(12) United States Patent
Acton, III et al.

(10) Patent No.: US 11,149,036 B2
(45) Date of Patent: Oct. 19, 2021

(54) 3-(1H-PYRAZOL-4-YL)PYRIDINE ALLOSTERIC MODULATORS OF THE M4 MUSCARINIC ACETYLCHOLINE RECEPTOR

(71) Applicants: John J. Acton, III, Bridgewater, NJ (US); Merck Sharp & Dohme Corp., Rahway, NJ (US); MSD R&D (China) Co., Ltd., Shanghai (CN); Jianming Bao, San Mateo, CA (US); Qiaolin Deng, Princeton, NJ (US); Melissa Egbertson, Ambler, PA (US); Ronald Ferguson, II, Scotch Plains, NJ (US); Xiaolei Gao, Bridgewater, NJ (US); Scott Timothy Harrison, Elkins Park, PA (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Zhaoyang Meng, Ambler, PA (US); Meng Na, Shanghai (CN); Michael T. Rudd, Collegeville, PA (US); Oleg Selyutin, West Windsor, NJ (US); David M. Tellers, Lansdale, PA (US); Ling Tong, Warren, NJ (US); Fengqi Zhang, Edison, NJ (US)

(72) Inventors: John J. Acton, III, Bridgewater, NJ (US); Jianming Bao, San Mateo, CA (US); Qiaolin Deng, Princeton, NJ (US); Melissa Egbertson, Ambler, PA (US); Ronald Ferguson, II, Scotch Plains, NJ (US); Xiaolei Gao, Bridgewater, NJ (US); Scott Timothy Harrison, Elkins Park, PA (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Zhaoyang Meng, Ambler, PA (US); Meng Na, Shanghai (CN); Michael T. Rudd, Collegeville, PA (US); Oleg Selyutin, West Windsor, NJ (US); David M. Tellers, Lansdale, PA (US); Ling Tong, Warren, NJ (US); Fengqi Zhang, Edison, NJ (US)

(73) Assignees: MSD R&D (China) Co., Ltd., Shanghai (CN); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/621,959

(22) PCT Filed: Jun. 22, 2018

(86) PCT No.: PCT/US2018/038888
§ 371 (c)(1),
(2) Date: Dec. 12, 2019

(87) PCT Pub. No.: WO2019/005587
PCT Pub. Date: Jan. 3, 2019

(65) Prior Publication Data
US 2020/0207758 A1    Jul. 2, 2020

(30) Foreign Application Priority Data
Jun. 27, 2017    (WO) ............... PCT/CN2017/090384

(51) Int. Cl.
*C07D 471/04*        (2006.01)
*C07D 401/04*        (2006.01)
(Continued)

(52) U.S. Cl.
CPC ......... *C07D 471/04* (2013.01); *C07D 401/04* (2013.01); *C07D 401/14* (2013.01);
(Continued)

(58) Field of Classification Search
CPC .. C07D 471/04; C07D 401/04; C07D 401/14; C07D 405/14; C07D 413/14; C07D 491/048; C07D 498/04
See application file for complete search history.

(56) References Cited

U.S. PATENT DOCUMENTS

| | | | |
|---|---|---|---|
| 5,574,044 | A | 11/1996 | Thompson et al. |
| 5,691,323 | A | 11/1997 | Thompson et al. |

(Continued)

FOREIGN PATENT DOCUMENTS

| | | |
|---|---|---|
| CN | 102015655 | 4/2011 |
| JP | 2014047192 | 3/2014 |

(Continued)

OTHER PUBLICATIONS

Chan; Proceedings of the National Academy of Sciences 2008, 105, 10978-10983. (Year: 2008).*

(Continued)

*Primary Examiner* — Daniel R Carcanague
(74) *Attorney, Agent, or Firm* — Eric A. Meade; John C. Todaro

(57) ABSTRACT

The present invention is directed to pyrazol-4-yl-pyridine compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

18 Claims, No Drawings

(51) Int. Cl.

| | |
|---|---|
| *C07D 401/14* | (2006.01) |
| *C07D 405/14* | (2006.01) |
| *C07D 413/14* | (2006.01) |
| *C07D 491/048* | (2006.01) |
| *C07D 498/04* | (2006.01) |

(52) U.S. Cl.
CPC ......... *C07D 405/14* (2013.01); *C07D 413/14* (2013.01); *C07D 491/048* (2013.01); *C07D 498/04* (2013.01)

(56) References Cited

U.S. PATENT DOCUMENTS

| | | |
|---|---|---|
| 6,699,880 B1 | 3/2004 | Yamakawa et al. |
| 6,900,224 B2 | 5/2005 | Ledoussal et al. |
| 7,074,801 B1 | 7/2006 | Yoshida et al. |
| 7,858,635 B2 | 12/2010 | Makings et al. |
| 7,964,602 B2 | 6/2011 | MacDonald et al. |
| 8,071,776 B2 | 12/2011 | Esteban et al. |
| 8,168,639 B2 | 5/2012 | Kogan |
| 8,349,850 B2 | 1/2013 | Tworowski et al. |
| 8,614,319 B2 | 12/2013 | Tworowski et al. |
| 9,034,872 B2 | 5/2015 | Tworowski et al. |
| 9,056,875 B2 | 6/2015 | Lindsley et al. |
| 9,056,876 B2 | 6/2015 | Conn et al. |
| 9,493,481 B2 | 11/2016 | Lindsley et al. |
| 9,593,106 B2 | 3/2017 | Livermore et al. |
| 9,637,498 B2 | 5/2017 | Lindsley et al. |
| 9,670,183 B2 | 6/2017 | Brown et al. |
| 9,758,506 B2 | 9/2017 | Brown et al. |
| 9,868,746 B2 | 1/2018 | Lindsley et al. |
| 10,329,289 B2 | 6/2019 | Bao et al. |
| 10,351,564 B2 | 7/2019 | Gao et al. |
| 10,512,638 B2 | 12/2019 | Rudd et al. |
| 10,933,056 B2 * | 3/2021 | Acton, III ............... A61P 25/16 |
| 2006/0100245 A1 | 5/2006 | Bakthavatchalam et al. |
| 2007/0004763 A1 | 1/2007 | Baindur et al. |
| 2008/0015193 A1 | 1/2008 | Mendoza |
| 2008/0306107 A1 | 12/2008 | Griffin et al. |
| 2011/0065683 A1 | 3/2011 | Thuring |
| 2012/0202784 A1 | 8/2012 | Aronov et al. |
| 2013/0096144 A1 | 4/2013 | Huang et al. |
| 2014/0194471 A1 | 7/2014 | Lindlsley et al. |
| 2014/0275175 A1 | 9/2014 | Adams et al. |
| 2014/0288084 A1 | 9/2014 | Lindsley et al. |
| 2015/0307451 A1 | 10/2015 | Yamada et al. |
| 2015/0307479 A1 | 10/2015 | Kuduk et al. |
| 2015/0307497 A1 | 10/2015 | Sugimoto et al. |
| 2015/0376179 A1 * | 12/2015 | Livermore ........... A61K 31/506 424/722 |
| 2016/0194321 A1 | 7/2016 | Ballard et al. |
| 2016/0200733 A1 | 7/2016 | Lindsley et al. |
| 2017/0096437 A1 | 4/2017 | Congreve et al. |
| 2017/0369505 A1 | 12/2017 | Lindsley et al. |
| 2019/0000824 A1 * | 1/2019 | Acton, III ............ A61K 31/437 |
| 2020/0069671 A1 * | 3/2020 | Acton, III ............ A61K 31/437 |
| 2020/0095262 A1 * | 3/2020 | Clausen ............. A61B 17/3472 |
| 2020/0109137 A1 * | 4/2020 | Bao ...................... C07D 487/04 |

FOREIGN PATENT DOCUMENTS

| | | |
|---|---|---|
| WO | WO2005100351 | 10/2005 |
| WO | WO2006/125180 | 11/2006 |
| WO | WO2009/135944 | 11/2009 |
| WO | WO2011033018 | 3/2011 |
| WO | WO2011087776 | 7/2011 |
| WO | WO2012020813 | 2/2012 |
| WO | WO2012116246 | 8/2012 |
| WO | WO2013055895 | 4/2013 |
| WO | WO2013055897 | 4/2013 |
| WO | WO2013063549 | 5/2013 |
| WO | WO2014077401 | 5/2014 |
| WO | WO2017112556 | 6/2017 |
| WO | WO-2019000237 A1 * | 1/2019 ............. A61P 25/00 |
| WO | WO-2019000238 A1 * | 1/2019 ........... C07D 413/14 |
| WO | WO-2020087202 A1 * | 5/2020 ........... C07D 401/14 |

OTHER PUBLICATIONS

Foster; Neuropsychiatric Disease and Treatment 2014, 10, 183-191. (Year: 2014).*

Scarr; CNS Neuroscience & Therapeutics 2012, 18, 369-379. (Year: 2012).*

Schubert; ChemMedChem 2019, 14, 943-951. (Year: 2019).*

Vardigan; Psychopharmacology 2015, 232, 1859-1866. (Year: 2015).*

European Search Report in Application EP18825469, dated Jan. 22, 2021. 4 Pages. (Year: 2021).*

Bewley, Blake R., et al., Discovery of a novel, CNS penetrant M4PAM chemotype based on a 6-fluoro-4-(piperiden-1-yl)quinoline-3-carbonitrile core, Bioorganic and Med Chem Letters, 2017, 4274-4279, 27.

Byun, Nellie B, et al., Antipsychotic Drug-like Effects of the Selective M4 Muscarinic Acetylcholine Receptor Positive Allosteric Modulator VU02552100, Neuropsychopharmacology, 2014, 1578-1593, 39.

Eglen, Richard M., Muscarinic receptor ligands and their therapeutic potential, Current Opinion in Chemical Biology, 1999, 426-432, 3.

International Search Report and Written Opinion for PCT/CN2017/090384 dated Mar. 29, 2018; 11 pages.

International Search Report and Written Opinion for PCT/US2018/038888 dated Sep. 12, 2018; 8 pages.

Kargbo, Robert B., Allosteric Modulators of the M4 Muuscarinic Acetylcholine Receptor, ACS Medicinal Chemistry Letters, 2017, 903-904, 8.

Lindsley, Craig W., et al., Discovery of the mAChR subtype selective M4 positive allosteric moduclators, Current Topics in Medicinal Chemistry, 2008, 531, 8-6.

Long, Madeline F., Discovery of a nove 2,4-dimethylquinoline-6-carboxamide M4 positive allosteric modulator (PAM) Chemotype via scaffold hopping, Bioorganic and Med Chem Letters, 2017, 4999-5001, 27.

Melancon, Bruce J., et al., Optimization of M4 Positive Allosteric Modulators (PAMs): The discovery of VUO476406, a non-human primate in vivo tool compound for translational pharmacology, Bioorganic and Med Chem Letters, 2017, 2296-2301,27.

Salovich, James M., et al., Discovery of N-(4-methoxy-7-methylbenzo[d]thiazol-2-yl) . . . , Bioorganic and Med Chem Letters, 2012, 5084-5088, 22.

Tarr, James C., Challenges in the development of an M4PAM preclinical candidate: The discovery, SAR and in vivo characterization of a . . . , Bioorganic and Med Chem Letters, 2017, 2990-2995, 27.

Tarr, James C., et al., Challenges in the development of an M4PAM Preclinical candidate: . . . , Bioorganic and Med Chem Letters, 2017, 5179-5184, 27.

Utley, Thomas, Synthesis and SAR of a novel metabotropic glutamate receptor 4 . . . , Bioorganic and Med Chem Letters, 2011, 6955-6959, 21.

Wood, Michael R., et al., Discovery and Optimization of a novel series of highly CNS penetrant M4PAMS based on a 5,6-dimethul-4-(piperidin-1-yl)thieno[2,3-d]pyrimidine core, Bioorganic and Med Chem Letters, 2016, 3029-3033, 26.

Wood, Michael R., et al., Discovery of VU0467485/AZ13713945: An M4PAM evaluated as a Preclinical candidate for the Treatment of Schizophrenia, ACS Medicinal Chemistry Letters, 2017, 233-238, 8.

RN: 1552923-38-2 Registry STN American Chemical Society; Feb. 23, 2014.

RN: 1546829-79-1 Registry STN American Chemical Society; Feb. 23, 2014.

RN: 1424588-49-7 Registry STN American Chemical Society; Feb. 23, 2014.

RN: 1394484-56-0 Registry STN American Chemical Society; Feb. 23, 2014.

(56) References Cited

OTHER PUBLICATIONS

PUBCHEM Substance Record for SID 215465399 dated Oct. 20, 2014.

* cited by examiner

3-(1H-PYRAZOL-4-YL)PYRIDINE ALLOSTERIC MODULATORS OF THE M4 MUSCARINIC ACETYLCHOLINE RECEPTOR

CROSS REFERENCE TO RELATED APPLICATIONS

This application is a U.S. National Phase application under 35 U.S.C. § 371 of PCT Application No. PCT/US18/038888, filed Jun. 22, 2018, which claims priority under 35 U.S.C. § 119(e) from PCT/CN2017/090384, filed Jun. 27, 2017.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system. Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42). One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to pyrazol-4-yl-pyridine compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

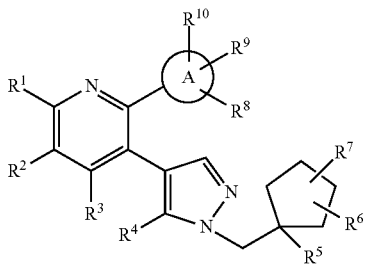

wherein:
A is selected from: benzoimidazole, benzoisoxazole, benzoxazole, benzotriazole, cinnoline, dihydrobenzofuranone, furopyridinone, imidazopyridine, indazole, isobenzofuranone, isoindolinone, isoquinoline, oxazolopyridine, phenyl, pyrazolopyridine, pyrrolopyridinone, quinoline, and triazolopyridine;
$R^1$ is selected from:
  (1) hydrogen,
  (2) halogen,
  (3) —CN,
  (4) —$C_{1-6}$alkyl, which is unsubstituted or substituted with a hydroxy, or 1-3 fluoro,
  (5) —O—$C_{1-6}$alkyl, which is unsubstituted or substituted with a hydroxy, or 1-3 fluoro,
  (6) —C≡CH,
  (7) -pyrazolyl,
  (8) —(C=O)—$NH_2$, and
  (9) —(C=O)—NH(—$C_{1-6}$alkyl);
$R^2$ is selected from:
  (1) hydrogen,
  (2) halogen,
  (3) —$C_{1-6}$alkyl, and
  (4) —$NH_2$;
$R^3$ is selected from:
  (1) hydrogen,
  (2) halogen,
  (3) —CN,
  (4) —$C_{1-6}$alkyl, and
  (5) —$NH_2$;
$R^4$ is selected from:
  (1) hydrogen,
  (2) —CN,
  (3) chloro, and
  (4) fluoro;
$R^5$ is selected from:
  (1) hydrogen,
  (2) fluoro, and
  (3) —$CH_3$;
each of $R^6$ and $R^7$ is independently selected from:
  (1) hydrogen,
  (2) fluoro, and
  (2) $C_{1-6}$alkyl,
  or $R^5$, $R^6$ and $R^7$ are joined together to form a bicycle [2.2.1]heptane ring,
  with the proviso that if A is pyrazolopyridine, then at least one of $R^6$ and $R^7$ is other than hydrogen;
each of $R^8$, $R^9$ and $R^{10}$ is independently selected from:
  (1) hydrogen,
  (2) halo,
  (3) —OH,
  (4) —$C_{1-6}$alkyl, which is unsubstituted or substituted with a hydroxy, —$OC_{1-6}$alkyl, cyclopropyl, cyclobutyl, or 1-3 fluoro,
  (5) —$OC_{1-6}$alkyl, which is unsubstituted or substituted with a hydroxy, —$OC_{1-6}$alkyl, cyclopropyl, cyclobutyl, or 1-3 fluoro,
  (6) —$C_{3-6}$cyclolkyl, which is unsubstituted or substituted with a hydroxy, methoxy, or 1-3 fluoro,
  (7) —$NH_2$, —NH($C_{1-6}$alkyl), or —N($C_{1-6}$alkyl)$_2$, wherein the —$C_{1-6}$alkyl, is unsubstituted or substituted with hydroxy, methoxy, or 1-3 fluoro,
  (8) azetidinyl, pyrrolidinyl, piperidinyl, or piperazinyl, wherein the azetidinyl, pyrrolidinyl, piperidinyl, or piperazinyl, is unsubstituted or substituted with hydroxy, methoxy, or 1-3 fluoro, and
  (9) —CN;
or a pharmaceutically acceptable salt thereof.

An embodiment of the present invention includes compounds of the formula Ia:

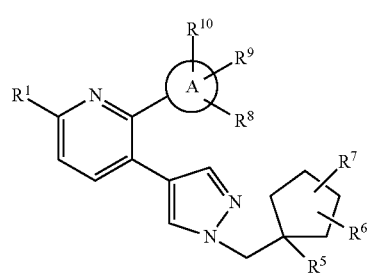

wherein A, $R^1$, $R^5$, $R^6$, $R^7$, $R^8$, $R^9$ and $R^{10}$ are defined herein; or a pharmaceutically acceptable salt thereof.

An embodiment of the present invention includes compounds of the formula Ib:

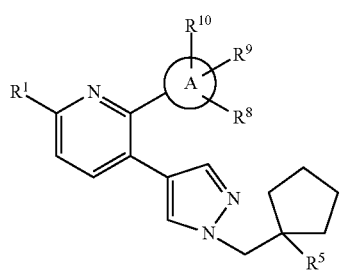

wherein A, $R^1$, $R^5$, $R^8$, $R^9$ and $R^{10}$ are defined herein; or a pharmaceutically acceptable salt thereof.

An embodiment of the present invention includes compounds wherein A is selected from: cinnoline, isoindolinone, phenyl, pyrrolopyridinone, and quinolone. An embodiment of the present invention includes compounds wherein A is quinolone. An embodiment of the present invention includes compounds wherein A is isoindolinone.

An embodiment of the present invention includes compounds wherein $R^1$ is selected from:
  (1) hydrogen,
  (2) fluoro,
  (3) chloro,
  (4) —CN, and
  (5) methyl.

An embodiment of the present invention includes compounds wherein $R^1$ is selected from:
  (1) hydrogen,
  (2) —CN, and
  (3) methyl.

An embodiment of the present invention includes compounds wherein $R^1$ is hydrogen. An embodiment of the present invention includes compounds wherein $R^1$ is methyl.

An embodiment of the present invention includes compounds wherein $R^2$ is selected from:
(1) hydrogen, and
(2) methyl.

An embodiment of the present invention includes compounds wherein $R^2$ is hydrogen.

An embodiment of the present invention includes compounds wherein $R^3$ is selected from:
(1) hydrogen,
(2) —CN, and
(2) methyl.

An embodiment of the present invention includes compounds wherein $R^3$ is hydrogen.

An embodiment of the present invention includes compounds wherein $R^4$ is hydrogen. An embodiment of the present invention includes compounds wherein $R^4$ is cyano. An embodiment of the present invention includes compounds wherein $R^4$ is fluoro.

An embodiment of the present invention includes compounds wherein $R^5$ is hydrogen. An embodiment of the present invention includes compounds wherein $R^5$ is methyl. An embodiment of the present invention includes compounds wherein $R^5$ is fluoro.

An embodiment of the present invention includes compounds wherein $R^6$ is selected from:
(1) hydrogen, and
(2) fluoro.

An embodiment of the present invention includes compounds wherein $R^6$ is hydrogen.

An embodiment of the present invention includes compounds wherein $R^7$ is selected from:
(1) hydrogen, and
(2) fluoro.

An embodiment of the present invention includes compounds wherein $R^7$ is hydrogen.

An embodiment of the present invention includes compounds wherein each of $R^8$, $R^9$ and $R^{10}$ is independently selected from:
(1) hydrogen,
(2) halo,
(3) —OH,
(4) —$C_{1-6}$alkyl, which is unsubstituted or substituted with a hydroxy, or 1-3 fluoro,
(5) —$OC_{1-6}$alkyl, which is unsubstituted or substituted with a hydroxy, or 1-3 fluoro, and
(6) cyclopropyl.

An embodiment of the present invention includes compounds wherein each of $R^8$, $R^9$ and $R^{10}$ is independently selected from:
(1) hydrogen,
(2) fluoro,
(3) —$CH_3$,
(4) —$CF_3$, and
(5) —$OCH_3$, and
(6) cyclopropyl.

An embodiment of the present invention includes compounds wherein each of $R^8$, $R^9$ and $R^{10}$ is hydrogen.

Certain embodiments of the present invention include a compound which is selected from the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Similarly, ($CH_{2-5}$ cycloalkyl-O—) indicates the presence of cyclopropoxy, cyclobutoxy, tetrahydrofuranyl, or tetrahydropyranyl ring. Substituents (such as $R^{1a}$, $R^{1b}$ and $R^{1c}$) may be absent if the valency of the group to which they are attached does not permit such substitution. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences,* 2001, 68:2517-2524. For a general description of the role of allosteric binding sites, see Christopoulos, *Nature Reviews: Drug Discovery,* 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as modulators of M4 muscarinic acetylcholine receptors may be readily determined without undue experimentation by methodology well known in the art, including monitoring the mobilization of intracellular Ca++, determining the levels of intracellular cAMP, or quantiting the exchange of GDP for [35S]γGTP.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gaqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 1000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 μM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, 0-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR 3 agonists; ApoE4 conformational modulators; NR2B antagonists; androgen receptor modulators; blockers of AP3 oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; CB-1 receptor antagonists or CB-1 receptor inverse agonists; antibiotics such as doxycycline and rifampin; N-methyl-D-aspartate (NMDA) receptor antagonists, such as memantine, neramexane and EVT 101; recombinant growth hormone; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or $M_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), (+)-2,3-dihydro-5, 6-dimethoxy-2-[[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK30 inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DAST: diethylaminosulfur trifluoride; DCM: dichloromethane; DCE: dichloroethane; DEA: diethylamine; DEAD: diethylazodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMSO: dimethylsulfoxide; dppf: 1,1'-bis(diphenylphosphino)ferrocene; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; HATU: (1-[bis(dimethylamino)methylene]-1H-1,2,3-triazolo[4,5-b]pyridinium 3-oxid hexafluorophosphate); HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; mCPBA: meta-chloroperbenzoic acid; MeOH: methanol; $MgSO_4$: magnesium sulfate; Ms: methanesulfonyl; MTBE: methyl tert-butyl ether; $NaHCO_3$: sodium bicarbonate; NaOH: sodium hydroxide; NCS: N-chlorosuccinimide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; TBAF: tetra-n-butylammonium fluoride; TFA: trifluoracetic acid; TFAA: trifluoroacetic anhydride; THF: tetrahydrofuran; TIPS: triisopropylsilyl; TLC: thin layer chromatography; Ts: toluenesulfonyl; X-Phos: 2-(dicyclohexyl-phosphino)-2',4',6'-triisopropylbiphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediates

Intermediate compounds of the present invention can be synthesized according to the schemes and procedures outlined below. Because the schemes are an illustration, the invention should not be construed as being limited by the chemical reactions and conditions expressed. The preparation of the various starting materials used in the schemes is within the skill of a person versed in the art.

SCHEME A

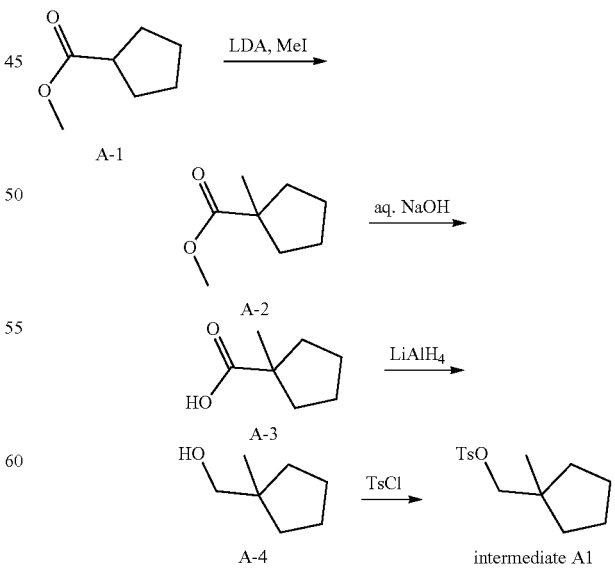

Intermediate A1 is prepared according to scheme A via alkylation of commercially available ester A-1. Subsequent saponification to acid A-3 and reduction provides alcohol A-4, which is then tosylated to yield intermediate A1.

Intermediate A1

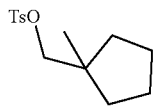

(1-Methylcyclopentyl)methyl 4-methylbenzenesulfonate (Scheme A)

Step 1: Methyl 1-methylcyclopentane-1-carboxylate

To a solution of diisopropylamine (276 mL, 1.97 mol) in THF (400 mL) was added n-BuLi (664 mL, 1.66 mol) at 0° C. The reaction mixture was stirred at this temperature for 15 min before warming to RT and aging for 45 min. The system was then cooled to −70° C. and a solution of methyl cyclopentanecarboxylate (100 g, 780 mmol) in THF (800 mL) was added dropwise. After stirring for 2 h at this temperature, iodomethane (166 g, 1.18 mol) was added dropwise and the reaction mixture was stirred for an additional for 16 h. The mixture poured into aqueous $NH_4Cl$ and was extracted with EtOAc (2×). The organic was washed with brine, dried and concentrated before distillation to obtain the title compound.

Step 2: 1-Methylcyclopentane-1-carboxylic acid

To a stirred suspension of methyl 1-methylcyclopentane-1-carboxylate (100 g, 0.704 mol) in MeOH (500 mL) at RT was added aq. NaOH (352 mL, 1.4 mol). The mixture was stirred for 4 h and was then acidified with 4 N HCl to pH=2-3. The organic was extracted with EtOAc (3×), washed with brine, dried over anhydrous $Na_2SO_4$, and concentrated to give the title compound.

Step 3: (1-Methylcyclopentyl)methanol

To a mixture of $LiAlH_4$ (53.5 g, 1.41 mol) in THF (600 mL) was added a solution of 1-methylcyclopentane-1-carboxylic acid (100 g, 781 mmol) in THF at 0° C. The system was stirred for 30 min at the same temperature before warming to RT and aging the reaction for an additional 16 h. The reaction mixture was quenched by cautious addition of water, 15% NaOH solution, and water again at 0° C. After stirring for 1 h, the mixture was filtered and the filtrate washed with brine, dried and concentrated to give the title compound.

Step 4: (1-Methylcyclopentyl)methyl 4-methylbenzenesulfonate

To a solution of (1-methylcyclopentyl)methanol (170 g, 1.49 mol) in pyridine (1.5 L) at RT was added TsCl (284 g, 1.49 mol) in one portion. After stirring for 16 h, the reaction was poured into 1N HCl and was extracted with EtOAc (3×). The combined organics were washed with 1N HCl, brine, dried over sodium sulfate and concentrated. Purification by silica gel chromatography (100:1-50:1 petroleum ether:EtOAc) yielded the title compound. $^1H$ NMR (500 MHz, $CDCl_3$): δ 7.81-7.79 (t, J=6.8 Hz, 2H), 7.37-7.28 (t, J=8.4 Hz, 2H), 3.77 (s, 2H), 2.46 (s, 3H), 1.63-1.27 (m, J=7.2 Hz, 8H), 0.98 (s, 3H).

SCHEME A2

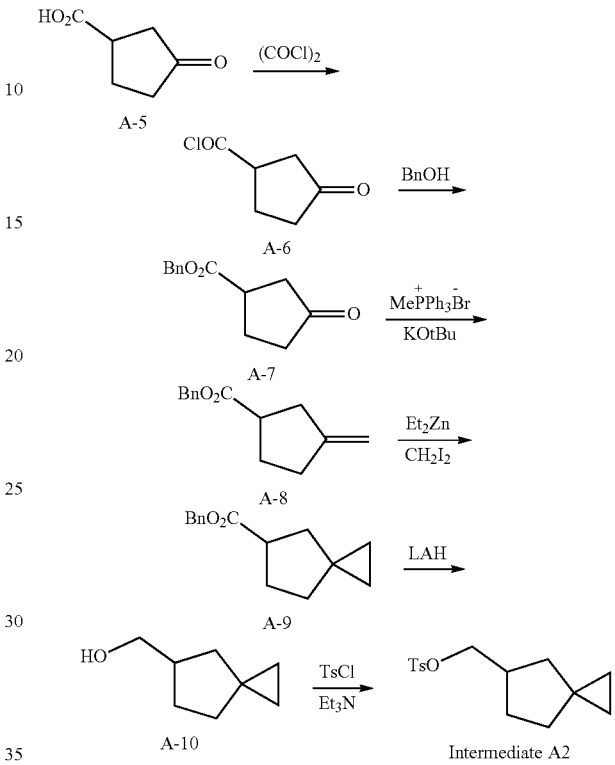

Intermediate A2 is prepared by a two step benzyl esterification of cyclopentanone carboxylate A-5, followed by Wittig reaction to provide alkene A-8. Simmons-Smith cyclopropanation followed by ester reduction and tosylation provides Intermediate A2.

Intermediate A2

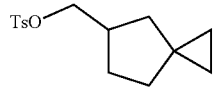 [SMILES: Cc1ccc(S(=O)(=O)OCC2CCC3(CC3)C2)cc1]

spiro[2.4]heptan-5-ylmethyl 4-methylbenzenesulfonate (Scheme A2)

Step 1: 3-oxocyclopentanecarbonyl chloride

To a solution of 3-oxocyclopentanecarboxylic acid (5 g, 39.0 mmol) in DCM (30 mL) was added oxalyl dichloride (5 ml, 39.0 mmol) dropwise at −10° C. for 30 min. The resulting mixture was stirred at 20° C. for 2 hours, then concentrated in vacuo. The residue was used directly without further purification or characterization.

Step 2: benzyl 3-oxocyclopentanecarboxylate

To a solution of benzyl alcohol (4.80 g, 44.3 mmol) in DCM (30 ml) was added $Et_3N$ (4.75 ml, 34.1 mmol) and DMAP (0.834 g, 6.82 mmol). 3-Oxocyclopentanecarbonyl chloride (5 g, 34.1 mmol) was then added dropwise at 0° C. The reaction mixture was stirred at 20° C. for 12h. Then the mixture was poured into water (45 mL) and extracted with three times with ethyl acetate. The combined organic layers were washed with brine (45 mL), dried over sodium sulfate, filtered and concentrated in vacuo. The residue was purified by column chromatography on silica gel (40% ethyl acetate in petroleum ether) to give the title compound. $^1$H NMR (400 MHz, CDCl$_3$): δ 7.35 (m, 5H), 5.15 (s, 2H), 3.12 (m, 1H), 2.60-2.10 (m, 6H).

Step 3: benzyl 3-methylenecyclopentanecarboxylate

To a solution of bromo(methyl)triphenylphosphorane (7.37 g, 20.62 mmol) in THF (20 ml) was added 1 N potassium tert-butoxide (20.62 ml, 20.62 mmol) in THF dropwise at 0° C. for 30 min, then was added dropwise benzyl 3-oxocyclopentanecarboxylate (3 g, 13.75 mmol) in THF (10 mL). The resulting mixture was stirred at −5° C. for 1 hour. The reaction mixture was diluted with water (40 mL) and extracted with EtOAc (100 mL×4). The combined organic layers were dried over anhydrous Na$_2$SO$_4$, filtered and the filtrate was concentrated in vacuo. The residue was purified by Prep-TLC (20% EtOAc in petroleum ether) to give the title compound. $^1$H NMR (400 MHz, CDCl$_3$): δ 7.34 (m, 5H), 5.12 (s, 2H), 4.87 (s, 2H), 2.88 (m, 1H), 2.59-2.29 (m, 4H), 2.05-1.90 (m, 2H).

Step 4: benzyl spiro[2.4]heptane-5-carboxylate

To a solution of diiodomethane (2477 mg, 9.25 mmol) in DCM (5 ml) was added diethylzinc (4.62 ml, 4.62 mmol) at −10° C. for 30 min, and then benzyl 3-methylenecyclopentanecarboxylate (500 mg, 2.312 mmol). The resulting mixture was stirred at 25° C. for 12 h. The reaction mixture was diluted with water (10 mL) and extracted with ethyl acetate (80 mL×4). The combined organic layers were dried over Na$_2$SO$_4$, filtered and evaporated to give the title compound, which was used directly without further purification. $^1$H NMR (400 MHz, CDCl$_3$): δ 6.97 (m, 5H), 4.74 (s, 2H), 2.63 (m, 1H), 1.75-1.55 (m, 3H), 1.40-1.10 (m, 3H), 0.15-0.00 (m, 4H).

Step 5: spiro[2.4]heptan-5-ylmethanol

To a solution of benzyl spiro[2.4]heptane-5-carboxylate (200 mg, 0.868 mmol) in THF (2 ml) was added LiAlH$_4$ (42.8 mg, 1.129 mmol) at 0° C. The mixture was stirred at 0° C. for 1 h, then it was diluted with water (50 mL) and extracted with EtOAc (70 mL×3). The combined organic layers were washed with brine (50 mL), dried over MgSO$_4$, filtered, and the filtrate was concentrated in vacuo to give the title compound as a mixture with benzyl alcohol. $^1$H NMR (400 MHz, CDCl$_3$): δ 7.35-7.15 (m, 5H), 4.62 (s, 2H), 3.49 (m, 2H), 2.24 (m, 1H), 1.85-1.25 (m, 6H), 0.34 (m, 4H).

Step 6: spiro[2.4]heptan-5-ylmethyl 4-methylbenzenesulfonate

To a solution of spiro[2.4]heptan-5-ylmethanol (85 mg, 0.674 mmol) in DCM (3 ml) was added Et$_3$N (0.235 ml, 1.684 mmol) and 4-methylbenzene-1-sulfonyl chloride (167 mg, 0.876 mmol) at 0° C. The mixture was stirred at 0° C. for 1 hour. The mixture was diluted with water (50 mL) and extracted with EtOAc (50 mL×2). The combined organic layers were washed with brine (50 mL), dried over MgSO$_4$, filtered, and the filtrate was concentrated in vacuo. The residue was purified by Prep TLC (PE:EA=20:1) to give the title compound. $^1$H NMR (400 MHz, CDCl$_3$): δ 7.72 (m, 2H), 7.27 (m, 2H), 3.88 (m, 2H), 2.38 (s, m, 4H), 1.78 (m, 1H), 1.55-1.25 (m, 4H), 1.15 (m, 1H), 0.28 (m, 4H).

Using other commercially available cyclopentyl esters, acids or cyclopentylmethyl alcohols the tosylates A3-A7 were prepared in a similar fashion as tosylates A1 and A2.

TABLE A

| Intermediate | Structure | Name | NMR |
| --- | --- | --- | --- |
| A3 | TsO, F (structure) | (1-fluorocyclopentyl)methyl 4-methylbenzenesulfonate | $^1$H NMR (400 MHz, CDCl$_3$): δ 7.80 (d, J = 8.2 Hz, 2H), 7.35 (d, J = 8.6 Hz, 2H), 4.11 (d, J = 19 Hz, 2H), 2.45 (s, 3H), 2.10-1.60 (m, 8H). |
| A4 | TsO, F, F (structure) | (3,3-difluorocyclopentyl)methyl 4-methylbenzenesulfonate | $^1$H NMR (400 MHz, CDCl$_3$): δ 7.79 (d, J = 8.4 Hz, 2H), 7.36 (d, J = 8 Hz, 2H), 3.96 (m, 2H), 2.47 (m, 1H), 2.46 (s, 3H), 2.28-1.85 (m, 4H), 1.77 (m, 1H), 1.52 (m, 1H). |
| A5 | TsO (structure) | bicyclo[2.2.1]heptan-1-ylmethyl 4-methylbenzenesulfonate | $^1$H NMR (400 MHz, CDCl$_3$): δ 7.79 (d, J = 8.2 Hz, 2H), 7.34 (d, J = 8.4 Hz, 2H), 4.10 (s, 2H), 2.45 (s, 3H), 2.21 (m, 1H), 1.70-1.15 (m, 10H). |

TABLE A-continued

| Intermediate | Structure | Name | NMR |
|---|---|---|---|
| A6 | OTs, ⋯F (cyclopentyl) | (1S,3S and 1R,3R)-3-fluorocyclopentyl)methyl 4-methylbenzenesulfonate | ¹H NMR (400 MHz, CDCl₃): δ 7.78 (m, 2H), 7.36 (m, 2H), 5.11 (dm, J = 53.5 Hz, 1H), 3.95 (d, 2H), 2.50 (m, 1H), 2.46 (s, 3H), 2.07 (m, 1H),1.90 (m, 3H), 1.41 (m, 2H). |
| A7 | OTs, F (cyclopentyl) | ((1R,3S and 1S,3R)-3-fluorocyclopentyl)methyl 4-methylbenzenesulfonate | ¹H NMR (400 MHz, CD₃OD): δ 7.76 (d, 2H), 7.43 (d, 2H), 5.02 (d, J = 54 Hz, 1H), 3.93 (m, 2H), 2.44 (s, 3H), 2.30 (m, 1H), 2.00-1.30 (m, 6H). |

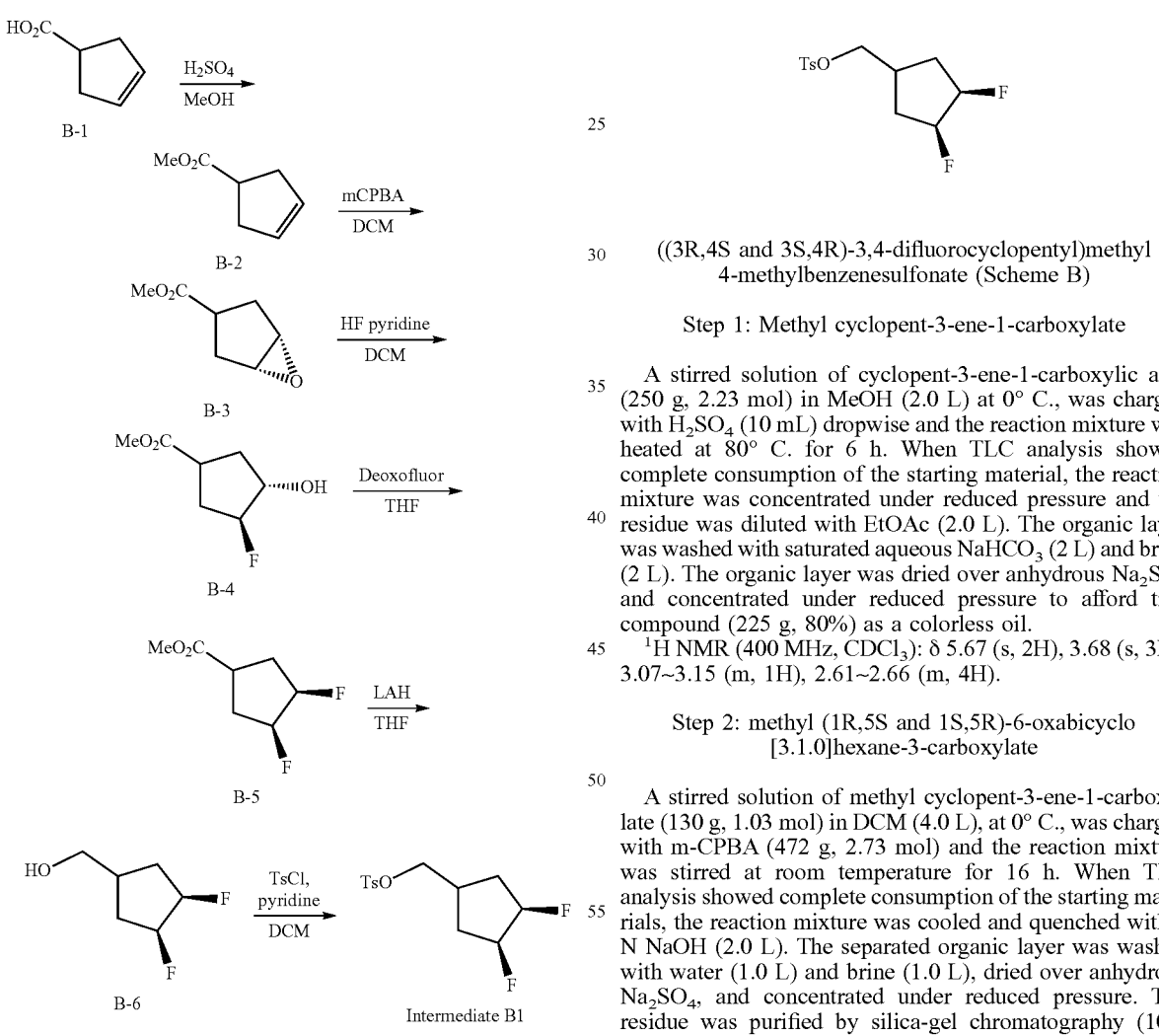

Intermediate B1 is prepared according to scheme B via epoxidation of ester B-2 followed by ring opening with HF•Pyridine to fluorocyclopentanol B-4. Subsequent fluorination of the hydroxycyclopentane to B-5 followed by reduction to alcohol B-6 and tosylation provides intermediate B1.

Intermediate B1

((3R,4S and 3S,4R)-3,4-difluorocyclopentyl)methyl 4-methylbenzenesulfonate (Scheme B)

Step 1: Methyl cyclopent-3-ene-1-carboxylate

A stirred solution of cyclopent-3-ene-1-carboxylic acid (250 g, 2.23 mol) in MeOH (2.0 L) at 0° C., was charged with H₂SO₄ (10 mL) dropwise and the reaction mixture was heated at 80° C. for 6 h. When TLC analysis showed complete consumption of the starting material, the reaction mixture was concentrated under reduced pressure and the residue was diluted with EtOAc (2.0 L). The organic layer was washed with saturated aqueous NaHCO₃ (2 L) and brine (2 L). The organic layer was dried over anhydrous Na₂SO₄ and concentrated under reduced pressure to afford title compound (225 g, 80%) as a colorless oil.

¹H NMR (400 MHz, CDCl₃): δ 5.67 (s, 2H), 3.68 (s, 3H), 3.07~3.15 (m, 1H), 2.61~2.66 (m, 4H).

Step 2: methyl (1R,5S and 1S,5R)-6-oxabicyclo[3.1.0]hexane-3-carboxylate

A stirred solution of methyl cyclopent-3-ene-1-carboxylate (130 g, 1.03 mol) in DCM (4.0 L), at 0° C., was charged with m-CPBA (472 g, 2.73 mol) and the reaction mixture was stirred at room temperature for 16 h. When TLC analysis showed complete consumption of the starting materials, the reaction mixture was cooled and quenched with 1 N NaOH (2.0 L). The separated organic layer was washed with water (1.0 L) and brine (1.0 L), dried over anhydrous Na₂SO₄, and concentrated under reduced pressure. The residue was purified by silica-gel chromatography (10% MTBE in hexanes) to afford title compound (78.0 g, 30%) as a colorless liquid.

Step 3: methyl (3S,4S and 3R,4R)-3-fluoro-4-hydroxycyclopentane-1-carboxylate

A stirred solution of methyl (1R,5S and 1S,5R)-6-oxabicyclo[3.1.0]hexane-3-carboxylate (50 g, 0.352 mol) in CH$_2$Cl$_2$ (500 mL) at 0° C. was charged with HF·Pyridine (30.7 mL, 1.23 mol) dropwise over 10 min. The reaction mixture was stirred at room temperature for 4 h. When TLC analysis showed complete consumption of the starting material, the reaction mixture was cooled to 0° C. and quenched with saturated aqueous NaHCO$_3$ (500 mL). The separated organic layer was washed with 2 M HCl (500 mL), water (300 mL), and brine (300 mL), dried over anhydrous Na$_2$SO$_4$, and concentrated under reduced pressure. The residue was purified by silica-gel chromatography eluted with PE:EtOAc=2:1 to afford title compound (22 g, 35%) as a colorless liquid. $^1$H NMR (400 MHz CDCl$_3$): δ 4.77-4.91 (m, 1H), 4.35-4.38 (m, 1H), 3.71 (s, 3H), 3.08-3.12 (m, 1H), 1.98-2.50 (m, 5H).

Step 4: methyl (3R,4S and 3S,4R)-3,4-difluorocyclopentane-1-carboxylate

To a solution of methyl (3S,4S and 3R,4R)-3-fluoro-4-hydroxycyclopentane-1-carboxylate (1.0 gram, 6.17 mmol) in 10 mL THF was added deoxofluor (1.5 gram, 6.78 mmol). The solution was heated to 65° C. for 90 minutes and then cooled back to room temperature. The reaction was treated with water and extracted twice with ethyl acetate. The combined extracts were then washed successively with saturated aqueous NaHCO$_3$ and saturated NaCl, then dried over MgSO$_4$, filtered and evaporated by rotary evaporation to give the crude title compound.

Step 5: ((3R,4S and 3S,4R)-3,4-difluorocyclopentyl)methanol

Methyl (3R,4S and 3 S,4R)-3,4-difluorocyclopentane-1-carboxylate (1.05 gram, 6.40 mmol) was dissolved in 20 ml of anhydrous diethyl ether and cooled to 0° C. The substrate was then treated with 1M lithium aluminum hydride in ether (12.8 mL, 12.8 mmol) and stirred for 1 hour at room temperature. Cooled the reaction again and quenched with 0.5 mL water, 0.5 mL of 2.5 M NaOH, and then 1.5 mL water. Stirred for 30 minutes at room temperature, then added 50 mL ether and MgSO$_4$, then stirred for an additional 30 minutes before filtering and evaporating the filtrate to produce the crude title compound.

Step 6: ((3R,4S and 3 S,4R)-3,4-difluorocyclopentyl)methyl 4-methylbenzenesulfonate To a solution of ((3R,4S and 3S,4R)-3,4-difluorocyclopentyl)methanol (590 mg, 4.33 mmol) in DCM (1.7 mL) was added pyridine (1.75 mL, 21.67 mmol) and TsCl (1.24 g, 6.5 mmol) in one portion. After stirring for 1 h, the reaction was poured into 1N HCl and was extracted with EtOAc (3×). The combined organics were washed with 1N HCl, brine, dried over sodium sulfate and concentrated. Purification by silica gel chromatography (gradient from 0-100% DCM in hexanes) yielded the title compound. $^1$H NMR (400 MHz, CDCl$_3$): δ 7.78 (d, J=6.2 Hz, 2H), 7.37 (d, J=8.5 Hz, 2H), 5.00 (m, 1H), 4.90 (m, 1H), 3.93 (d, J=5.1 Hz, 2H), 2.72 (m, 1H), 2.46 (s, 3H), 2.12 (m, 2H), 1.70 (m, 2H).

SCHEME C

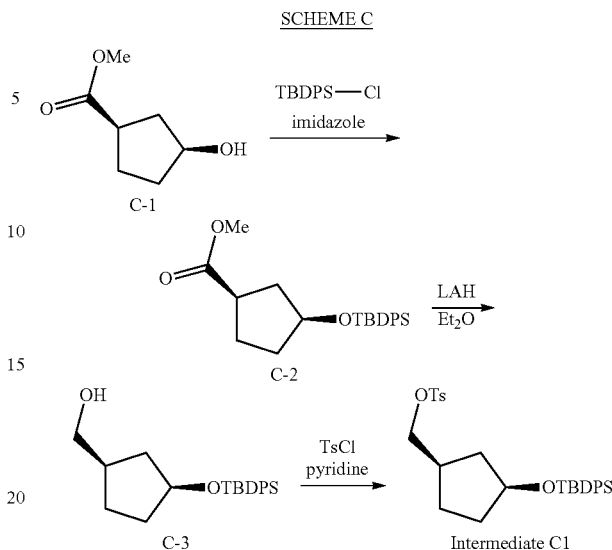

The commercially available alcohol C-1 was treated with TBDPS-Cl and imidazole, then reduced with LAH and the alcohol C-3 treated with tosyl chloride/pyridine to give intermediate C1.

((1R,3S and 1S,3R)-3-((tert-butyldiphenylsilyl)oxy)cyclopentyl)methyl 4-methylbenzenesulfonate (Scheme C)

Step 1: Methyl (1R,3S and 1 S,3R)-3-((tert-butyldiphenylsilyl)oxy)cyclopentane-1-carboxylate Methyl (1R,3S and 1S,3R)-3-hydroxycyclopentane-1-carboxylate (1.71 g, 11.86 mmole) was dissolved in 20 ml DCM and treated sequentially with TBDPS-Cl (3.59 g, 13.05 mmole) and imidazole (1.62 g, 23.72 mmole). Th reaction exotherms. The reaction was stirred at ambient temperature for 2 days. Added 20 ml water and partitioned the resulting layers. The aqueous was back extracted with 20 ml DCM. The combined organic extracts were washed with 0.1N HCl to acidic pH, and then 10 ml brine. Dried over MgSO4, filtered and evaporated in vacuo. The crude isolate was carried to the next step without further purification. MS(M+1): 383.

Step 2: ((1R,3S and 1S,3R)-3-((tert-butyldiphenylsilyl)oxy)cyclopentyl)methanol Methyl (1R,3S and 1S,3R)-3-((tert-butyldiphenylsilyl)oxy)cyclopentane-1-carboxylate (4.99 g, 13.04 mmole) was dissolved in 30 ml diethyl ether under nitrogen and cooled over dry ice/acetone bath for 5 minutes. LAH (495 mg, 13.04 mmole) was added slowly over 5 minutes, after which the cooling bath was removed. Stirred at ambient temperature for 1 hour. The reaction was again cooled over a dry ice/acetone bath and then quenched with 495 µl water. This mixture was removed from the cooling bath and treated with 495 µl of 2.5M aqueous NaOH and then 1480 µl water. Stirred at room temperature for 10 minutes. Diluted with 50 ml ether and filtered, rinsing the pad with 20 ml ether. The filtrate was washed with 10 ml brine, dried over MgSO$_4$, filtered and evaporated in vacuo to give the title compound, which was used in the next step without further purification. MS(M+1): 355.

Step 3: ((1R,3S and 1S,3R)-3-((tert-butyldiphenylsilyl)oxy)cyclopentyl)methyl 4-methylbenzenesulfonate ((1R,3S and 1S,3R)-3-((tert-butyldiphenylsilyl)oxy)cyclopentyl)methanol (4.2 grams, 11.85 mmole) was dissolved in DCM (5 mL) and pyridine (4.8 ml, 59.2 mmole) and then treated with TsCl (2.48 grams, 13.03 mmole). The reaction mixture became warm; it was allowed to stand at ambient temperature for an hour. The reaction was concentrated in vacuo. This residue was dissolved in 50 ml DCM and washed with 20 ml water and then 10 ml 0.1M HCl. The organic layer was dried with $MgSO_4$, filtered and evaporated in vacuo. This residue was purified by silica gel chromatography eluting with 0-100% DCM/hexanes to give the title compound. $^1$H NMR (400 MHz $CDCl_3$): δ 7.79 (m, 2H), 7.58 (m, 4H), 7.36 (m, 8H), 4.21 (t, J=4.5 Hz, 1H), 4.01 (m, 2H), 2.42 (s, 3H), 2.18 (m, 1H), 1.80-1.22 (m, 6H), 0.98 (s, 9H).

Using the trans alcohol B-4 (prepared in scheme B), the intermediate in Table C was prepared in a similar fashion to Intermediate C1.

Intermediate D1 is prepared according to Scheme D by displacement of tosylate A1 with 4-bromo-1H-pyrazole to yield bromide D-2. A Miyaura borylation provides intermediate D1.

Intermediate D1

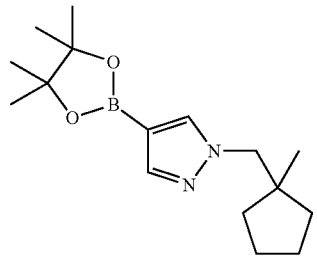 [SMILES: CC1(Cn2cc(B3OC(C)(C)C(C)(C)O3)cn2)CCCC1]

TABLE C

| Intermediate | Structure | Name | LCMS/NMR |
|---|---|---|---|
| C2 | TsO⟶⟨cyclopentyl with OTBDPS and F⟩ | ((3S,4S and (3R,4R))-3-((tert-butyldiphenylsilyl)oxy)-4-fluorocyclopentyl)methyl 4-methylbenzenesulfonate | $^1$H NMR (400 MHz $CDCl_3$): δ 7.76-7.78 (m, 2H), 7.58-7.60 (m, 4H), 7.34-7.40 (m, 8H), 4.66-4.80 (m, 1H), 4.24-4.26 (m, 1H), 3.90-3.92 (d, 2H), 2.66-2.67 (m, 1H), 2.44 (s, 3H), 2.25-2.45 (m, 1H), 1.78-1.83 (m, 1H), 1.40-1.42 (m, 1H), 1.07 (s, 9H). |

1-((1-Methylcyclopentyl)methyl)-4-(4,4,5,5-tetramethyl-1,3,2-dioxaborolan-2-yl)-1H-pyrazole (Scheme D)

SCHEME D

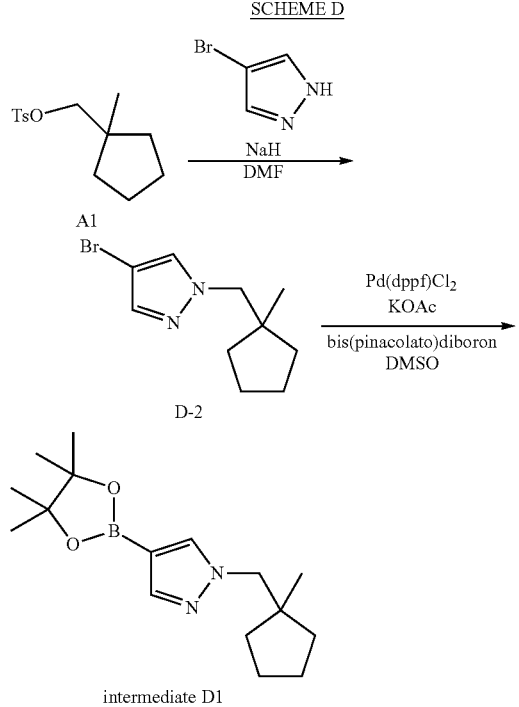

Step 1: 4-Bromo-1-((1-methylcyclopentyl)methyl)-1H-pyrazole

Into a 3 L, 4-necked round-bottom flask purged and maintained with an inert atmosphere of nitrogen, was placed a solution of sodium hydride (53 g, 1.32 mol) in DMF (500 mL), 4-bromo-1H-imidazole (172 g, 1.17 mol). After stirring for 30 min at 40° C., a solution of (1-methylcyclopentyl)methyl methanesulfonate (Intermediate A1, 150 g, 780 mmol) in DMF (1 L) was added portionwise. The resulting solution was stirred overnight at 90° C. The reaction mixture was cooled to 20° C. with a water/ice bath and was quenched by the addition of water (3 L). The organic was extracted with ethyl acetate (1 L×3) and the combined organic layers were washed with brine (1 L), dried over anhydrous sodium sulfate and concentrated under vacuum. The residue was applied onto a silica gel column (1:15 ethyl acetate:petroleum ether) to provide the title compound.

Step 2: 1-((1-Methylcyclopentyl)methyl)-4-(4,4,5,5-tetramethyl-1,3,2-dioxaborolan-2-yl)-1H-pyrazole Into a 3 L, 4-necked round-bottom flask purged and maintained with an inert atmosphere of nitrogen, was placed 4-bromo-1-[(1-methylcyclopentyl)methyl]-1H-imidazole (140 g, 576 mmol), 4,4,5,5-tetramethyl-2-(tetramethyl-1,3, 2-dioxaborolan-2-yl)-1,3,2-dioxaborolane (205 g, 807 mmol), Pd(dppf)Cl$_2$ (80 g, 109 mmol), KOAc (119 g, 1.2 mol), DMSO (1.5 L). The resulting solution was stirred overnight at 80° C. The reaction mixture was cooled to RT and was quenched by the addition of water (3 L). The resulting solution was extracted with ethyl acetate (1 L×3) and the organic layers combined and washed with brine (1 L×2). The mixture was dried over anhydrous sodium sulfate, concentrated under reduced pressure and was purified by silica gel chromatography (1:10 ethyl acetate:petroleum ether) to yield the title compound. MS: 291 (M+1).

The intermediates in table D were prepared according to scheme D using the procedures outlined in the synthesis of intermediate D1. The cyclopentylmethyl halides or tosylates utilized in this scheme are either commercially available or their synthesis has been described in Schemes A and B. Chiral Intermediates D4 and D5 are synthesized by displacement of tosylate A6 with 4-bromo-1H-pyrazole to yield the trans racemic bromide. Separation of the trans racemic bromide by chiral SFC to the (S,S) and (R,R) enantiomers followed by borylation of each gives Intermediates D4 and D5 respectively.

TABLE D

| Intermediate | Structure | Name | MS (M + 1) |
| --- | --- | --- | --- |
| D2 | 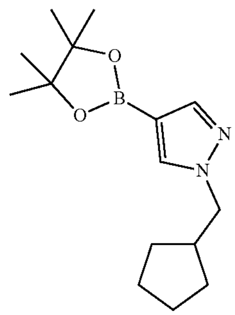 [SMILES: CC1(C)OB(c2cnn(CC3CCCC3)c2)OC1(C)C] | 1-(cyclopentylmethyl)-4-(4,4,5,5-tetramethyl-1,3,2-dioxaborolan-2-yl)-1H-pyrazole | 276.3 |
| D3 | 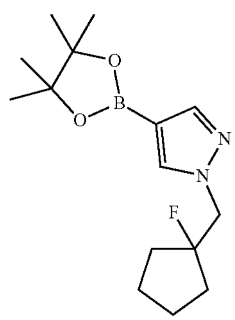 [SMILES: CC1(C)OB(c2cnn(CC3(F)CCCC3)c2)OC1(C)C] | 1-((1-fluorocyclopentyl)methyl)-4-(4,4,5,5-tetramethyl-1,3,2-dioxaborolan-2-yl)-1H-pyrazole | 295.3 |
| D4 | 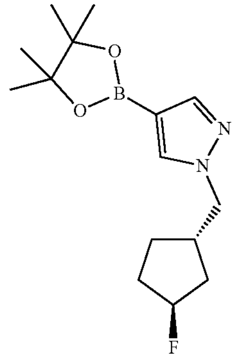 [SMILES: CC1(C)OB(c2cnn(C[C@H]3CC[C@H](F)C3)c2)OC1(C)C] | 1-(((1S,3S)-3-fluorocyclopentyl)methyl)-4-(4,4,5,5-tetramethyl-1,3,2-dioxaborolan-2-yl)-1H-pyrazole | NMR* |

TABLE D-continued
| Intermediate | Structure | Name | MS (M + 1) |
|---|---|---|---|
| D5 | 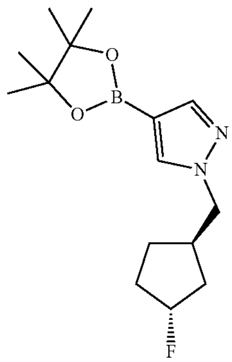 [SMILES: CC1(C)OB(c2cnn(C[C@@H]3CC[C@@H](F)C3)c2)OC1(C)C] | 1-(((1R,3R)-3-fluorocyclopentyl)methyl)-4-(4,4,5,5-tetramethyl-1,3,2-dioxaborolan-2-yl)-1H-pyrazole | NMR** |
*¹H-NMR (CDCl3, 400 MHz) δ 7.78 (s, 1H), 7.67 (s, 1H), 5.20-5.07 (m, 1H), 4.10-4.08 (m, 2H), 2.80-2.73 (m, 1H), 2.06-1.87 (m, 4H), 1.40-1.32 (m, 2H), 1.23 (s, 12H).
**¹H-NMR (CDCl3, 400 MHz) δ 7.75 (s, 1H), 7.66 (s, 1H), 5.18-5.03 (m, 1H), 4.09-4.07 (m, 2H), 2.79-2.73 (m, 1H), 2.04-1.86 (m, 4H), 1.39-1.30 (m, 2H), 1.22 (s, 12H).
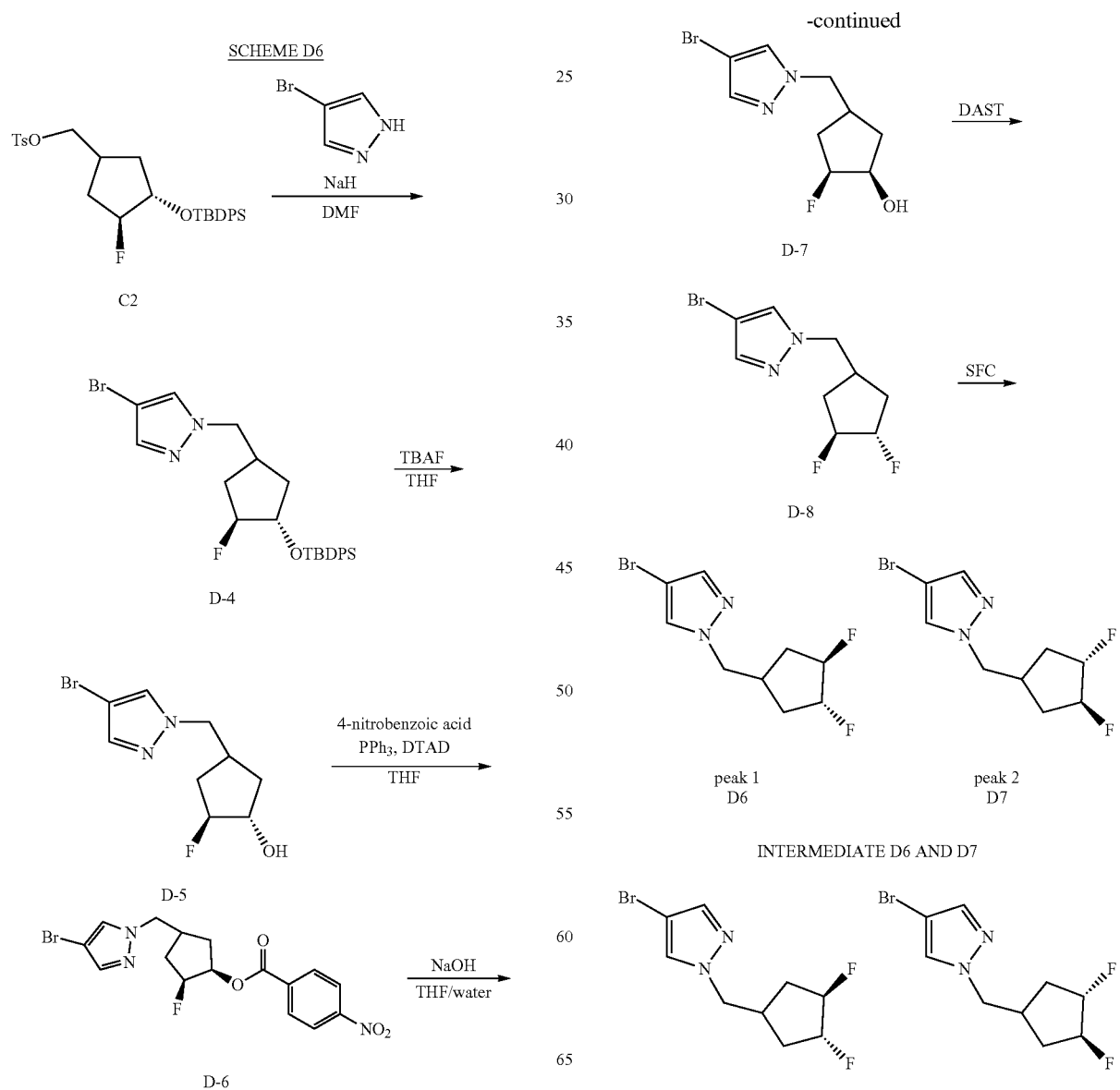
INTERMEDIATE D6 AND D7

4-Bromo-1-(((3R,4R) and (3 S,4S)-3,4-difluorocyclopentyl)methyl)-1H-pyrazole (Scheme D6)

Step 1: 4-bromo-1-(((3 S,4S) and (3R,4R)-3-((tert-butyldiphenylsilyl)oxy)-4-fluorocyclopentyl)methyl)-1H-pyrazole In three large reaction vessels, ((3 S,4S) and (3R,4R)-3-((tert-butyldiphenylsilyl)oxy)-4-fluorocyclopentyl)methyl 4-methylbenzenesulfonate (INTERMEDIATE C2; 360 g, 683 mmol, 1.0 eq) and 4-bromopyrazole (105 g, 718 mmol, 1.05 eq) were dissolved in DMF (1.1 L). Each vessel was degassed under vacuum and purged with nitrogen three times, then cooled to 0° C. with an ice bath. Each reaction vessel was then treated with NaH (31.4 g, 786 mmol, 60% purity, 1.15 eq), which was added in portions over 30 minutes to modulate gas evolution. An off-white suspension formed. The reactions were warmed to 25-30° C. and stir for 12 hrs. The three reactions were combined for workup. The combined reactions were poured into cold saturated ammonium chloride (5 L), then extracted 3× with 2 L of MTBE. The combined organic layer was washed with brine (2 L), dried over anhydrous sodium sulfate and filtered. The filtrate was concentrated under reduced pressure at 40° C. to give athe title compound, which was used directly without further purification. $^1$H NMR (400 MHz, CDCl$_3$): δ 7.70-7.77 (m, 1H), 7.57-7.68 (m, 3H), 7.30-7.51 (m, 7H), 4.70-4.95 (m, 1H), 4.26-4.38 (m, 1H), 4.06-4.17 (m, 1H), 4.01 (d, J=7.6 Hz, 1H), 2.81-2.95 (m, 1H), 2.68 (m, 1H), 2.18-2.40 (m, 1H), 1.73-2.08 (m, 2H), 1.37-1.72 (m, 2H), 0.99-1.13 (m, 9H).

Step 2: (1S,2S) and (1R,2R)-4-((4-bromo-1H-pyrazol-1-yl)methyl)-2-fluorocyclopentan-1-ol In two separate reaction vessels, 4-bromo-1-(((3S,4S) and (3R,4R)-3-((tert-butyldiphenylsilyl)oxy)-4-fluorocyclopentyl)methyl)-1H-pyrazole (515 g, 1.03 mol) was dissolved in THF (4.1 L). To each reaction, TBAF.3H$_2$O (357 g, 1.13 mol) was added in one portion at 25-30° C. The reaction was stirred at 25-30° C. for 2 hrs. The two reactions were combined for workup. The combined reaction was poured into water (10 L) and extracted with twice with EtOAc (3 L each).

The combined organic layer was washed with brine (3 L), dried over anhydrous sodium sulfate and filtered. The filtrate was concentrated under reduced pressure at 40° C. to give the crude product. The crude product was purified by silica gel chromatography eluting with petroleum ether/ethyl acetate=10/1-2/1 to give the title compound. $^1$H NMR (400 MHz, CDCl$_3$): δ 7.46 (s, 1H), 7.41 (s, 1H), 4.71-4.99 (m, 1H), 4.26-4.42 (m, 1H), 4.01-4.16 (m, 2H), 2.56-2.91 (m, 1H), 2.10-2.37 (m, 2H), 1.94-2.04 (m, 1H), 1.71-1.93 (m, 2H), 1.54-1.70 (m, 1H), 1.42-1.52 (m, 1H).

Step 3: (1R,2S) and (1S,2R)-4-((4-bromo-1H-pyrazol-1-yl)methyl)-2-fluorocyclopentyl 4-nitrobenzoate In two separate reaction vessels, (1 S,2S) and (1R,2R)-4-((4-bromo-1H-pyrazol-1-yl)methyl)-2-fluorocyclopentan-1-ol (215 g, 0.817 mol) was dissolved in anhydrous THF (1.0 L). To each reaction was added p-nitrobenzoic acid (205 g, 1.23 mol) and PPh$_3$ (321 g, 1.23 mol). The reactions were degassed by vacuum and purged with nitrogen three times, then cooled to 0° C. with an ice bath. To each reaction was then added dropwise a solution of DTAD (282 g, 1.23 mol) in anhydous THF (1.0 L) at 0° C. over 1 hr. The reactions were then warmed to 25-30° C. and stirred for 5 hrs. The reactions were combined for workup; they were poured into water (5 L) and brine (1 L). Lots of solid appeared in the organic phase. The two phases were separated and the organic phase was filtered to collect the solid. The filtered solid was washed with MTBE (500 mL). The solid was dried under reduced pressure to give the pure title compound. Additional product was recovered by extracting the filtrate twice with MTBE (2 L each), then washing the combined organic layer with brine (2 L), drying over anhydrous sodium sulfate and filtering. The filtrate was concentrated under reduced pressure at 40° C. to give the crude product, which was purified by silica gel chromatography eluting with petroleum ether/ethyl acetate=30/1-3/1 to give product contained with some impurity. This secondary product was washed with MTBE (300 mL) to give additional pure title compound. $^1$H NMR (400 MHz, CDCl$_3$): δ 8.27-8.36 (m, 2H), 8.18-8.27 (m, 2H), 7.62-7.76 (m, 1H), 7.46 (d, J=14.4 Hz, 2H), 5.06-5.33 (m, 2H), 4.08-4.26 (m, 2H), 2.64-2.82 (m, 1H), 2.34 (td, J=7.50, 13.2 Hz, 1H), 2.06-2.27 (m, 1H), 1.80-1.97 (m, 2H), 1.60 (s, 1H), 1.48 (s, 1H).

Step 4: (1R,2S) and (1 S,2R)-4-((4-bromo-1H-pyrazol-1-yl)methyl)-2-fluorocyclopentan-1-ol In two separate reaction vessels (1R,2S) and (1S,2R)-4-((4-bromo-1H-pyrazol-1-yl)methyl)-2-fluorocyclopentyl 4-nitrobenzoate (185 g, 449 mmol) was added to THF (1.4 L), forming a white suspension. To each reaction was added solid NaOH (26.9 g, 673 mmol) in one portion at 25-30° C. The internal temperature arises to 35° C. After stirring for 1 hour, the suspension had turned from white to yellow. The two reactions were combined for workup; they were poured into 4 L water and 1 L brine, then extracted twice with 2 L of ethyl acetate. The combined organic layer was washed twice with saturated sodium bicarbonate (2 L) and once with brine (2 L). Then the organic layer was dried over sodium sulfate, filtered and the filtrate evaporated under reduced pressure at 40° C. to give the crude product. The crude product was purified by silica gel chromatography, eluting with petroleum ether/ethyl acetate=20/1-3/1 to obtain the title compound. $^1$H NMR (400 MHz, CDCl$_3$): δ 7.44-7.49 (m, 1H), 7.38-7.43 (m, 1H), 4.74-5.03 (m, 1H), 3.99-4.21 (m, 3H), 2.89 (spt, J=7.6 Hz, 1H), 2.47-2.66 (m, 1H), 2.17-2.30 (m, 1H), 1.96-2.15 (m, 2H), 1.66-1.84 (m, 1H), 1.41-1.55 (m, 1H).

Step 5: 4-bromo-1-(((3 S,4S) and (3R,4R)-3,4-difluorocyclopentyl)methyl)-1H-pyrazole In two separate reaction vessels (1R,2S) and (1S,2R)-4-((4-bromo-1H-pyrazol-1-yl)methyl)-2-fluorocyclopentan-1-ol (90 g, 342 mmol) was dissolved in anhydrous DCM (810 mL). Both vessels were then cooled to 0° C. DAST (110 g, 684 mmol) was then added dropwise over 30 mins. The reactions were then heated to 40° C. and stirred for 12 hrs. The two reactions were combined for workup; they were poured into ice water (2 L), keeping the temperature from exceeding 0° C. The organic layer was partitioned, then the aqueous phase was extracted twice with dichloromethane (500 mL each). The combined organic layer was washed with brine (500 mL), dried over sodium sulfate, filtered and the filtrate evaporated under reduced pressure at 40° C. to give the crude product. The crude was purified by silica gel chromatography, eluting with petroleum ether/ethyl acetate=20/1-5/1 to give the title compound. $^1$H NMR (400

MHz, CDCl₃): δ 7.47 (s, 1H), 7.41 (s, 1H), 5.08-5.20 (m, 1H), 4.96-5.07 (m, 1H), 4.05-4.13 (m, 2H), 2.77-2.93 (m, 1H), 2.02-2.38 (m, 2H), 1.63-1.90 (m, 2H).

Step 6: 4-bromo-1-(((3R,4R)-3,4-difluorocyclopentyl)methyl)-1H-pyrazole (D6) and 4-bromo-1-(((3S,4S)-3,4-difluorocyclopentyl)methyl)-1H-pyrazole (D7)

The racemic compound was separated by chiral SFC. Equal amounts of the faster eluting isomer and slower eluting isomer were obtained.
Column: AD, 250×50 mmI.D. 10 μm
Mobile phase: A for CO₂ and B for MeOH
Gradient: B 20%
Flow rate: 200 mL/min
Back pressure: 100 bar
Column temperature: 38° C.
Wavelength: 220 nm
Cycletime: 4 min
Sample preparation: Compound was dissolved in Ethanol and DCM to ~50 mg/mL
Injection: 2 mL per injection.

D6: ¹H NMR (400 MHz, CDCl₃): δ 7.48 (s, 1H), 7.41 (s, 1H), 5.14-5.17 (m, 1H), 5.01-5.05 (m, 1H), 4.09 (d, J=7.6 Hz, 2H), 2.81-2.89 (m, 1H), 2.05-2.24 (m, 2H), 1.58-1.77 (m, 2H).

D7: ¹H NMR (400 MHz, CDCl₃): δ 7.47 (s, 1H), 7.41 (s, 1H), 5.14-5.17 (m, 1H), 5.01-5.05 (m, 1H), 4.09 (d, J=7.6 Hz, 2H), 2.83-2.89 (m, 1H), 2.07-2.29 (m, 2H), 1.61-1.77 (m, 2H).

SCHEME E

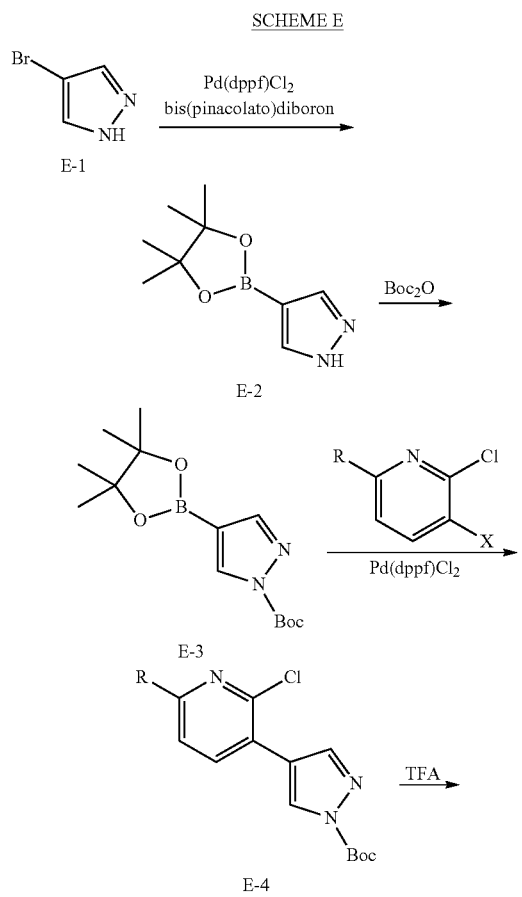

Intermediate E

Intermediate E is prepared from a commercial bromopyrazole E-1, which is borylated to provide boronic ester E-2. Protection of the pyrazole enables a Suzuki cross-coupling with a known iodide or bromide to yield product E-4. Deprotection with HCl/dioxane provides intermediate E.

Intermediate E1

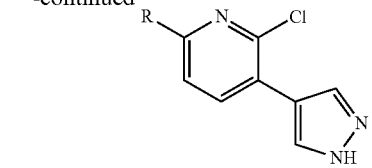

2-Chloro-3-(1H-pyrazol-4-yl)pyridine (Scheme E)

Step 1: 4-(4,4,5,5-Tetramethyl-1,3,2-dioxaborolan-2-yl)-1H-pyrazole

A flask charged with Pd(dppf)Cl₂ (20 g, 0.023 mol), KOAc (264 g, 2.72 mol), and bis(pinacolato)diboron (380 g, 1.48 mol) was flushed with N₂. Dioxane (3 L) and 4-bromo-1H-pyrazole (200 g×2, 1.36 mol) were then added. After being stirred at 80° C. for an appropriate period, the mixture was cooled and poured into water. The organic was extracted with EtOAc and then washed with water and brine, and dried over anhydrous Na₂SO₄ before concentrating to dryness. The residue was purified by silica gel column (5:1 petroleum ether:EtOAc) to give the title compound.

Step 2: tert-Butyl 4-(4,4,5,5-tetramethyl-1,3,2-dioxaborolan-2-yl)-1H-pyrazole-1-carboxylate Boc₂O (96 g, 0.48 mol) and DMAP (64 g, 0.64 mol) were added to a solution of 4-(4,4,5,5-tetramethyl-1,3,2-dioxaborolan-2-yl)-1H-pyrazole in DMF (1 L). The reaction mixture was stirred at room temperature for 7 hours before the mixture was poured into water and EtOAc. The organic layer was separated and washed with water and brine, and dried over anhydrous Na₂SO₄ before concentrating to dryness. The resulting residue was purified by silica gel column (10:1 petroleum ether:EtOAc) to give the title compound.

Step 3: tert-Butyl 4-(2-chloropyridin-3-yl)-1H-pyrazole-1-carboxylate

2-Chloro-3-iodopyridine (100 g×2, 0.42 mol) and tert-butyl 4-(2-chloropyridin-3-yl)-1H-pyrazole-1-carboxylate (123 g, 0.42 mol) was dissolved in dioxane (2 L). The system was placed under N₂ and Pd(dppf)Cl₂ (15 g, 17 mmol) was added to the solution and the reaction was heated to 65° C. for 3 h. The reaction was cooled to RT and the mixture was poured into water and partitioned with EtOAc.

The organic was washed with water and brine, then dried over anhydrous Na₂SO₄ before concentrating to dryness. The title compound was obtained and was used without further purification.

Step 4: 2-Chloro-3-(1H-pyrazol-4-yl)pyridine

A solution of tert-butyl 4-(2-chloropyridin-3-yl)-1H-pyrazole-1-carboxylate (90 g, 0.32 mmol) in dioxane (600 mL) and 4 N HCl (400 mL in dioxane) was stirred at room temperature for 5 hours. The mixture was filtered and the solids were washed with EtOAc and then dissolved into water (adjust pH=9 with aqueous NaOH). The layers were separated, then the organic was washed with water and brine, dried over anhydrous Na₂SO₄, and concentrated to give the title compound. MS: 313 (M+1). $^1$H NMR (500 MHz, CDCl₃): δ 8.33-8.31 (dd, J=1.6, 8.8 Hz, 1H), 8.04 (s, 2H), 7.84-7.81 (dd, J=2.0, 7.6 Hz, 1H), 7.31-7.28 (dd, J=4.8, 7.6 Hz, 1H).

The following intermediates in table E were prepared according to scheme E using the procedure outlined in the synthesis of intermediate E1 using commercially available 2-halopyridines and the commercial bromopyrazole E-1.

Tosylates prepared in schemes A, B or C are displaced with Intermediates E in the presence of base (typically NaH or cesium carbonate) to give Intermediate F.

Intermediate F1

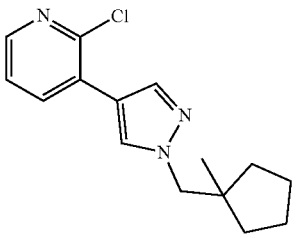

2-chloro-3-(1-((1-methylcyclopentyl)methyl)-1H-pyrazol-4-yl)pyridine (Scheme F)

2-Chloro-3-(1H-pyrazol-4-yl)pyridine (INTERMEDIATE E1, 569 mg, 3.17 mmol) was dissolved in anhydrous DMF (6 mL) in a 20 mL pressure vial, and was purged under

TABLE E

| Intermediate | Structure | Name | MS (M + 1) |
|---|---|---|---|
| E2 | 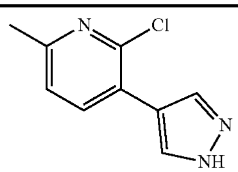 | 2-chloro-6-methyl-3-(1H-pyrazol-4-yl)pyridine | 194 |
| E3 | 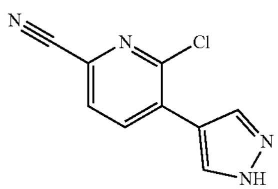 [SMILES: N#Cc1ccc(-c2cn[nH]c2)c(Cl)n1] | 6-chloro-5-(1H-pyrazol-4-yl)picolinonitrile | 205 |

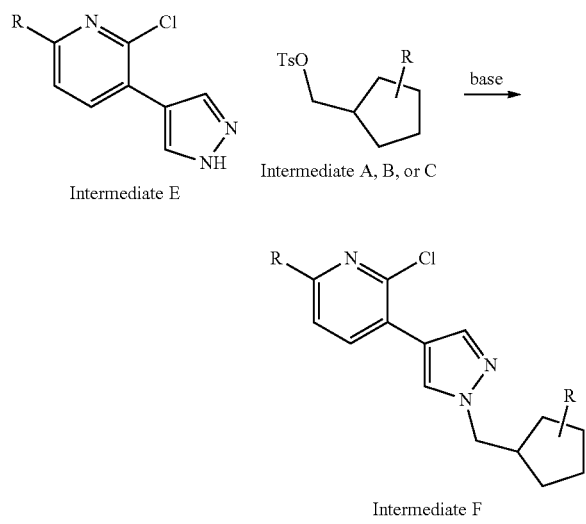

SCHEME F

N₂. Solid NaH (177 mg, 4.43 mmol) was added with vigorous stirring and rapid effervescence was observed. After stirring for 10 minutes (1-methylcyclopentyl)methyl 4-methylbenzenesulfonate (INTERMEDIATE A1, 850 mg, 3.17 mmol) was added and continued to stir at 50° C. Monitored the reaction by LC/MS until completion or no further progress is observed. Then the reaction mixture was cooled in ice, and quenched with water. It was diluted with EtOAc (100 mL). Partitioned the EtOAc extract with water (20 mL) and back extracted (2×10 mL), washed the EtOAc extract with brine and dried using anhydrous Na₂SO₄. After filtration, the filtrate was concentrated via rotary evaporation to obtain the crude as a light yellow oil. Pumped on vacuum to remove residual DMF. Dissolved crude in DCM (3 mL) and loaded onto a silica gel column, eluting with 0% to 100% EtOAc/hexanes in a step gradient. Product eluted at 20-25% EtOAc. Concentrated desired fractions on and dried on vacuum to obtain the title compound as a colorless oil. LC/MS: MH+=(276). NMR (500 MHz, DMSO-d6): δ 8.28 (dd, J=1.7, 4.7 Hz, 1H), 8.27 (s, 1H), 8.07 (dd, J=1.7, 7.7 Hz, 1H), 7.93, (s, 1H), 7.45 (dd, J=4.7, 7.7 Hz, 1H), 4.07 (s, 2H), 1.61 (m, 6H), 1.28 (m, 2H), 0.94 (s, 3H).

The following intermediates in Table F were prepared as in scheme F above, using Intermediates E and commercial halides or tosylates, or those prepared as Intermediates A, B, or C above in the presence of base.

TABLE F

| Intermediate | Structure | Name | MS (M + 1) |
|---|---|---|---|
| F2 | 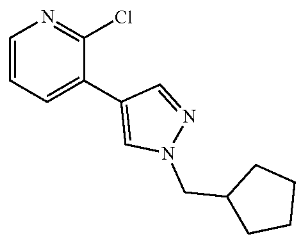 [SMILES: Clc1ncccc1-c1cnn(CC2CCCC2)c1] | 2-chloro-3-(1-(cyclopentylmethyl)-1H-pyrazol-4-yl)pyridine | 262 |
| F3 | 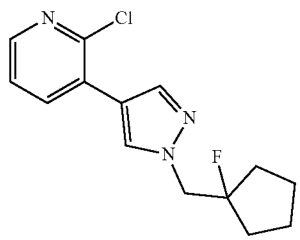 [SMILES: FC1(Cn2cc(-c3cccnc3Cl)cn2)CCCC1] | 2-chloro-3-(1-((1-fluorocyclopentyl)methyl)-1H-pyrazol-4-yl)pyridine | 280 |
| F4 | 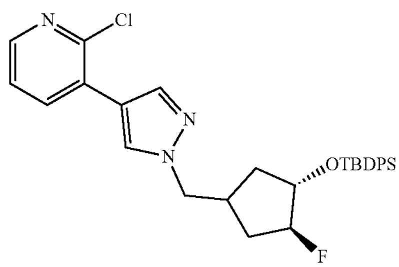 | 3-(1-(((3S,4S and (3R,4R))-3-((tert-butyldiphenylsilyl)oxy)-4-fluorocyclopentyl)methyl)-1H-pyrazol-4-yl)-2-chloropyridine | 534 |
| F5 | 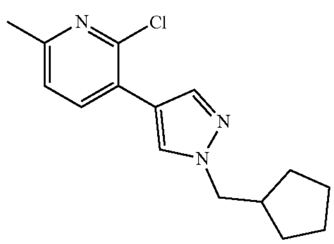 [SMILES: Cc1ccc(-c2cnn(CC3CCCC3)c2)c(Cl)n1] | 2-chloro-3-(1-(cyclopentylmethyl)-1H-pyrazol-4-yl)-6-methylpyridine | 276 |
| F6 | 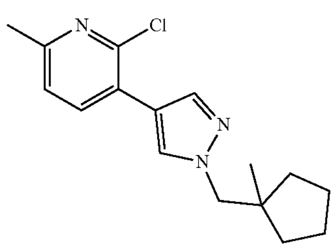 [SMILES: Cc1ccc(-c2cnn(CC3(C)CCCC3)c2)c(Cl)n1] | 2-chloro-6-methyl-3-(1-((1-methylcyclopentyl)methyl)-1H-pyrazol-4-yl)pyridine | 290 |
| F7 | 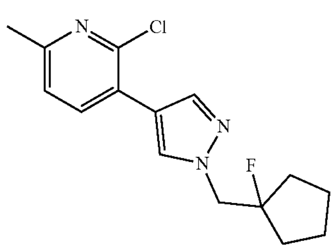 [SMILES: Cc1ccc(-c2cnn(CC3(F)CCCC3)c2)c(Cl)n1] | 2-chloro-3-(1-((1-fluorocyclopentyl)methyl)-1H-pyrazol-4-yl)-6-methylpyridine | 294 |

TABLE F-continued

| Intermediate | Name | MS (M + 1) |
|---|---|---|
| F8 | 3-(1-(bicyclo[2.2.1]heptan-1-ylmethyl)-1H-pyrazol-4-yl)-2-chloro-6-methylpyridine | 302 |
| F9 | 2-chloro-3-(1-(((1S,3S and 1R,3R)-3-fluorocyclopentyl)methyl)-1H-pyrazol-4-yl)-6-methylpyridine | 294 |
| F10 | 2-chloro-3-(1-(((3R,4S and 3S,4R)-3,4-difluorocyclopentyl)methyl)-1H-pyrazol-4-yl)-6-methylpyridine | 312 |
| F11 | 3-(1-(((3S,4S and 3R,4R)-3-((tert-butyldiphenylsilyl)oxy)-4-fluorocyclopentyl)methyl)-1H-pyrazol-4-yl)-2-chloro-6-methylpyridine | 548 |
| F12 | 2-chloro-3-(1-((3,3-difluorocyclopentyl)methyl)-1H-pyrazol-4-yl)-6-methylpyridine | 312 |
| F13 | 2-chloro-3-(1-((6,6-difluorobicyclo[3.1.0]hexan-3-yl)methyl)-1H-pyrazol-4-yl)-6-methylpyridine | 324 |

TABLE F-continued

| Intermediate | Structure | Name | MS (M + 1) |
|---|---|---|---|
| F14 | 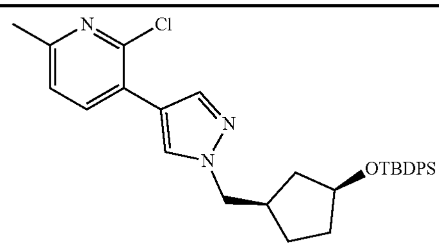 | 3-(1-(((1R,3S and 1S,3R)-3-((tert-butyldiphenylsilyl)oxy)cyclopentyl)methyl)-1H-pyrazol-4-yl)-2-chloro-6-methylpyridine | 530 |

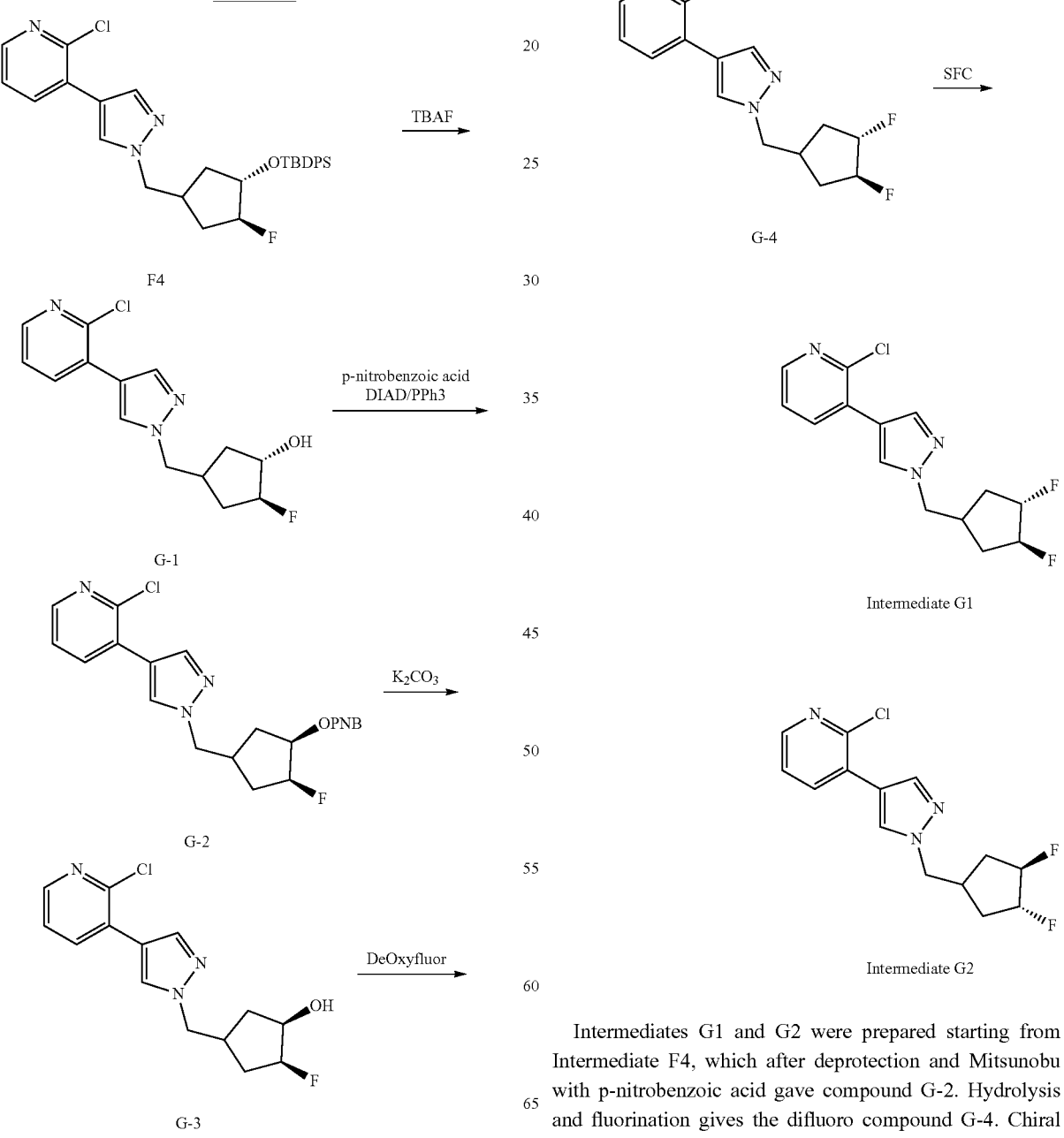

Intermediates G1 and G2 were prepared starting from Intermediate F4, which after deprotection and Mitsunobu with p-nitrobenzoic acid gave compound G-2. Hydrolysis and fluorination gives the difluoro compound G-4. Chiral SFC provides Intermediates G1 and G2.

INTERMEDIATES G1 and G2

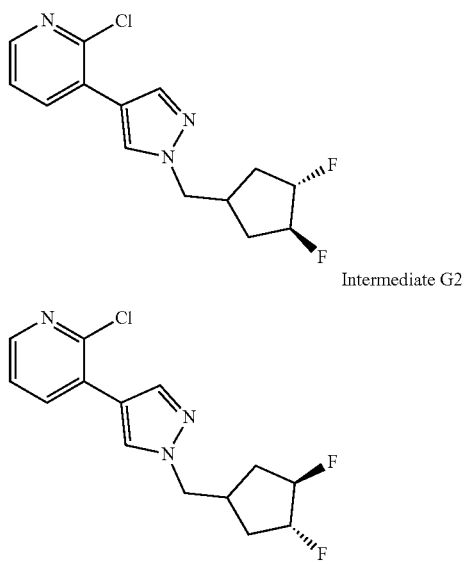

Intermediate G1

Intermediate G2

2-chloro-3-(1-(((3 S,4S)-3,4-difluorocyclopentyl) methyl)-1H-pyrazol-4-yl)pyridine and 2-chloro-3-(1-(((3R,4R)-3,4-difluorocyclopentyl)methyl)-1H-pyrazol-4-yl)pyridine (Scheme G)

Step 1: (1S,2S and 1R,2R)-4-((4-(2-chloropyridin-3-yl)-1H-pyrazol-1-yl)methyl)-2-fluorocyclopentan-1-ol To a solution of 3-(1-(((3S,4S and 3R,4R)-3-((tert-butyldiphenylsilyl)oxy)-4-fluorocyclopentyl)methyl)-1H-pyrazol-4-yl)-2-chloropyridine (INTERMEDIATE F4, 38 g, 0.71 mol) in THF (300 mL) was added TBAF (24.8 g, 0.78 mol) at room temperature. Then the reaction mixture was stirred at room temperature overnight. TLC showed the reaction was completed. After the solvent was removed, the residue was rediluted in EtOAc (300 mL). The mixture was washed with saturated aqueous NH₄Cl (300 mL), brine (300 mL), dried over Na₂SO₄ and concentrated. The residue was purified by silica gel column chromatography eluted with PE:EtOAc=1:1 to give the title compound. MS(M+1): 296.

Step 2: (1R,2S and 1 S,2R)-4-((4-(2-chloropyridin-3-yl)-1H-pyrazol-1-yl)methyl)-2-fluorocyclopentyl 4-nitrobenzoate To a solution of (1S,2S and 1R,2R)-4-((4-(2-chloropyridin-3-yl)-1H-pyrazol-1-yl)methyl)-2-fluorocyclopentan-1-ol (70 g, 0.237 mol) in THF (700 mL) was added p-nitrobenzoic acid (51.5 g, 0.308 mol) and Ph₃P (51.5 g, 0.308 mol) at room temperature. After cooling to 0~5° C., DIAD (67 g, 0.331 mol) was added dropwise. Then the reaction mixture was stirred at room temperature overnight. TLC showed the reaction was completed. 1 L of ice-water was added, and extracted with EtOAc (3×800 mL). The organic layers were washed with brine (1.5 L), dried over Na₂SO₄ and concentrated. The residue was purified by silica gel column chromatography eluted with PE:EtOAc=2:1 to give the title compound. MS(M+1): 445.

Step 3: (1R,2S and 1 S,2R)-4-((4-(2-chloropyridin-3-yl)-1H-pyrazol-1-yl)methyl)-2-fluorocyclopentan-1-ol To a solution of (1R,2S and 1 S,2R)-4-((4-(2-chloropyridin-3-yl)-1H-pyrazol-1-yl)methyl)-2-fluorocyclopentyl 4-nitrobenzoate (175 g, 0.393 mol) in MeOH (2 L) was added K₂CO₃ (163 g, 1.18 mol) at room temperature. Then the reaction mixture was stirred at room temperature overnight. TLC showed the reaction was completed. After the solvent was removed, 2 L of water was added, and extracted with EtOAc (3×2 L). The organic layers were washed with brine (3 L), dried over Na₂SO₄ and concentrated. The residue was purified by silica gel column chromatography eluted with PE:EtOAc=1:1 to give the title compound. MS(M+1): 296.

Step 4: 2-chloro-3-(1-(((3S,4S and 3R,4R)-3,4-difluorocyclopentyl)methyl)-1H-pyrazol-4-yl)pyridine To a solution of (1R,2S and 1 S,2R)-4-((4-(2-chloropyridin-3-yl)-1H-pyrazol-1-yl)methyl)-2-fluorocyclopentan-1-ol (50 g, 0.169 mol) in THF (500 mL) was added DeOxyfluor (56 g, 0.253 mol) dropwise at 0-10° C. Then the reaction mixture was stirred at room temperature overnight. TLC showed the reaction was completed. The reaction mixture was poured into saturated aqueous NH₄Cl (1 L), and extracted with EtOAc (3×1 L). The organic layers were washed with brine (2 L), dried over Na₂SO₄ and concentrated. The residue was purified by silica gel column chromatography eluted with PE:EtOAc=5:1 to give the title compound. MS(M+1): 298.

Step 5: 2-chloro-3-(1-(((3S,4S)-3,4-difluorocyclopentyl)methyl)-1H-pyrazol-4-yl)pyridine (Intermediate G1) and 2-chloro-3-(1-(((3R,4R)-3,4-difluorocyclopentyl)methyl)-1H-pyrazol-4-yl)pyridine (Intermediate G2)

SFC was used to separate the chiral mixture under the following conditions: A Chiralpak AD-3 150×4.6 mm I.D., 3 um column was eluted with ethanol (0.05% DEA) in C02 from 5% to 40% at 2.35 mL/min and monitored at 220 nm.

Intermediate G1 elutes at 3.94 minutes.

$^1$H NMR (400 MHz CDCl₃): δ 8.28-8.30 (m, 1H), 7.91 (s, 1H), 7.83 (s, 1H), 7.79-7.81 (m, 1H), 7.26-7.29 (m, 1H), 5.01-5.17 (m, 2H), 4.18-4.20 (d, 2H), 2.89-2.96 (m, 1H), 2.09-2.35 (m, 2H), 1.71-1.91 (m, 2H).

Intermediate G2 elutes at 4.28 min $^1$H NMR (400 MHz CDCl₃): δ 8.28-8.30 (m, 1H), 7.91 (s, 1H), 7.83 (s, 1H), 7.79-7.81 (m, 1H), 7.26-7.29 (m, 1H), 5.01-5.17 (m, 2H), 4.18-4.20 (d, 2H), 2.89-2.96 (m, 1H), 2.09-2.35 (m, 2H), 1.71-1.91 (m, 2H).

The following intermediates in table G were prepared in an analogous fashion starting from intermediates F14 and F11. Unlike G1 and G2, they were not subject to chiral resolution.

TABLE G

| Intermediate | Structure | Name | MS (M + 1) |
|---|---|---|---|
| G3 | 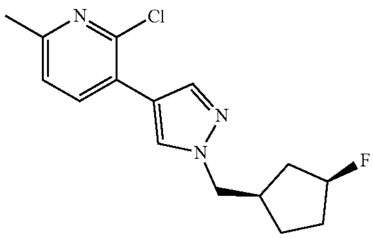 [SMILES: Cc1ccc(-c2cnn(C[C@@H]3CC[C@H](F)C3)c2)c(Cl)n1] | 2-chloro-3-(1-(((1R,3S and 1S,3R)-3-fluorocyclopentyl)methyl)-1H-pyrazol-4-yl)-6-methylpyridine | 294 |
| G4 | 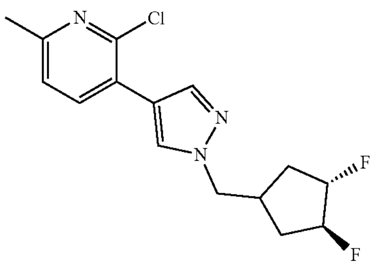 [SMILES: Cc1ccc(-c2cnn(CC3C[C@H](F)[C@@H](F)C3)c2)c(Cl)n1] | 2-chloro-3-(1-(((3S,4S and 3R,4R)-3,4-difluorocyclopentyl)methyl)-1H-pyrazol-4-yl)-6-methylpyridine | 312 |

SCHEME H

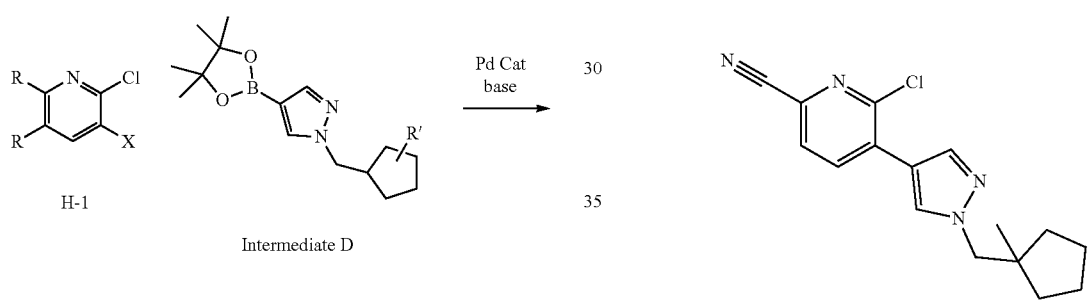

Intermediate H

Intermediate H is prepared via a Suzuki reaction of a commercially available, known or prepared pyridine (H-1) and boronic ester D, which is prepared as outlined in scheme D. Prepared pyridines (H-1) are shown in schemes I, J, K, U and V.

Intermediate H1

6-Chloro-5-(1-((1-methylcyclopentyl)methyl)-1H-pyrazol-4-yl)picolinonitrile (Scheme H)

Into a 5 L, 4-necked round-bottom flask purged and maintained with an inert atmosphere of nitrogen, was placed 1-[(1-methylcyclopentyl)methyl]-4-(tetramethyl-1,3,2-dioxaborolan-2-yl)-1H-pyrazole (INTERMEDIATE D1, 46.5 g, 160.23 mmol), 5-bromo-6-chloropyridine-2-carbonitrile (for preparation, see: Pettersson, M.; et. al. Bioorganic & Medicinal Chemistry Letters, 2012, 22(8), 2906-2911 or Am Ende, C. W.; et. al. PCT Int. Appl., 2012131539, 4 Oct. 2012) (42 g, 193 mmol), Pd(dppf)Cl$_2$ (28.5 g, 40 mmol), potassium carbonate (55.3 g, 400.72 mmol), dioxane (1.45 L), and water (580 mL). The resulting solution was stirred for 10 min at 25° C. and then at 100° C. for 3 h. The reaction was then quenched by the addition of water (2 L) and was partitioned with EtOAc (3 L×3). The combined organic layers were dried over anhydrous sodium sulfate and concentrated under reduced pressure. The residue was applied onto a silica gel column (5:1 petroleum ether:EtOAc) to yield the title compound. MS: 301 (M+1). $^1$H NMR (400 MHz, CDCl$_3$): δ 1.01 (3H, s), 1.38-1.42 (2H, m), 1.42-1.74 (6H, m), 4.09 (2H, s), 7.63-7.65 (1H, s), 7.86 (1H, s), 7.92-7.94 (1H, m), 8.00 (1H, s).

The following intermediates in table H were prepared according to scheme H using the procedure outlined in the synthesis of intermediate H1 using INTERMEDIATE D1-D7 or 1-(cyclopentylmethyl)-4-(4,4,5,5-tetramethyl-1,3,2-dioxaborolan-2-yl)-1H-pyrazole (CAS: 1233526-51-6) and commercially available, known (i.e., Frei, Beat; et. al. PCT Int. Appl. WO 2014086705, Jun. 12, 2014) or prepared 2-halopyridines. Alternative conditions can be used in this reaction, such that the catalyst is 1,1'-bis(di-tert-butylphosphino)ferrocene palladium dichloride or the solvent is THF and temperature can range from RT to 110° C. as appropriate for each substrate.

TABLE H

| Intermediate | Structure | Name | MS (M + 1) |
|---|---|---|---|
| H2 | 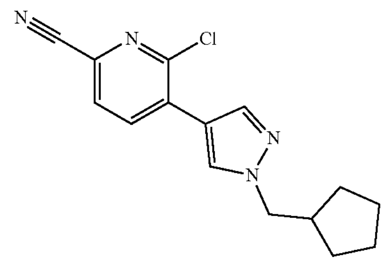 [SMILES: N#Cc1ccc(-c2cnn(CC3CCCC3)c2)c(Cl)n1] | 6-chloro-5-(1-(cyclopentylmethyl)-1H-pyrazol-4-yl)picolinonitrile | 287 |
| H3 | 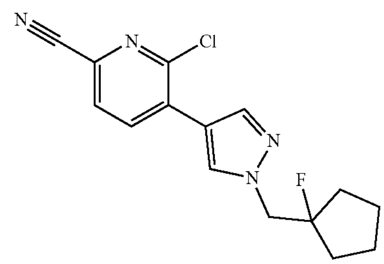 [SMILES: N#Cc1ccc(-c2cnn(CC3(F)CCCC3)c2)c(Cl)n1] | 6-chloro-5-(1-((1-fluorocyclopentyl)methyl)-1H-pyrazol-4-yl)picolinonitrile | 305 |
| H4 | 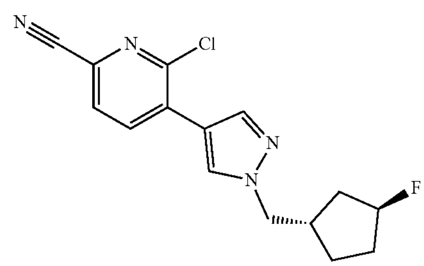 [SMILES: N#Cc1ccc(-c2cnn(C[C@H]3CC[C@H](F)C3)c2)c(Cl)n1] | 6-chloro-5-(1-(((1S,3S)-3-fluorocyclopentyl)methyl)-1H-pyrazol-4-yl)picolinonitrile | 305 |
| H5 | 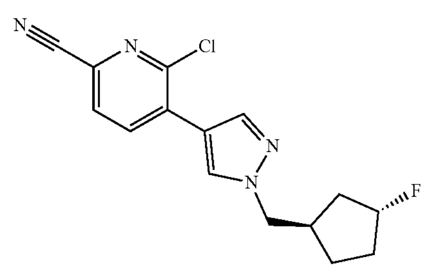 [SMILES: N#Cc1ccc(-c2cnn(C[C@@H]3CC[C@@H](F)C3)c2)c(Cl)n1] | 6-chloro-5-(1-(((1R,3R)-3-fluorocyclopentyl)methyl)-1H-pyrazol-4-yl)picolinonitrile | NMR* |
| H6 | 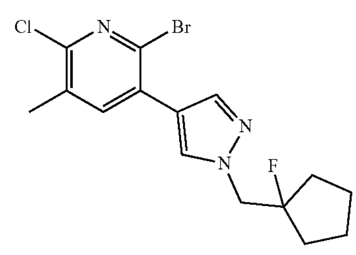 [SMILES: Cc1cc(-c2cnn(CC3(F)CCCC3)c2)c(Br)nc1Cl] | 2-bromo-6-chloro-3-(1-((1-fluorocyclopentyl)methyl)-1H-pyrazol-4-yl)-5-methylpyridine | 372 374 |

TABLE H-continued

| Intermediate | Structure | Name | MS (M + 1) |
|---|---|---|---|
| H7 | 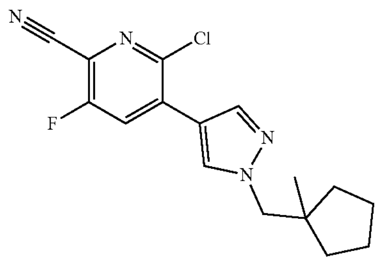 [SMILES: CC1(Cn2cc(-c3cc(F)c(C#N)nc3Cl)cn2)CCCC1] | 6-chloro-3-fluoro-5-(1-((1-methylcyclopentyl)methyl)-1H-pyrazol-4-yl)picolinonitrile | 319 |
| H8 | 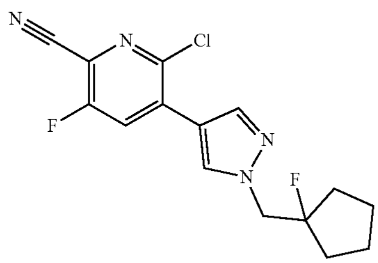 | 6-chloro-3-fluoro-5-(1-((1-fluorocyclopentyl)methyl)-1H-pyrazol-4-yl)picolinonitrile | 323 |
| H9 | 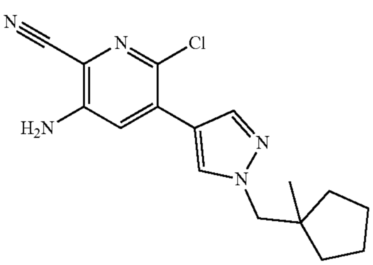 [SMILES: CC1(Cn2cc(-c3cc(N)c(C#N)nc3Cl)cn2)CCCC1] | 3-amino-6-chloro-5-(1-((1-methylcyclopentyl)methyl)-1H-pyrazol-4-yl)picolinonitrile | 316 |
| H10 | 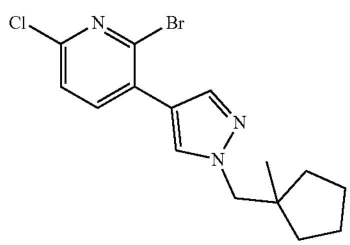 [SMILES: CC1(Cn2cc(-c3ccc(Cl)nc3Br)cn2)CCCC1] | 2-bromo-6-chloro-3-(1-((1-methylcyclopentyl)methyl)-1H-pyrazol-4-yl)pyridine | 354<br>356 |
| H11 | 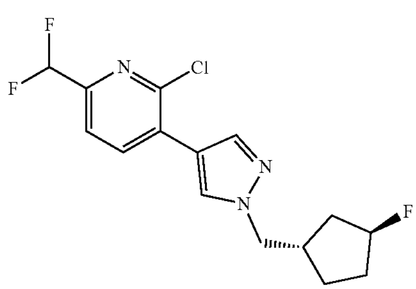 [SMILES: FC(F)c1ccc(-c2cnn(C[C@H]3CC[C@H](F)C3)c2)c(Cl)n1] | 2-chloro-6-(difluoromethyl)-3-(1-((((1S,3S)-3-fluorocyclopentyl)methyl)-1H-pyrazol-4-yl)pyridine | NMR** |
| H12 | 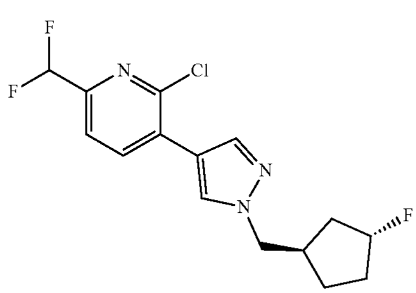 [SMILES: FC(F)c1ccc(-c2cnn(C[C@@H]3CC[C@@H](F)C3)c2)c(Cl)n1] | 2-chloro-6-(difluoromethyl)-3-(1-((((1R,3R)-3-fluorocyclopentyl)methyl)-1H-pyrazol-4-yl)pyridine | NMR# |

TABLE H-continued

| Intermediate | Structure | Name | MS (M + 1) |
|---|---|---|---|
| H13 | 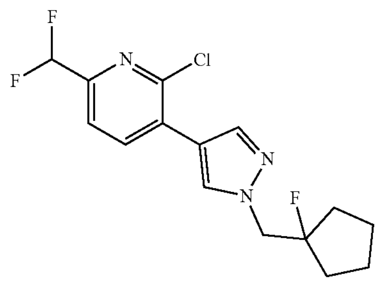 [SMILES: FC(F)c1ccc(-c2cnn(CC3(F)CCCC3)c2)c(Cl)n1] | 2-chloro-6-(difluoromethyl)-3-(1-((1-fluorocyclopentyl)methyl)-1H-pyrazol-4-yl)pyridine | NMR## |
| H14 | 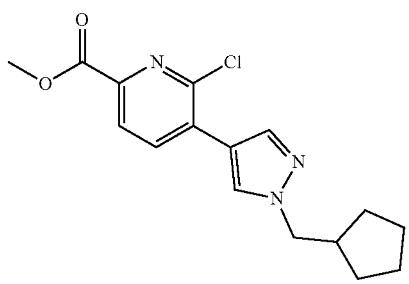 [SMILES: COC(=O)c1ccc(-c2cnn(CC3CCCC3)c2)c(Cl)n1] | methyl 6-chloro-5-(1-(cyclopentylmethyl)-1H-pyrazol-4-yl)picolinate | 320 |
| H15 | 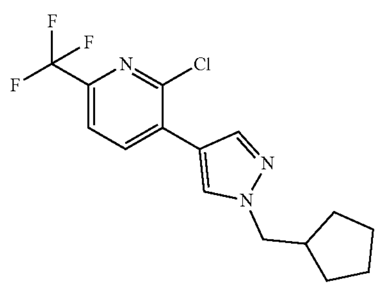 [SMILES: FC(F)(F)c1ccc(-c2cnn(CC3CCCC3)c2)c(Cl)n1] | 2-chloro-3-(1-(cyclopentylmethyl)-1H-pyrazol-4-yl)-6-(trifluoromethyl)pyridine | 330 |
| H16 | 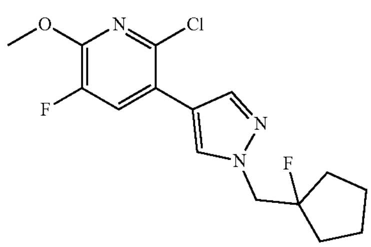 [SMILES: COc1nc(Cl)c(-c2cnn(CC3(F)CCCC3)c2)cc1F] | 2-chloro-5-fluoro-3-(1-((1-fluorocyclopentyl)methyl)-1H-pyrazol-4-yl)-6-methoxypyridine | 328 |
| H17 | 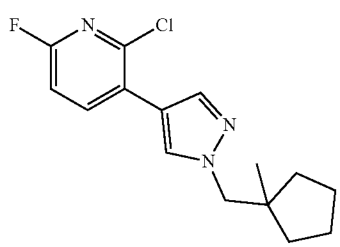 [SMILES: CC1(Cn2cc(-c3ccc(F)nc3Cl)cn2)CCCC1] | 2-chloro-6-fluoro-3-(1-((1-methylcyclopentyl)methyl)-1H-pyrazol-4-yl)pyridine | 294 |
| H18 | 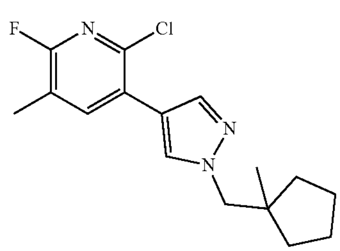 [SMILES: Cc1cc(-c2cnn(CC3(C)CCCC3)c2)c(Cl)nc1F] | 2-chloro-6-fluoro-5-methyl-3-(1-((1-methylcyclopentyl)methyl)-1H-pyrazol-4-yl)pyridine | 308 |

TABLE H-continued

| Intermediate | Structure | Name | MS (M + 1) |
|---|---|---|---|
| H19 | 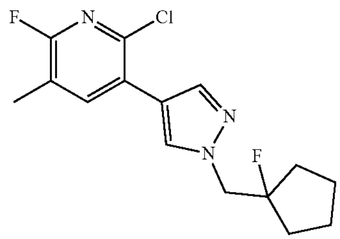 [SMILES: Cc1cc(-c2cnn(CC3(F)CCCC3)c2)c(Cl)nc1F] | 2-chloro-6-fluoro-3-(1-((1-fluorocyclopentyl)methyl)-1H-pyrazol-4-yl)-5-methylpyridine | 312 |
| H20 | 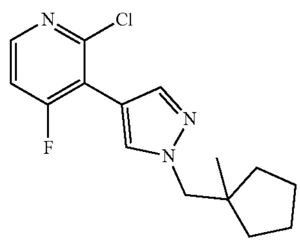 [SMILES: CC1(Cn2cc(-c3c(F)ccnc3Cl)cn2)CCCC1] | 2-chloro-4-fluoro-3-(1-((1-methylcyclopentyl)methyl)-1H-pyrazol-4-yl)pyridine | 294 |
| H21 | 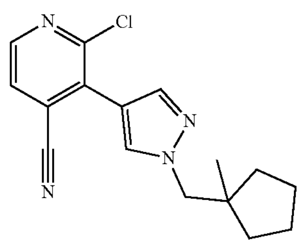 [SMILES: CC1(Cn2cc(-c3c(C#N)ccnc3Cl)cn2)CCCC1] | 2-chloro-3-(1-((1-methylcyclopentyl)methyl)-1H-pyrazol-4-yl)isonicotinonitrile | 301 |
| H22 | 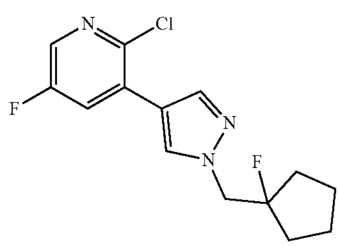 [SMILES: Fc1cnc(Cl)c(-c2cnn(CC3(F)CCCC3)c2)c1] | 2-chloro-5-fluoro-3-(1-((1-fluorocyclopentyl)methyl)-1H-pyrazol-4-yl)pyridine | 298 |
| H23 | 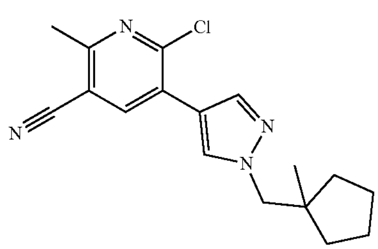 [SMILES: Cc1nc(Cl)c(-c2cnn(CC3(C)CCCC3)c2)cc1C#N] | 6-chloro-2-methyl-5-(1-((1-methylcyclopentyl)methyl)-1H-pyrazol-4-yl)nicotinonitrile | 315 |
| H24 | 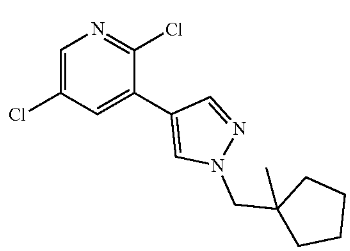 [SMILES: CC1(Cn2cc(-c3cc(Cl)cnc3Cl)cn2)CCCC1] | 2,5-dichloro-3-(1-((1-methylcyclopentyl)methyl)-1H-pyrazol-4-yl)pyridine | 310 |

TABLE H-continued

| Intermediate | Structure | Name | MS (M + 1) |
|---|---|---|---|
| H25 | 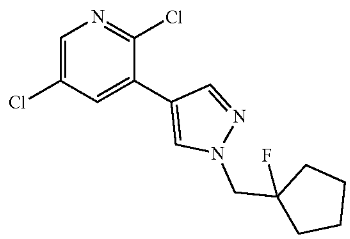 [SMILES: FC1(Cn2cc(-c3cc(Cl)cnc3Cl)cn2)CCCC1] | 2,5-dichloro-3-(1-((1-fluorocyclopentyl)methyl)-1H-pyrazol-4-yl)pyridine | 314 |
| H26 | 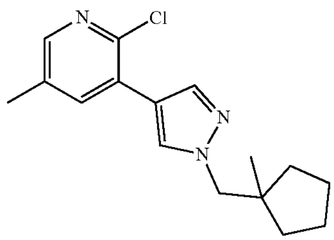 [SMILES: Cc1cnc(Cl)c(-c2cnn(CC3(C)CCCC3)c2)c1] | 2-chloro-5-methyl-3-(1-((1-methylcyclopentyl)methyl)-1H-pyrazol-4-yl)pyridine | 290 |
| H27 | 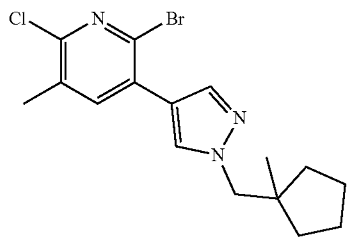 [SMILES: Cc1cc(-c2cnn(CC3(C)CCCC3)c2)c(Br)nc1Cl] | 2-bromo-6-chloro-5-methyl-3-(1-((1-methylcyclopentyl)methyl)-1H-pyrazol-4-yl)pyridine | 368<br>370<br>372 |
| H28 | 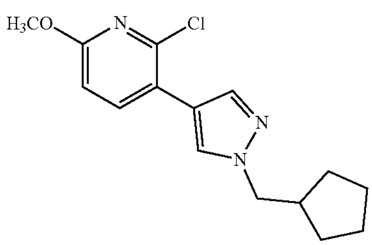 [SMILES: COc1ccc(-c2cnn(CC3CCCC3)c2)c(Cl)n1] | 2-chloro-3-(1-(cyclopentylmethyl)-1H-pryazol-4-yl)-6-methoxypyridine | 292 |

*$^1$H NMR (400 MHz, CDCl$_3$): δ 8.02 (s, 1H), 7.93 (d, J = 8 Hz, 1H), 7.88 (s, 1H), 7.65 (d, J = 8 Hz, 1H), 5.17 (dm, J = 52 Hz, 1H), 4.18 (d, J = 7.2 Hz, 2H), 2.81 (m, 1H), 2.00 (m, 4H), 1.43 (m, 1H).
**$^1$H NMR (400 MHz, CDCl$_3$): δ 7.93 (m, 2H), 7.83 (s, 1H), 7.58 (d, J = 8 Hz, 1H), 6.58 (t, J = 56 Hz, 1H), 5.22-5.09 (dm, J = 52 Hz, 1H), 4.15 (d, J = 7.2 Hz, 2H), 2.78 (m, 1H), 2.12-1.91 (m, 4H), 1.41 (m, 2H).
$^1$H NMR (400 MHz, CDCl$_3$): δ 7.88 (m, 2H), 7.78 (s, 1H), 7.54 (d, J = 8 Hz, 1H), 6.53 (t, J = 56 Hz, 1H), 5.10 (dm, J = 52 Hz, 1H), 4.10 (d, J = 6.8 Hz, 2H), 2.73 (m, 1H), 2.05 (m, 1H), 1.93 (m, 3H), 1.36 (m, 2H).
$^1$H NMR (400 MHz, CDCl$_3$): δ 8.05 (s, 1H), 7.95 (d, J = 8 Hz, 1H), 7.87 (s, 1H), 7.60 (d, J = 7.6 Hz, 1H), 6.60 (t, J = 55 Hz, 1H), 4.46 (d, J = 22 Hz, 2H), 1.86-1.71 (m, 8H).

Intermediate H29

2-chloro-3-(1-(((3R,4R)-3,4-difluorocyclopentyl)methyl)-1H-pyrazol-4-yl)-5-fluoropyridine

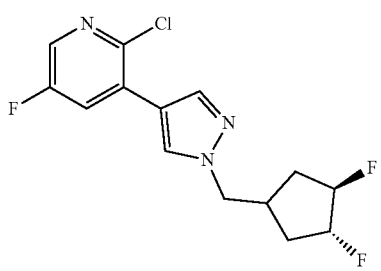 [SMILES: Fc1cnc(Cl)c(-c2cnn(CC3C[C@@H](F)[C@H](F)C3)c2)c1]

A mixture of 4-bromo-1-(((3R,4R)-3,4-difluorocyclopentyl)methyl)-1H-pyrazole (INTERMEDIATE D6, 80 mg, 0.302 mmol), bis(pinacolato)diboron (92 mg, 0.362 mmol), PdCl$_2$(dppf) (22.1 mg, 0.030 mmol) and KOAc (59.2 mg, 0.604 mmol) in 1,4-dioxane (3 ml) was stirred at 80° C. for 16 hours under N$_2$. LCMS confirmed boronate formation. 3-Bromo-2-chloro-5-fluoropyridine (95 mg, 0.452 mmol), K$_3$PO$_4$ (241 mg, 0.903 mmol) and PdCl$_2$(dppf) (22.0 mg, 0.030 mmol) were then added, the vessel evacuated and charged with nitrogen, then water (1 ml) was added and the reaction stirred at 80° C. for 16 hours under N$_2$. The mixture was dissolved in EtOAc (20 ml), washed with water (5 ml), dried over Na$_2$SO$_4$, filtrated and the filtrate was concen trated, purified by silica gel chromatography (pet. ether: THF=80:20) to give the title compound. MS (M+1): 316.

SCHEME I

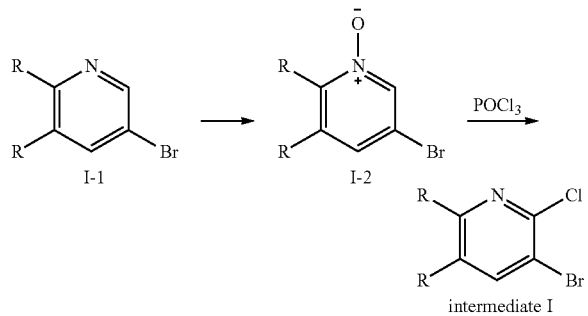

Intermediate I is prepared from a commercial 2-unsubstituted pyridine (I-1) according to scheme I via N-oxide formation followed by chlorination to provide a 2-chloropyridine.

Intermediate I1

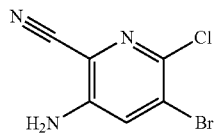

3-Amino-5-bromo-6-chloropicolinonitrile (Scheme I)

Step 1: 3-Amino-5-bromo-2-cyanopyridine 1-oxide

To a solution of 3-amino-5-bromopicolinonitrile (300 mg, 1.51 mmol) in 1,2-dichloroethane (5 mL) was added m-CPBA (1.23 g, 6.06 mmol) at 0° C. The reaction mixture was stirred 0° C. for 1 h and then 80° C. for 20 h. The reaction quenched with saturated aqueous $Na_2S_2O_3$ (10 mL) and then extracted with DCM (10 mL×3). The combined organics were dried over anhydrous $Na_2SO_4$ and concentrated. The residue was purified by silica gel chromatography (20%-80% EtOAc/petroleum ether) to give the title compound. MS: 214, 216 (M+1).

Step 2: 3-Amino-5-bromo-6-chloropicolinonitrile

3-Amino-5-bromo-2-cyanopyridine 1-oxide (50 mg, 0.23 mmol) in phosphoryl trichloride (358 mg, 2.336 mmol) was stirred 16 h at 25° C. The reaction solution was carefully added to water. The mixture was extracted with DCM (3×10 mL) and the combined organics were dried over anhydrous $Na_2SO_4$ and concentrated. The residue was purified by prep TLC (1:1 petroleum ether:EtOAc, $R_f$=0.7) to give the title compound. MS: 232, 234, 236 (M+1).

The following intermediate in table I was prepared according to scheme I using the procedure outlined in the synthesis of intermediate I1 using a commercially available pyridine.

TABLE I

| Intermediate | Structure | Name | MS (M + 1) |
|---|---|---|---|
| 12 | 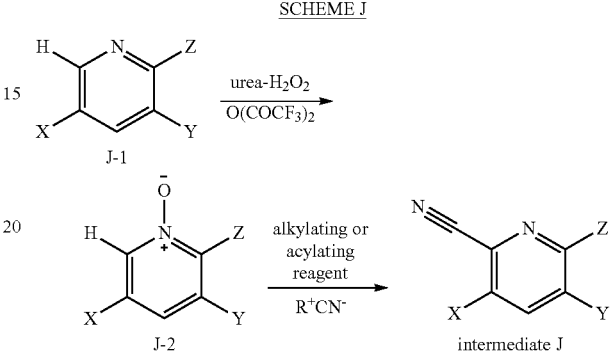 | 3-bromo-2-chloro-6-fluoro-5-methylpyridine | 224, 226 |

SCHEME J

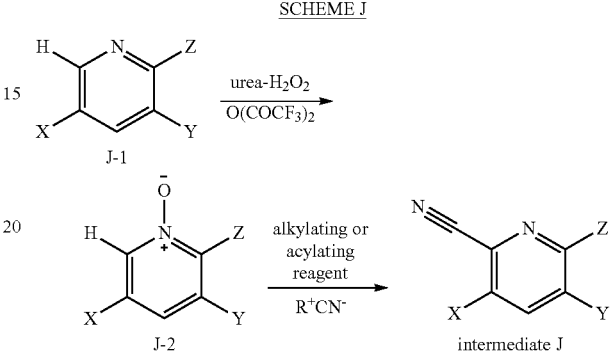

Intermediate J is prepared according to scheme J beginning with commercial pyridine J-1. Oxidation with urea.hydrogen peroxide in the presence of trifluoroacetic anhydride provides N-oxide J-2. Subsequent o-methylation with dimethyl sulfite followed by Reissert-Kaufmann reaction with sodium cyanide affords intermediate J.

Intermediate J1

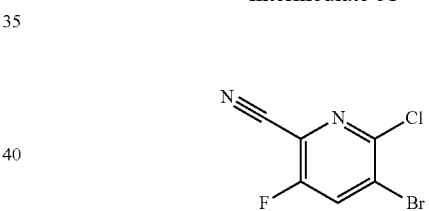

3-Fluoro-5-bromo-6-chloropicolinonitrile (Scheme J)

Step 1: 3-Fluoro-5-bromo-2-cyanopyridine 1-oxide

To a solution of urea compound with hydrogen peroxide (1:1) (1.34, 14.3 mole) and trifluoroacetic anhydride (2 mL, 14.3 mole) in 10 mL dichloromethane at 0° C. for at least 15 minutes was added 3-fluoro-5-bromopicolinonitrile (500 mg, 2.38 mmol). The reaction mixture was stirred at 40° C. for 2 hours. The reaction quenched with saturated aqueous $NaHCO_3$ (20 mL) and then extracted with DCM (20 mL×5). The combined organics were dried over anhydrous $Na_2SO_4$ and concentrated to give the crude title compound, which was carried forward without purification. MS: 226, 228 (M+1).

Step 2: 3-Fluoro-5-bromo-6-chloropicolinonitrile

To a round-bottom flask were added dimethyl sulfate (0.188 ml, 1.987 mmol) and 3-bromo-2-chloro-5-fluoropyridine 1-oxide (150 mg, 0.662 mmol). The mixture was heated to 100° C. for 30 mins. After being cooled to 0° C., the neat mixture was diluted with water (2 mL). To the stirred aqueous solution was added sodium cyanide (50.3 mg, 1.027 mmol) at 0° C. The mixture was stirred at 0° C. for 1 h under $N_2$ atmosphere. LCMS indicated the reaction was completed. The mixture was extracted with ethyl acetate (5 mL×3). The combined organic layer was dried over anhydrous sodium sulfate, filtered and the filtrate was concentrated in vacuo and the residue was purified by silica gel chromatography (petroleum ether:ethyl acetate 100:1) to give the title compound. MS: 235 (M+1).

The following intermediates in Table J were prepared in a similar fashion to intermediate J1. Intermediates G1 or G2 were converted to their N-oxides, then acylated with dimethylcarbamic chloride and treated with zinc cyanide (J3) or acylated with acetyl chloride and treated with trimethylsilylcyanide (J2).

Intermediate K1

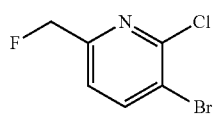

3-Bromo-2-chloro-6-(fluoromethyl)pyridine (Scheme K)

To a solution of (5-bromo-6-chloropyridin-2-yl)methanol (200 mg, 0.90 mmol) in DCM (5 mL) was added DAST (0.36 mL, 2.7 mmol) at 25° C. The resulting mixture was stirred for 12 h at 25° C., before the reaction mixture was quenched with saturated aqueous $NaHCO_3$ (15 mL). The organic was extracted with DCM (20 mL×3) and the combined organic layers were washed with water (10 mL) then brine (10 mL), dried over anhydrous sodium sulfate, filtered and concentrated to give the title compound. The material was used without further purification. MS: 224, 226 (M+1).

The following intermediate in table K was prepared according to scheme K using the procedure outlined in the synthesis intermediate K1 using the corresponding commercial aldehyde with the reaction carried out at 0° C. for 3 hours.

TABLE J

| Intermediate | Structure | Name | MS (M + 1) |
| --- | --- | --- | --- |
| J2 | 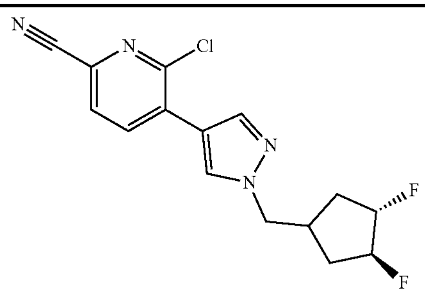 | 6-chloro-5-(1-(((3S,4S)-3,4-difluorocyclopentyl)methyl)-1H-pyrazol-4-yl)picolinonitrile | 323 |
| J3 | 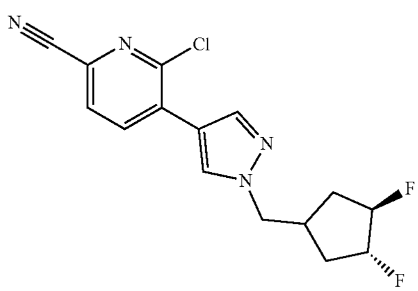 [SMILES: N#Cc1ccc(-c2cnn(CC3C[C@@H](F)[C@H](F)C3)c2)c(Cl)n1] | 6-chloro-5-(1-(((3R,4R)-3,4-difluorocyclopentyl)methyl)-1H-pyrazol-4-yl)picolinonitrile | 323 |

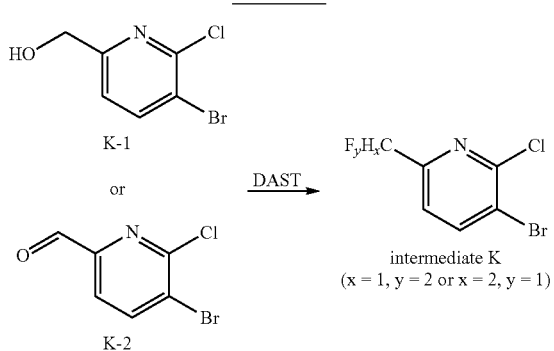

SCHEME K intermediate K (x = 1, y = 2 or x = 2, y = 1)

Intermediate K is prepared according to scheme K from treatment with DAST with either commercial alcohol K-1 or aldehyde K-2.

TABLE K

| Intermediate | Structure | Name | MS (M + 1) |
| --- | --- | --- | --- |
| K2 | 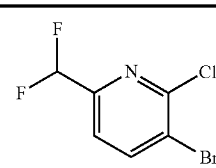 | 3-bromo-2-chloro-6-(difluoromethyl)pyridine | *see NMR data |

*intermediate K2: $^1$H NMR (400 MHz, $CDCl_3$): δ 8.07 (d, J = 8.4 Hz, 1H), 7.44 (d, J = 8.0 Hz, 1H), 6.54 (t, J = 55 Hz, 1 H).

SCHEME L

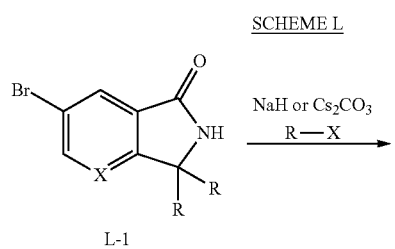

Intermediate L1

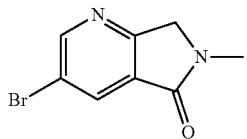

3-Bromo-6-methyl-6,7-dihydro-5H-pyrrolo[3,4-b]pyridin-5-one (Scheme L)

3-Bromo-6,7-dihydro-5H-pyrrolo[3,4-b]pyridin-5-one (320 mg, 1.5 mmol) was suspended using a freshly opened bottle of anhydrous DMF (12 mL) under an atmosphere of nitrogen. Sodium hydride (66 mg, 1.65 mmol) was added portionwise and after stirring for 30 minutes, a solution of iodomethane (103 μL, 1.65 mmol) in DMF (3 mL) was added dropwise. After 3 hours, the reaction was partitioned between water and ethyl acetate and the organic was washed with water (4×). The solution was dried over sodium sulfate, filtered and evaporated before purifying by silica gel chromatography (25-100% EtOAc/hexanes) to give the title compound. MS: 227, 229 (M+1). The following intermediates in table L were prepared using the procedure outlined in the synthesis intermediate L1 with commercially available aryl or heteroaryl lactams in the presence of an appropriate alkyl bromide or iodide. Alternative bases such as cesium carbonate can in some cases be employed.

Intermediate L is prepared according to Scheme L via alkylation using a base (NaH or cesium carbonate) in the presence of an alkyl halide.

TABLE L

| Intermediate | Structure | Name | MS (M + 1) |
| --- | --- | --- | --- |
| L2 | 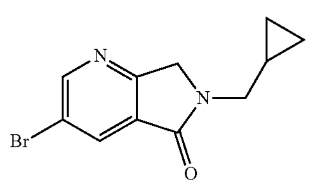 [SMILES: O=C1c2cc(Br)cnc2CN1CC1CC1] | 3-bromo-6-(cyclopropylmethyl)-6,7-dihydro-5H-pyrrolo[3,4-b]pyridin-5-one | 267, 269 |
| L3 | 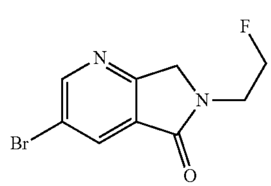 [SMILES: O=C1c2cc(Br)cnc2CN1CCF] | 3-bromo-6-(2-fluoroethyl)-6,7-dihydro-5H-pyrrolo[3,4-b]pyridin-5-one | 259, 261 |
| L4 | 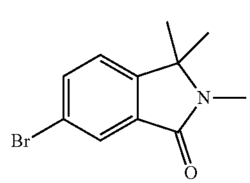 | 6-bromo-2,3,3-trimethylisoindolin-1-one | 254, 256 |

SCHEME M

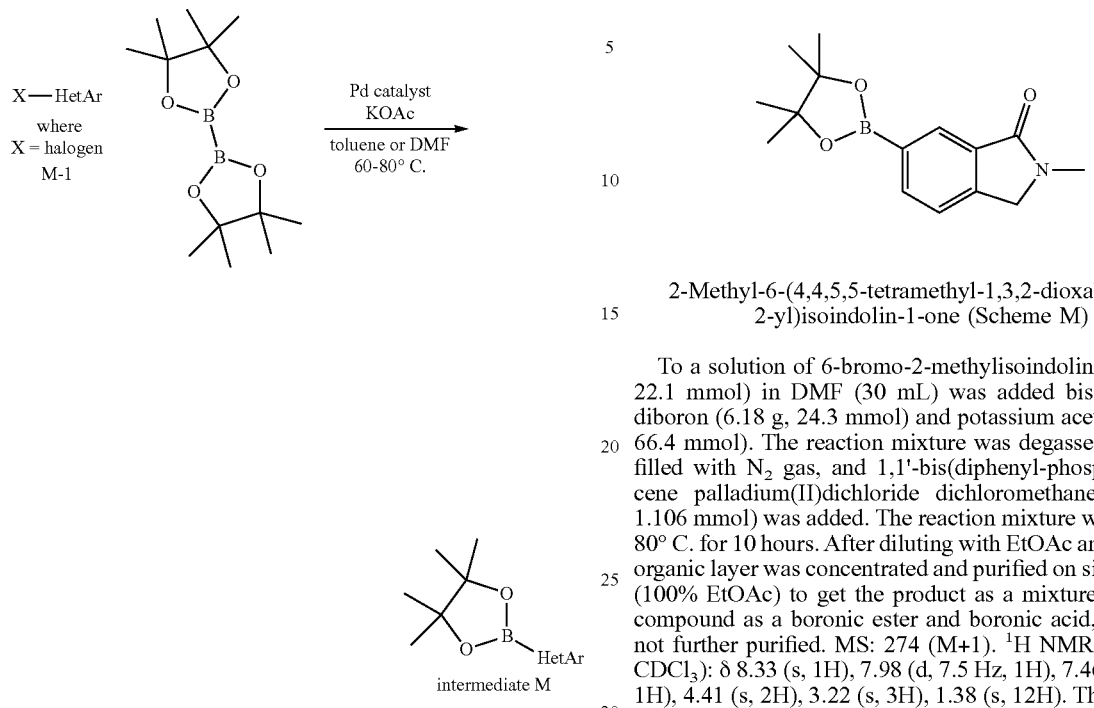

Intermediate M is prepared via a Miyaura borylation reaction that can be performed in either toluene or DMF with either 1,1'-bis(di-tert-butylphosphino)ferrocene palladium dichloride or 1,1'-bis(diphenylphosphino)ferrocene palladium(II)dichloride dichloromethane complex as the palladium catalyst. Other catalysts can be used as well, including but not limited to Xphos G2 Precatalyst with KOAc as base.

Intermediate M1

2-Methyl-6-(4,4,5,5-tetramethyl-1,3,2-dioxaborolan-2-yl)isoindolin-1-one (Scheme M)

To a solution of 6-bromo-2-methylisoindolin-1-one (5 g, 22.1 mmol) in DMF (30 mL) was added bis(pinacolato)diboron (6.18 g, 24.3 mmol) and potassium acetate (6.51 g, 66.4 mmol). The reaction mixture was degassed and back-filled with $N_2$ gas, and 1,1'-bis(diphenyl-phosphino)ferrocene palladium(II)dichloride dichloromethane (0.903 g, 1.106 mmol) was added. The reaction mixture was stirred at 80° C. for 10 hours. After diluting with EtOAc and water, the organic layer was concentrated and purified on silica column (100% EtOAc) to get the product as a mixture of the title compound as a boronic ester and boronic acid, which was not further purified. MS: 274 (M+1). $^1$H NMR (500 MHz, $CDCl_3$): δ 8.33 (s, 1H), 7.98 (d, 7.5 Hz, 1H), 7.46 (d, 7.5 Hz, 1H), 4.41 (s, 2H), 3.22 (s, 3H), 1.38 (s, 12H). The following intermediates in table M were prepared according to scheme M using the procedure outlined in the synthesis intermediate M1. The procedure can utilize 1,1'-bis(di-tert-butylphosphino)ferrocene palladium dichloride or 1,1'-bis(diphenylphosphino) ferrocene palladium(II)dichloride dichloromethane complex as the palladium catalyst with toluene or DMF as the reaction solvent. The starting material bromide was either commercially available, known in the literature, or prepared using the protocol in scheme L.

TABLE M

| Intermediate | Structure | Name | MS (M + 1) |
| --- | --- | --- | --- |
| M2 | 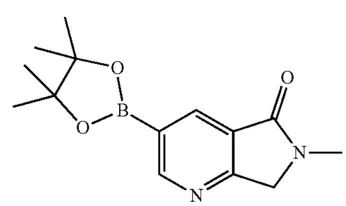 | 6-methyl-3-(4,4,5,5-tetramethyl-1,3,2-dioxaborolan-2-yl)-6,7-dihydro-5H-pyrrolo[3,4-b]pyridin-5-one | 193* |
| M3 | 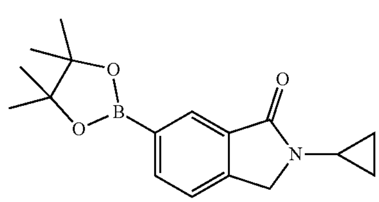 [SMILES: CC1(C)OB(c2ccc3c(c2)C(=O)N(C2CC2)C3)OC1(C)C] | 2-cyclopropyl-6-(4,4,5,5-tetramethyl-1,3,2-dioxaborolan-2-yl)isoindolin-1-one | 300 |

TABLE M-continued

| Intermediate | Name | MS (M + 1) |
|---|---|---|
| M4 | 2-(cyclopropylmethyl)-6-(4,4,5,5-tetramethyl-1,3,2-dioxaborolan-2-yl)isoindolin-1-one | 314 |
| M5 | 3,3-dimethyl-6-(4,4,5,5-tetramethyl-1,3,2-dioxaborolan-2-yl)isoindolin-1-one | 288 |
| M6 | 2,3,3-trimethyl-6-(4,4,5,5-tetramethyl-1,3,2-dioxaborolan-2-yl)isoindolin-1-one | 302 |
| M7 | (7-(4,4,5,5-tetramethyl-1,3,2-dioxaborolan-2-yl)imidazo[1,2-a]pyridin-2-yl)methanol | 193* |
| M8 | 3-methoxy-7-(4,4,5,5-tetramethyl-1,3,2-dioxaborolan-2-yl)cinnoline | 287<br>205* |
| M9 | (2-methylimidazo[1,2-a]pyridin-7-yl)boronic acid | 177* |
| M10 | 3-fluoro-7-(4,4,5,5-tetramethyl-1,3,2-dioxaborolan-2-yl)quinoline | 274 |

TABLE M-continued

| Intermediate | Structure | Name | MS (M + 1) |
|---|---|---|---|
| M11 | 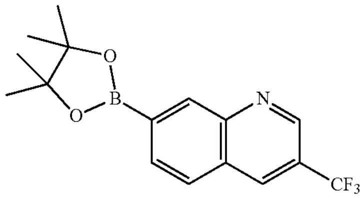 [SMILES: CC1(C)OB(c2ccc3cc(C(F)(F)F)cnc3c2)OC1(C)C] | 7-(4,4,5,5-tetramethyl-1,3,2-dioxaborolan-2-yl)-3-(trifluoromethyl)quinoline | 242* |
| M12 | 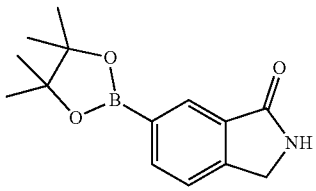 [SMILES: CC1(C)OB(c2ccc3c(c2)C(=O)NC3)OC1(C)C] | 6-(4,4,5,5-tetramethyl-1,3,2-dioxaborolan-2-yl)isoindolin-1-one | 260 |
| M13 | 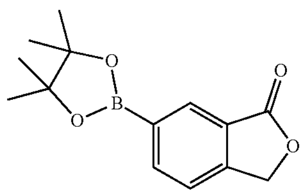 [SMILES: CC1(C)OB(c2ccc3c(c2)C(=O)OC3)OC1(C)C] | 6-(4,4,5,5-tetramethyl-1,3,2-dioxaborolan-2-yl)isobenzofuran-1(3H)-one | 261 |
| M14 | 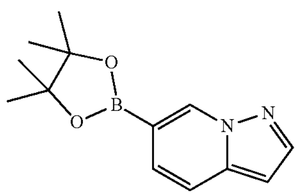 [SMILES: CC1(C)OB(c2ccc3ccnn3c2)OC1(C)C] | 6-(4,4,5,5-tetramethyl-1,3,2-dioxaborolan-2-yl)pyrazolo[1,5-a]pyridine | 245 |
| M15 | 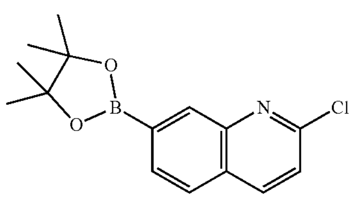 [SMILES: CC1(C)OB(c2ccc3ccc(Cl)nc3c2)OC1(C)C] | 2-chloro-7-(4,4,5,5-tetramethyl-1,3,2-dioxaborolan-2-yl)quinoline | 290 |
| M16 | 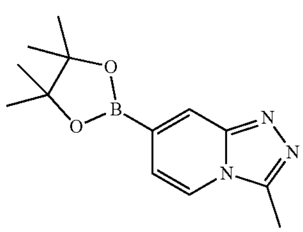 [SMILES: Cc1nnc2cc(B3OC(C)(C)C(C)(C)O3)ccn12] | 3-methyl-7-(4,4,5,5-tetramethyl-1,3,2-dioxaborolan-2-yl)-[1,2,4]triazolo[4,3-a]pyridine | 178* |
| M17 | 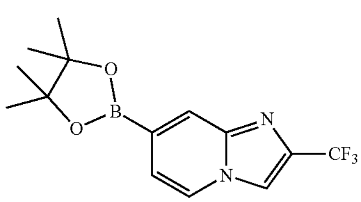 [SMILES: CC1(C)OB(c2ccn3cc(C(F)(F)F)nc3c2)OC1(C)C] | 7-(4,4,5,5-tetramethyl-1,3,2-dioxaborolan-2-yl)-2-(trifluoromethyl)imidazo[1,2-a]pyridine | 231 |

TABLE M-continued

| Intermediate | Name | MS (M + 1) |
|---|---|---|
| M18 | 1,2-dimethyl-5-(4,4,5,5-tetramethyl-1,3,2-dioxaborolan-2-yl)-1H-benzo[d]imidazole | 272 |
| M19 | 2-methyl-7-(4,4,5,5-tetramethyl-1,3,2-dioxaborolan-2-yl)-[1,2,4]triazolo[1,5-a]pyridine | 178* |
| M20 | 6-(4,4,5,5-tetramethyl-1,3,2-dioxaborolan-2-yl)benzo[c]isoxazole | 246 |
| M21 | 2,3-dimethyl-6-(4,4,5,5-tetramethyl-1,3,2-dioxaborolan-2-yl)-3H-imidazo[4,5-b]pyridine | 192* |
| M22 | 2,3-dimethyl-7-(4,4,5,5-tetramethyl-1,3,2-dioxaborolan-2-yl)imidazo[1,2-a]pyridine | 191* |
| M23 | 3-chloro-7-(4,4,5,5-tetramethyl-1,3,2-dioxaborolan-2-yl)cinnoline | 209* |
| M24 | 3-chloro-7-(4,4,5,5-tetramethyl-1,3,2-dioxaborolan-2-yl)quinoline | 290<br>208* |

TABLE M-continued

| Intermediate | Structure | Name | MS (M + 1) |
|---|---|---|---|
| M25 | 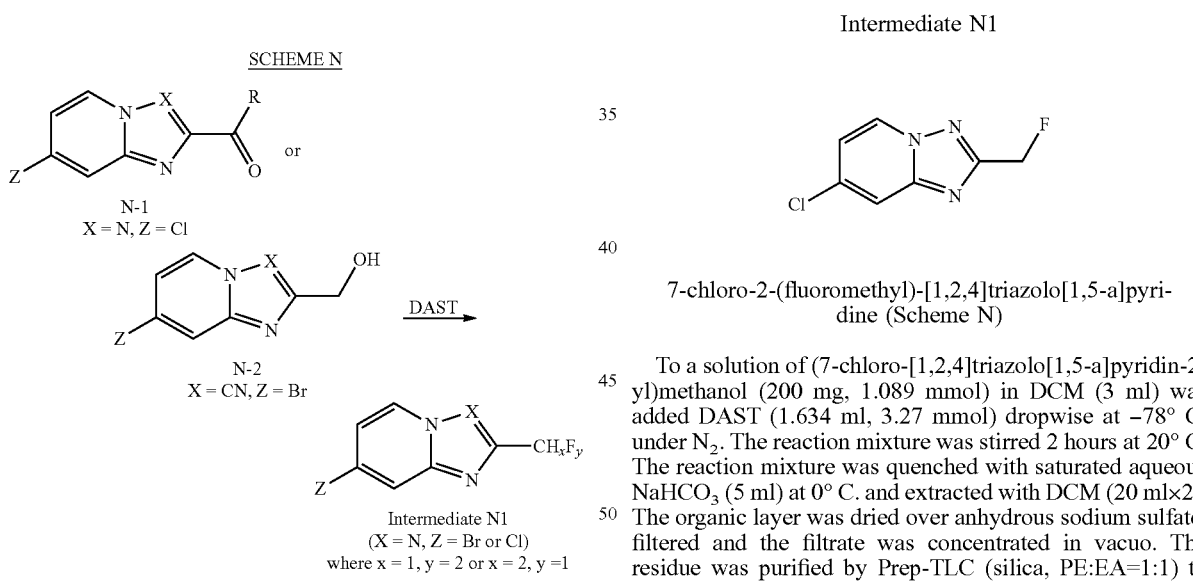 | 1-methyl-5-(4,4,5,5-tetramethyl-1,3,2-dioxaborolan-2-yl)-1H-benzo[d][1,2,3]triazole compound with 1-methyl-6-(4,4,5,5-tetramethyl-1,3,2-dioxaborolan-2-yl)-1H-benzo[d][1,2,3]triazole and 2-methyl-5-(4,4,5,5-tetramethyl-1,3,2-dioxaborolan-2-yl)-2H-benzo[d][1,2,3]triazole (1:1:1) | 260 |

*(M + 1) of parent boronic acid.

SCHEME N

N-1
X = N, Z = Cl

N-2
X = CN, Z = Br

Intermediate N1
(X = N, Z = Br or Cl)
where x = 1, y = 2 or x = 2, y =1

Intermediate N is prepared according to scheme N from treatment with DAST with either aldehyde N-1 or commercial alcohol N-2.

Intermediate N1

7-chloro-2-(fluoromethyl)-[1,2,4]triazolo[1,5-a]pyridine (Scheme N)

To a solution of (7-chloro-[1,2,4]triazolo[1,5-a]pyridin-2-yl)methanol (200 mg, 1.089 mmol) in DCM (3 ml) was added DAST (1.634 ml, 3.27 mmol) dropwise at −78° C. under $N_2$. The reaction mixture was stirred 2 hours at 20° C. The reaction mixture was quenched with saturated aqueous $NaHCO_3$ (5 ml) at 0° C. and extracted with DCM (20 ml×2). The organic layer was dried over anhydrous sodium sulfate, filtered and the filtrate was concentrated in vacuo. The residue was purified by Prep-TLC (silica, PE:EA=1:1) to give the title compound. MS: 224, 226 (M+1).

Intermediate N2 in Table N was prepared according to Scheme N by treating the commercial aldehyde N-1 with DAST.

TABLE N

| Intermediate | Structure | Name | MS (M + 1) |
|---|---|---|---|
| N2 | 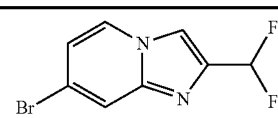 | 7-bromo-2-(difluoromethyl)imidazo[1,2-a]pyridine | *see NMR data |

*intermediate N2: $^1$H NMR (400 MHz, $CDCl_3$): δ 8.01 (d, J = 7.2 Hz, 1H), 7.83 (s, 1H), 7.79 (s, 1H), 6.98 (dd, J = 1.8, 7.2 Hz, 1H), 6.84 (t, J = 55 Hz, 1 H).

SCHEME O

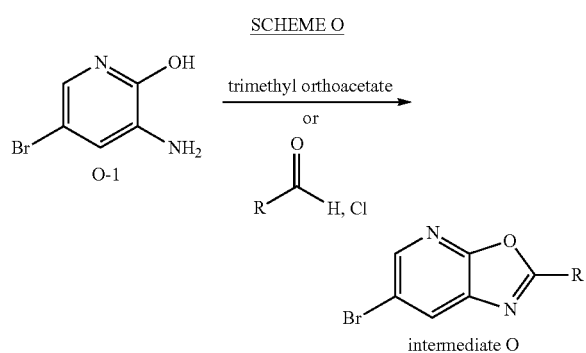

Intermediate O can be prepared by mixing intermediate O-1 with trimethyl orthoacetate. Alternatively, the amine can be acylated with an acid chloride in the presence of triethylamine, followed by a dehydrative ring closure in the presence of hexachloroethane/triphenylphosphine.

Intermediate O1

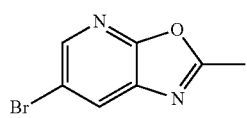

6-bromo-2-methyloxazolo[5,4-b]pyridine (Scheme O)

3-amino-5-bromopyridin-2-ol (473 mg, 2.5 mmol) was suspended in trimethyl orthoacetate (3.2 mL, 25.00 mmol) and heated to 120° C. via microwave heating for 30 minutes and 140° C. for an additional 30 minutes. The trimethylorthoacetate was evaporated, then reconstituted in DCM and filtered over celite. Purified by silica gel chromatography, eluting with 10-50% EtOAc/hexanes. Evaporated the major fractions to isolate the title compound. $^1$H NMR (500 MHz, CDCl$_3$): δ 8.36 (d, J=2.2 Hz, 1H), 8.08 (d, J=2.2 Hz, 1H), 2.69 (s, 3H).

Intermediate O2

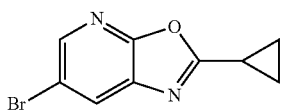 [SMILES: Brc1cnc2oc(C3CC3)nc2c1]

6-bromo-2-cyclopropyloxazolo[5,4-b]pyridine (Scheme O)

Step 1: N-(5-bromo-2-hydroxypyridin-3-yl)cyclopropanecarboxamide

3-Amino-5-bromopyridin-2-ol (473 mg, 2.5 mmol) was suspended in DCM (12.5 mL) and treated with cyclopropanecarbonyl chloride (250 μl, 2.75 mmol) followed by triethylamine (871 μl, 6.25 mmol). The reaction stirred overnight at room temperature. LCMS shows about 2/3 conversion to product. Added an additional 0.100 mL of cyclopropanecarbonyl chloride and 0.5 mL Et3N, then continued stirring. Once progress was halted, the reaction was diluted with additional DCM and washed with aqueous NH$_4$Cl. Dried over sodium sulfate, filtered and evaporated. Purified by silica gel chromatography, eluting with 20-100% EtOAc/hexanes. The main peak was isolated without the front shoulder to give the title compound. MS 257, 259 (M+1).

Step 2: 6-bromo-2-cyclopropyloxazolo[5,4-b]pyridine

Hexachloroethane (46.0 mg, 0.194 mmol) was dissolved in 0.300 mL of CH$_2$Cl$_2$. Then triphenylphosphine (61.2 mg, 0.233 mmol) and Et$_3$N (87 μl, 0.622 mmol) were added and the reaction was stirred for 5 minutes. Then a suspension of N-(5-bromo-2-hydroxypyridin-3-yl)cyclopropanecarboxamide (20 mg, 0.078 mmol) in 0.300 mL of CH$_2$Cl$_2$ was added and the reaction stirred for 2 hours. The reaction was worked up by diluting with CH$_2$Cl$_2$ and washing with saturated aqueous NH$_4$Cl followed by saturated aqueous NaHCO$_3$ and brine. Dried the organic over sodium sulfate, filtered and evaporated. Pumped on high vacuum briefly. Purified by silica gel chromatography, eluting with 5-30% EtOAc/hexanes to give the title compound. $^1$H NMR (500 MHz, CDCl$_3$): δ 8.29 (d, J=2.2 Hz, 1H), 7.99 (d, J=2.2 Hz, 1H), 2.22 (m, 1H), 1.35 (m, 2H), 1.25 (m, 2H).

SCHEME P

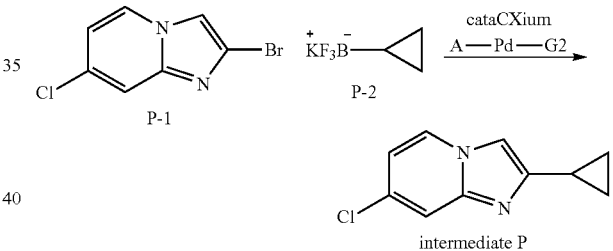

Intermediate P is prepared according to scheme P from commercial bromide P-1 and Molander reagent P-2 in the presence of catalyst to give intermediate P.

Intermediate P1

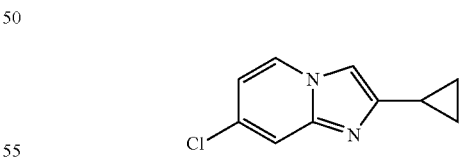

7-chloro-2-cyclopropylimidazo[1,2-a]pyridine (Scheme P)

2-Bromo-7-chloroimidazo[1,2-a]pyridine (116 mg, 0.5 mmol), potassium cyclopropyltrifluoroborate (89 mg, 0.600 mmol) and chloro[(di(1-adamantyl)-N-butylphosphine)-2-(2-aminobiphenyl)]palladium(II) (20.06 mg, 0.030 mmol) were added to a reaction vial and evacuated and charged with nitrogen. Dissolved/suspended the solid mixture in toluene (4 mL), degassed, then added 1.5 M aqueous Cs$_2$CO$_3$ (1000 μl, 1.500 mmol). Stirred at 90° C. overnight, then at 100° C. for an additional 6 hours. Filtered over a bed of sodium sulfate and purified the filtrate directly on a silica gel column, eluting with 10-50% 3:1 EtOAc:EtOH in hexanes to give the title compound. MS 193 (M+1).

Propionaldehyde (722 μl, 10.00 mmol) was added, then the stirred reaction was exposed to ambient air. After 10 minutes 2 ml of 2N KOH was added, and at 1 hour 3 mL of 2N KOH was added. At 2 hours the reaction was partitioned between ethyl acetate and water. Extracted the aqueous a second time

SCHEME Q

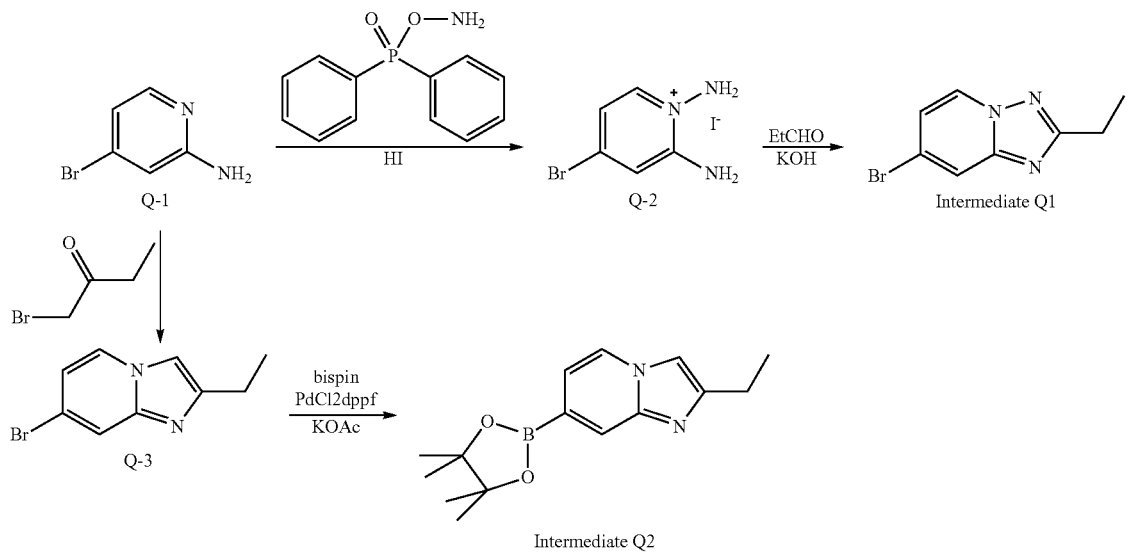

Intermediate Q1 was prepared by N-amination of the 2-aminopyridine Q-1 followed by condensation with propionaldehyde to give bicyclic intermediate Q1. Intermediate Q2 was prepared by treating aminopyridine Q-1 with 1-bromo-2-butanone followed by borylation via Miyaura reaction to give intermediate Q2.

Intermediate Q1

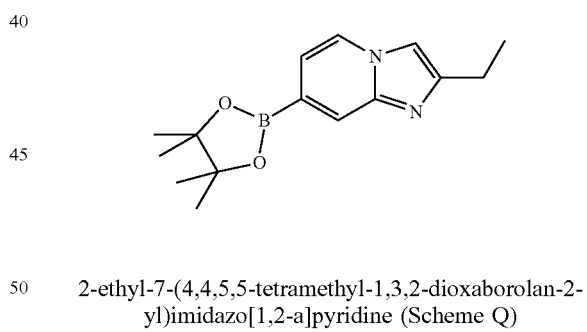

7-bromo-2-ethyl-[1,2,4]triazolo[1,5-a]pyridine (Scheme Q)

Step 1: 1,2-diamino-4-bromopyridin-1-ium iodide 4-bromopyridin-2-amine (3.46 g, 20 mmol) was dissolved in CH$_2$Cl$_2$ (100 ml). Added O-diphenylphosphinylhydroxylamine (7.00 g, 30.0 mmol) and stirred. Suspension was thinned out and allowed to stir overnight. Reaction mixture was quenched carefully with aqueous HI (2.64 ml, 20.00 mmol) and allowed to stir for another 30 minutes. The solids were filtered and washed with DCM, then hexanes. Transferred the solid to a flask and pumped off remaining solvent. The material was used directly in the following step. MS 188, 190 (M+1).

Step 2: 7-bromo-2-ethyl-[1,2,4]triazolo[1,5-a]pyridine 1,2-Diamino-4-bromopyridin-1-ium iodide (632 mg, 2.000 mmol) was suspended in THF (10 mL) with stirring.

with EtOAc, then washed the combined organics with brine, dried over sodium sulfate, filtered and evaporated. Purified by silica gel chromatography, eluting with 5-40% EtOAc in hexanes to give the title compound. MS 225, 227 (M+1).

Intermediate Q2

2-ethyl-7-(4,4,5,5-tetramethyl-1,3,2-dioxaborolan-2-yl)imidazo[1,2-a]pyridine (Scheme Q)

Step 1: 7-bromo-2-ethylimidazo[1,2-a]pyridine

2-Amino-4-bromopyridine (150 mg, 0.867 mmol) was dissolved in ethanol (3 mL) and dioxane (1 mL) followed by the addition of 1-bromobutan-2-one (96 μl, 0.954 mmol). The reaction mixture was vigorously stirred for 12 hours at 80° C. Solvent was then evaporated to give the title compound, which was used as is in the next step. MS (M+1): 225, 227.

Step 2: 2-ethyl-7-(4,4,5,5-tetramethyl-1,3,2-dioxaborolan-2-yl)imidazo[1,2-a]pyridine 7-Bromo-2-ethylimidazo[1,2-a]pyridine (270 mg, 0.840 mmol) was added to mixture of the PdCl$_2$(dppf)-CH$_2$Cl$_2$ adduct (68.6 mg, 0.084 mmol), bispinacolatodiboron (256 mg, 1.008 mmol), potassium acetate (247 mg, 2.52 mmol) in 1,4-dioxane (15 ml). The reaction was degassed for 1 minute and stirred at 90° C. for 5 hours. The solution was used as is in subsequent Suzuki reaction (see EXAMPLE 57). MS(M+1): 191 (M+1 of parent boronic acid).

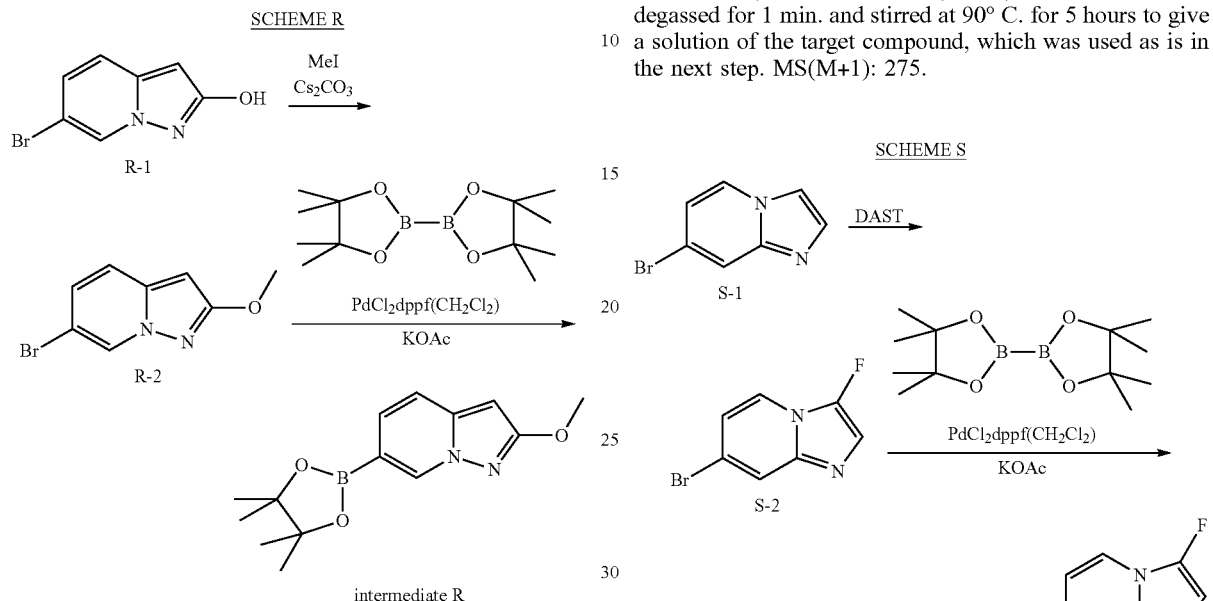

Intermediate R is prepared using scheme R, by first methylating the commercial reagent R-1, followed by Miyaura borylation to give Intermediate R.

Intermediate R1

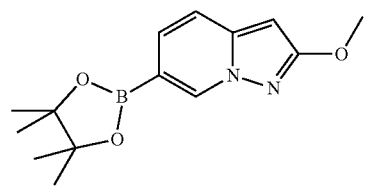

2-methoxy-6-(4,4,5,5-tetramethyl-1,3,2-dioxaborolan-2-yl)pyrazolo[1,5-a]pyridine (Scheme R)

Step 1: 6-bromo-2-methoxypyrazolo[1,5-a]pyridine

Iodomethane (0.059 ml, 0.939 mmol), cesium carbonate (306 mg, 0.939 mmol), and 6-bromopyrazolo[1,5-a]pyridin-2-ol (200 mg, 0.939 mmol) were added to a reaction vial with DMF (3 ml) and stirred for 12 hours. The reaction mixture was dissolved in water and extracted with ethyl acetate twice. The combined organics were then washed an additional three times with water and once with brine, dried over anhydrous Na₂SO₄, filtered and the filtrate evaporated to give the title compound, which was used as is without purification. MS(M+1): 227, 229.

Step 2: 2-methoxy-6-(4,4,5,5-tetramethyl-1,3,2-dioxaborolan-2-yl)pyrazolo[1,5-a]pyridine 6-Bromo-2-methoxypyrazolo[1,5-a]pyridine (150 mg, 0.661 mmol) was added to a mixture of the PdCl₂(dppf)-CH₂Cl₂ adduct (53.9 mg, 0.066 mmol), bispinacolatodiboron (185 mg, 0.727 mmol), and potassium acetate (195 mg, 1.982 mmol) in 1,4-dioxane (15 ml). The reaction was degassed for 1 min. and stirred at 90° C. for 5 hours to give a solution of the target compound, which was used as is in the next step. MS(M+1): 275.

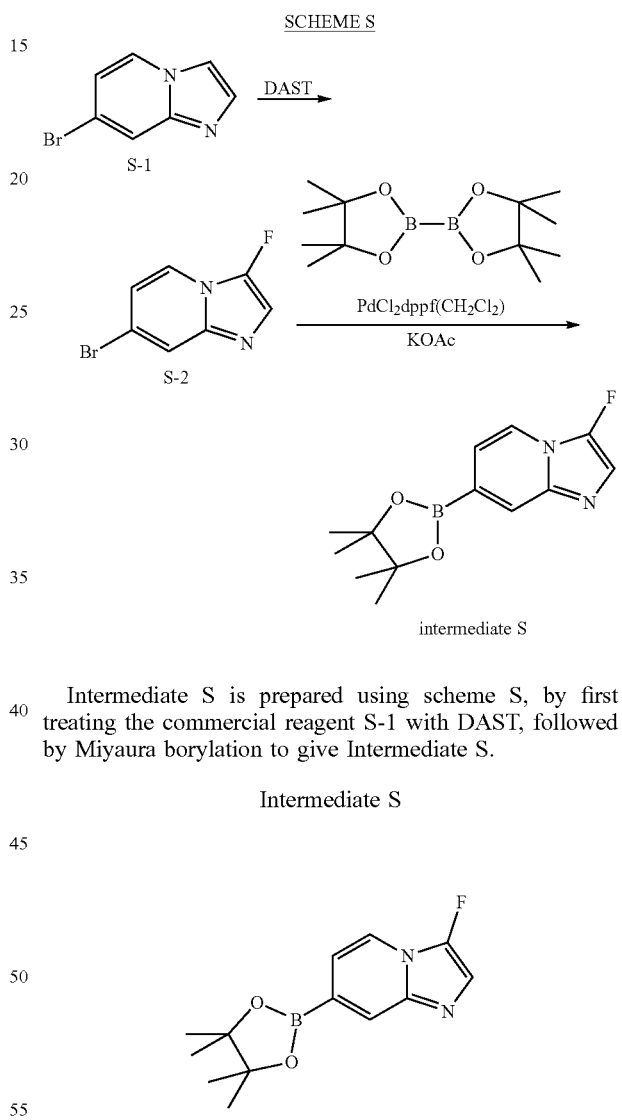

Intermediate S is prepared using scheme S, by first treating the commercial reagent S-1 with DAST, followed by Miyaura borylation to give Intermediate S.

Intermediate S 3-fluoro-7-(4,4,5,5-tetramethyl-1,3,2-dioxaborolan-2-yl)imidazo[1,2-a]pyridine (Scheme S)

Step 1: 7-bromo-3-fluoroimidazo[1,2-a]pyridine

To a solution of 7-bromoimidazo[1,2-a]pyridine (60 mg, 0.305 mmol) in THF (6 ml) was added 60% sodium hydride (8.77 mg, 0.365 mmol) at −5° C. for 10 min. Then added DAST (216 mg, 0.609 mmol).The reaction mixture was stirred at 60° C. for 16h. The mixture was diluted with water (5 mL) at 0° C. The mixture was then extracted with ethyl acetate (15 mL×2). The combined organic layers were washed with brine (5 mL×2), dried over sodium sulfate, filtered and filtrate was concentrated. The residue was purified by prep-TLC (SiO₂, 50% EA in PE) to give the title compound. MS (M+H): 215.1.

Step 2: 3-fluoro-7-(4,4,5,5-tetramethyl-1,3,2-dioxaborolan-2-yl)imidazo[1,2-a]pyridine To a solution of 7-bromo-3-fluoroimidazo[1,2-a]pyridine (30 mg, 0.140 mmol) in 1,4-dioxane (4 ml) were added bispinacolatodiboron (53.1 mg, 0.209 mmol), potassium acetate (41.1 mg, 0.419 mmol), PdCl₂(dppf) (10.2 mg, 0.014 mmol) at 27° C. The reaction mixture was stirred at 90° C. for 2 hours under nitrogen atmosphere. The reaction mixture was diluted with water (15 mL) and extracted with EtOAc (10 mL×3). The combined organic layers were washed with brine (10 mL), dried over Na₂SO₄, filtered and the filtrate was concentrated in vacuo to give the title compound, which was carried forward without further purification. MS (M+1): 263.1

SCHEME T

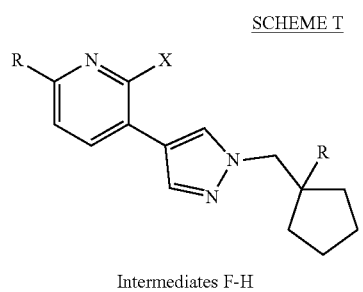

Intermediates F-H

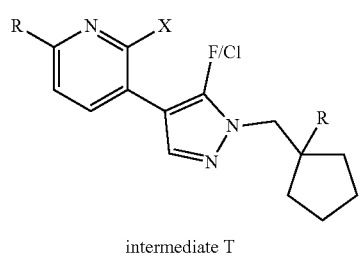

intermediate T

Intermediate T is prepared according to scheme T by treatment of any of the intermediates F-H with Selectfluor® or NCS to result in the pyrazole halogenation.

Intermediates T1 and T2

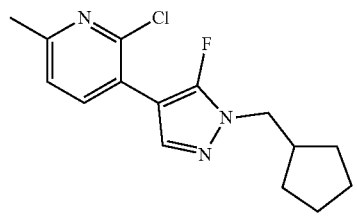 [SMILES: Cc1ccc(-c2cnn(CC3(F)CCCC3)c2F)c(Cl)n1]

Intermediate T1

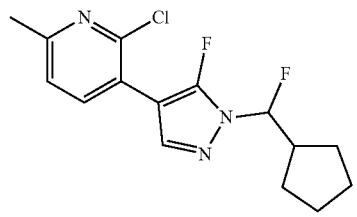

Intermediate T2

2-chloro-3-(1-(cyclopentylmethyl)-5-fluoro-1H-pyrazol-4-yl)-6-methylpyridine (T1) and 2-chloro-3-(1-(cyclopentYlfluoromethyl)-5-fluoro-1H-pyrazol-4-yl)-6-methylpyridine (T2) (Scheme T)

Selectfluor® (5.1 g 14.41 mmol) was added to a mixture of 2-chloro-3-(1-(cyclopentylmethyl)-1H-pyrazol-4-yl)-6-methylpyridine (INTERMEDIATE F5, 1.33 g, 4.80 mmol) in MeCN (24 mL) and the mixture was stirred at 60° C. for 72 hours under microwave conditions. The reaction mixture was filtered and the filtrate concentrated and the residue was purified by column chromatography on silica gel (0-30% EtOAc:hexane) to give both title compounds. Intermediate T1 MS: 294 (M+1) and Intermediate T2 MS: 312 (M+1).

The intermediates in table T were prepared according to scheme T by treating prepared intermediates (from table F-H) with DAST to give T3 or utilizing N-chlorosuccinimide in acetonitrile at 100° C. (microwave irradiation) to yield the corresponding chloropyrazole product T4.

TABLE T

| Intermediate | Structure | Name | MS (M + 1) |
|---|---|---|---|
| T3 | ![structure] | 2-chloro-3-(5-fluoro-1-((1-fluorocyclopentyl)methyl)-1H-pyrazol-4-yl)-6-methylpyridine | 312 |

TABLE T-continued

| Intermediate | Structure | Name | MS (M + 1) |
|---|---|---|---|
| T4 | 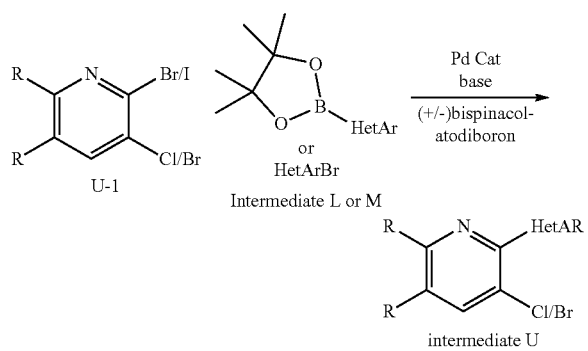 | 6-chloro-5-(5-chloro-1-((1-methylcyclopentyl)methyl)-1H-pyrazol-4-yl)picolinonitrile | 335, 337 |

SCHEME U

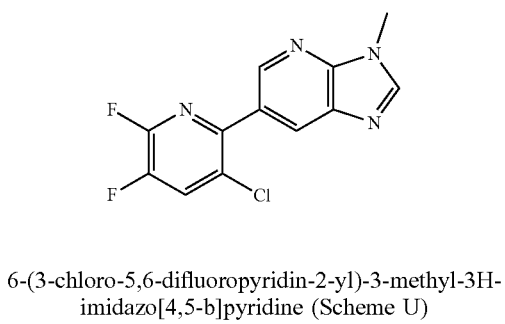

Intermediate U is prepared via a Suzuki coupling of commercial intermediate U-1 with Intermediate M or a commercial boronate. Alternatively, intermediate U can be prepared by a tandem Miyaura borylation-Suzuki coupling of intermediate L or a commercial heteroaryl halide with U-1.

Intermediate U1

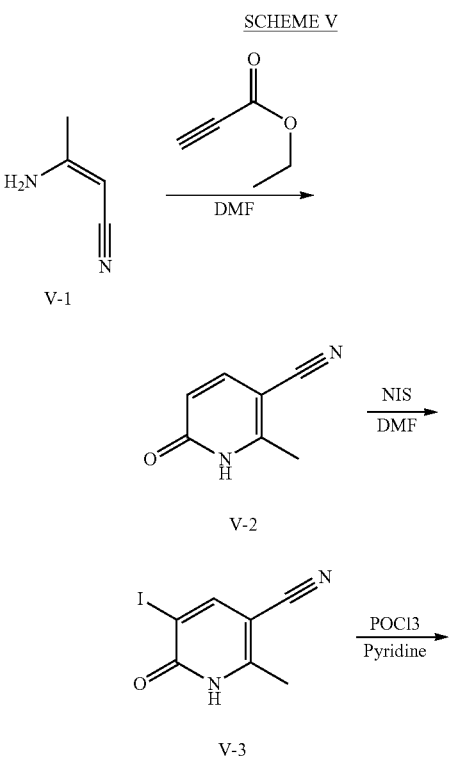

6-(3-chloro-5,6-difluoropyridin-2-yl)-3-methyl-3H-imidazo[4,5-b]pyridine (Scheme U)

3-Chloro-5,6-difluoro-2-iodopyridine (200 mg, 0.726 mmol), 3-methyl-6-(4,4,5,5-tetramethyl-1,3,2-dioxaborolan-2-yl)-3H-imidazo[4,5-b]pyridine (188 mg, 0.726 mmol), PdCl$_2$(dppf) (53.1 mg, 0.073 mmol) and potassium carbonate (2.90 ml, 2.90 mmol) were added in a reaction tube with 1,4-dioxane (5 ml) and it was degassed three times before it was heated to 50° C. for 4 hr. The reaction mixture was worked up by diluting with ethyl acetate and washing with water (3×), then drying the organic over sodium sulfate, filtering and evaporating the filtrate. The crude residue was purified by silica gel chromatography, eluting with EtOAc/ EtOH (3:1) in hexanes 0% to 50% to give the title compound. MS(M+1): 281. The following intermediates in table U were prepared according to scheme U using the procedure outlined in the synthesis of intermediate U1 using commercially available or prepared pyridine 2,3-dihalides.

TABLE U

| Intermediate | Structure | Name | MS (M + 1) |
|---|---|---|---|
| U2 | 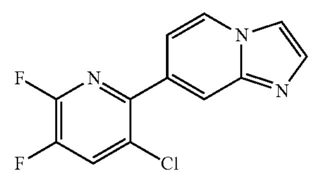 [SMILES: Fc1cc(Cl)c(-c2ccn3ccnc3c2)nc1F] | 7-(3-chloro-5,6-difluoropyridin-2-yl)imidazo[1,2-a]pyridine | 266 |

SCHEME V

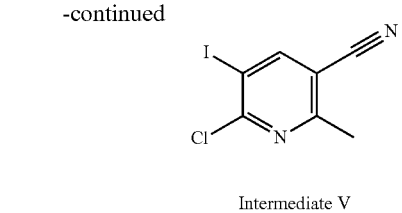

Intermediate V

Diels-Alder condensation of V-1 with ethyl prop-2-ynoate provides pyridone intermediate V-2. Iodination with NIS followed by POCl$_3$/pyridine treatment provides intermediate V.

Intermediate V1

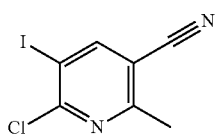

6-chloro-5-iodo-2-methylnicotinonitrile (Scheme V)

Step 1: 2-methyl-6-oxo-1,6-dihydropyridine-3-carbonitrile

Into a 3000-mL 3-necked round-bottom flask, was placed (2Z)-3-aminobut-2-enenitrile (393 g, 4.79 mol, 1.00 equiv), DMF (1500 mL), ethyl prop-2-ynoate (469.7 g, 4.79 mol, 1.00 equiv). The resulting solution was stirred for 1 h at 25° C. and then 3 days at 150° C. The reaction mixture was cooled to 25° C. with a water/ice bath. The solid was collected by filtration and washed with 2×200 mL of methanol to give the target compound as a light brown solid, which was used in next step.

Step 2: 5-iodo-2-methyl-6-oxo-1,6-dihydropyridine-3-carbonitrile

Into a 3000-mL 3-necked round-bottom flask, was placed 2-methyl-6-oxo-1,6-dihydropyridine-3-carbonitrile (148.5 g, 1.11 mol, 1.00 equiv), DMF (1500 mL), NIS (375 g, 1.67 mol, 1.50 equiv). The resulting solution was stirred for 30 min at 120° C. in an oil bath and then cooled to 25° C. with a water/ice bath, followed by dilution of the reaction with 1500 mL of ethyl acetate. The solid was collected by filtration and washed with 2×200 mL of ethyl acetate to give the target compound as a yellow solid, which was used as is in next step.

Step 3: 6-chloro-5-iodo-2-methylpyridine-3-carbonitrile

Into a 3000-mL 3-necked round-bottom flask, was placed 5-iodo-2-methyl-6-oxo-1,6-dihydropyridine-3-carbonitrile (120 g, 461.48 mmol, 1.00 equiv), POCl$_3$ (1200 mL), pyridine (3.65 g, 46.14 mmol, 0.10 equiv). The resulting solution was stirred for 3 h at 101° C. in an oil bath and then cooled to 25° C. and concentrated under vacuum. The solid was washed with water till the pH of the filtrate was 7. The solid was collected by filtration to give the title compound. MS (M+1): 279.

SCHEME W

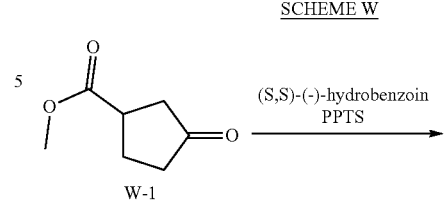

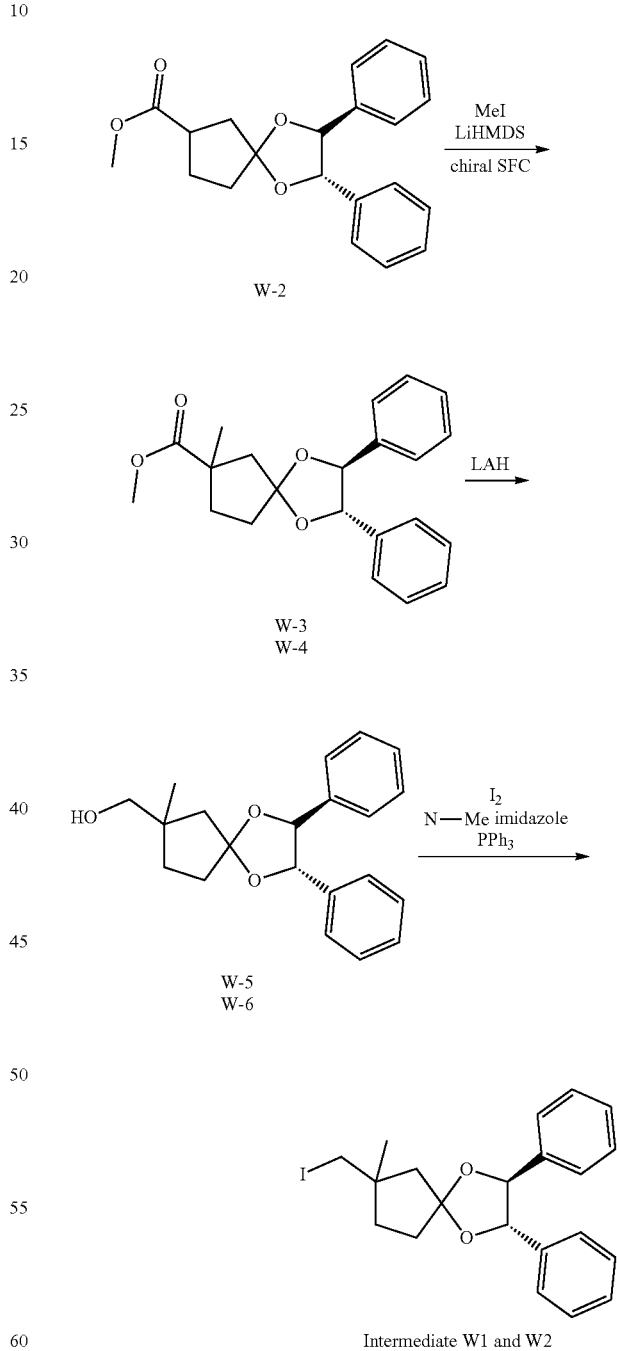

Cyclopentanone W-1 was protected as the cyclic diether W-2. α-Methylation of the ester followed by chiral SFC separation gave intermediates W-3 and W-4. Reduction of these two esters gave the alochols W-5 and W-6. Iodination of the alcohols provided intermediates W1 and W2.

INTERMEDIATE W1 and W2

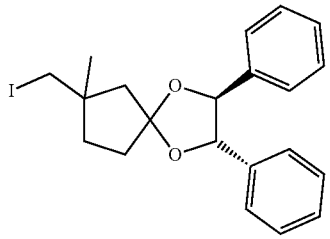

(2S,3S)-7-(iodomethyl)-7-methyl-2,3-diphenyl-1,4-dioxaspiro[4.4]nonane Isomer A (W1) and Isomer B (W2) (Scheme W)

Step 1: (2S,3S)-methyl 2,3-diphenyl-1,4-dioxaspiro[4.4]nonane-7-carboxylate

A solution of (S,S)-(−)-hydrobenzoin (7.54 g, 35.2 mmol), methyl 3-oxocyclopentanecarboxylate (5 g, 35.2 mmol), and pyridinium p-toluenesulfonate (0.884 g, 3.52 mmol) in toluene (50 ml) was refluxed with a Dean-Stark trap for 14 hours. The reaction was then cooled and partitioned between ethyl acetate and water. The organic was dried over sodium sulfate, filtered and the filtrate evaporated. The crude was purified by silica gel chromatography, eluting with 25% EtOAc in hexanes to get the title compound.

Step 2: (2S,3S)-methyl 7-methyl-2,3-diphenyl-1,4-dioxaspiro[4.4]nonane-7-carboxylate isomer B To a solution of (2S,3S)-methyl 2,3-diphenyl-1,4-dioxaspiro[4.4]nonane-7-carboxylate (3.8 g, 11.23 mmol) in THF (50 ml) was added lithium bis(trimethylsilylamide) (16.84 ml, 16.84 mmol) at −78° C. After it was stirred at −78° C. for 30 minutes, iodomethane (0.843 ml, 13.48 mmol) was added. The reaction solution was slowly warmed to room temperature, and stirred over night (14 hours). The reaction was partitioned between EtOAc and water. The organic layer was collected and purified by silica gel chromatography, eluting with EtOAc in hexanes to get the product as a mixture of two diastereomers. SFC chromatography using a Chiralcel AD column and eluting with 20% MeOH/CO$_2$ separates the two diastereomers. The faster moving isomer is assigned as isomer A: $^1$H NMR (CDCl$_3$, 500 MHz): δ 7.37-7.34 (m, 6H), 7.27-7.23 (m, 4H), 4.70 (s, 2H), 3.76 (s, 3H), 2.83 (d, 14.0 Hz, 1H), 2.39-2.23 (m, 3H), 2.09 (d, 14.0 hz, 1H), 1.82 (m, 1H), 1.43 (s, 3H). The slower moving isomer is assigned as isomer B: $^1$H NMR (CDCl$_3$, 500 MHz): δ 7.39-7.33 (m, 6H), 7.27-7.23 (m, 4H), 4.72 (s, 2H), 3.73 (s, 3H), 2.83 (d, 14.0 Hz, 1H), 2.43 (m, 1H), 2.30 (m, 1H), 2.22 (m, 1H), 2.16 (d, 14.0 hz, 1H), 1762 (m, 1H), 1.46 (s, 3H).

Step 3: ((2S,3S)-7-methyl-2,3-diphenyl-1,4-dioxaspiro[4.4]nonan-7-yl)methanol isomer To a solution of (2S,3S)-methyl 7-methyl-2,3-diphenyl-1,4-dioxaspiro[4.4]nonane-7-carboxylate isomer B (1130 mg, 3.21 mmol) in THF (20 ml), was added LAH (2.79 ml, 6.41 mmol) at −78° C. The reaction solution was then slowly warmed up to room temperature and stirred for 14 hours. It was cooled to −78° C., and quenched with water. It was then partitioned between EtOAc and 1 N aqueous HCl. The organic phase was collected, dried over MgSO$_4$, filtered and evaporated to give the crude title compound. $^1$H NMR (CDCl$_3$, 500 MHz): δ 7.349 (m, 6H), 7.255 (m, 4H), 4.73 s., 2H), 3.53 (abq, 2H), 2.24 (m, 1H), 2.17 (d, 13.5 Hz, 1H), 2.10 (d, 12.0 Hz, 1H), 2.03 (d, 14.0 Hz, 1H), 1.92 (m, 1H), 1.60 (m, 1H), 1.21 (s, 3H). Isomer A was treated in the same fashion to give ((2S,3S)-7-methyl-2,3-diphenyl-1,4-dioxaspiro[4.4]nonan-7-yl)methanol isomer A. $^1$H NMR (CDCl$_3$, 500 MHz): δ 7.35 (m, 6H), 7.255 (m, 4H), 4.72 (abq., 2H), 3.54 (abq. 2H), 2.32 (m, 1H), 2.24 (d, 13.5 Hz, 1H), 2.17 (m, 1H), 1.97 (d, 14.0 Hz, 1H), 1.86 (m, 1H), 1.62 (m, 1H), 1.19 (s, 3H).

Step 4: (2S,3S)-7-(iodomethyl)-7-methyl-2,3-diphenyl-1,4-dioxaspiro[4.4]nonane isomer B To a solution of iodine (1119 mg, 4.41 mmol) in DCM (10 ml) was added triphenylphosphine (1156 mg, 4.41 mmol) at 0° C. After addition, it was stirred at 0° C. for 1 hour. Then, 1-methylimidazole (0.405 ml, 5.09 mmol) was added. After 20 more minutes at 0° C., ((2S,3S)-7-methyl-2,3-diphenyl-1,4-dioxaspiro[4.4]nonan-7-yl)methanol isomer B (1100 mg, 3.39 mmol) was added, and the reaction solution was stirred at 0° C. overnight. The reaction was partitioned between ether and water. The organic layer was dried over MgSO$_4$, filtered and the filtrate evaporated. The crude isolate was purified by silica gel chromatography, eluting with 10% EtOAc in hexanes to get the title compound. $^1$H NMR (CDCl$_3$, 500 MHz): δ 7.36-7.34 (m, 6H), 7.26-7.23 (m, 4H), 4.70 (s, 2H), 3.43 (s, 2H), 2.36-2.18 (m, 4H), 1.94 (m, 1H), 1.81 (m, 1H), 1.33 (s, 3H). Isomer A was treated in the same fashion to give ((2S,3S)-7-methyl-2,3-diphenyl-1,4-dioxaspiro[4.4]nonan-7-yl)methanol isomer A. $^1$H NMR (CDCl$_3$, 500 MHz): δ 7.36-7.34 (m, 6H), 7.26-7.23 (m, 4H), 4.68 (abQ, 2H), 3.43 (abq, 2H), 2.40-2.26 (m, 3H), 2.11 (d, 13.5 hz, 1H), 1.90-1.78 (m, 2H), 1.30 (s, 3H).

SCHEME X

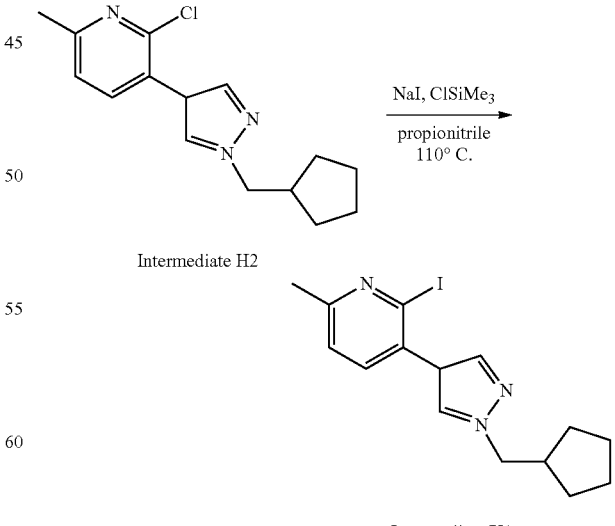

Intermediate H2

Intermediate X1

Intermediate H2 was treated with NaI and chlorotrimethylsilane to give the 2-iodopyridine intermediate X1.

Intermediate X1

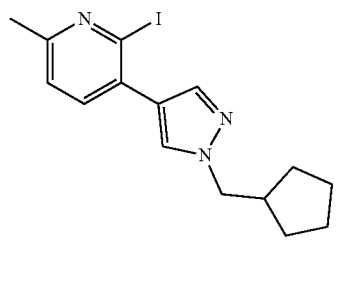 [SMILES: Cc1ccc(-c2cnn(CC3CCCC3)c2)c(I)n1]

3-(1-(cyclopentylmethyl)-1H-pyrazol-4-yl)-2-iodo-6-methylpyridine (Scheme X)

2-chloro-3-(1-(cyclopentylmethyl)-1H-pyrazol-4-yl)-6-methylpyridine (INTERMEDIATE H2, 2.00 g, 7.25 mmol), sodium iodide (4.35 g, 29.0 mmol) and propionitrile (7.25 ml) were added to a pressure flask followed by chlorotrimethylsilane (0.463 ml, 3.63 mmol) and heated to 110° C. for 24 hours. The reaction was then cooled to room temperature and washed with aqueous sodium bisulfite, water and brine sequentially. Extracted with EtOAc and dried over sodium sulfate, filtered and evaporated to dryness. Purified by silica gel chromatography, eluting with 0-100% ethyl acetate in hexanes to provide the title compound. MS(M+1); 368.

SCHEME Y

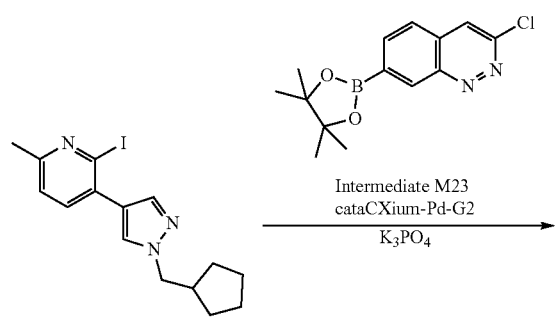

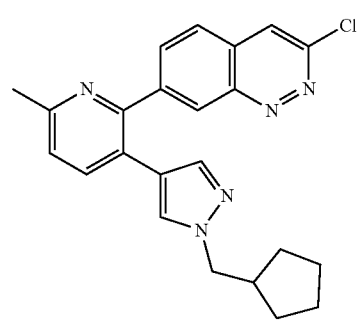

Treatment of Intermediate X1 with Intermediate M23 under Suzuki coupling conditions provides intermediate Y1.

Intermediate Y1

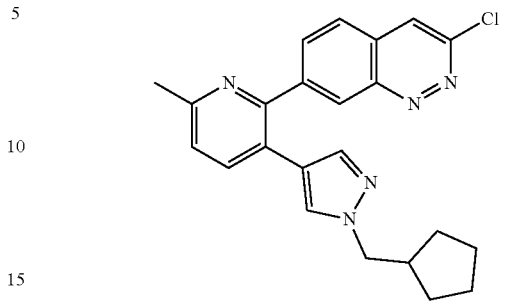

3-chloro-7-(3-(1-(cyclopentylmethyl)-1H-pyrazol-4-yl)-6-methylpyridin-2-yl)cinnoline (Scheme Y)

3-chloro-7-(4,4,5,5-tetramethyl-1,3,2-dioxaborolan-2-yl)cinnoline (INTERMEDIATE M23, 1.029 g, 3.54 mmol), 3-(1-(cyclopentylmethyl)-1H-pyrazol-4-yl)-2-iodo-6-methylpyridine (INTERMEDIATE X1, 1.3 g, 3.54 mmol), cataCXium-Pd-G2 catalyst (0.237 g, 0.354 mmol) and potassium phosphate (2.254 g, 10.62 mmol) was added a flask. THF (35.4 ml) was added followed by purging with nitrogen. The reaction was heated to 80° C. for 10 hours, then cooled to room temperature and filtered over a pad of celite. The celite pad was washed with EtOAc and the combined filtrate was evaporated to dryness. The crude isolate was purified on by silica gel chromatography, eluting with a gradient from 0-100% ethyl acetate in hexanes to provide the title compound. MS(M+1): 404.

SCHEME Z

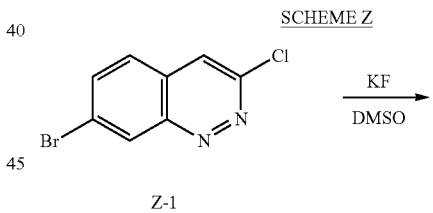

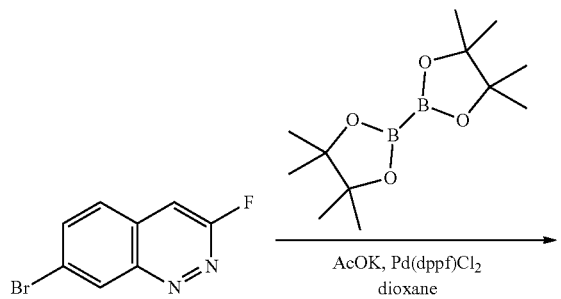

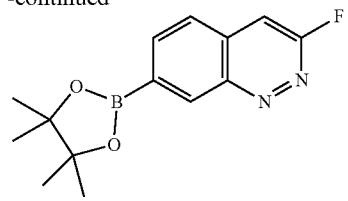

Z1

Chlorocinnoline Z-1 can be treated with KF in DMSO with heating to provide the fluorocinnoline Z-2. A Miyaura borylation of Z-2 can provide intermediate Z1.

Intermediate Z1

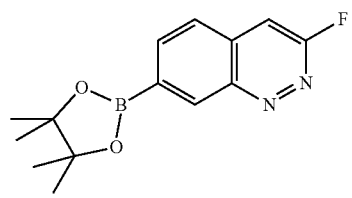 [SMILES: CC1(C)OB(c2ccc3cc(F)nnc3c2)OC1(C)C]

3-fluoro-7-(4,4,5,5-tetramethyl-1,3,2-dioxaborolan-2-yl)cinnoline (Scheme Z)

Step 1: 7-bromo-3-fluorocinnoline

A mixture of 7-bromo-3-chlorocinnoline (120 mg, 0.492 mmol), KF (43.0 mg, 0.739 mmol) in DMSO (2 mL) were stirred at 100° C. for 16 hours. LC-MS showed target was formed. Then the mixture was extracted with EtOAc (10 mL×3). The organic phase was washed with brine (20 mL×2), dried over $Na_2SO_4$, filtered, concentrated in vacuo and purified by prep-TLC ($SiO_2$, petroleum ether: ethyl acetate=4:1) to yield the title compound. MS (M+H): 227, 229

Step 2: 3-fluoro-7-(4,4,5,5-tetramethyl-1,3,2-dioxaborolan-2-yl)cinnoline

To a solution of 7-bromo-3-fluorocinnoline (40 mg, 0.176 mmol), bis(pinacolato)diboron (53.7 mg, 0.211 mmol) and potassium acetate (51.9 mg, 0.528 mmol) in dioxane (2 mL) was added Pd(dppf)Cl$_2$ (6.4 mg, 0.0088 mmol) under nitrogen atmosphere. Then the mixture was stirred at 60° C. for 16 hours. LC-MS showed the reaction was completed and the mixture was used directly in next step. MS (M+H): 275

SCHEME AA

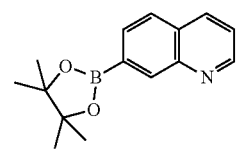

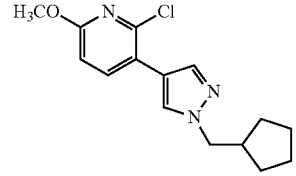

Intermediate H28

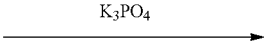

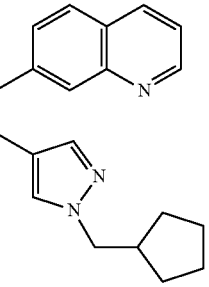

AA-1

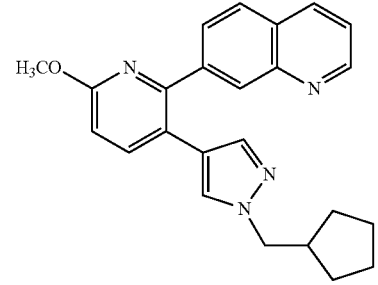

Intermediate AA1

Suzuki coupling of I INTERMEDIATE H28 and 7-(4,4,5,5-tetramethyl-1,3,2-dioxaborolan-2-yl)quinoline provides intermediate AA-1. Demethylation of the methoxypyridine provides Intermediate AA1.

Intermediate AA1

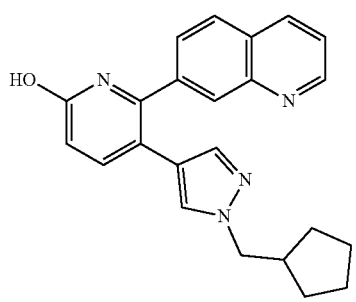 [SMILES: Oc1ccc(-c2cnn(CC3CCCC3)c2)c(-c2ccc3cccnc3c2)n1]

5-(1-(cyclopentylmethyl)-1H-pyrazol-4-yl)-6-(quinolin-7-yl)pyridin-2-ol (SchemeAA)

Step 1: 7-(3-(1-(cyclopentylmethyl)-1H-pyrazol-4-yl)-6-methoxypyridin-2-yl)quinoline 1,1'-Bis(di-tert-butylphosphino)ferrocene palladium dichloride (20.1 mg, 0.031 mmol) was added to a stirred mixture of 7-(4,4,5,5-tetramethyl-1,3,2-dioxaborolan-2-yl)quinoline (157 mg, 0.617 mmol), 2-chloro-3-(1-(cyclopentylmethyl)-1H-pyrazol-4-yl)-6-methoxypyridine (INTERMEDIATE H28, 180 mg, 0.617 mmol), $K_3PO_4$ (393 mg, 1.851 mmol) in dioxane (5 ml) and water (1 ml) and the mixture was stirred at 90° C. for 18 hours. The mixture was cooled, then solvent was evaporated under reduced pressure. The residue was diluted with DCM (10 mL) and washed with water (2×10 mL), dried over sodium sulfate, filtered and the solvent was evaporated under reduced pressure.

The residue was purified by TLC eluting with petroleum ether/ethyl acetate (1:1) to give the title compound. MS(M+1): 385.7.

Step 2: 5-(1-(cyclopentylmethyl)-1H-pyrazol-4-yl)-6-(quinolin-7-yl)pyridin-2-ol Chlorotrimethylsilane (0.030 ml, 0.234 mmol) was added to a stirred mixture of sodium iodide (35.1 mg, 0.234 mmol) and 7-(3-(1-(cyclopentylmethyl)-1H-pyrazol-4-yl)-6-methoxypyridin-2-yl)quinoline (30 mg, 0.078 mmol) in acetonitrile (3 ml). The mixture was stirred at 60° C. for 18 hours. The mixture was then cooled, and the solvent was evaporated under reduced pressure. The residue was diluted with DCM (10 mL) and washed with water (2×10 mL), dried ($Na_2SO_4$), filtered and the solvent was evaporated under reduced pressure. The residue was purified by TLC eluting with petroleum ether/ethyl acetate (1:2) to give the title compound. $^1$H NMR (CDCl$_3$, 400 MHz): δ 8.98 (s, 1H), 8.18 (m, 2H), 7.79 (d, J=8.4 Hz, 1H), 7.57 (d, J=9.6 Hz, 1H), 7.49 (m, 1H), 7.42 (d, J=8.8 Hz, 1H), 7.21 (s, 1H), 6.86 (s, 1H), 6.64 (d, J=8.8 Hz, 1H), 3.83 (d, J=7.6 Hz, 2H), 2.20 (m, 1H), 1.46 (m, 6H), 1.02 (m, 2H).

Compounds of formula (I) are prepared from a 2-step, 1-pot protocol for the in situ formation of a boronic ester or acid of bromide 1-3 that undergoes a subsequent Suzuki-coupling reaction with chloropyridine 1-1 mediated by palladium catalysts.

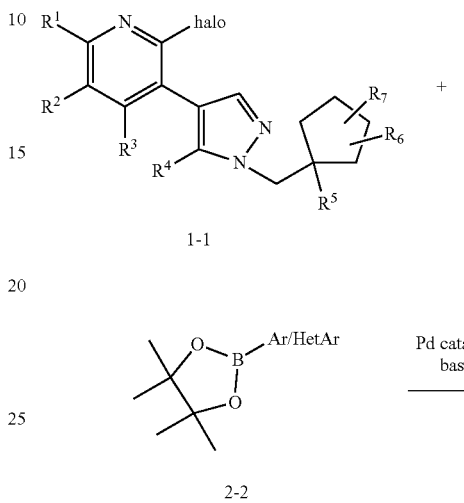

SCHEME 2

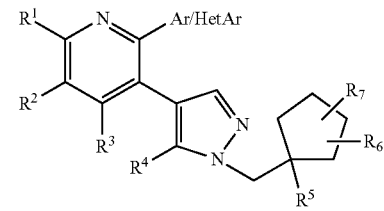

Compounds of formula (I) are synthesized from a palladium-catalyzed Suzuki coupling reaction of prepared intermediate halide 1-1 and a prepared or known boronic ester or acid 2-2.

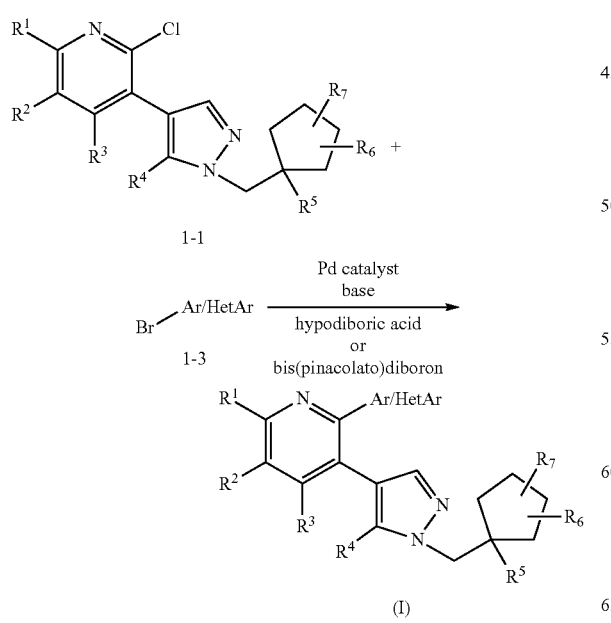

SCHEME 1

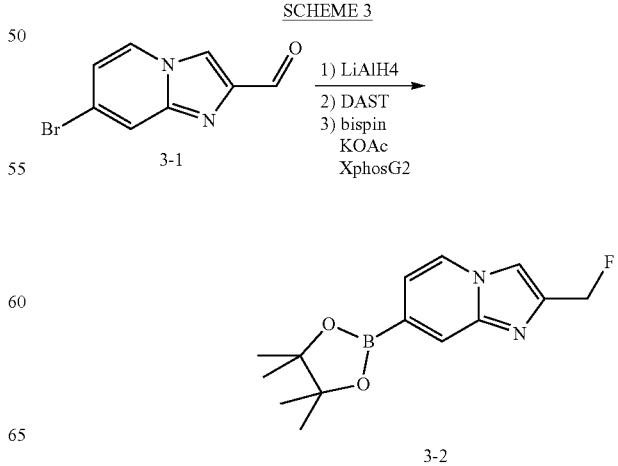

SCHEME 3

-continued

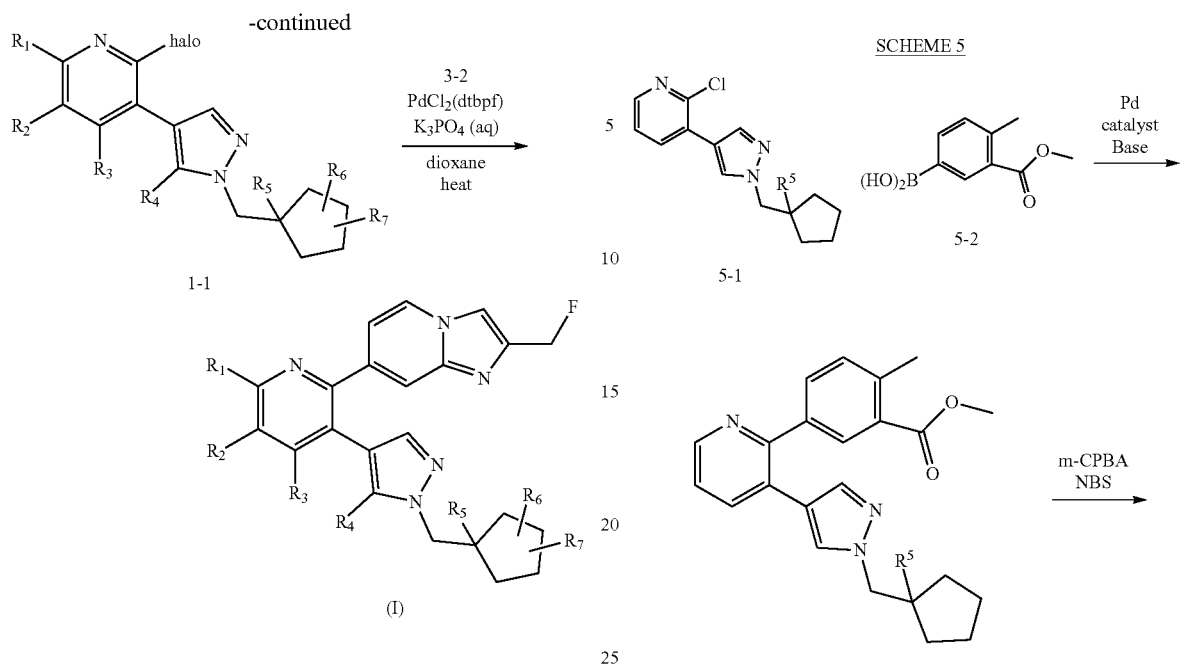

Compounds of formula (I) are synthesized from a palladium-catalyzed Suzuki coupling reaction of prepared intermediate halide 1-1 and the prepared boronic ester 3-2. Ester 3-2 is prepared by reducing the formyl functionality of heterocycle 3-1 to a primary alcohol, followed by treatment with DAST to give the fluoride.

Compounds of formula (I) are prepared from a commercial 2-iodopyridine 13-1 which was coupled to intermediate U1,U2 via a palladium-mediated Suzuki coupling reaction. A second Suzuki reaction of the resultant 3-chloropyridine U with intermediates D1-D5 provides the target compounds.

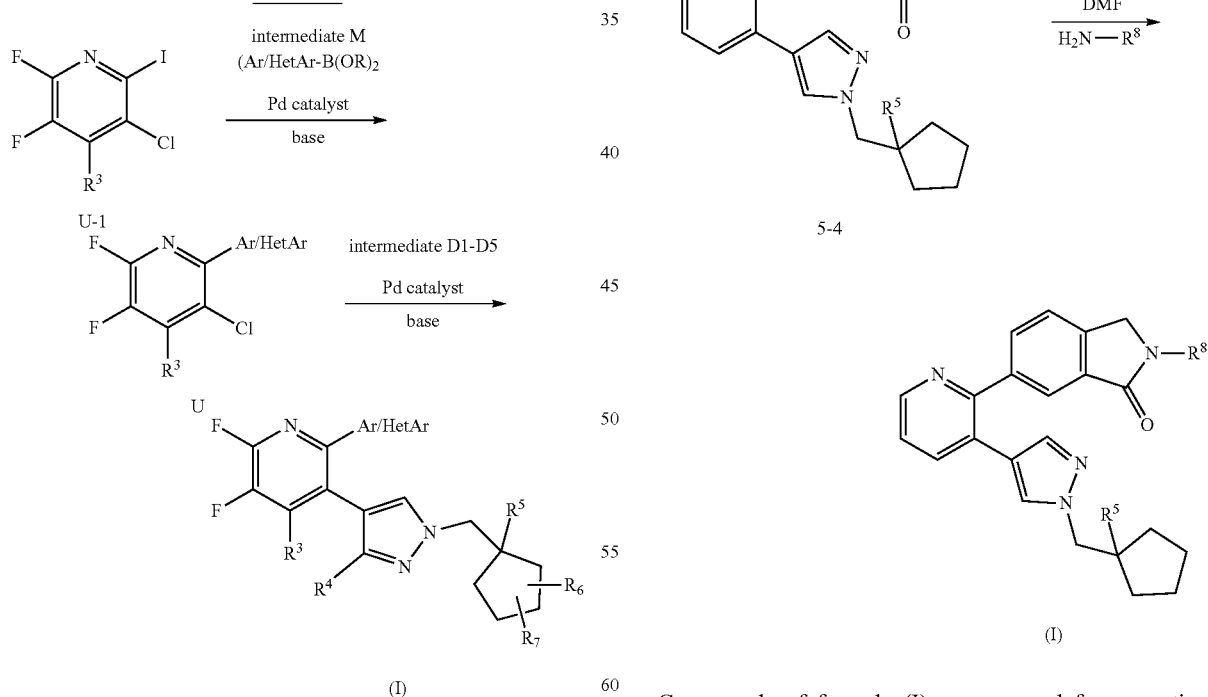

Compounds of formula (I) are prepared from reaction sequence that begins with Suzuki coupling reaction mediated by palladium catalyst of prepared intermediate halide 5-1 and commercial boronic acid 5-2. A radical bromination of tolyl-intermediate 5-3 provides the penultimate benzyl bromide 5-4. Condensation of 5-4 with amines provides compounds of the formula (I).

SCHEME 6

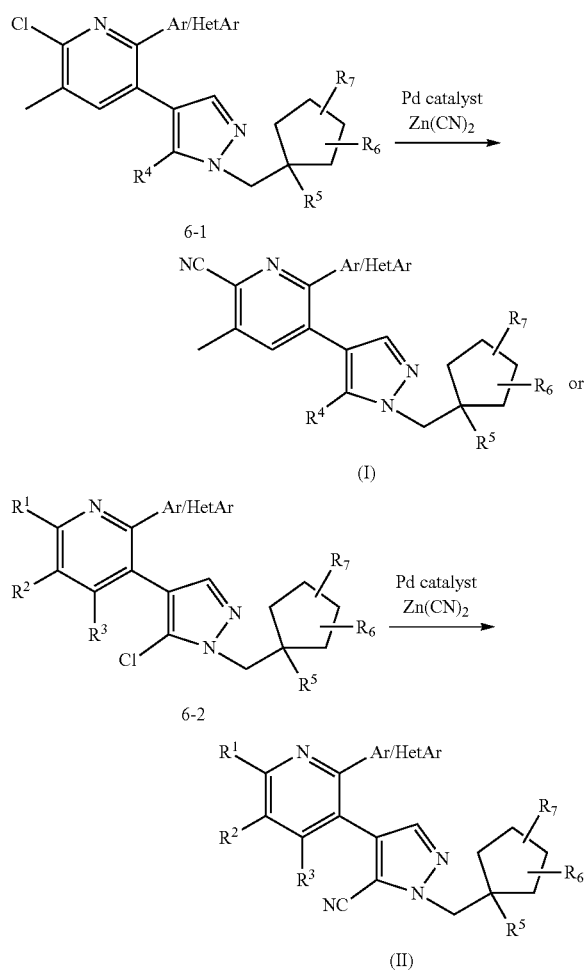

Compounds of formula (I) are prepared via a palladium-catalyzed Negishi coupling reaction of prepared chloropyridine 6-1 with zinc cyanide. Negishi coupling of chloropyrazole 6-2 with zinc cyanide provide compounds of formula (II).

SCHEME 7

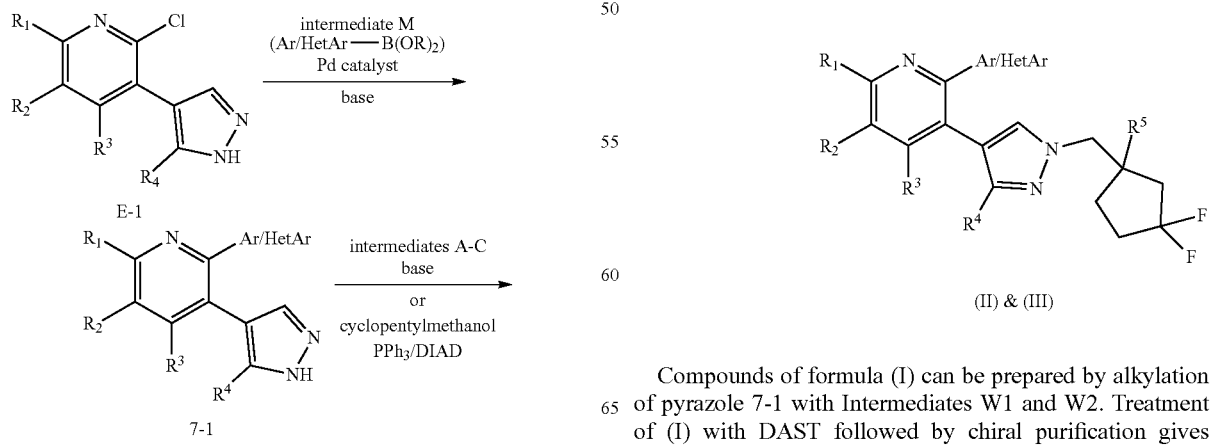

Compounds of formula (I) can be prepared via Suzuki coupling of Intermediate E-1 followed by Mitsunobu reaction of the pyrazole with cyclopentylmethanol. Alternatively, the pyrazole 7-1 can be alkylated with Intermediates A-C in the presence of base to give the target compounds.

SCHEME 8

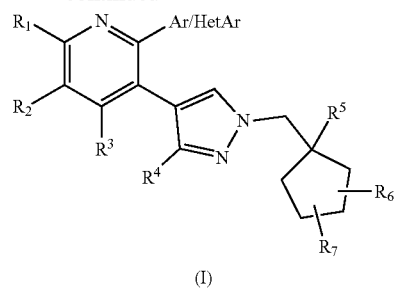

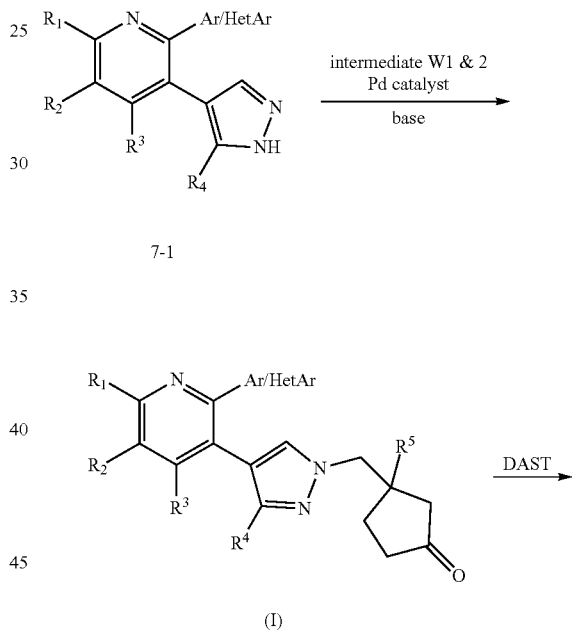

Compounds of formula (I) can be prepared by alkylation of pyrazole 7-1 with Intermediates W1 and W2. Treatment of (I) with DAST followed by chiral purification gives compounds of formulas (II) and (III).

SCHEME 9

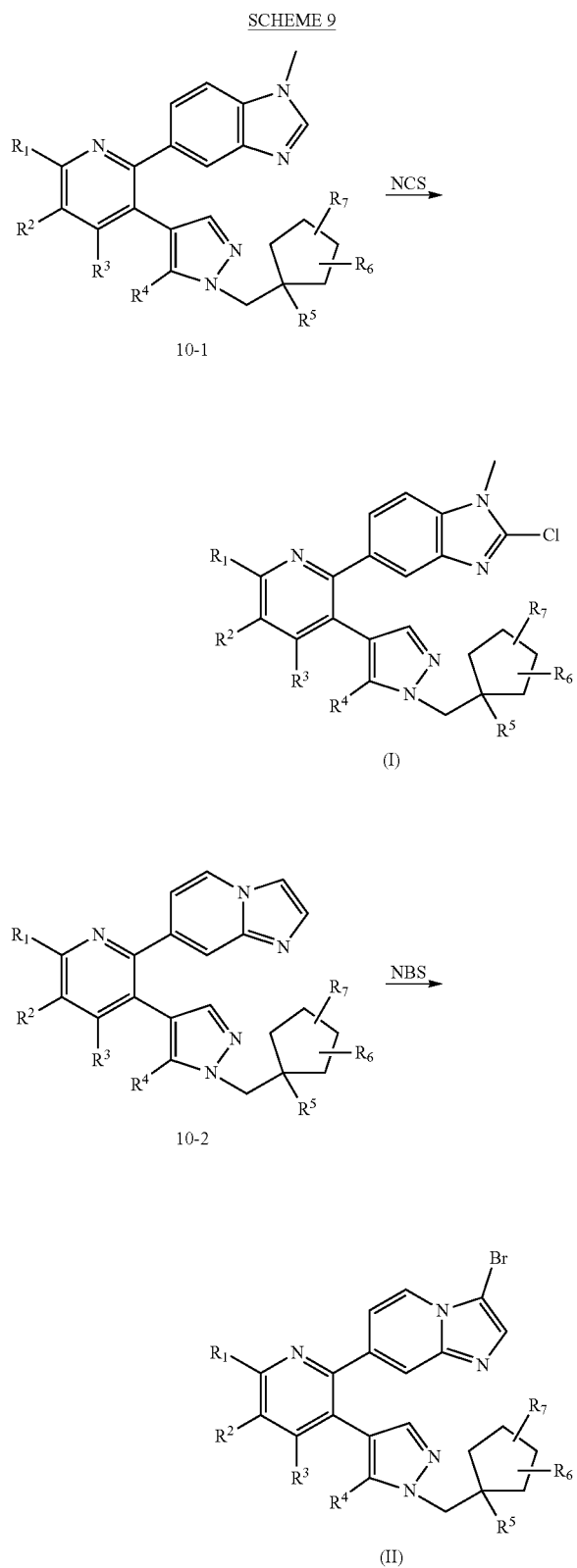

Compounds of formula (I) are prepared according to Scheme 10 by treating benzimidazole 10-1 with NCS. Similarly, compounds of formula (II) are prepared by treating imidazopyridine 10-2 with NBS.

SCHEME 11

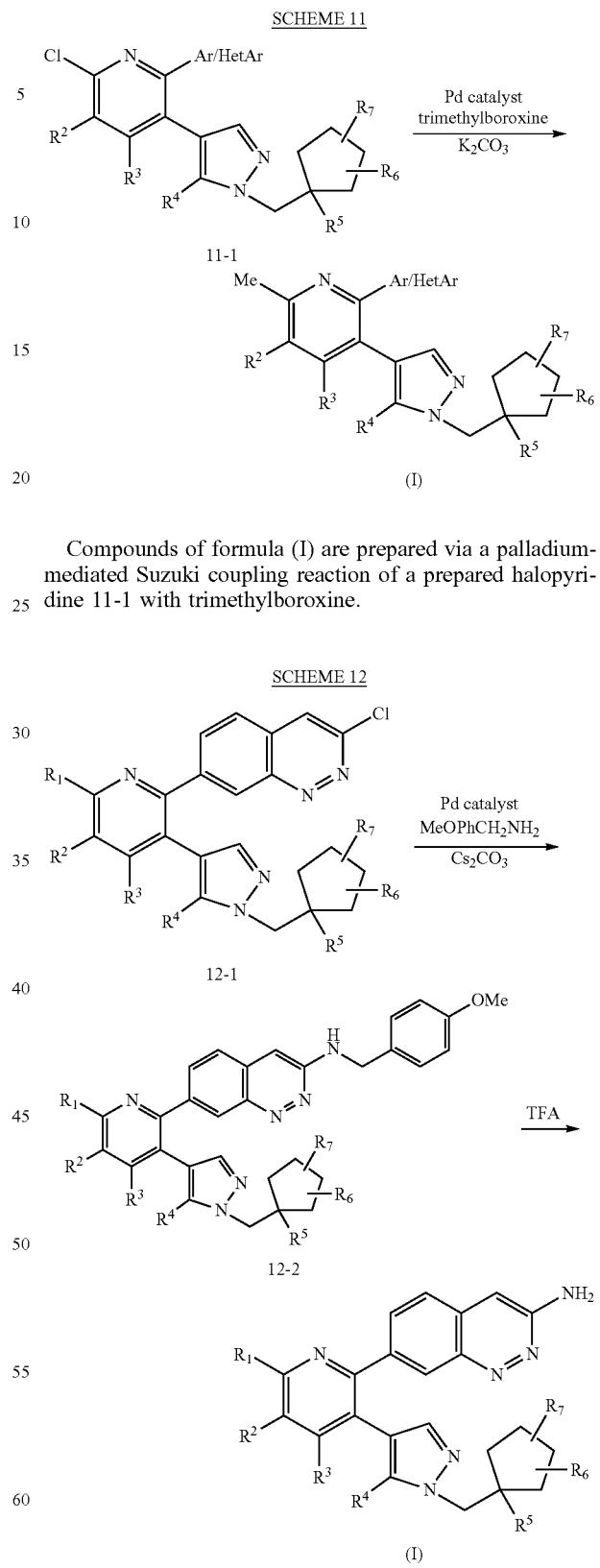

Compounds of formula (I) are prepared via a palladium-mediated Suzuki coupling reaction of a prepared halopyridine 11-1 with trimethylboroxine.

SCHEME 12

Compounds of formula (I) can be prepared by Pd catalyzed C—N coupling of 12-1 and 4-methoxybenzylamine, followed by TFA deprotection.

SCHEME 13

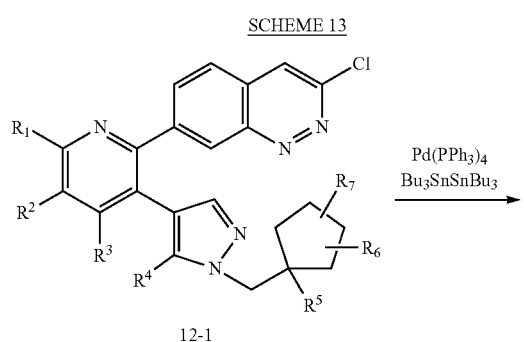

12-1

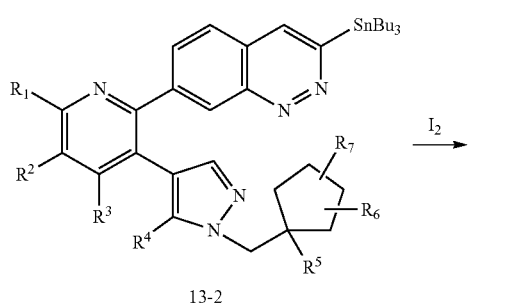

13-2

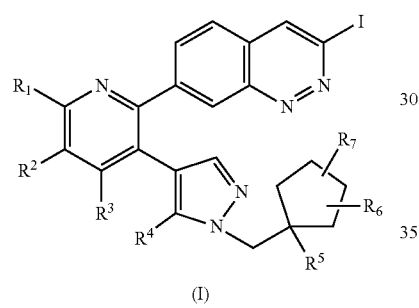

(I)

Compounds of formula (I) can be prepared by stannylation of Intermediate 12-1 followed by iodine displacement of the aromatic stannyl group.

SCHEME 14

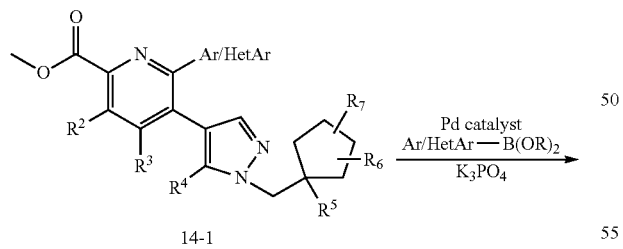

14-1

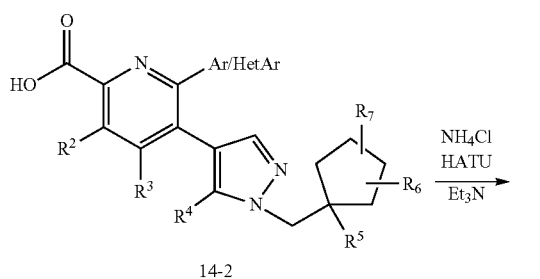

14-2

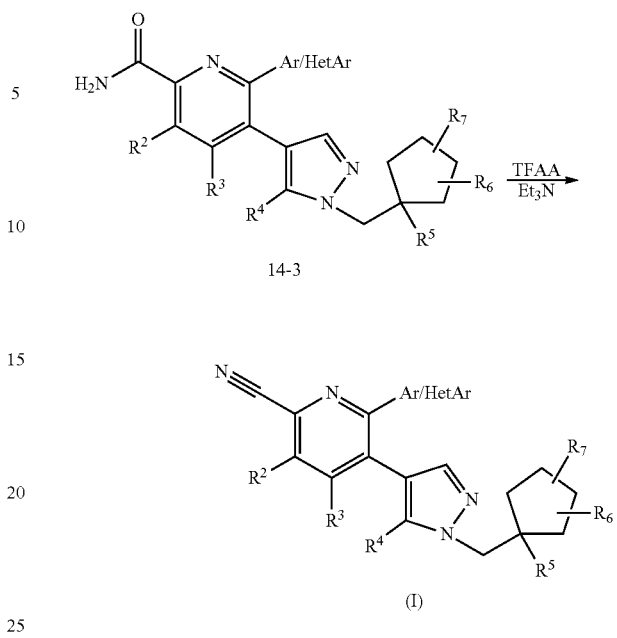

14-3

(I)

An alternative to Schemes 1 and 2 to make compounds of formula (I) where $R_1$=CN starts with Suzuki coupling of the picolinate ester 15-1, resulting in the hydrolyzed product 15-2. Conversion of 15-2 to the primary amide 15-3 followed by dehydration gives (I). Alternatively, one can start with $R_1$=CN as in portions of schemes 1 and 2.

SCHEME 15

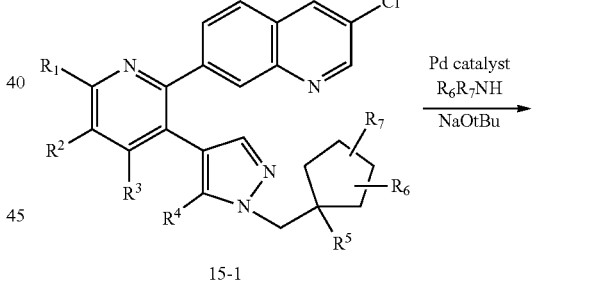

15-1

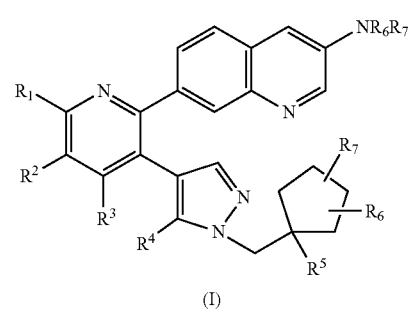

(I)

Compounds of formula (I) can be prepared by Pd catalyzed C—N coupling of intermediate 15-1 with primary and secondary amines in the presence of bases such as sodium t-butoxide.

SCHEME 16

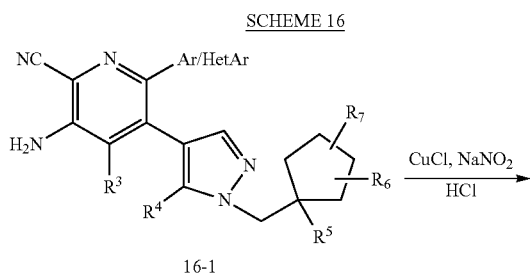

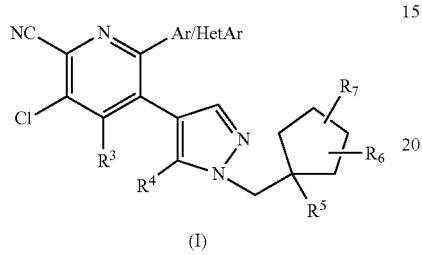

Compounds of formula (I) can be prepared by diazotization/chlorination of aminopyridine 16-1 to give the target compound.

SCHEME 17

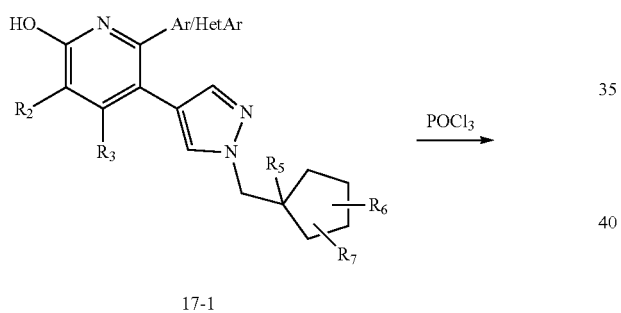

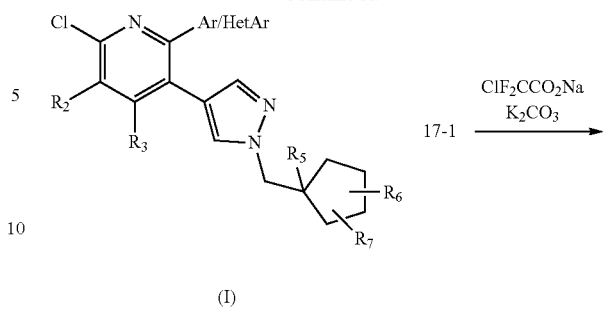

Compounds of formula (I) can be prepared by treating pyridone/pyridinol 18-1 with phosphorous oxychloride. Reaction of the pyridine/pyridinol 17-1 with sodium 2-chloro-2,2-difluoroacetate and potassium carbonate results in compounds of formula (II).

SCHEME 18

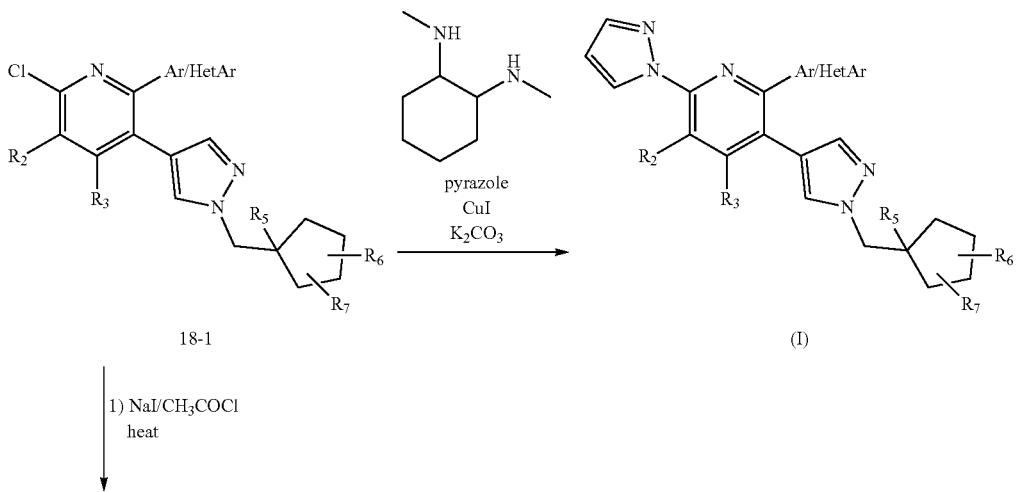

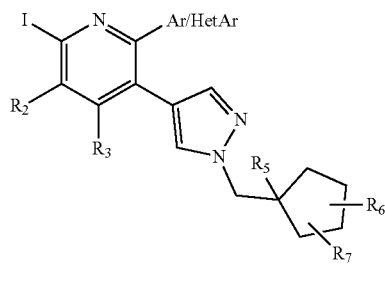 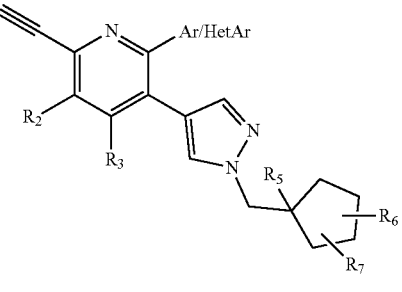

18-2                       (III)

Treatment of the chloropyridine 18-1 and pyrazole with CuI, potassium carbonate and catalytic N,N'-dimethylcyclohexane-1,2-diamine results in the formation of compounds of formula (I). Conversion of 18-1 to iodide 18-2 followed by a Sonogashira reaction with TMS-acetylene and cleavage of the TMS group with mild basic conditions provides compounds of formula (II).

EXAMPLES

Example compounds of the present invention can be synthesized according to the schemes and procedures outlined below. Because the schemes are an illustration, the invention should not be construed as being limited by the chemical reactions and conditions expressed. The preparation of the various starting materials used in the schemes is within the skill of a person versed in the art. Absolute stereochemistry of separate stereoisomers in the examples and intermediates was not determined unless stated otherwise in an example.

Example 1

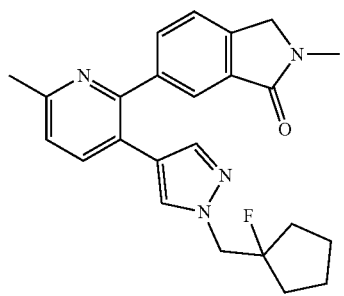

6-(3-(1-((1-fluorocyclopentyl)methyl)-1H-pyrazol-4-yl)-6-methylpyridin-2-yl)-2-methylisoindolin-1-one Potassium acetate (294 mg, 3.00 mmol), bis(pinacolato)diboron (305 mg, 1.200 mmol), 6-bromo-2-methylisoindolin-1-one (271 mg, 1.200 mmol) and 2nd Generation XPHOS precatalyst (59.0 mg, 0.075 mmol) were added to a 8 mL reaction vial equipped with a stir bar. The vial was evacuated and charged 3× with nitrogen. 1,4-Dioxane (8 mL) was added, the vial was again evacuated and charged (3×) with nitrogen, and the borylation reaction was heated to 100° C. Monitored by LCMS; once borylation was complete the reaction was cooled to room temperature and 2-chloro-3-(1-((1-fluorocyclopentyl)methyl)-1H-pyrazol-4-yl)-6-methylpyridine (INTERMEDIATE F7; 294 mg, 1.0 mmol) and 1,1'-bis(di-tert-butylphosphino)ferrocene palladium dichloride (48.9 mg, 0.075 mmol) were added to the reaction. The vial was evacuated and charged 3× with nitrogen, then added 3M aqueous $K_2CO_3$ (1.0 mL, 3.00 mmol). The reaction was then heated to 70° C. overnight. LCMS shows reaction is substantially complete. Cooled to room temperature, then partitioned between water and ethyl acetate. The organic was filtered over a bed of sodium sulfate. The aqueous was extracted twice more with ethyl acetate, and the organic from those extractions was used to wash the sodium sulfate as well. The combined filtrate was evaporated and taken up again in DCM, then purified by silica gel chromatography, eluting with 20-100% 3:1 EtOAc:EtOH in hexanes. The major peak was isolated and the volatiles were evaporated. The solid was scraped to a small particle size and treated with diethyl ether. The suspension was filtered and the solid was collected as the title compound. MS: 405 (M+1). $^1$H NMR (500 MHz, CDCl$_3$): δ 7.89 (s, 1H), 7.67 (d, J=7.5 Hz, 1H), 7.58 (d, J=7.7 Hz, 1H), 7.39 (d, J=7.7 Hz, 1H), 7.21 (s, 1H), 7.18 (d, J=7.8 Hz, 1H), 7.04 (s, 1H), 4.39 (s, 2H), 4.23 (d, J=21.6 Hz, 2H), 3.20 (s, 3H), 2.62 (s, 3H), 1.77-1.58 (m, 8H).

Example 2

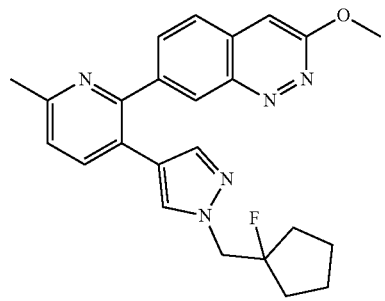

7-(3-(1-((1-fluorocyclopentyl)methyl)-1H-pyrazol-4-yl)-6-methylpyridin-2-yl)-3-methoxycinnoline 2-Chloro-3-(1-((1-fluorocyclopentyl)methyl)-1H-pyrazol-4-yl)-6-methylpyridine (INTERMEDIATE F7; 525 mg, 1.787 mmol), 3-methoxy-7-(4,4,5,5-tetramethyl-1,3,2-dioxaborolan-2-yl)cinnoline (INTERMEDIATE M8; 767 mg, 2.68 mmol) and 1,1'-bis(di-tert-butylphospino)ferrocene palladium dichloride (58.2 mg, 0.089 mmol) were dissolved in degassed potassium phosphate (2M aq) (2.68 mL, 5.36 mmol) and THF (4.5 mL). The resulting solution was degassed again by sparging with N₂ for 5 min and was then heated to 60° C. for 16h. The reaction mixture was diluted with 200 mL ethyl acetate and 100 mL saturated sodium bicarbonate and the layers separated. Washed the organics with 2×50 mL water and 50 mL brine, dried over magnesium sulfate, filter, and concentrated. Diluted with DCM and purified by silica gel chromatography (0-100% ethyl acetate/hexanes). Combined product containing fractions, concentrated and partitioned the remaining crude product between EtOAc (100 mL×3) and sat. sodium bicarbonate (100 mL). Combined organic layers and washed with water (20 mL) and brine (100 mL). Dried over Na₂SO₄, filtered and concentrated to obtain the title compound. MS: 418 (M+1). ¹H NMR (500 MHz, CD₃CN): δ 8.57 (s, 1H), 8.37 (d, J=8.2 Hz, 1H), 7.73 (d, J=8.4 Hz, 1H), 7.56 (dd, J=1.7, 7.8 Hz, 1H), 7.49 (s, 1H), 7.36 (s, 1H), 7.20 (s, 1H), 4.24 (s, 3H), 4.21 (d, J=21.1 Hz, 2H), 2.96 (s, 3H), 1.70-1.45 (m, 8H).

Example 3

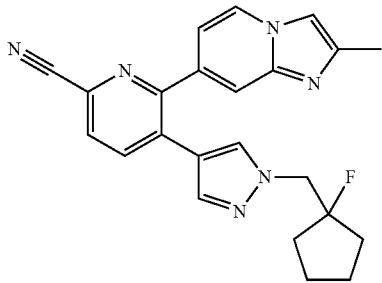 [SMILES: Cc1cn2ccc(-c3nc(C#N)ccc3-c3cnn(CC4(F)CCCC4)c3)cc2n1]

5-(1-((1-fluorocyclopentyl)methyl)-1H-pyrazol-4-yl)-6-(2-methylimidazo[1,2-a]pyridin-7-yl)picolinonitrile (2-Methylimidazo[1,2-a]pyridin-7-yl)boronic acid (INTERMEDIATE M9; 28.9 mg, 0.164 mmol), 6-chloro-5-(1-((1-fluorocyclopentyl)methyl)-1H-pyrazol-4-yl)picolinonitrile (INTERMEDIATE H3; 50 mg, 0.164 mmol), 1,1'-bis(di-tert-butylphosphino)ferrocene palladium dichloride (10.69 mg, 0.016 mmol) and K₂CO₃ (68.0 mg, 0.492 mmol) were added to a reaction vial with dioxane (3 ml) and water (0.5 ml) and it was degassed three times. The reaction was then heated to 90° C. for 5 hours. Diluted the reaction mixture with ethyl acetate and saturated sodium bicarbonate and separated layers. Washed the organics with water and brine, dried over magnesium sulfate, filtered, and concentrated. The crude material was purified by silica gel chromatography, eluting with a gradient of 0-40% of 3:1 ethyl acetate:EtOH in hexanes to give the title compound. MS: 401 (M+1). ¹H NMR (500 MHz, CDCl₃): δ 8.01 (d, J=7.2 Hz, 1H), 7.86 (d, J=7.6 Hz, 1H), 7.66 (d, J=8.4 Hz, 1H), 7.61 (s, 1H), 7.41 (s, 1H), 7.34 (d, J=14.8 Hz, 1H), 6.84 (d, J=4.4 Hz, 1H), 4.28 (d, J=22 Hz, 2H), 2.45 (s, 3H), 1.82-1.50 (m, 8H).

The following compounds were prepared according to the general procedure provided in examples 1-3 and procedures herein using known or prepared pyridyl chlorides or bromides with known or prepared (hetero)aryl boronic esters or acids or (hetero)aryl halides, as described in the reaction schemes and examples herein. The requisite starting materials are either prepared as described in the intermediates section, commercially available, or may be prepared from commercially available reagents using conventional reactions well known in the art without undue experimentation. The reaction can be performed with either 1,1'-bis(diphenylphosphino)ferrocene palladium(II)dichloride dichloromethane complex or 1,1'-bis(di-tert-butylphosphino)ferrocene palladium dichloride under the conditions outlined in Examples 1, 2 and 3 with the reaction temperature ranging from room temperature to 110° C. as appropriate for each substrate. For a tandem borylation/Suzuki reaction as outlined in Example 1, the borylation step can be effected using 2$^{nd}$ generation Xphos Precatalyst or bis(diphenylphosphino)ferrocene palladium(II)dichloride dichloromethane complex in the presence of bispinacolatodiboron and potassium acetate at elevated temperatures or other suitable borylation strategies as found in the literature.

TABLE 1

| Example | Structure | Name | MS (M + 1) |
|---|---|---|---|
| 4 | 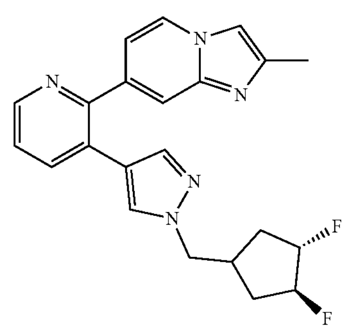 [SMILES: Cc1cn2ccc(-c3ncccc3-c3cnn(CC4C[C@H](F)[C@@H](F)C4)c3)cc2n1] | 7-(3-(1-(((3S,4S)-3,4-difluorocyclopentyl)methyl)-1H-pyrazol-4-yl)pyridin-2-yl)-2-methylimidazo[1,2-a]pyridine | 394 |

TABLE 1-continued

| Example | Structure | Name | MS (M + 1) |
|---|---|---|---|
| 5 | 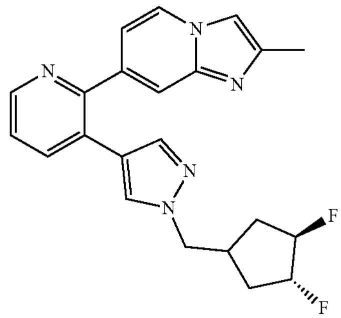 [SMILES: Cc1cn2ccc(-c3ncccc3-c3cnn(CC4C[C@@H](F)[C@H](F)C4)c3)cc2n1] | 7-(3-(1-(((3R,4R)-3,4-difluorocyclopentyl)methyl)-1H-pyrazol-4-yl)pyridin-2-yl)-2-methylimidazo[1,2-a]pyridine | 394 |
| 6 | 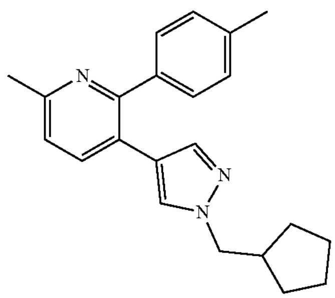 [SMILES: Cc1ccc(-c2nc(C)ccc2-c2cnn(CC3CCCC3)c2)cc1] | 3-(1-(cyclopentylmethyl)-1H-pyrazol-4-yl)-6-methyl-2-(p-tolyl)pyridine | 331 |
| 7 | 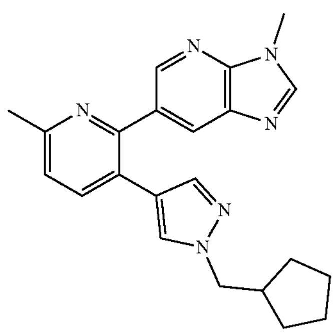 [SMILES: Cc1ccc(-c2cnn(CC3CCCC3)c2)c(-c2cnc3c(c2)ncn3C)n1] | 6-(3-(1-(cyclopentylmethyl)-1H-pyrazol-4-yl)-6-methylpyridin-2-yl)-3-methyl-3H-imidazo[4,5-b]pyridine | 373 |
| 8 | 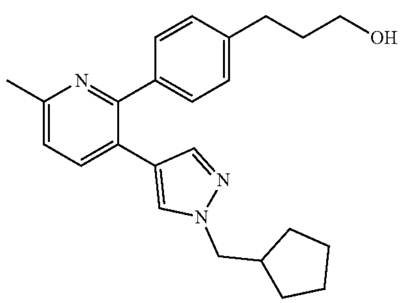 [SMILES: Cc1ccc(-c2cnn(CC3CCCC3)c2)c(-c2ccc(CCCO)cc2)n1] | 3-(4-(3-(1-(cyclopentylmethyl)-1H-pyrazol-4-yl)-6-methylpyridin-2-yl)phenyl)propan-1-ol | NMR* |
| 9 | 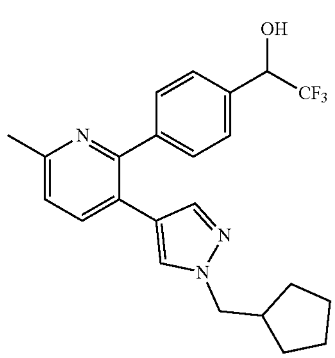 [SMILES: Cc1ccc(-c2cnn(CC3CCCC3)c2)c(-c2ccc(C(O)C(F)(F)F)cc2)n1] | 1-(4-(3-(1-(cyclopentylmethyl)-1H-pyrazol-4-yl)-6-methylpyridin-2-yl)phenyl)-2,2,2-trifluoroethan-1-ol | NMR** |

TABLE 1-continued

| Example | Structure | Name | MS (M + 1) |
|---|---|---|---|
| 10 | 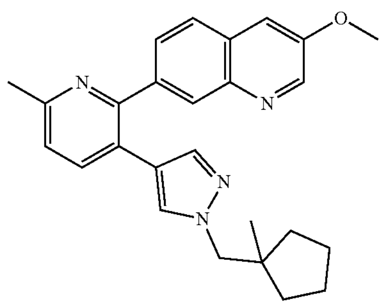 | 3-methoxy-7-(6-methyl-3-(1-((1-methylcyclopentyl)methyl)-1H-pyrazol-4-yl)pyridin-2-yl)quinoline | 399 |
| 11 | 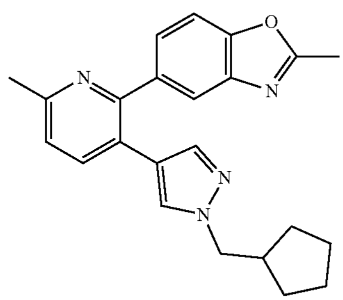 | 5-(3-(1-(cyclopentylmethyl)-1H-pyrazol-4-yl)-6-methylpyridin-2-yl)-2-methylbenzo[d]oxazole | 373 |
| 12 | 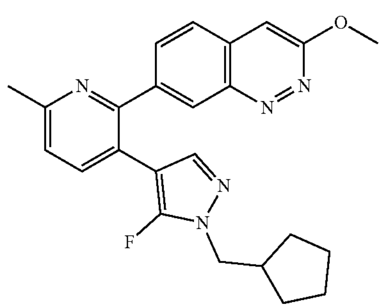 | 7-(3-(1-(cyclopentylmethyl)-5-fluoro-1H-pyrazol-4-yl)-6-methylpyridin-2-yl)-3-methoxycinnoline | 418 |
| 13 | 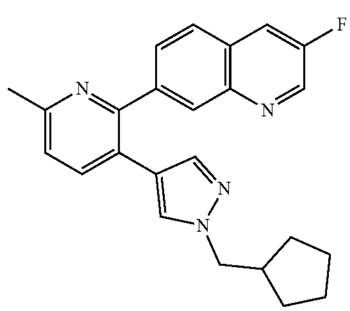 [SMILES: Cc1ccc(-c2cnn(CC3CCCC3)c2)c(-c2ccc3cc(F)cnc3c2)n1] | 7-(3-(1-(cyclopentylmethyl)-1H-pyrazol-4-yl)-6-methylpyridin-2-yl)-3-fluoroquinoline | 387 |
| 14 | 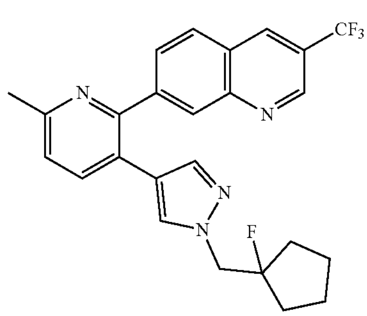 [SMILES: Cc1ccc(-c2cnn(CC3(F)CCCC3)c2)c(-c2ccc3cc(C(F)(F)F)cnc3c2)n1] | 7-(3-(1-((1-fluorocyclopentyl)methyl)-1H-pyrazol-4-yl)-6-methylpyridin-2-yl)-3-(trifluoromethyl)quinoline | 454 |

TABLE 1-continued

| Example | Structure | Name | MS (M + 1) |
|---|---|---|---|
| 15 | 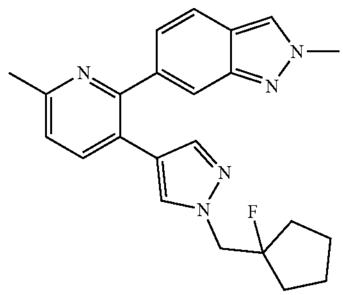 | 5-(3-(1-((1-fluorocyclopentyl)methyl)-1H-pyrazol-4-yl)-6-methylpyridin-2-yl)-1-methyl-1H-benzo[d]imidazole | 389 |
| 16 | 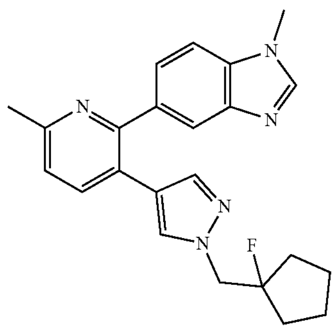 [SMILES: Cc1ccc(-c2cnn(CC3(F)CCCC3)c2)c(-c2ccc3c(c2)ncn3C)n1] | 5-(3-(1-((1-fluorocyclopentyl)methyl)-1H-pyrazol-4-yl)-6-methylpyridin-2-yl)-1-methyl-1H-benzo[d]imidazole | 389 |
| 17 | 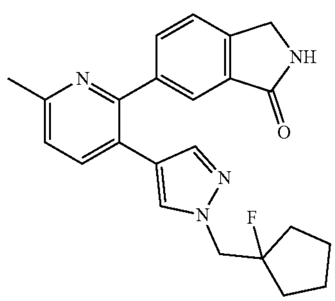 [SMILES: Cc1ccc(-c2cnn(CC3(F)CCCC3)c2)c(-c2ccc3c(c2)C(=O)NC3)n1] | 6-(3-(1-((1-fluorocyclopentyl)methyl)-1H-pyrazol-4-yl)-6-methylpyridin-2-yl)isoindolin-1-one | 391 |
| 18 | 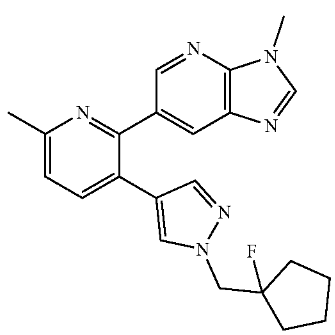 [SMILES: Cc1ccc(-c2cnn(CC3(F)CCCC3)c2)c(-c2cnc3c(c2)ncn3C)n1] | 6-(3-(1-((1-fluorocyclopentyl)methyl)-1H-pyrazol-4-yl)-6-methylpyridin-2-yl)-3-methyl-3H-imidazo[4,5-b]pyridine | 391 |
| 19 | 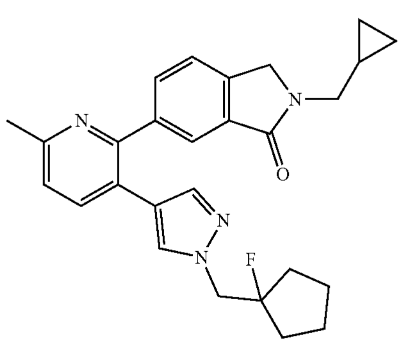 [SMILES: Cc1ccc(-c2cnn(CC3(F)CCCC3)c2)c(-c2ccc3c(c2)C(=O)N(CC2CC2)C3)n1] | 2-(cyclopropylmethyl)-6-(3-(1-((1-fluorocyclopentyl)methyl)-1H-pyrazol-4-yl)-6-methylpyridin-2-yl)isoindolin-1-one | 445 |

TABLE 1-continued

| Example | Structure | Name | MS (M + 1) |
|---|---|---|---|
| 20 | 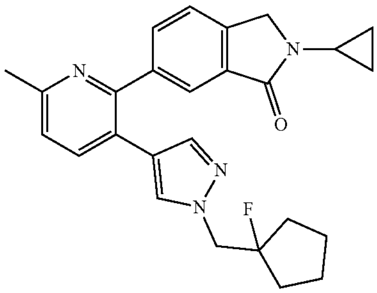 [SMILES: Cc1ccc(-c2cnn(CC3(F)CCCC3)c2)c(-c2ccc3c(c2)C(=O)N(C2CC2)C3)n1] | 2-cyclopropyl-6-(3-(1-((1-fluorocyclopentyl)methyl)-1H-pyrazol-4-yl)-6-methylpyridin-2-yl)isoindolin-1-one | 431 |
| 21 | 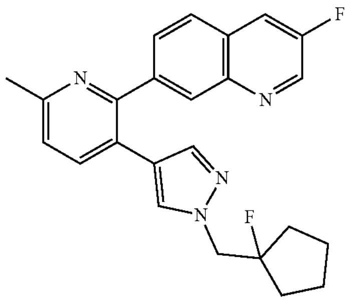 [SMILES: Cc1ccc(-c2cnn(CC3(F)CCCC3)c2)c(-c2ccc3cc(F)cnc3c2)n1] | 3-fluoro-7-(3-(1-((1-fluorocyclopentyl)methyl)-1H-pyrazol-4-yl)-6-methylpyridin-2-yl)quinoline | 405 |
| 22 | 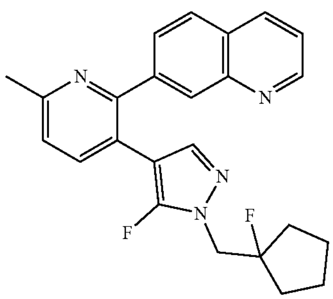 [SMILES: Cc1ccc(-c2cnn(CC3(F)CCCC3)c2F)c(-c2ccc3cccnc3c2)n1] | 7-(3-(5-fluoro-1-((1-fluorocyclopentyl)methyl)-1H-pyrazol-4-yl)-6-methylpyridin-2-yl)quinoline | 405 |
| 23 | 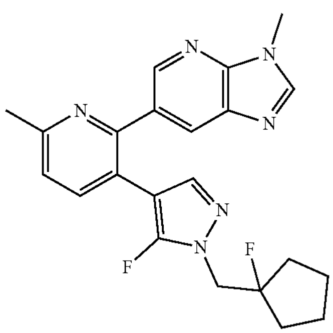 [SMILES: Cc1ccc(-c2cnn(CC3(F)CCCC3)c2F)c(-c2cnc3c(c2)ncn3C)n1] | 6-(3-(5-fluoro-1-((1-fluorocyclopentyl)methyl)-1H-pyrazol-4-yl)-6-methylpyridin-2-yl)-3-methyl-3H-imidazo[4,5-b]pyridine | 409 |
| 24 | 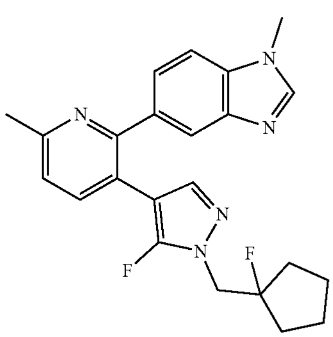 [SMILES: Cc1ccc(-c2cnn(CC3(F)CCCC3)c2F)c(-c2ccc3c(c2)ncn3C)n1] | 5-(3-(5-fluoro-1-((1-fluorocyclopentyl)methyl)-1H-pyrazol-2-yl)-1-methylpyridin-2-yl)-1-methyl-1H-benzo[d]imidazole | 408 |

TABLE 1-continued

| Example | Structure | Name | MS (M + 1) |
|---|---|---|---|
| 25 | 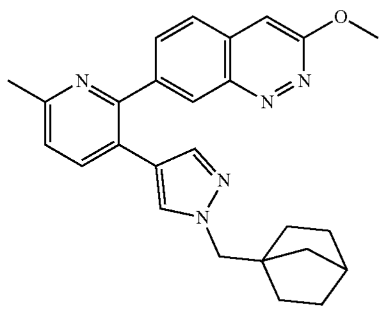 | 7-(3-(1-(bicyclo[2.2.1]heptan-1-ylmethyl)-1H-pyrazol-4-yl)-6-methylpyridin-2-yl)-3-methoxycinnoline | 426 |
| 26 | 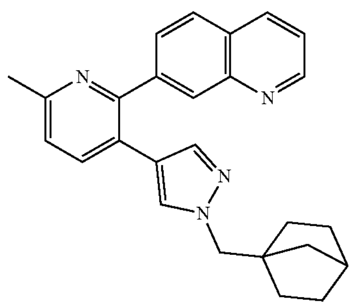 [SMILES: Cc1ccc(-c2cnn(CC34CCC(CC3)C4)c2)c(-c2ccc3cccnc3c2)n1] | 7-(3-(1-(bicyclo[2.2.1]heptan-1-ylmethyl)-1H-pyrazol-4-yl)-6-methylpyridin-2-yl)quinoline | 395 |
| 27 | 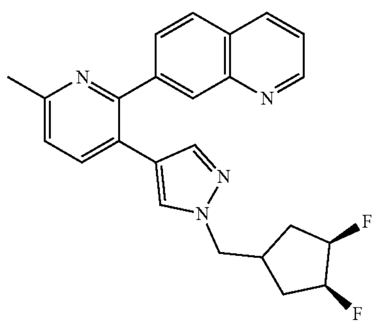 [SMILES: Cc1ccc(-c2cnn(CC3C[C@@H](F)[C@@H](F)C3)c2)c(-c2ccc3cccnc3c2)n1] | 7-(3-(1-(((3R,4S and 3S,4R)-3,4-difluorocyclopentyl)methyl)-1H-pyrazol-4-yl)-6-methylpyridin-2-yl)quinoline (+/−) | 405 |
| 28 | 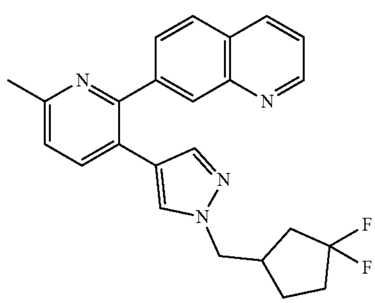 [SMILES: Cc1ccc(-c2cnn(CC3CCC(F)(F)C3)c2)c(-c2ccc3cccnc3c2)n1] | 7-(3-(1-((3,3-difluorocyclopentyl)methyl)-1H-pyrazol-4-yl)-6-methylpyridin-2-yl)quinoline | 405 |
| 29 | 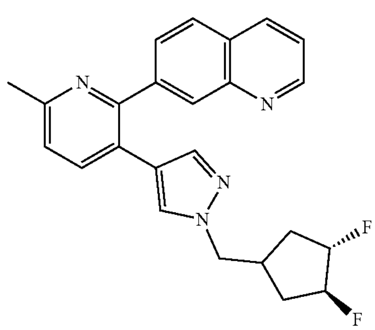 [SMILES: Cc1ccc(-c2cnn(CC3C[C@H](F)[C@@H](F)C3)c2)c(-c2ccc3cccnc3c2)n1] | 7-(3-(1-(((3S,4S and 3R,4R)-3,4-difluorocyclopentyl)methyl)-1H-pyrazol-4-yl)-6-methylpyridin-2-yl)quinoline | 405 |

TABLE 1-continued

| Example | Structure | Name | MS (M + 1) |
|---|---|---|---|
| 30 | 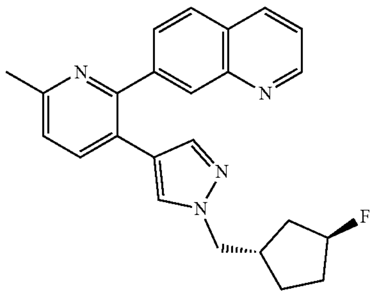 [SMILES: Cc1ccc(-c2cnn(C[C@H]3CC[C@H](F)C3)c2)c(-c2ccc3cccnc3c2)n1] | 7-(3-(1-(((1S,3S and 1R,3R)-3-fluorocyclopentyl)methyl)-1H-pyrazol-4-yl)-6-methylpyridin-2-yl)quinoline | 387 |
| 31 | 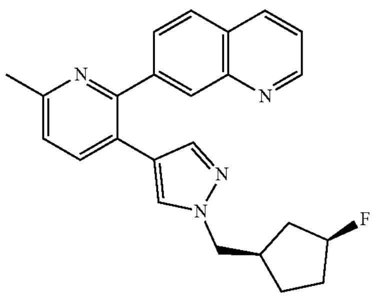 [SMILES: Cc1ccc(-c2cnn(C[C@@H]3CC[C@H](F)C3)c2)c(-c2ccc3cccnc3c2)n1] | 7-(3-(1-(((1R,3S and 1S,3R)-3-fluorocyclopentyl)methyl)-1H-pyrazol-4-yl)-6-methylpyridin-2-yl)quinoline | 387 |
| 32 | 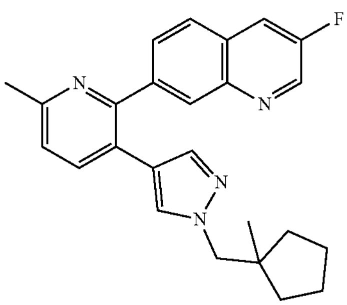 [SMILES: Cc1ccc(-c2cnn(CC3(C)CCCC3)c2)c(-c2ccc3cc(F)cnc3c2)n1] | 3-fluoro-7-(6-methyl-3-(1-((1-methylcyclopentyl)methyl)-1H-pyrazol-4-yl)pyridin-2-yl)quinoline | 401 |
| 33 | 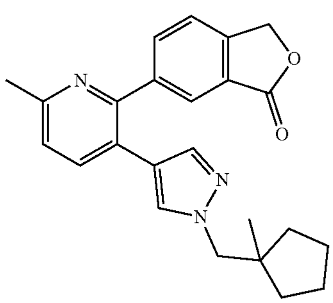 [SMILES: Cc1ccc(-c2cnn(CC3(C)CCCC3)c2)c(-c2ccc3c(c2)C(=O)OC3)n1] | 6-(6-methyl-3-(1-((1-methylcyclopentyl)methyl)-1H-pyrazol-4-yl)pyridin-2-yl)isobenzofuran-1(3H)-one | 388 |
| 34 | 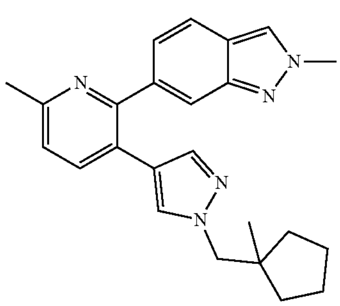 | 2-methyl-6-(6-methyl-3-(1-((1-methylcyclopentyl)methyl)-1H-pyrazol-4-yl)pyridin-2-yl)-2H-indazole | 386 |

TABLE 1-continued

| Example | Name | MS (M + 1) |
|---|---|---|
| 35 | 2-methyl-7-(6-methyl-3-(1-((1-methylcyclopentyl)methyl)-1H-pyrazol-4-yl)pyridin-2-yl)isoquinolin-1(2H)-one | 413 |
| 36 | 7-(3-(1-(cyclopentylfluoromethyl)-5-fluoro-1H-pyrazol-4-yl)-6-methylpyridin-2-yl)-3-methoxycinnoline | 436 |
| 37 | 7-(3-(1-((6,6-difluorobicyclo[3.1.0]hexan-3-yl)methyl)-1H-pyrazol-4-yl)-6-methylpyridin-2-yl)-3-methoxycinnoline | 448 |
| 38 | 5-(1-(cyclopentylmethyl)-1H-pyrazol-4-yl)-6-(pyrazolo[1,5-a]pyridin-6-yl)picolinonitrile | 369 |
| 39 | 5-(1-(cyclopentylmethyl)-1H-pyrazol-4-yl)-6-(2-methyl-1-oxo-1,2-dihydroisoquinolin-7-yl)picolinonitrile | 410 |

TABLE 1-continued

| Example | Structure | Name | MS (M + 1) |
|---|---|---|---|
| 40 | 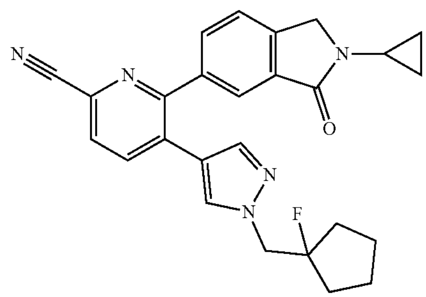 [SMILES: N#Cc1ccc(-c2cnn(CC3(F)CCCC3)c2)c(-c2ccc3c(c2)C(=O)N(C2CC2)C3)n1] | 6-(2-cyclopropyl-3-oxoisoindolin-5-yl)-5-(1-((1-fluorocyclopentyl)methyl)-1H-pyrazol-4-yl)picolinonitrile | 442 |
| 41 | 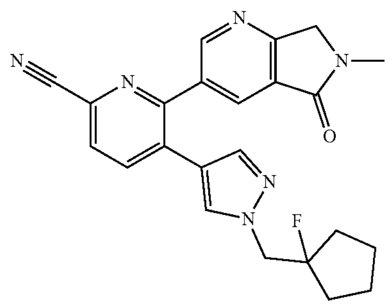 [SMILES: CN1Cc2ncc(-c3nc(C#N)ccc3-c3cnn(CC4(F)CCCC4)c3)cc2C1=O] | 5-(1-((1-fluorocyclopentyl)methyl)-1H-pyrazol-4-yl)-6-(6-methyl-5-oxo-6,7-dihydro-5H-pyrrolo[3,4-b]pyridin-3-yl)picolinonitrile | 417 |
| 42 | 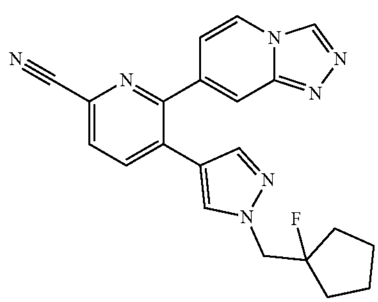 [SMILES: N#Cc1ccc(-c2cnn(CC3(F)CCCC3)c2)c(-c2ccn3cnnc3c2)n1] | 6-([1,2,4]triazolo[4,3-a]pyridin-7-yl)-5-(1-((1-fluorocyclopentyl)methyl)-1H-pyrazol-4-yl)picolinonitrile | 388 |
| 43 | 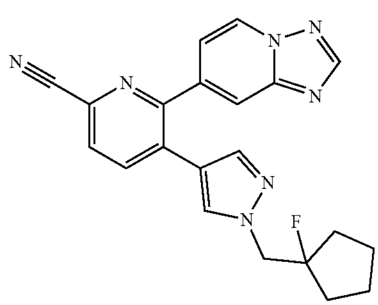 [SMILES: N#Cc1ccc(-c2cnn(CC3(F)CCCC3)c2)c(-c2ccn3ncnc3c2)n1] | 6-([1,2,4]triazolo[1,5-a]pyridin-7-yl)-5-(1-((1-fluorocyclopentyl)methyl)-1H-pyrazol-4-yl)picolinonitrile | 388 |
| 44 | 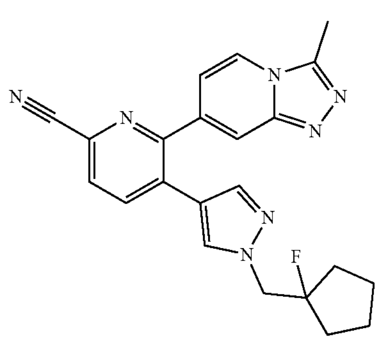 [SMILES: Cc1nnc2cc(-c3nc(C#N)ccc3-c3cnn(CC4(F)CCCC4)c3)ccn12] | 5-(1-((1-fluorocyclopentyl)methyl)-1H-pyrazol-4-yl)-6-(3-methyl-[1,2,4]triazolo[4,3-a]pyridin-7-yl)picolinonitrile | 402 |

TABLE 1-continued

| Example | Structure | Name | MS (M + 1) |
|---|---|---|---|
| 45 | 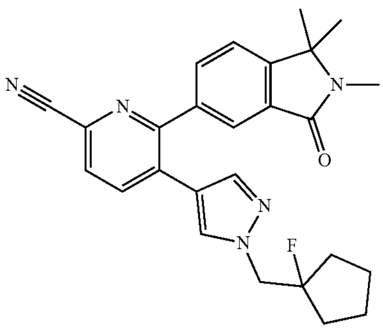 [SMILES: CN1C(=O)c2cc(-c3nc(C#N)ccc3-c3cnn(CC4(F)CCCC4)c3)ccc2C1(C)C] | 5-(1-((1-fluorocyclopentyl)methyl)-1H-pyrazol-4-yl)-6-(1,1,2-trimethyl-3-oxoisoindolin-5-yl)picolinonitrile | 444 |
| 46 | 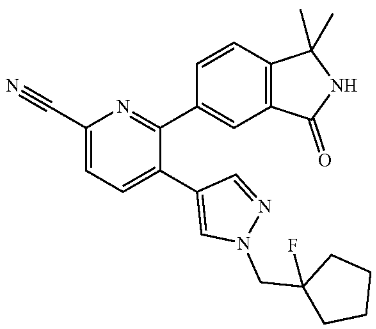 [SMILES: CC1(C)NC(=O)c2cc(-c3nc(C#N)ccc3-c3cnn(CC4(F)CCCC4)c3)ccc21] | 6-(1,1-dimethyl-3-oxoisoindolin-5-yl)-5-(1-((1-fluorocyclopentyl)methyl)-1H-pyrazol-4-yl)picolinonitrile49 | 430 |
| 47 | 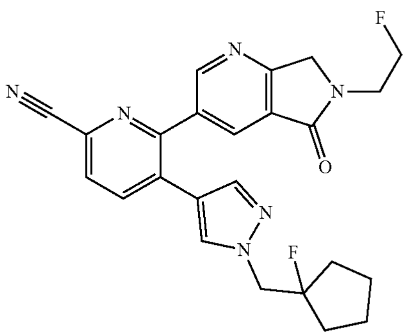 [SMILES: N#Cc1ccc(-c2cnn(CC3(F)CCCC3)c2)c(-c2cnc3c(c2)C(=O)N(CCF)C3)n1] | 5-(1-((1-fluorocyclopentyl)methyl)-1H-pyrazol-4-yl)-6-(6-(2-fluoroethyl)-5-oxo-6,7-dihydro-5H-pyrrolo[3,4-b]pyridin-3-yl)picolinonitrile | 449 |
| 48 | 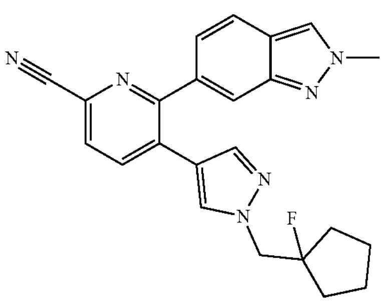 [SMILES: Cn1cc2ccc(-c3nc(C#N)ccc3-c3cnn(CC4(F)CCCC4)c3)cc2n1] | 5-(1-((1-fluorocyclopentyl)methyl)-1H-pyrazol-4-yl)-6-(2-methyl-2H-indazol-6-yl)picolinonitrile | 401 |
| 49 | 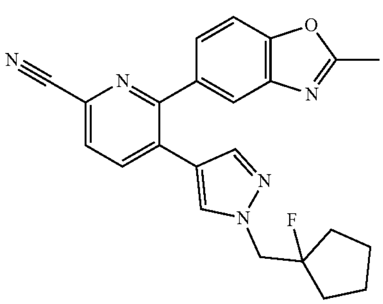 [SMILES: Cc1nc2cc(-c3nc(C#N)ccc3-c3cnn(CC4(F)CCCC4)c3)ccc2o1] | 5-(1-((1-fluorocyclopentyl)methyl)-1H-pyrazol-4-yl)-6-(2-methylbenzo[d]oxazol-5-yl)picolinonitrile | 402 |

TABLE 1-continued

| Example | Structure | Name | MS (M + 1) |
|---|---|---|---|
| 50 | 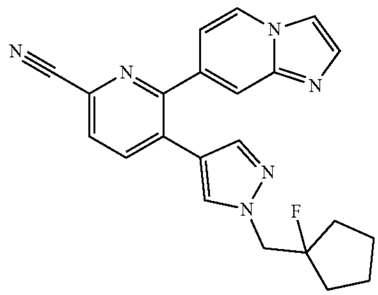 [SMILES: N#Cc1ccc(-c2cnn(CC3(F)CCCC3)c2)c(-c2ccn3ccnc3c2)n1] | 5-(1-((1-fluorocyclopentyl)methyl)-1H-pyrazol-4-yl)-6-(imidazo[1,2-a]pyridin-7-yl)picolinonitrile | 387 |
| 51 | 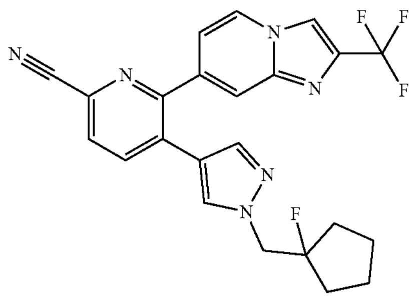 [SMILES: N#Cc1ccc(-c2cnn(CC3(F)CCCC3)c2)c(-c2ccn3cc(C(F)(F)F)nc3c2)n1] | 5-(1-((1-fluorocyclopentyl)methyl)-1H-pyrazol-4-yl)-6-(2-(trifluoromethyl)imidazo[1,2-a]pyridin-7-yl)picolinonitrile | 455 |
| 52 | 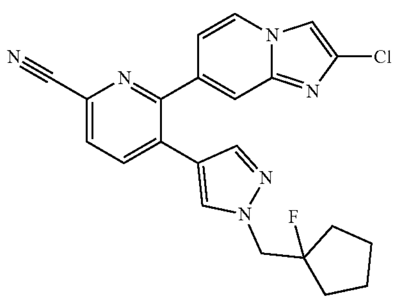 [SMILES: N#Cc1ccc(-c2cnn(CC3(F)CCCC3)c2)c(-c2ccn3cc(Cl)nc3c2)n1] | 6-(2-chloroimidazo[1,2-a]pyridin-7-yl)-5-(1-((1-fluorocyclopentyl)methyl)-1H-pyrazol-4-yl)picolinonitrile | 421 |
| 53 | 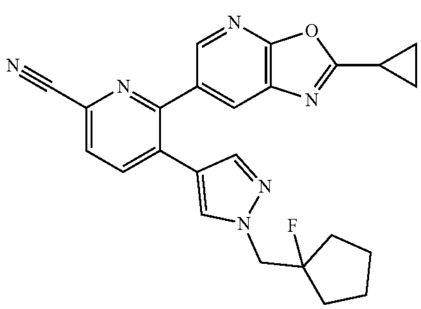 [SMILES: N#Cc1ccc(-c2cnn(CC3(F)CCCC3)c2)c(-c2cnc3oc(C4CC4)nc3c2)n1] | 6-(2-cyclopropyloxazolo[5,4-b]pyridin-6-yl)-5-(1-((1-fluorocyclopentyl)methyl)-1H-pyrazol-4-yl)picolinonitrile | 429 |
| 54 | 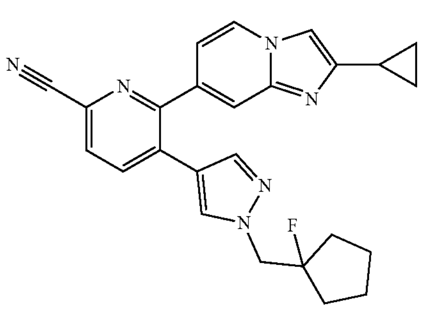 [SMILES: N#Cc1ccc(-c2cnn(CC3(F)CCCC3)c2)c(-c2ccn3cc(C4CC4)nc3c2)n1] | 6-(2-cyclopropylimidazo[1,2-a]pyridin-7-yl)-5-(1-((1-fluorocyclopentyl)methyl)-1H-pyrazol-4-yl)picolinonitrile | 427 |

TABLE 1-continued

| Example | Structure | Name | MS (M + 1) |
|---|---|---|---|
| 55 | 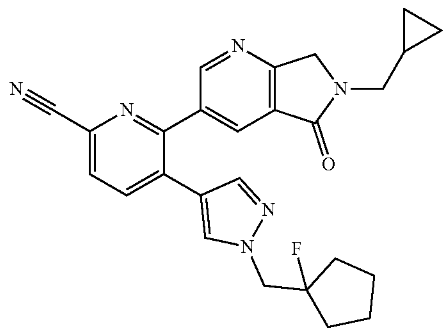 [SMILES: N#Cc1ccc(-c2cnn(CC3(F)CCCC3)c2)c(-c2cnc3c(c2)C(=O)N(CC2CC2)C3)n1] | 6-(6-(cyclopropylmethyl)-5-oxo-6,7-dihydro-5H-pyrrolo[3,4-b]pyridin-3-yl)-5-(1-((1-fluorocyclopentyl)methyl)-1H-pyrazol-4-yl)picolinonitrile | 457 |
| 56 | 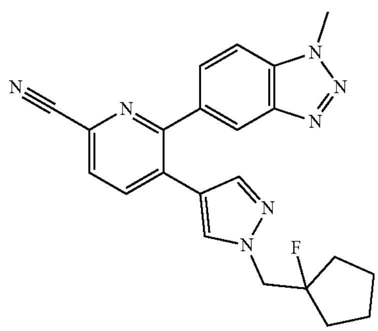 [SMILES: Cn1nnc2cc(-c3nc(C#N)ccc3-c3cnn(CC4(F)CCCC4)c3)ccc21] | 5-(1-((1-fluorocyclopentyl)methyl)-1H-pyrazol-4-yl)-6-(1-methyl-1H-benzo[1,2,3]triazol-5-yl)picolinonitrile | 402 |
| 57 | 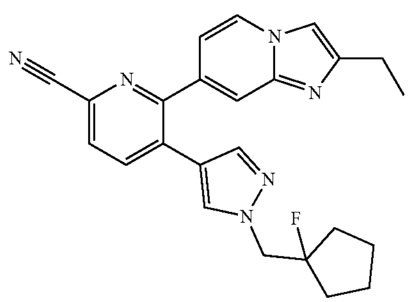 [SMILES: CCc1cn2ccc(-c3nc(C#N)ccc3-c3cnn(CC4(F)CCCC4)c3)cc2n1] | 6-(2-ethylimidazo[1,2-a]pyridin-7-yl)-5-(1-((1-fluorocyclopentyl)methyl)-1H-pyrazol-4-yl)picolinonitrile | 415 |
| 58 | 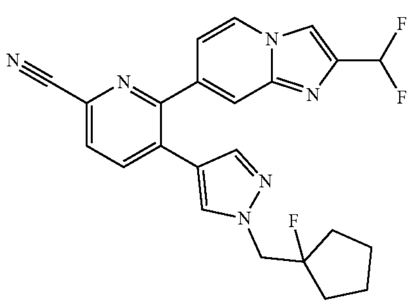 [SMILES: N#Cc1ccc(-c2cnn(CC3(F)CCCC3)c2)c(-c2ccn3cc(C(F)F)nc3c2)n1] | 6-(2-(difluoromethyl)imidazo[1,2-a]pyridin-7-yl)-5-(1-((1-fluorocyclopentyl)methyl)-1H-pyrazol-4-yl)picolinonitrile | 437 |
| 59 | 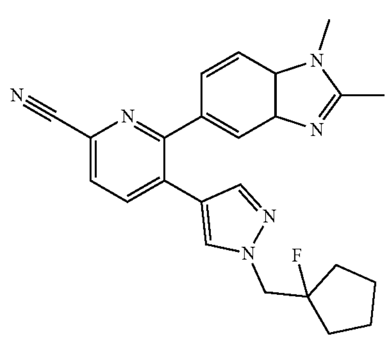 [SMILES: CC1=NC2C=C(c3nc(C#N)ccc3-c3cnn(CC4(F)CCCC4)c3)C=CC2N1C] | 6-(1,2-dimethyl-1H-benzo[d]imidazol-5-yl)-5-(1-((1-fluorocyclopentyl)methyl)-1H-pyrazol-4-yl)picolinonitrile | 415 |

TABLE 1-continued

| Example | Structure | Name | MS (M + 1) |
|---|---|---|---|
| 60 | 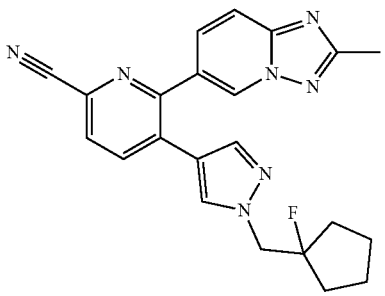 [SMILES: Cc1nc2ccc(-c3nc(C#N)ccc3-c3cnn(CC4(F)CCCC4)c3)cn2n1] | 5-(1-((1-fluorocyclopentyl)methyl)-1H-pyrazol-4-yl)-6-(2-methyl-[1,2,4]triazolo[1,5-a]pyridin-6-yl)picolinonitrile | 402 |
| 61 | 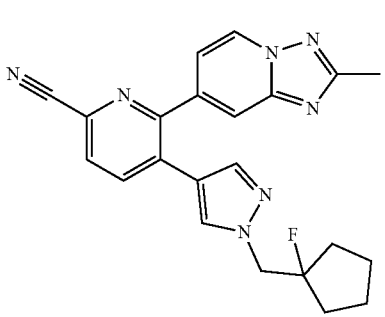 [SMILES: Cc1nc2cc(-c3nc(C#N)ccc3-c3cnn(CC4(F)CCCC4)c3)ccn2n1] | 5-(1-((1-fluorocyclopentyl)methyl)-1H-pyrazol-4-yl)-6-(2-methyl-[1,2,4]triazolo[1,5-a]pyridin-7-yl)picolinonitrile | 402 |
| 62 | 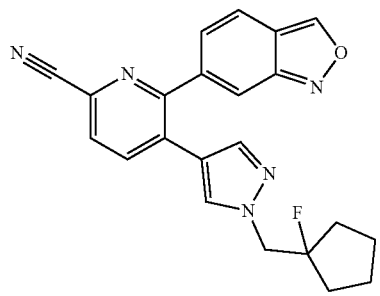 [SMILES: N#Cc1ccc(-c2cnn(CC3(F)CCCC3)c2)c(-c2ccc3conc3c2)n1] | 6-(benzo[c]isoxazol-6-yl)-5-(1-((1-fluorocyclopentyl)methyl)-1H-pyrazol-4-yl)picolinonitrile | 388 |
| 63 | 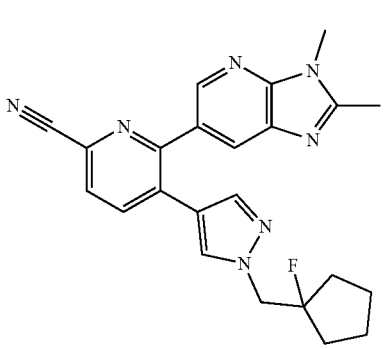 [SMILES: Cc1nc2cc(-c3nc(C#N)ccc3-c3cnn(CC4(F)CCCC4)c3)cnc2n1C] | 6-(2,3-dimethyl-3H-imidazo[4,5-b]pyridin-6-yl)-5-(1-((1-fluorocyclopentyl)methyl)-1H-pyrazol-4-yl)picolinonitrile | 416 |
| 64 | 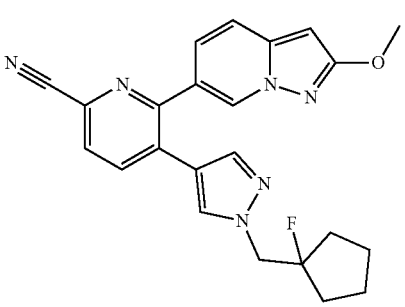 [SMILES: COc1cc2ccc(-c3nc(C#N)ccc3-c3cnn(CC4(F)CCCC4)c3)cn2n1] | 5-(1-((1-fluorocyclopentyl)methyl)-1H-pyrazol-4-yl)-6-(2-methoxypyrazolo[1,5-a]pyridin-6-yl)picolinonitrile | 417 |

TABLE 1-continued

| Example | Structure | Name | MS (M + 1) |
|---|---|---|---|
| 65 | 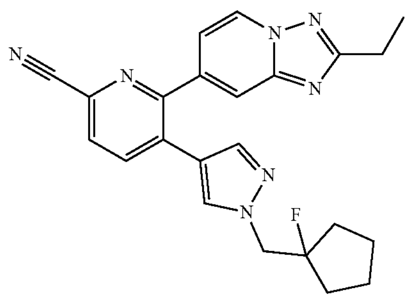 [SMILES: CCc1nc2cc(-c3nc(C#N)ccc3-c3cnn(CC4(F)CCCC4)c3)ccn2n1] | 6-(2-ethyl-[1,2,4]triazolo[1,5-a]pyridin-7-yl)-5-(1-((1-fluorocyclopentyl)methyl)-1H-pyrazol-4-yl)picolinonitrile | 416 |
| 66 | 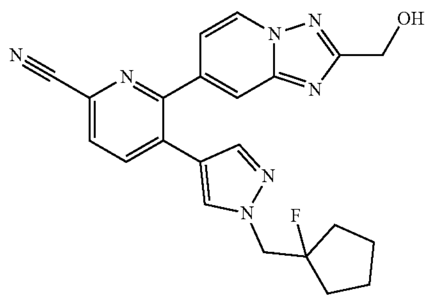 [SMILES: N#Cc1ccc(-c2cnn(CC3(F)CCCC3)c2)c(-c2ccn3nc(CO)nc3c2)n1] | 5-(1-((1-fluorocyclopentyl)methyl)-1H-pyrazol-4-yl)-6-(2-(hydroxymethyl)-[1,2,4]triazolo[1,5-a]pyridin-7-yl)picolinonitrile | 418 |
| 67 | 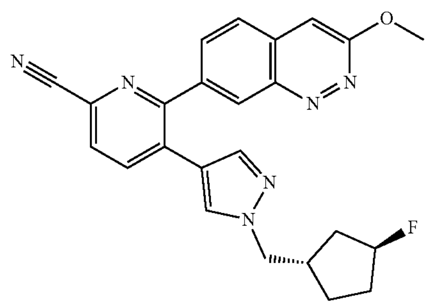 [SMILES: COc1cc2ccc(-c3nc(C#N)ccc3-c3cnn(C[C@H]4CC[C@H](F)C4)c3)cc2nn1] | 5-(1-(((1S,3S)-3-fluorocyclopentyl)methyl)-1H-pyrazol-4-yl)-6-(3-methoxycinnolin-7-yl)picolinonitrile | 429 |
| 68 | 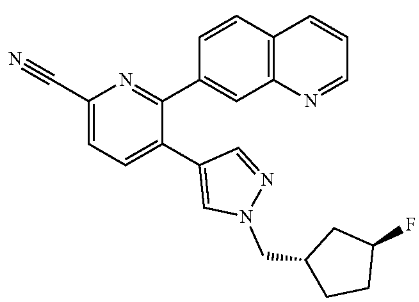 [SMILES: N#Cc1ccc(-c2cnn(C[C@H]3CC[C@H](F)C3)c2)c(-c2ccc3cccnc3c2)n1] | 5-(1-(((1S,3S)-3-fluorocyclopentyl)methyl)-1H-pyrazol-4-yl)-6-(quinolin-7-yl)picolinonitrile | 398 |
| 69 | 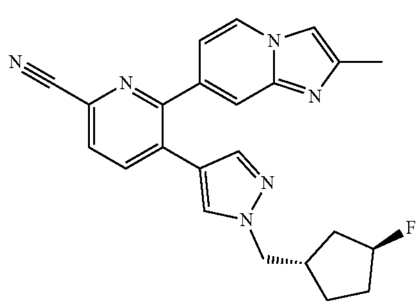 [SMILES: Cc1cn2ccc(-c3nc(C#N)ccc3-c3cnn(C[C@H]4CC[C@H](F)C4)c3)cc2n1] | 5-(1-(((1S,3S)-3-fluorocyclopentyl)methyl)-1H-pyrazol-4-yl)-6-(2-methylimidazo[1,2-a]pyridin-7-yl)picolinonitrile | 401 |

TABLE 1-continued

| Example | Name | MS (M + 1) |
|---|---|---|
| 70 | 5-(1-(((1R,3R)-3-fluorocyclopentyl)methyl)-1H-pyrazol-4-yl)-6-(1-methyl-1H-benzo[d]imidazol-5-yl)picolinonitrile | 401 |
| 71 | 5-(1-(((3S,4S)-3,4-difluorocyclopentyl)methyl)-1H-pyrazol-4-yl)-6-(imidazo[1,2-a]pyridin-7-yl)picolinonitrile | 405 |
| 72 | 5-(1-(((3S,4S)-3,4-difluorocyclopentyl)methyl)-1H-pyrazol-4-yl)-6-(1-methyl-1H-benzo[d]imidazol-5-yl)picolinonitrile | 419 |
| 73 | 5-(1-((1-methylcyclopentyl)methyl)-1H-pyrazol-4-yl)-6-(5-oxo-5,7-dihydrofuro[3,4-b]pyridin-3-yl)picolinonitrile | 400 |

TABLE 1-continued

| Example | Structure | Name | MS (M + 1) |
|---|---|---|---|
| 74 | 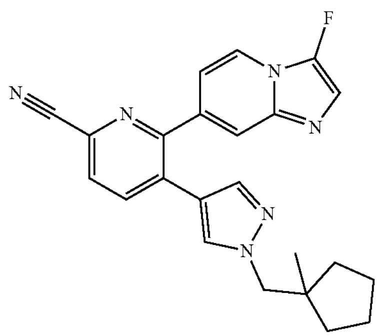 [SMILES: CC1(Cn2cc(-c3ccc(C#N)nc3-c3ccn4c(F)cnc4c3)cn2)CCCC1] | 6-(3-fluoroimidazo[1,2-a]pyridin-7-yl)-5-(1-((1-methylcyclopentyl)methyl)-1H-pyrazol-4-yl)picolinonitrile | 401 |
| 75 | 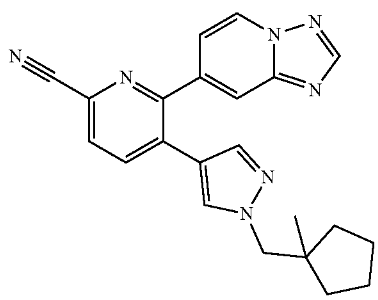 [SMILES: CC1(Cn2cc(-c3ccc(C#N)nc3-c3ccn4ncnc4c3)cn2)CCCC1] | 6-([1,2,4]triazolo[1,5-a]pyridin-7-yl)-5-(1-((1-methylcyclopentyl)methyl)-1H-pyrazol-4-yl)picolinonitrile | 384 |
| 76 | 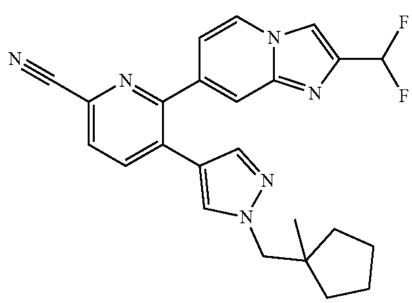 [SMILES: CC1(Cn2cc(-c3ccc(C#N)nc3-c3ccn4cc(C(F)F)nc4c3)cn2)CCCC1] | 6-(2-(difluoromethyl)imidazo[1,2-a]pyridin-7-yl)-5-(1-((1-methylcyclopentyl)methyl)-1H-pyrazol-4-yl)picolinonitrile | 433 |
| 77 | 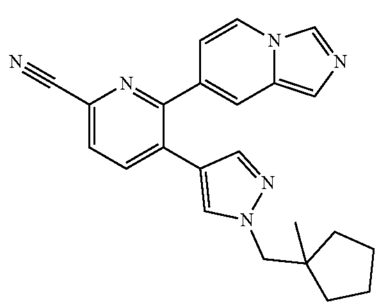 [SMILES: CC1(Cn2cc(-c3ccc(C#N)nc3-c3ccn4cncc4c3)cn2)CCCC1] | 6-(imidazo[1,5-a]pyridin-7-yl)-5-(1-((1-methylcyclopentyl)methyl)-1H-pyrazol-4-yl)picolinonitrile | 383 |
| 78 | 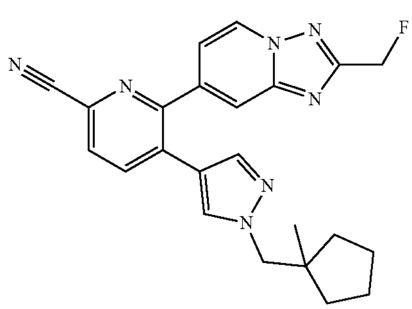 [SMILES: CC1(Cn2cc(-c3ccc(C#N)nc3-c3ccn4nc(CF)nc4c3)cn2)CCCC1] | 6-(2-(fluoromethyl)-[1,2,4]triazolo[1,5-a]pyridin-7-yl)-5-(1-((1-methylcyclopentyl)methyl)-1H-pyrazol-4-yl)picolinonitrile | 416 |

TABLE 1-continued

| Example | Structure | Name | MS (M + 1) |
|---|---|---|---|
| 79 | 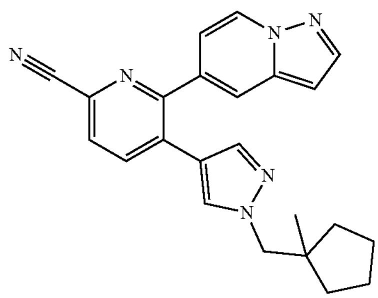 [SMILES: CC1(Cn2cc(-c3ccc(C#N)nc3-c3ccn4nccc4c3)cn2)CCCC1] | 5-(1-((1-methylcyclopentyl)methyl)-1H-pyrazol-4-yl)-6-(pyrazolo[1,5-a]pyridin-5-yl)picolinonitrile | 383 |
| 80 | 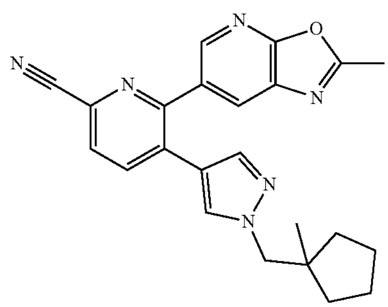 [SMILES: Cc1nc2cc(-c3nc(C#N)ccc3-c3cnn(CC4(C)CCCC4)c3)cnc2o1] | 5-(1-((1-methylcyclopentyl)methyl)-1H-pyrazol-4-yl)-6-(2-methyloxazolo[5,4-b]pyridin-6-yl)picolinonitrile | 399 |
| 81 | 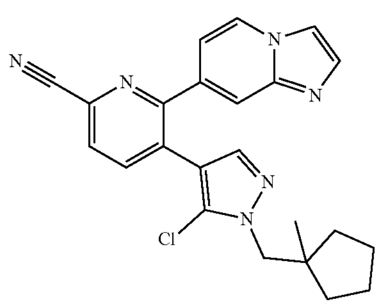 [SMILES: CC1(Cn2ncc(-c3ccc(C#N)nc3-c3ccn4ccnc4c3)c2Cl)CCCC1] | 5-(5-chloro-1-((1-methylcyclopentyl)methyl)-1H-pyrazol-4-yl)-6-(imidazo[1,2-a]pyridin-7-yl)picolinonitrile | 417 |
| 82 | 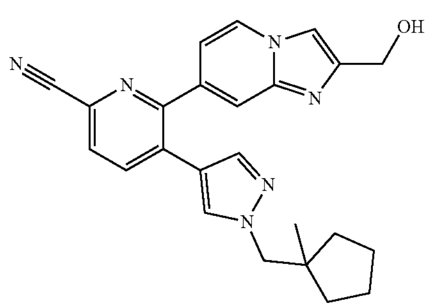 [SMILES: CC1(Cn2cc(-c3ccc(C#N)nc3-c3ccn4cc(CO)nc4c3)cn2)CCCC1] | 6-(2-(hydroxymethyl)imidazo[1,2-a]pyridin-7-yl)-5-(1-((1-methylcyclopentyl)methyl)-1H-pyrazol-4-yl)picolinonitrile | 413 |
| 83 | 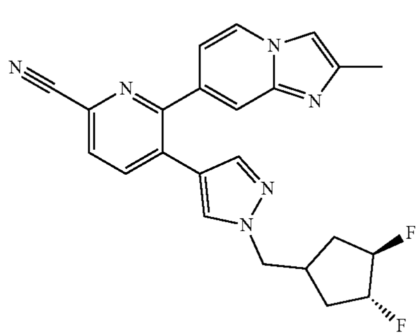 [SMILES: Cc1cn2ccc(-c3nc(C#N)ccc3-c3cnn(CC4C[C@@H](F)[C@H](F)C4)c3)cc2n1] | 5-(1-(((3R,4R)-3,4-difluorocyclopentyl)methyl)-1H-pyrazol-4-yl)-6-(2-methylimidazo[1,2-a]pyridin-7-yl)picolinonitrile | 419 |

TABLE 1-continued

| Example | Structure | Name | MS (M + 1) |
|---|---|---|---|
| 84 | 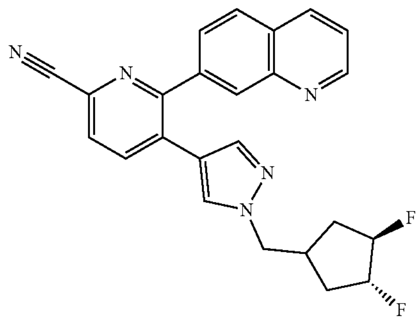 [SMILES: N#Cc1ccc(-c2cnn(CC3C[C@@H](F)[C@H](F)C3)c2)c(-c2ccc3cccnc3c2)n1] | 5-(1-(((3R,4R)-3,4-difluorocyclopentyl)methyl)-1H-pyrazol-4-yl)-6-(quinolin-7-yl)picolinonitrile | 416 |
| 85 | 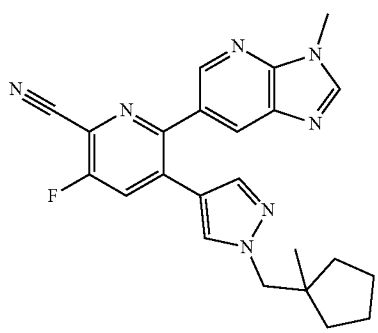 [SMILES: Cn1cnc2cc(-c3nc(C#N)c(F)cc3-c3cnn(CC4(C)CCCC4)c3)cnc21] | 3-fluoro-6-(3-methyl-3H-imidazo[4,5-b]pyridin-6-yl)-5-(1-((1-methylcyclopentyl)methyl)-1H-pyrazol-4-yl)picolinonitrile | 416 |
| 86 | 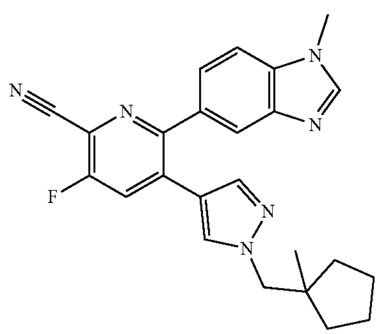 [SMILES: Cn1cnc2cc(-c3nc(C#N)c(F)cc3-c3cnn(CC4(C)CCCC4)c3)ccc21] | 3-fluoro-6-(1-methyl-1H-benzo[d]imidazol-5-yl)-5-(1-((1-methylcyclopentyl)methyl)-1H-pyrazol-4-yl)picolinonitrile | 415 |
| 87 | 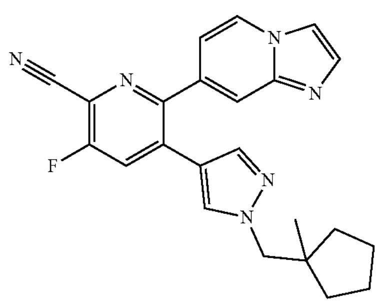 [SMILES: CC1(Cn2cc(-c3cc(F)c(C#N)nc3-c3ccn4ccnc4c3)cn2)CCCC1] | 3-fluoro-6-(imidazo[1,2-a]pyridin-7-yl)-5-(1-((1-methylcyclopentyl)methyl)-1H-pyrazol-4-yl)picolinonitrile | 401 |
| 88 | 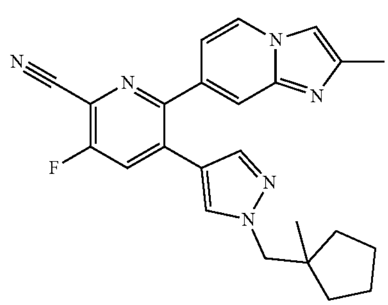 [SMILES: Cc1cn2ccc(-c3nc(C#N)c(F)cc3-c3cnn(CC4(C)CCCC4)c3)cc2n1] | 3-fluoro-5-(1-((1-methylcyclopentyl)methyl)-1H-pyrazol-4-yl)-6-(2-methylimidazo[1,2-a]pyridin-7-yl)picolinonitrile | 415 |

TABLE 1-continued

| Example | Structure | Name | MS (M + 1) |
|---|---|---|---|
| 89 | 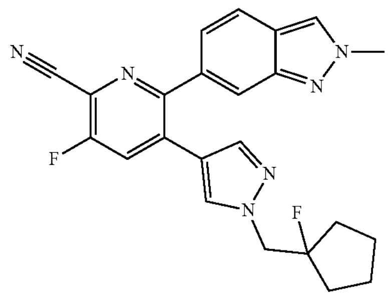 [SMILES: Cn1cc2ccc(-c3nc(C#N)c(F)cc3-c3cnn(CC4(F)CCCC4)c3)cc2n1] | 3-fluoro-5-(1-((1-fluorocyclopentyl)methyl)-1H-pyrazol-4-yl)-6-(2-methyl-2H-indazol-6-yl)picolinonitrile | 419 |
| 90 | 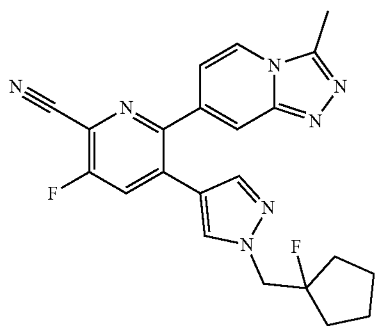 [SMILES: Cc1nnc2cc(-c3nc(C#N)c(F)cc3-c3cnn(CC4(F)CCCC4)c3)ccn12] | 3-fluoro-5-(1-((1-fluorocyclopentyl)methyl)-1H-pyrazol-4-yl)-6-(3-methyl-[1,2,4]triazolo[4,3-a]pyridin-7-yl)picolinonitrile | 420 |
| 91 | 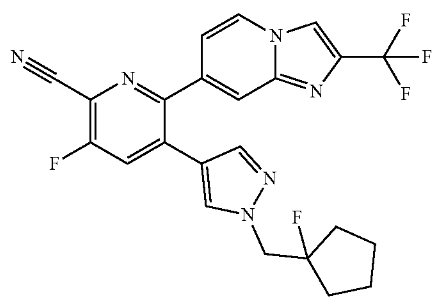 [SMILES: N#Cc1nc(-c2ccn3cc(C(F)(F)F)nc3c2)c(-c2cnn(CC3(F)CCCC3)c2)cc1F] | 3-fluoro-5-(1-((1-fluorocyclopentyl)methyl)-1H-pyrazol-4-yl)-6-(2-(trifluoromethyl)imidazo[1,2-a]pyridin-7-yl)picolinonitrile | 473 |
| 92 | 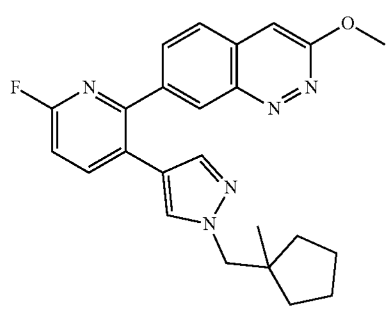 [SMILES: COc1cc2ccc(-c3nc(F)ccc3-c3cnn(CC4(C)CCCC4)c3)cc2nn1] | 7-(6-fluoro-3-(1-((1-methylcyclopentyl)methyl)-1H-pyrazol-4-yl)pyridin-2-yl)-3-methoxycinnoline | 418 |
| 93 | 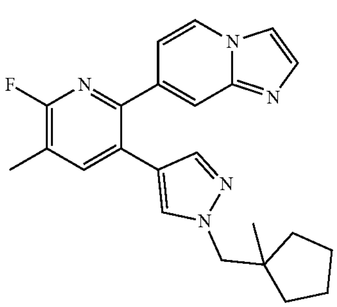 [SMILES: Cc1cc(-c2cnn(CC3(C)CCCC3)c2)c(-c2ccn3ccnc3c2)nc1F] | 7-(6-fluoro-5-methyl-3-(1-((1-methylcyclopentyl)methyl)-1H-pyrazol-4-yl)pyridin-2-yl)imidazo[1,2-a]pyridine | 390 |

TABLE 1-continued

| Example | Structure | Name | MS (M + 1) |
|---|---|---|---|
| 94 | 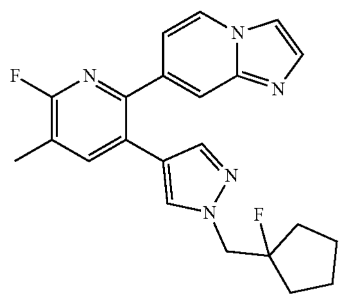 [SMILES: Cc1cc(-c2cnn(CC3(F)CCCC3)c2)c(-c2ccn3ccnc3c2)nc1F] | 7-(6-fluoro-3-(1-((1-fluorocyclopentyl)methyl)-1H-pyrazol-4-yl)-5-methylpyridin-2-yl)imidazo[1,2-a]pyridine | 394 |
| 95 | 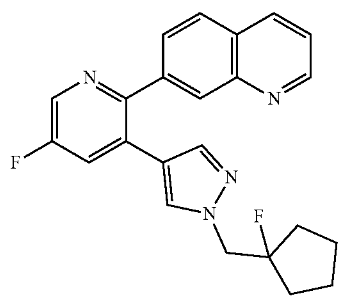 [SMILES: Fc1cnc(-c2ccc3cccnc3c2)c(-c2cnn(CC3(F)CCCC3)c2)c1] | 7-(5-fluoro-3-(1-((1-fluorocyclopentyl)methyl)-1H-pyrazol-4-yl)pyridin-2-yl)quinoline | 391 |
| 96 | 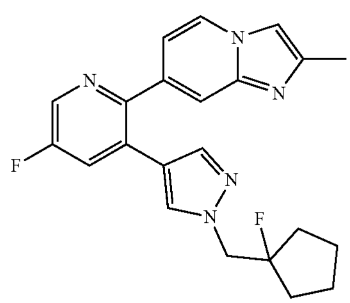 [SMILES: Cc1cn2ccc(-c3ncc(F)cc3-c3cnn(CC4(F)CCCC4)c3)cc2n1] | 7-(5-fluoro-3-(1-((1-fluorocyclopentyl)methyl)-1H-pyrazol-4-yl)pyridin-2-yl)-2-methylimidazo[1,2-a]pyridine | 394 |
| 97 | 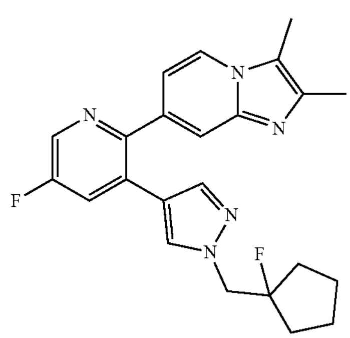 [SMILES: Cc1nc2cc(-c3ncc(F)cc3-c3cnn(CC4(F)CCCC4)c3)ccn2c1C] | 7-(5-fluoro-3-(1-((1-fluorocyclopentyl)methyl)-1H-pyrazol-4-yl)pyridin-2-yl)-2,3-dimethylimidazo[1,2-a]pyridine | 408 |
| 98 | 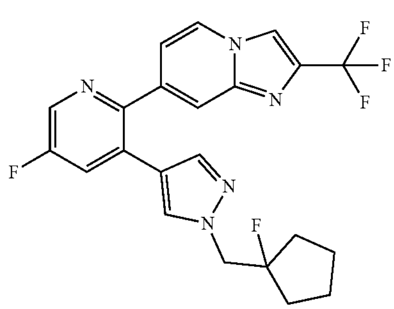 [SMILES: Fc1cnc(-c2ccn3cc(C(F)(F)F)nc3c2)c(-c2cnn(CC3(F)CCCC3)c2)c1] | 7-(5-fluoro-3-(1-((1-fluorocyclopentyl)methyl)-1H-pyrazol-4-yl)pyridin-2-yl)-2-(trifluoromethyl)imidazo[1,2-a]pyridine | 448 |

TABLE 1-continued

| Example | Structure | Name | MS (M + 1) |
|---|---|---|---|
| 99 | 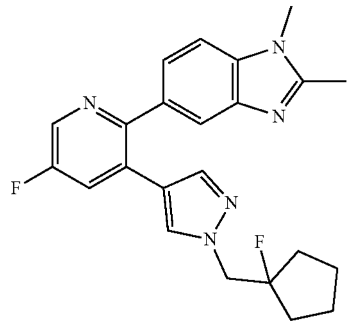 [SMILES: Cc1nc2cc(-c3ncc(F)cc3-c3cnn(CC4(F)CCCC4)c3)ccc2n1C] | 5-(5-fluoro-3-(1-((1-fluorocyclopentyl)methyl)-1H-pyrazol-4-yl)pyridin-2-yl)-1,2-dimethyl-1H-benzo[d]imidazole | 408 |
| 100 | 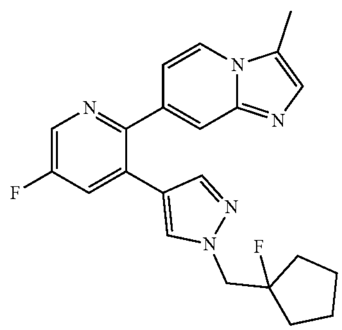 [SMILES: Cc1cnc2cc(-c3ncc(F)cc3-c3cnn(CC4(F)CCCC4)c3)ccn12] | 7-(5-fluoro-3-(1-((1-fluorocyclopentyl)methyl)-1H-pyrazol-4-yl)pyridin-2-yl)-3-methyl-[1,2,4]triazolo[4,3-a]pyridine | 395 |
| 101 | 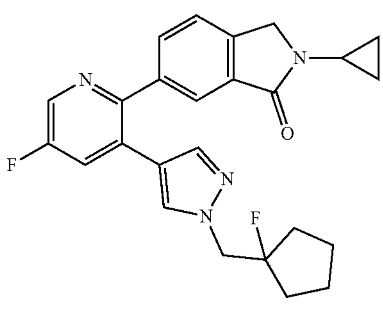 [SMILES: O=C1c2cc(-c3ncc(F)cc3-c3cnn(CC4(F)CCCC4)c3)ccc2CN1C1CC1] | 2-cyclopropyl-6-(5-fluoro-3-(1-((1-fluorocyclopentyl)methyl)-1H-pyrazol-4-yl)pyridin-2-yl)isoindolin-1-one | 435 |
| 102 | 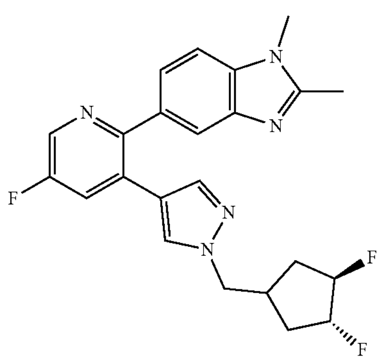 [SMILES: Cc1nc2cc(-c3ncc(F)cc3-c3cnn(CC4C[C@@H](F)[C@H](F)C4)c3)ccc2n1C] | 5-(3-(1-(((3R,4R)-3,4-difluorocyclopentyl)methyl)-1H-pyrazol-4-yl)-5-fluoropyridin-2-yl)-1,2-dimethyl-1H-benzo[d]imidazole | 412 |

TABLE 1-continued

| Example | Structure | Name | MS (M + 1) |
|---|---|---|---|
| 103 | 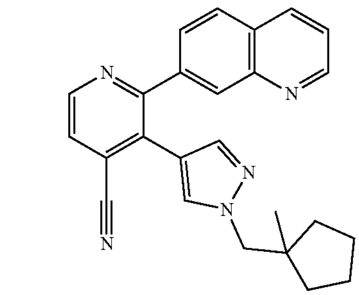 [SMILES: CC1(Cn2cc(-c3c(C#N)ccnc3-c3ccc4cccnc4c3)cn2)CCCC1] | 3-(1-((1-methylcyclopentyl)methyl)-1H-pyrazol-4-yl)-2-(quinolin-7-yl)isonicotinonitrile | 394 |
| 104 | 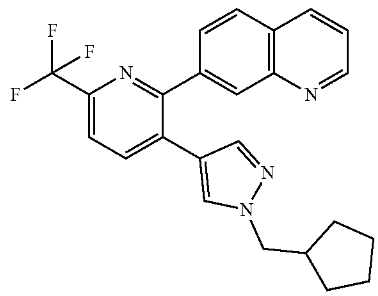 [SMILES: FC(F)(F)c1ccc(-c2cnn(CC3CCCC3)c2)c(-c2ccc3cccnc3c2)n1] | 7-(3-(1-(cyclopentylmethyl)-1H-pyrazol-4-yl)-6-(trifluoromethyl)pyridin-2-yl)quinoline | 423 |
| 105 | 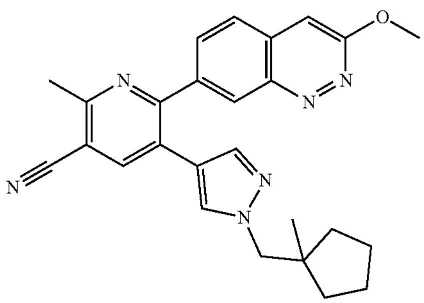 [SMILES: COc1cc2ccc(-c3nc(C)c(C#N)cc3-c3cnn(CC4(C)CCCC4)c3)cc2nn1] | 6-(3-methoxycinnolin-7-yl)-2-methyl-5-(1-((1-methylcyclopentyl)methyl)-1H-pyrazol-4-yl)nicotinonitrile | 439 |
| 106 | 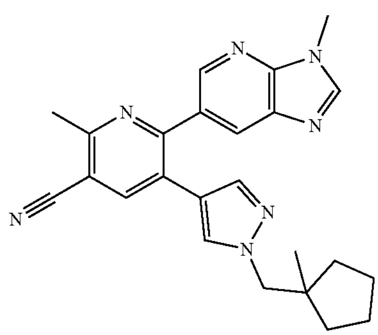 [SMILES: Cc1nc(-c2cnc3c(c2)ncn3C)c(-c2cnn(CC3(C)CCCC3)c2)cc1C#N] | 2-methyl-6-(3-methyl-3H-imidazo[4,5-b]pyridin-6-yl)-5-(1-((1-methylcyclopentyl)methyl)-1H-pyrazol-4-yl)nicotinonitrile | 412 |
| 107 | 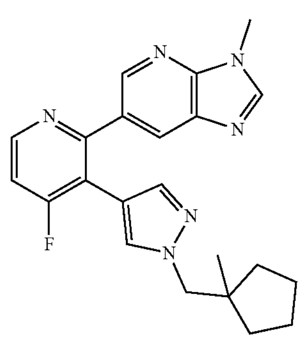 [SMILES: Cn1cnc2cc(-c3nccc(F)c3-c3cnn(CC4(C)CCCC4)c3)cnc21] | 6-(4-fluoro-3-(1-((1-methylcyclopentyl)methyl)-1H-pyrazol-4-yl)pyridin-2-yl)-3-methyl-3H-imidazo[4,5-b]pyridine | 391 |

TABLE 1-continued

| Example | Structure | Name | MS (M + 1) |
|---|---|---|---|
| 108 | 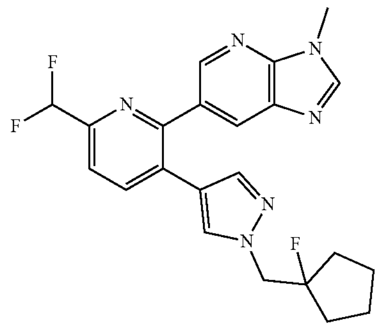 [SMILES: Cn1cnc2cc(-c3nc(C(F)F)ccc3-c3cnn(CC4(F)CCCC4)c3)cnc21] | 6-(6-(difluoromethyl)-3-(1-((1-fluorocyclopentyl)methyl)-1H-pyrazol-4-yl)pyridin-2-yl)-3-methyl-3H-imidazo[4,5-b]pyridine | 427 |
| 109 | 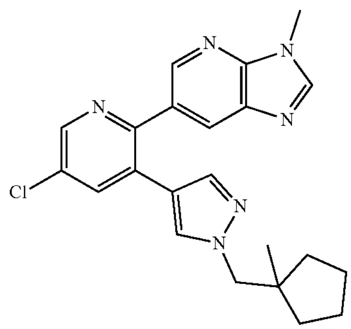 [SMILES: Cn1cnc2cc(-c3ncc(Cl)cc3-c3cnn(CC4(C)CCCC4)c3)cnc21] | 6-(5-chloro-3-(1-((1-methylcyclopentyl)methyl)-1H-pyrazol-4-yl)pyridin-2-yl)-3-methyl-3H-imidazo[4,5-b]pyridine | 407 |
| 110 | 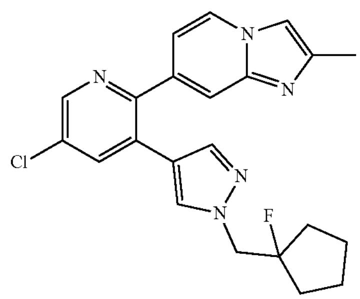 [SMILES: Cc1cn2ccc(-c3ncc(Cl)cc3-c3cnn(CC4(F)CCCC4)c3)cc2n1] | 7-(5-chloro-3-(1-((1-fluorocyclopentyl)methyl)-1H-pyrazol-4-yl)pyridin-2-yl)-2-methylimidazo[1,2-a]pyridine | 410 |
| 111 | 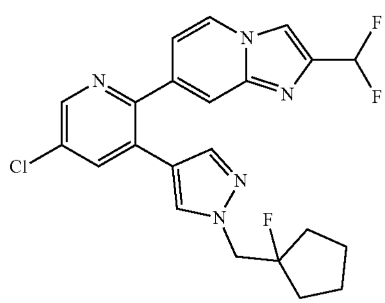 [SMILES: FC(F)c1cn2ccc(-c3ncc(Cl)cc3-c3cnn(CC4(F)CCCC4)c3)cc2n1] | 7-(5-chloro-3-(1-((1-fluorocyclopentyl)methyl)-1H-pyrazol-4-yl)pyridin-2-yl)-2-(difluoromethyl)imidazo[1,2-a]pyridine | 446 |
| 112 | 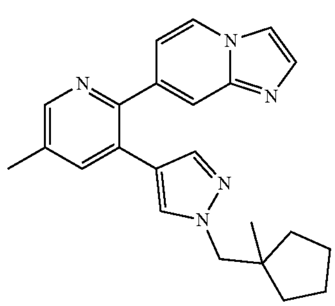 [SMILES: Cc1cnc(-c2ccn3ccnc3c2)c(-c2cnn(CC3(C)CCCC3)c2)c1] | 7-(5-methyl-3-(1-((1-methylcyclopentyl)methyl)-1H-pyrazol-4-yl)pyridin-2-yl)imidazo[1,2-a]pyridine | 372 |

TABLE 1-continued

| Example | Structure | Name | MS (M + 1) |
|---|---|---|---|
| 113 | 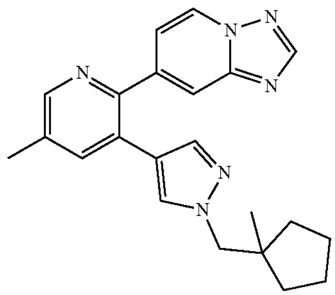 [SMILES: Cc1cnc(-c2ccn3ncnc3c2)c(-c2cnn(CC3(C)CCCC3)c2)c1] | 7-(5-methyl-3-(1-((1-methylcyclopentyl)methyl)-1H-pyrazol-4-yl)pyridin-2-yl)-[1,2,4]triazolo[1,5-a]pyridine | 373 |
| 114 | 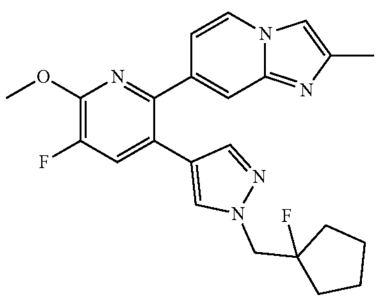 | 7-(5-fluoro-3-(1-((1-fluorocyclopentyl)methyl)-1H-pyrazol-4-yl)-6-methoxypyridin-2-yl)-2-methylimidazo[1,2-a]pyridine | 424 |
| 115 | 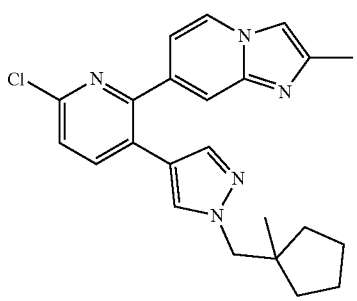 [SMILES: Cc1cn2ccc(-c3nc(Cl)ccc3-c3cnn(CC4(C)CCCC4)c3)cc2n1] | 7-(6-chloro-3-(1-((1-methylcyclopentyl)methyl)-1H-pyrazol-4-yl)pyridin-2-yl)-2-methylimidazo[1,2-a]pyridine | 406 |
| 116 | 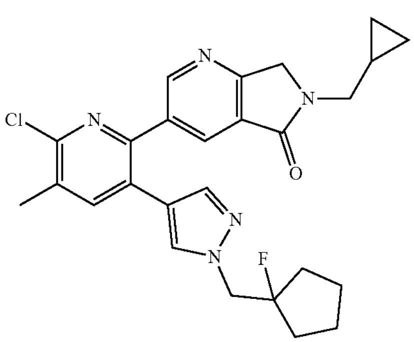 [SMILES: Cc1cc(-c2cnn(CC3(F)CCCC3)c2)c(-c2cnc3c(c2)C(=O)N(CC2CC2)C3)nc1Cl] | 3-(6-chloro-3-(1-((1-fluorocyclopentyl)methyl)-1H-pyrazol-4-yl)-5-methylpyridin-2-yl)-6-(cyclopropylmethyl)-6,7-dihydro-5H-pyrrolo[3,4-b]pyridin-5-one | 480 |
| 117 | 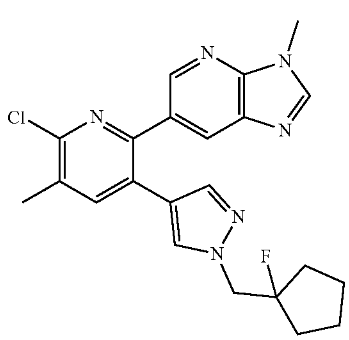 [SMILES: Cc1cc(-c2cnn(CC3(F)CCCC3)c2)c(-c2cnc3c(c2)ncn3C)nc1Cl] | 6-(6-chloro-3-(1-((1-fluorocyclopentyl)methyl)-1H-pyrazol-4-yl)-5-methylpyridin-2-yl)-3-methyl-3H-imidazo[4,5-b]pyridine | 425 |

TABLE 1-continued

| Example | Structure | Name | MS (M + 1) |
|---|---|---|---|
| 118 | 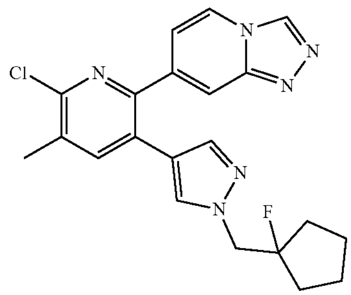 [SMILES: Cc1cc(-c2cnn(CC3(F)CCCC3)c2)c(-c2ccn3cnnc3c2)nc1Cl] | 7-(6-chloro-3-(1-((1-fluorocyclopentyl)methyl)-1H-pyrazol-4-yl)-5-methylpyridin-2-yl)-[1,2,4]triazolo[4,3-a]pyridine | 411 |
| 119 | 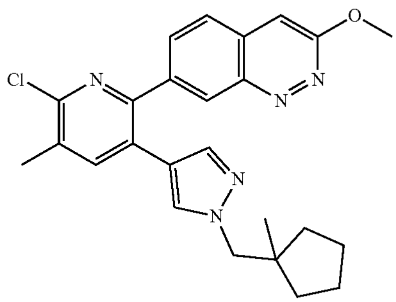 [SMILES: COc1cc2ccc(-c3nc(Cl)c(C)cc3-c3cnn(CC4(C)CCCC4)c3)cc2nn1] | 7-(6-chloro-5-methyl-3-(1-((1-methylcyclopentyl)methyl)-1H-pyrazol-4-yl)pyridin-2-yl)-3-methoxycinnoline | 448 |
| 120 | 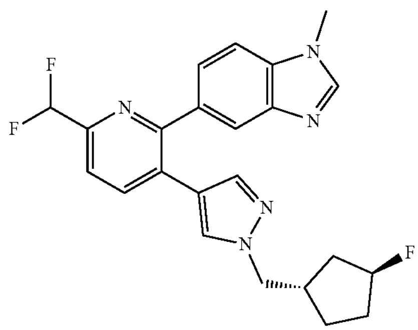 [SMILES: Cn1cnc2cc(-c3nc(C(F)F)ccc3-c3cnn(C[C@H]4CC[C@H](F)C4)c3)ccc21] | 5-(6-(difluoromethyl)-3-(1-(((1S,3S)-3-fluorocyclopentyl)methyl)-1H-pyrazol-4-yl)pyridin-2-yl)-1-methyl-1H-benzo[d]imidazole | 426 |
| 121 | 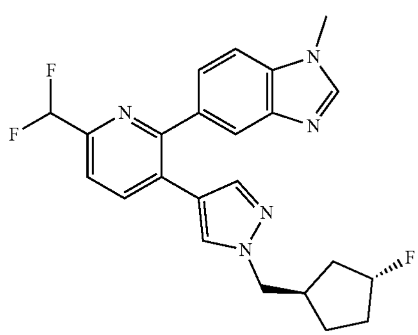 [SMILES: Cn1cnc2cc(-c3nc(C(F)F)ccc3-c3cnn(C[C@@H]4CC[C@@H](F)C4)c3)ccc21] | 5-(6-(difluoromethyl)-3-(1-(((1R,3R)-3-fluorocyclopentyl)methyl)-1H-pyrazol-4-yl)pyridin-2-yl)-1-methyl-1H-benzo[d]imidazole | 426 |
| 122 | 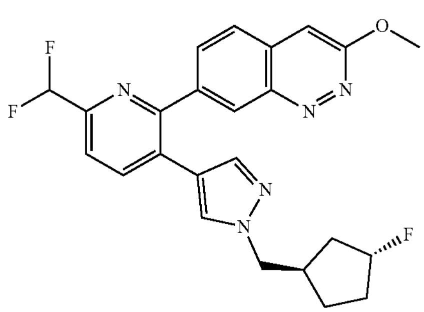 [SMILES: COc1cc2ccc(-c3nc(C(F)F)ccc3-c3cnn(C[C@@H]4CC[C@@H](F)C4)c3)cc2nn1] | 7-(6-(difluoromethyl)-3-(1-(((1R,3R)-3-fluorocyclopentyl)methyl)-1H-pyrazol-4-yl)pyridin-2-yl)-3-methoxycinnoline | 454 |

TABLE 1-continued

| Example | Structure | Name | MS (M + 1) |
|---|---|---|---|
| 123 | 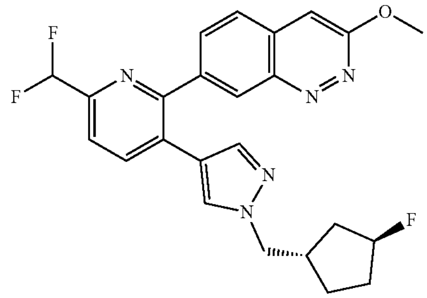 [SMILES: COc1cc2ccc(-c3nc(C(F)F)ccc3-c3cnn(C[C@H]4CC[C@H](F)C4)c3)cc2nn1] | 7-(6-(difluoromethyl)-3-(1-(((1S,3S)-3-fluorocyclopentyl)methyl)-1H-pyrazol-4-yl)pyridin-2-yl)-3-methoxy-cinnoline | 454 |
| 124 | 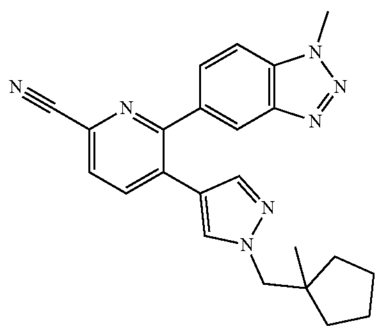 [SMILES: Cn1nnc2cc(-c3nc(C#N)ccc3-c3cnn(CC4(C)CCCC4)c3)ccc21] | 6-(1-methyl-1H-benzo[d][1,2,3]triazol-5-yl)-5-(1-((1-methylcyclopentyl)methyl)-1H-pyrazol-4-yl)picolinonitrile | 398 |
| 125 | 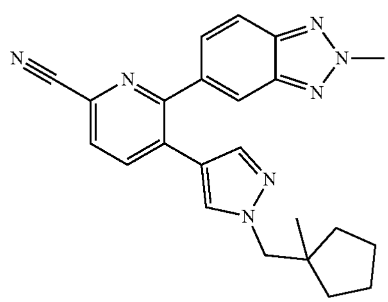 [SMILES: Cn1nc2ccc(-c3nc(C#N)ccc3-c3cnn(CC4(C)CCCC4)c3)cc2n1] | 6-(2-methyl-2H-benzo[d][1,2,3]triazol-5-yl)-5-(1-((1-methylcyclopentyl)methyl)-1H-pyrazol-4-yl)picolinonitrile | 398 |
| 126 | 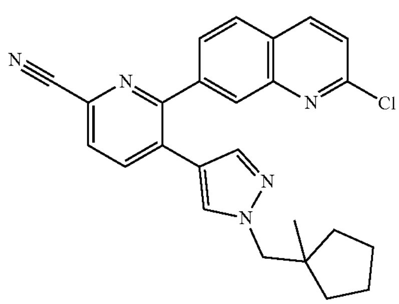 [SMILES: CC1(Cn2cc(-c3ccc(C#N)nc3-c3ccc4ccc(Cl)nc4c3)cn2)CCCC1] | 6-(2-chloro-quinolin-7-yl)-5-(1-((1-methylcyclopentyl)methyl)-1H-pyrazol-4-yl)picolinonitrile | 428 |
| 127 | 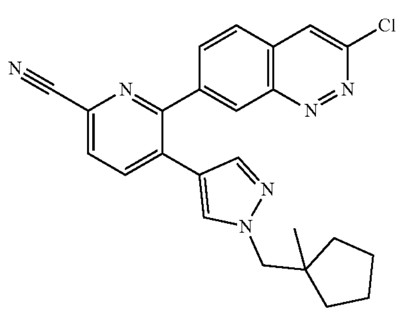 [SMILES: CC1(Cn2cc(-c3ccc(C#N)nc3-c3ccc4cc(Cl)nnc4c3)cn2)CCCC1] | 6-(3-chlorocinnolin-7-yl)-5-(1-((1-methylcyclopentyl)methyl)-1H-pyrazol-4-yl)picolinonitrile | 429 |

TABLE 1-continued

| Example | Structure | Name | MS (M + 1) |
|---|---|---|---|
| 128 | 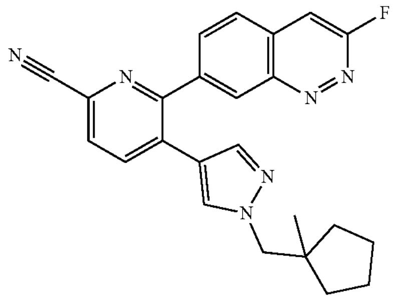 [SMILES: CC1(Cn2cc(-c3ccc(C#N)nc3-c3ccc4cc(F)nnc4c3)cn2)CCCC1] | 6-(3-fluorocinnolin-7-yl)-5-(1-((1-methylcyclopentyl)methyl)-1H-pyrazol-4-yl)picolinonitrile | 413 |

*¹H NMR (500 MHz, DMSO-d6): δ 7.6-7.3 (m, 8H), 3.85 (d, 2H), 2.85 (m, 2H), 2.6-2.4 (m, 4H + DMSO), 2.20 (m, 1H), 1.75 (m, 3H), 1.50 (m, 6H), 1.10 (m, 2H).

Example 129 and 130

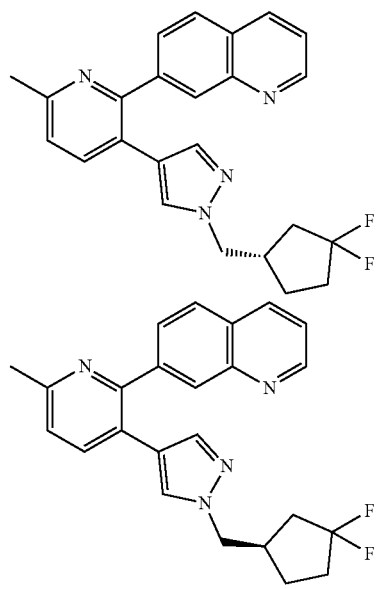

(S or R)-7-(3-(1-(((3,3-difluorocyclopentyl)methyl)-1H-pyrazol-4-yl)-6-methylpyridin-2-yl)quinoline (EXAMPLE 129) and (R or S)-7-(3-(1-(((3,3-difluorocyclopentyl)methyl)-1H-pyrazol-4-yl)-6-methylpyridin-2-yl)quinoline (EXAMPLE 130)

SFC was used to separate EXAMPLE 28 under the following conditions: A Chiralpak OZ 150×4.6 mm I.D., 3 um column was eluted with 25% isopropanol (0.05% DEA) in $CO_2$ to give EXAMPLE 129 and 130. Absolute configuration was not determined.

Using SFC with chiral stationary phases and either ethanol or isopropanol (with or without 0.05% DEA) single enantiomers were isolated from EXAMPLE 30 and 31 and are shown in TABLE 2. Absolute configuration was not determined in any of these examples.

TABLE 2

| Example | Structure | Name | MS (M + 1) |
|---|---|---|---|
| 131 | 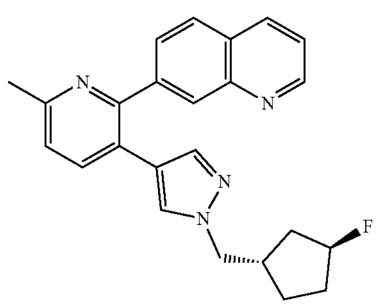 [SMILES: Cc1ccc(-c2cnn(C[C@H]3CC[C@H](F)C3)c2)c(-c2ccc3cccnc3c2)n1] | 7-(3-(1-(((1S,3S) or (1R,3R)-3-fluorocyclopentyl)methyl)-1H-pyrazol-4-yl)-6-methylpyridin-2-yl)quinoline | 387 |

TABLE 2-continued

| Example | Structure | Name | MS (M + 1) |
|---|---|---|---|
| 132 | 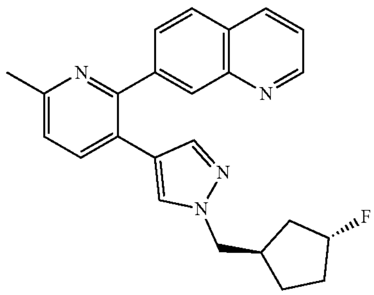 [SMILES: Cc1ccc(-c2cnn(C[C@@H]3CC[C@@H](F)C3)c2)c(-c2ccc3cccnc3c2)n1] | 7-(3-(1-(((1R,3R) or (1S,3S)-3-fluorocyclopentyl)methyl)-1H-pyrazol-4-yl)-6-methylpyridin-2-yl)quinoline | 387 |
| 133 | 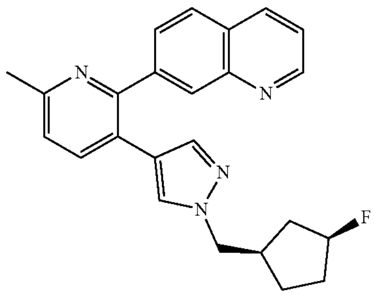 [SMILES: Cc1ccc(-c2cnn(C[C@@H]3CC[C@H](F)C3)c2)c(-c2ccc3cccnc3c2)n1] | 7-(3-(1-(((1R,3S) or (1S,3R)-3-fluorocyclopentyl)methyl)-1H-pyrazol-4-yl)-6-methylpyridin-2-yl)quinoline | 387 |
| 134 | 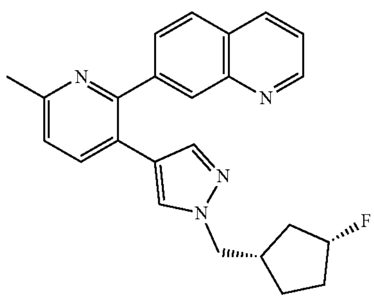 [SMILES: Cc1ccc(-c2cnn(C[C@H]3CC[C@@H](F)C3)c2)c(-c2ccc3cccnc3c2)n1] | 7-(3-(1-(((1S,3R) or (1R,3S)-3-fluorocyclopentyl)methyl)-1H-pyrazol-4-yl)-6-methylpyridin-2-yl)quinoline | 387 |

Example 135

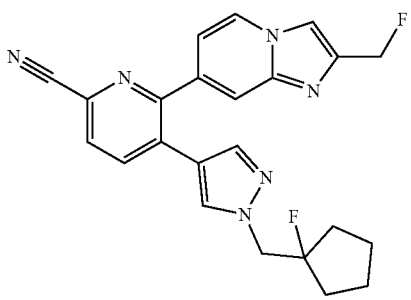 [SMILES: N#Cc1ccc(-c2cnn(CC3(F)CCCC3)c2)c(-c2ccn3cc(CF)nc3c2)n1]

5-(1-((1-fluorocyclopentyl)methyl)-1H-pyrazol-4-yl)-6-(2-(fluoromethyl)imidazo[1,2-a]pyridin-7-yl)picolinonitrile Step 1: (7-bromoimidazo[1,2-a]pyridin-2-yl)methanol To a solution of ethyl 7-bromoimidazo[1,2-a]pyridine-2-carboxylate (400 mg, 1.486 mmol) in dry THF (3 mL) at 0° C. was added LiAlH$_4$ (56.4 mg, 1.486 mmol) in a schlenk tube. After the mixture stirred for 16 hours at 25° C., TLC indicated the reaction was completed. The mixture was diluted with saturated aqueous NH$_4$Cl (20 mL) and extracted with ethyl acetate (70 mL×3). The combined organic layers were washed with water (40 mL) and brine (50 mL), dried over anhydrous sodium sulfate, filtered and concentrated. The crude product was purified by silica gel chromatography (pet. ether/ethyl acetate) to give the title compound.

Step 2: 7-bromo-2-(fluoromethyl)imidazo[1,2-a]pyridine

To a solution of (7-bromoimidazo[1,2-a]pyridin-2-yl)methanol (20 mg, 0.088 mmol) in DCM (3 ml) was added DAST (0.035 ml, 0.264 mmol) dropwise at −78° C. under nitrogen atmosphere. The reaction mixture was stirred 3 hours at 0° C. The reaction mixture was quenched with saturated aqueous NaHCO$_3$ (5 ml) and extracted with DCM (20 ml×2). The organic layer was dried over anhydrous sodium sulfate, filtered and the filtrate was concentrated in vacuo to give the title compound, which was moved forward without further purification. MS(M+1): 229.

Step 3: 2-(Fluoromethyl)-7-(4,4,5,5-tetramethyl-1,3,2-dioxaborolan-2-yl)imidazo[1,2-a]pyridine To a solution of 7-bromo-2-(fluoromethyl)imidazo[1,2-a]pyridine (20 mg, 0.061 mmol) in dioxane (4 ml) were added potassium acetate (18.0 mg, 0.183 mmol), bis(pinacolato)diboron (23.3 mg, 0.092 mmol), PdCl₂(dppf) (4.5 mg, 6.11 μmol) at 20° C. under nitrogen atmosphere. The reaction mixture was stirred at 90° C. for 2.5 hours. The reaction mixture was diluted with water (5 mL) and extracted with EtOAc (10 mL×3). The combined organic layers were washed with brine (10 mL), dried over Na₂SO₄, filtered and the filtrate was concentrated in vacuo to give the title compound, which was carried forward without purification.

Step 4: 5-(1-((1-fluorocyclopentyl)methyl)-1H-pyrazol-4-yl)-6-(2-(fluoromethyl)imidazo[1,2-a]pyridin-7-yl)picolinonitrile To a solution of 6-chloro-5-(1-((1-fluorocyclopentyl)methyl)-1H-pyrazol-4-yl)picolinonitrile (INTERMEDIATE H3, 20 mg, 0.066 mmol), 2-(fluoromethyl)-7-(4,4,5,5-tetramethyl-1,3,2-dioxaborolan-2-yl)imidazo[1,2-a]pyridine (18.1 mg, 0.066 mmol) and 1,1'-bis(di-tert-butylphosphino)ferrocene palladium dichloride (4.3 mg, 6.56 μmol) in 1,4-dioxane (2 ml) and H₂O (0.5 ml) was added potassium phosphate trihydrate (52.4 mg, 0.197 mmol) at 20° C. and the mixture was stirred at 80° C. for 2 hours under nitrogen atmosphere. The mixture was diluted with water (10 mL) and extracted with ethyl acetate (10 mL×3). The combined organic layers were washed with brine (10 ml), dried over sodium sulfate, filtered and the filtrate was concentrated in vacuo. The residue was purified by prep-HPLC (C18 stationary phase, CH₃CN/water modified with TFA) to give the title compound. ¹H NMR (400 MHz, CDCl₃): δ 8.24 (d, J=7.2 Hz, 1H), 8.20 (s, 1H), 7.94 (d, J=7.6 Hz, 1H), 7.76 (m, 2H), 7.43 (s, 1H), 7.34 (m, 2H), 5.70 (d, J=46.8 Hz, 2H), 4.32 (d, J=22.4 Hz, 2H), 1.77-1.69 (m, 8H). MS(M+1): 419.

Using the method above and utilizing intermediate H7 in the final step, EXAMPLE 136 was prepared and is shown in table 3 below.

Example 137

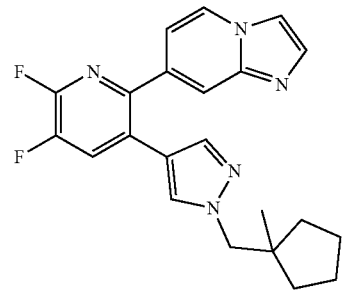

7-(5,6-difluoro-3-(1-((1-methylcyclopentyl)methyl)-1H-pyrazol-4-yl)pyridin-2-yl)imidazo[1,2-a]pyridine 1-((1-Methylcyclopentyl)methyl)-4-(4,4,5,5-tetramethyl-1,3,2-dioxaborolan-2-yl)-1H-pyrazole (INTERMEDIATE D1, 24.0 mg, 0.083 mmol), 7-(3-chloro-5,6-difluoropyridin-2-yl)imidazo[1,2-a]pyridine (INTERMEDIATE U2, 22 mg, 0.083 mmol), 1,1'-bis(di-tert-butylphosphino)ferrocene palladium dichloride (4.3 mg, 6.63 μmol) and 1M aqueous potassium carbonate (0.248 mL, 0.248 mmol) solution were added to a reaction vial with 1,4-dioxane (1 mL). The vial was evacuated and charged 3× with nitrogen, then heated to 100° C. for 2 hours. The reaction mixture was cooled to room temperature and diluted with ethyl acetate. The organic was washed 3× with water and then with brine, dried over sodium sulfate, filtered and the filtrate was evaporated. The crude material was purified by preparative reverse phase chromatography (C18), eluting with 10-55% acetonitrile/water (modified with 0.1% TFA) to give the title compound. MS: 394 (M+1). ¹H NMR (500 MHz, CDCl₃): δ 8.44 (s, 1H), 8.23 (d, 1H), 7.90 (s, 1H), 7.76-7.64 (s, m, 2H), 7.43 (s, 1H), 7.37 (d, 1H), 7.24 (s, 1H), 3.99 (s, 2H), 1.77-1.50 (m, 6H), 1.34 (m, 2H), 0.93 (s, 3H).

The following examples in Table 4 were prepared according to Scheme 4 using the procedure outlined in the synthesis of EXAMPLE 137.

TABLE 3

| Example | Structure | Name | MS |
|---|---|---|---|
| 136 | 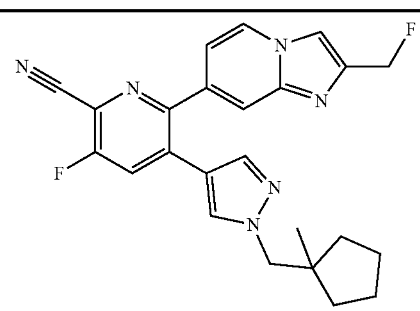 | 3-fluoro-6-(2-(fluoromethyl)imidazo[1,2-a]pyridin-7-yl)-5-(1-((1-methylcyclopentyl)methyl)-1H-pyrazol-4-yl)picolinonitrile | 433 |

TABLE 4

| Example | Structure | Name | MS (M + 1) |
|---|---|---|---|
| 138 | 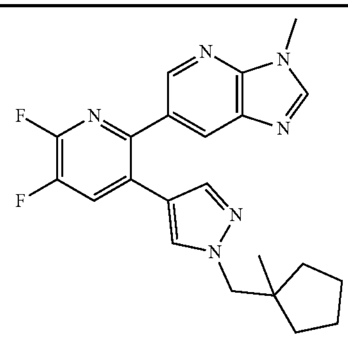 | 6-(5,6-difluoro-3-(1-((1-methylcyclopentyl)methyl)-1H-pyrazol-4-yl)pyridin-2-yl)-3-methyl-3H-imidazo[4,5-b]pyridine | 409 |

Example 139

2-cyclobutyl-6-(3-(1-((1-fluorocyclopentyl)methyl)-1H-pyrazol-4-yl)pyridin-2-yl)isoindolin-1-one Step 1: methyl 5-(3-(1-((1-fluorocyclopentyl)methyl)-1H-pyrazol-4-yl)pyridin-2-yl)-2-methylbenzoate Combined (3-(methoxycarbonyl)-4-methylphenyl)boronic acid (416 mg, 2.145 mmol), 2-chloro-3-(1-((1-fluorocyclopentyl)methyl)-1H-pyrazol-4-yl)pyridine (INTERMEDIATE F3, 400 mg, 1.430 mmol), and di-tert-butylphoshinoferrocene palladium dichloride (100 mg, 0.154 mmol) in a large reaction vial. Sealed the vial and inerted the atmosphere with nitrogen. Added THF (14.3 mL), and 1M aqueous tripotassium phosphate (4.3 mL, 4.3 mmol). The reaction was heated to 100° C. for 6 hours. Cooled and partitioned the organic from the aqueous. Washed the organic with water (2×10 mL). Dried the organic over sodium sulfate, filtered and evaporated the filtrate. Purified by silica gel chromatography, eluting with 0-100% Hex/EtOAc to give the title compound. MS(M+1): 394.

Step 2: methyl 2-(bromomethyl)-5-(3-(1-((1-fluorocyclopentyl)methyl)-1H-pyrazol-4-yl)pyridin-2-yl)benzoate Combined NBS (27.1 mg, 0.152 mmol), benzoyl peroxide (15.39 mg, 0.064 mmol), and methyl 5-(3-(1-((1-fluorocyclopentyl)methyl)-1H-pyrazol-4-yl)pyridin-2-yl)-2-methylbenzoate (50 mg, 0.127 mmol) in 2-5 mL microwave vial. Added CCl$_4$ (1.2 mL), sealed, and heated to 80° C. for 1 hour. Cooled, filtered, and evaporated filtrate, which was used as is without further purification.

MS(M+1): 472, 474.

Step 3: 2-cyclobutyl-6-(3-(1-((1-fluorocyclopentyl)methyl)-1H-pyrazol-4-yl)pyridin-2-yl)isoindolin-1-one Combined cyclobutylamine (11 μl, 0.128 mmol), methyl 2-(bromomethyl)-5-(3-(1-((1-fluorocyclopentyl)methyl)-1H-pyrazol-4-yl)pyridin-2-yl)benzoate (30 mg, 0.064 mmol), and DIEA (11.1 μl, 0.064 mmol) in a reaction vial. Added DMF (529 μl) and stirred for 30 minutes. Diluted with ethyl acetate and washed repeatedly with water, then dried over sodium sulfate, filtered and evaporated the filtrate. The crude material was purified by preparative reverse phase chromatography (C18), eluting with 5-95% acetonitrile/water (modified with 0.1% TFA) to give the title compound. MS: 431 (M+1); $^1$H NMR (500 MHz, DMSO-d6): δ 8.58 (s, 1H), 7.94 (d, 1H), 7.64 (m, 2H), 7.61 (s, 1H), 7.42 (m, 1H), 7.27 (m, 2H), 4.75 (m, 1H), 4.58 (s, 2H), 4.28 (d, 2H), 2.30 (m, 2H), 2.08 (m, 2H), 1.80-1.40 (m, 10H).

The following examples in Table 5 were prepared according to Scheme 5 using the procedure outlined in the synthesis of Example 139.

TABLE 5

| Example | Structure | Name | MS(M + 1) |
|---|---|---|---|
| 140 | 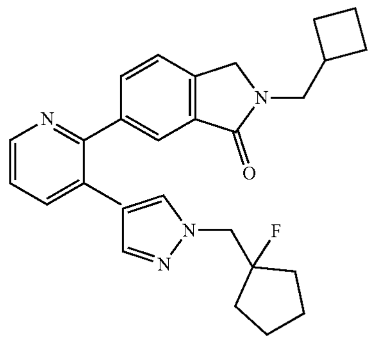 | 2-(cyclobutylmethyl)-6-(3-(1-((1-fluorocyclopentyl)methyl)-1H-pyrazol-4-yl)pyridin-2-yl)isoindolin-1-one | 445 |

Example 141

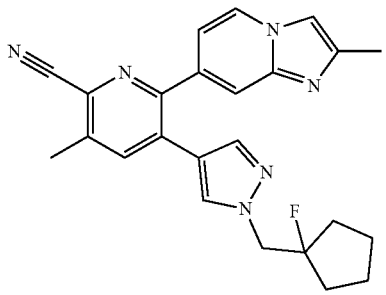

5-(1-((1-fluorocyclopentyl)methyl)-1H-pyrazol-4-yl)-3-methyl-6-(2-methyl-[1,2,4]triazolo[15-a]pyridin-7-yl)picolinonitrile Step 1: 7-(6-chloro-3-(1-((1-fluorocyclopentyl)methyl)-1H-pyrazol-4-yl)-5-methylpyridin-2-yl)-2-methyl-[1,2,4]triazolo[1,5-a]pyridine 7-bromo-2-methyl-[1,2,4]triazolo[1,5-a]pyridine (50.9 mg, 0.240 mmol), potassium acetate (70.7 mg, 0.720 mmol), 2nd generation XPhos precatalyst (14.16 mg, 0.018 mmol) and bis(pinacolato)diboron (60.9 mg, 0.240 mmol) were added to a 40 mL reaction vial and evacuated and charged multiple times with nitrogen. Added dioxane (1920 µl), then evacuated and charged the vessel again with nitrogen (3×). Heated to 100° C. and monitored by LCMS for loss of bromopyrazole. Once bromopyrazole was consumed, the reaction was cooled to room temperature and 2-bromo-6-chloro-3-(1-((1-fluorocyclopentyl)methyl)-1H-pyrazol-4-yl)-5-methylpyridine (INTERMEDIATE H6, 89 mg, 0.240 mmol) was added along with 1,1'-bis(di-tert-butylphosphino)ferrocene palladium dichloride (9.39 mg, 0.014 mmol). The reaction was evacuated and charged 3× with nitrogen, followed by the addition of 3M aqueous potassium carbonate (240 µl, 0.720 mmol). Heated to 50° C. overnight. Partitioned between water and ethyl acetate. Extracted the aqueous twice more with ethyl acetate. The organics were passed over a bed of sodium sulfate and the filtrate evaporated. Purified by silica gel chromatography, eluting with 20-100% 3:1 EtOAc:EtOH in hexanes to give the title compound. MS(M+1): 425.

Step 2: 5-(1-((1-fluorocyclopentyl)methyl)-1H-pyrazol-4-yl)-3-methyl-6-(2-methyl-[1,2,4]triazolo[1,5-a]pyridin-7-yl)picolinonitrile Zinc (II) cyanide (0.044 g, 0.372 mmol), 7-(6-chloro-3-(1-((1-fluorocyclopentyl)methyl)-1H-pyrazol-4-yl)-5-methylpyridin-2-yl)-2-methyl-[1,2,4]triazolo[1,5-a]pyridine (0.079 g, 0.186 mmol) and 2nd generation XPhos precatalyst (0.015 g, 0.019 mmol) were placed in a microwave vial and evacuated and charged with nitrogen. Added DMF (1.0 ml), sealed the vial and heated to 180° C. by microwave for 30 minutes. Partitioned between ethyl acetate and water. Washed the organic twice more with water, dried over sodium sulfate, filtered and evaporated. The crude was purified by silica gel chromatography, eluting with 20-75% 3:1 EtOAc:EtOH in hexanes to give the title compound. MS: 416 (M+1); $^1$H NMR (500 MHz, DMSO-d6): δ 8.47 (d, J=6.7 Hz, 1H), 7.76 (s, 1H), 7.72 (s, 1H), 7.40 (s, 1H), 7.30 (s, 1H), 7.04 (d, J=6.9 Hz, 1H), 4.29 (d, J=23.6 Hz, 2H), 2.65 (s, 3H), 2.62 (s, 3H), 1.79-1.67 (m, 8H).

The examples in TABLE 6 are prepared from INTERMEDIATE H6 in a similar fashion to EXAMPLE 141; the initial coupling reaction can either be a tandem Miyaura-Suzuki with a bromide starting material, or a traditional Suzuki reaction with a boronic ester or acid starting material (like Intermediate M). In the case of EXAMPLE 142, the product of step 1 happens to be EXAMPLE 117.

TABLE 6

| Example | Structure | Name | MS(M + 1) |
|---|---|---|---|
| 142 | 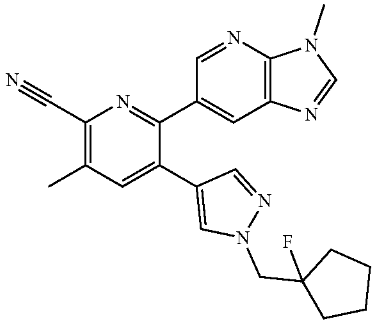 [SMILES: Cc1cc(-c2cnn(CC3(F)CCCC3)c2)c(-c2cnc3c(c2)ncn3C)nc1C#N] | 5-(1-((1-fluorocyclopentyl)methyl)-1H-pyrazol-4-yl)-3-methyl-6-(3-methyl-3H-imidazo[4,5-b]pyridin-6-yl)picolinonitrile | 416 |
| 143 | 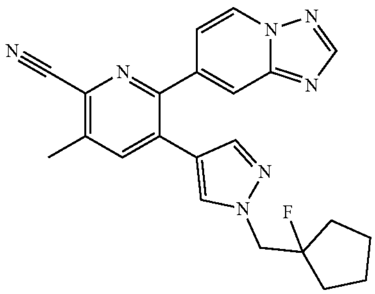 [SMILES: Cc1cc(-c2cnn(CC3(F)CCCC3)c2)c(-c2ccn3ncnc3c2)nc1C#N] | 6-([1,2,4]triazolo[1,5-a]pyridin-7-yl)-5-(1-((1-fluorocyclopentyl)methyl)-1H-pyrazol-4-yl)-3-methylpicolinonitrile | 402 |

Example 144

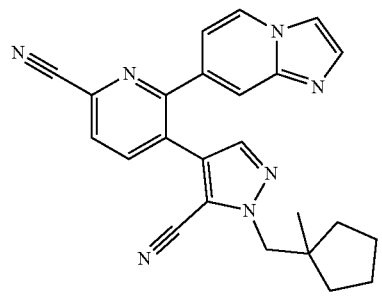 [SMILES: CC1(Cn2ncc(-c3ccc(C#N)nc3-c3ccn4ccnc4c3)c2C#N)CCCC1]

5-(5-cyano-1-((1-methylcyclopentyl)methyl)-1H-pyrazol-4-yl)-6-(imidazo[1,2-a]pyridin-7-yl)picolinonitrile A mixture of 5-(5-chloro-1-((1-methylcyclopentyl)methyl)-1H-pyrazol-4-yl)-6-(imidazo[1,2-a]pyridin-7-yl)picolinonitrile (EXAMPLE 81, 21 mg, 0.050 mmol), dicyanozinc (11.8 mg, 0.101 mmol) and Xphos G2 (4.0 mg, 5.04 µmol) in DMF (4 ml) was reacted at 200° C. under microwave irradiation for 30 minutes and concentrated. The residue was purified by column chromatography on silica gel, eluting with CH₂Cl₂/MeOH (20/1) to give the title compound. MS(M+1): 408; ¹H NMR (500 MHz, CDCl₃): δ 8.24 (d, 1H), 7.98 (d, 1H), 7.80 (d, 1H), 7.70 (s, 1H), 7.65 (s, 1H), 7.55 (d, 2H), 7.09 (d, 1H), 4.18 (s, 2H), 1.75-1.35 (m, 8H), 0.93 (s, 3H).

Example 145

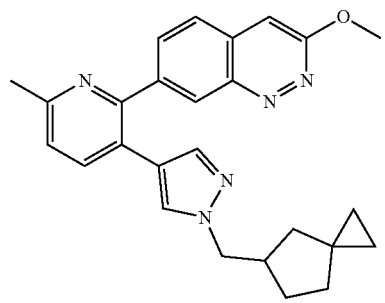

3-methoxy-7-(6-methyl-3-(1-(spiro[2.4]heptan-5-ylmethyl)-1H-pyrazol-4-yl)pyridin-2-yl)cinnoline Step 1: 3-methoxy-7-(6-methyl-3-(1H-pyrazol-4-yl)pyridin-2-yl)cinnoline A mixture of Na₂CO₃ (1.095 g, 10.33 mmol), 2-chloro-6-methyl-3-(1H-pyrazol-4-yl)pyridine (INTERMEDIATE E2, 2.00 g, 10.33 mmol), 3-methoxy-7-(4,4,5,5-tetramethyl-1,3,2-dioxaborolan-2-yl)cinnoline (INTERMEDIATE M8, 3.25 g, 11.36 mmol), PdCl₂(dppf) (0.756 g, 1.033 mmol) in THF (24 ml) and water (6 ml) was stirred at 100° C. overnight under nitrogen atmosphere. The reaction mixture was diluted with water and extracted with ethyl acetate. The organic layer was washed with brine, dried with Na₂SO₄, filtered and concentrated. The crude product was purified by silica gel chromatography (PE:EA=10: 1-0:1) to give the title compound. ¹H NMR (500 MHz, DMSO-d6): δ 12.83 (s, 1H), 8.25 (s, 1H), 7.84 (m, 2H), 7.64 (m, 1H), 7.57 (s, 1H), 7.32 (m, 1H), 7.19 (s, 1H), 4.14 (s, 3H), 2.52 (s, 3H).

Step 2: 3-methoxy-7-(6-methyl-3-(1-(spiro[2.4]heptan-5-ylmethyl)-1H-pyrazol-4-yl)pyridin-2-yl)cinnoline To a solution of 3-methoxy-7-(6-methyl-3-(1H-pyrazol-4-yl)pyridin-2-yl)cinnoline hydrochloride (46 mg, 0.130 mmol) in DMF (3 ml) was added $Cs_2CO_3$ (169 mg, 0.520 mmol) and spiro[2.4]heptan-5-ylmethyl 4-methylbenzenesulfonate (INTERMEDIATE A2, 43.7 mg, 0.156 mmol) at 60° C. The mixture was stirred at 60° C. for 1.5 hours. The mixture was diluted with water (30 mL) and extracted with EtOAc (50 mL×2). The combined organic layers were washed with brine (50 mL), dried over $MgSO_4$, filtered, and the filtrate was concentrated in vacuo. The residue was purified by preparative HPLC (C18, 5-95% $CH_3CN$/water (0.1% $NH_4OH$) to give the title compound. MS(M+1): 426; $^1$H NMR (500 MHz, $CD_3OD$): δ 8.08 (s, 1H), 7.66 (m, 2H), 7.47 (d, J=8.4 Hz, 1H), 7.39 (s, 1H), 7.18 (m, 2H), 7.06 (s, 1H), 4.03 (s, 3H), 3.73 (m, 2H), 2.41 (s, 3H), 2.21 (m, 1H), 1.41 (m, 1H), 1.24 (m, 2H), 1.06 (m, 2H), 0.89 (m, 1H), 0.14-0.01 (m, 4H).

EXAMPLE 146 in Table 7 was prepared by the same two step sequence utilizing 1,1'-bis(di-tert-butylphosphino)ferrocene palladium dichloride and $K_2CO_3$ with INTERMEDIATE E3 and 7-(4,4,5,5-tetramethyl-1,3,2-dioxaborolan-2-yl)quinoline for the Suzuki coupling to give the C-2 functionalized compound, followed by NaH alkylation of the pyrazole with INTERMEDIATE A7 to give the diastereomeric mixture. Chiral SFC (Chiralpak AD-H 250×4.6 mm I.D., 5 um Mobile phase: methanol (0.05% DEA) in $CO_2$ from 5% to 40%) provided the single diastereomer as the later eluting peak.

7-(3-(1-(cyclopentylmethyl)-1H-pyrazol-4-yl)pyridin-2-yl)quinoline

Step 1: 2-chloro-3-(1-(4-methoxybenzyl)-1H-pyrazol-4-yl)pyridine

2-Chloro-3-(1H-pyrazol-4-yl)pyridine (INTERMEDIATE E1, 100 mg, 0.557 mmol) was dissolved in DMF (1 mL) and treated sequentially with potassium carbonate (115 mg, 0.835 mmol) and 4-methoxybenzyl chloride (91 μL, 0.668 mmol). Stirred at 40° C. for 3 hours, then allowed to stand at ambient temperature overnight. Added 6 ml ethyl acetate and 3 ml water and partitioned the resulting layers. The aqueous was back extracted with 2 ml ethyl acetate. The combined extracts were washed with 2 ml brine, dried over $MgSO_4$, filtered and evaporated in vacuo. Purified by silica gel chromatography eluting with 0-10% EtOAc/DCM to give the title compound. MS(M+1): 300.

Step 2: 7-(3-(1-(4-methoxybenzyl)-1H-pyrazol-4-yl)pyridin-2-yl)quinoline 2-chloro-3-(1-(4-methoxybenzyl)-1H-pyrazol-4-yl)pyridine (100 mg, 0.334 mmol), quinolin-7-ylboronic acid (69.2 mg, 0.400 mmol) and 1,1'-bis(di-tert-butylphosphino)ferrocene palladium dichloride (21.7 mg, 0.033 mmol) were combined in 1 ml THF and purged with nitrogen bubbling for 2 minutes. Added 2.0 M aqueous sodium carbonate (0.25 mL, 0.500 mmol), then heated to 65° C. for 18 hours. Diluted with 5 ml ethyl acetate and washed with 2 ml water and then 2 ml brine. Dried over $MgSO_4$, filtered and evaporated in vacuo. Purified by silica gel chromatography

TABLE 7

| Example | Structure | Name | MS(M + 1) |
|---|---|---|---|
| 146 | 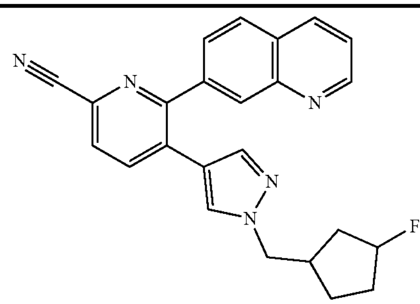 | 5-(1-(((1R,3S) or (1S,3R)-3-fluorocyclopentyl)methyl)-1H-pyrazol-4-yl)-6-(quinolin-7-yl)picolinonitrile | 398 |

Example 147

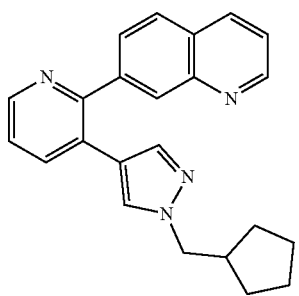 [SMILES: c1cnc(-c2ccc3cccnc3c2)c(-c2cnn(CC3CCCC3)c2)c1]

eluting with 20-100% EtOAc/hexanes for 10 minutes and then 100% EtOAc until the peak eluted to give the title compound. MS(M+1): 393.

Step 3: 7-(3-(1H-pyrazol-4-yl)pyridin-2-yl)quinoline 7-(3-(1-(4-methoxybenzyl)-1H-pyrazol-4-yl)pyridin-2-yl)quinoline (84 mg, 0.214 mmol) was dissolved in TFA (2 mL, 26 mmol) and allowed to stand at room temperature for 2 hours. LC-MS shows no desired product. Heated to 60° C. for 5 hours, after which LC-MS indicates reaction is substantially complete. The TFA was evaporated and the crude was purified by silica gel chromatography eluting with 0-10% aq $NH_4OH/CH_3CN$ to give the title compound. MS(M+1): 273.

Step 4: 7-(3-(1-(cyclopentylmethyl)-1H-pyrazol-4-yl)pyridin-2-yl)quinoline

Combined 7-(3-(1H-pyrazol-4-yl)pyridin-2-yl)quinoline (50 mg, 0.184 mmol), triphenylphosphine (72.2 mg, 0.275 mmol) and cyclopentylmethanol (36.8 mg, 0.367 mmol) in THF (1 mL), purged with nitrogen and then treated with DIAD (54 mL, 0.275 mmol). The reaction was heated to 65° C. for 1.5 hours. The reaction was concentrated in vacuo and purified by Prep HPLC (C18, eluting with 10-90% water/CH$_3$CN with 0.1% TFA. Desired fraction was lyophilized overnight to give the titled compound. $^1$H NMR (CDCl$_3$, 400 MHz): δ 9.26 (dd, J=5, 1.5 Hz, 1H), 8.80 (m, 1H), 8.73 (d, J=8.4 Hz, 1H), 8.58 (s, 1H), 8.07 (m, 2H), 7.89 (m, 2H), 7.64 (m, 1H), 7.26 (s, m, CHCl3+1H), 7.22 (s, 1H), 3.93 (d, J=7.5 Hz, 2H), 2.29 (m, 1H), 1.60-1.47 (m, 6H), 1.08 (m, 2H).

Example 148

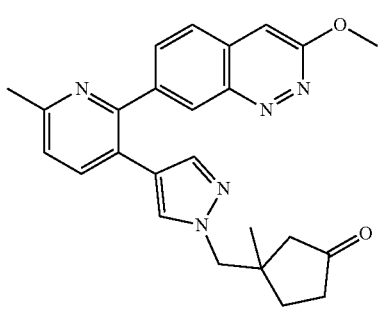

(S or R)-3-((4-(2-(3-methoxycinnolin-7-yl)-6-methylpyridin-3-yl)-1H-pyrazol-1-yl)methyl)-3-methyl-cyclopentan-1-one Step 1: 3-methoxy-7-(6-methyl-3-(1-(((2S,3 S)-7-methyl-2,3-diphenyl-1,4-dioxaspiro[4.4]nonan-7-yl)methyl)-1H-pyrazol-4-yl)pyridin-2-yl)cinnoline isomer B A mixture of 3-methoxy-7-(6-methyl-3-(1H-pyrazol-4-yl)pyridin-2-yl)cinnoline (100 mg, 0.315 mmol), (2S,3 S)-7-(iodomethyl)-7-methyl-2,3-diphenyl-1,4-dioxaspiro[4.4]nonane isomer B (INTERMEDIATE W2, 137 mg, 0.315 mmol), and cesium carbonate (257 mg, 0.788 mmol) in DMF (5 ml) was stirred at 100° C. for 1 hour. It was partitioned between EtOAc and water. The organic layer was dried over sodium sulfate, filtered and the filtrate evaporated. The crude was purified by silica gel chromatography, eluting with 60% EtOAc in hexanes to get the title compound. MS(M+1): 624

Step 2: (S or R)-3-((4-(2-(3-methoxycinnolin-7-yl)-6-methylpyridin-3-yl)-1H-pyrazol-1-yl)methyl)-3-methylcyclopentan-1-one 3-methoxy-7-(6-methyl-3-(1-(((2S,3 S)-7-methyl-2,3-diphenyl-1,4-dioxaspiro[4.4]nonan-7-yl)methyl)-1H-pyrazol-4-yl)pyridin-2-yl)cinnoline isomer B (161 mg, 0.258 mmol) was dissolved in 10 mL of MeOH. Then 10 mL of aqueous 3 N HCl was added. The reaction solution was stirred at 50° C. for 1 hour. The reaction was carefully quenched with saturated NaHCO$_3$ (CAUTION GAS EVOLUTION) and EtOAc. The organic layer was dried over sodium sulfate, filtered and the filtrate evaporated. The crude was purified by silica gel chromatography, eluting with 10% MeOH in DCM to get the title compound. MS (M+1): 428; $^1$H NMR (CDCl$_3$, 500 MHz): δ 8.53 (d, J=1.0 Hz, 1H), 7.73 (d, J=8.5 Hz, 1H), 7.66 (s, 2H), 7.44 (s, 1H), 7.29-7.27 (m, 2H), 6.96 (s, 1H), 4.34 (s, 3H), 3.91 (s, 2H), 2.70 (s, 3H), 2.28-2.08 (m, 3H), 1.92 (d, 18.0 Hz, 1H), 1.83 (m, 1H), 1.62 (m, 1H), 0.93 (s, 3H).

INTERMEDIATE W1 was subjected to steps 1 and 2 above to give the example shown in Table 8.

TABLE 8

| Example | Structure | Name | MS(M + 1) |
|---|---|---|---|
| 149 | 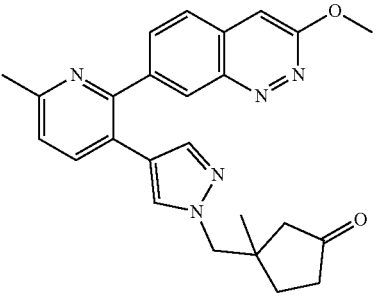 | (R or S)-3-((4-(2-(3-methoxycinnolin-7-yl)-6-methylpyridin-3-yl)-1H-pyrazol-1-yl)methyl)-3-methylcyclopentan-1-one | 428 |

Example 150

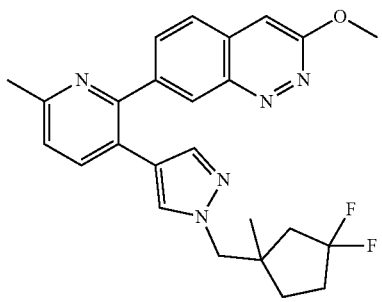

(R or S)-7-(3-(1-((3,3-difluoro-1-methylcyclopentyl)methyl)-1H-pyrazol-4-yl)-6-methylpyridin-2-yl)-3-methoxycinnoline 3-((4-(2-(3-methoxycinnolin-7-yl)-6-methylpyridin-3-yl)-1H-pyrazol-1-yl)methyl)-3-methylcyclopentan-1-one isomer A (EXAMPLE 149, 101 mg, 0.236 mmol) was dissolved in 4 mL of DCM. It was then treated with DAST (311 μL, 2.36 mmol) and heated to 40° C. for 24 hours. The reaction was worked up with saturated aqueous NaHCO$_3$ at 0° C. (CAUTION GAS EVOLUTION). The organic layer was dried over Na$_2$SO$_4$, filtered, and the filtrate evaporated. The crude was purified by silica gel chromatography, eluting with 70% EtOAc in hexanes to give the title compound. MS (M+1): 450; $^1$H NMR (CDCl$_3$, 500 MHz): δ 8.53 (s, 1H), 7.73 (d, J=8.0 Hz, 1H), 7.65 (m, 2H), 7.34 (s, 1H), 7.26 (d, J=8.0 Hz, 1H), 7.25 (s, 1H), 6.94 (s, 1H), 4.33 (s, 3H), 3.88 (m, 2H), 2.69 (s, 3H), 2.17-2.00 (m, 3H), 1.79-1.70 (m, 2H), 1.47 (m, 1H), 0.93 (s, 3H).

(S or R)-3-((4-(2-(3-methoxycinnolin-7-yl)-6-methylpyridin-3-yl)-1H-pyrazol-1-yl)methyl)-3-methylcyclopentan-1-one isomer B (EXAMPLE 148) was treated in the same fashion as EXAMPLE 149 above to give the product in Table 9.

Example 152

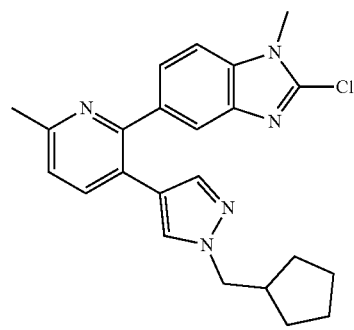 [SMILES: Cc1ccc(-c2cnn(CC3CCCC3)c2)c(-c2ccc3c(c2)nc(Cl)n3C)n1]

2-chloro-5-(3-(1-(cyclopentylmethyl)-1H-pyrazol-4-yl)-6-methylpyridin-2-yl)-1-methyl-1H-benzo[d]imidazole A solution of 6-(3-(1-(cyclopentylmethyl)-1H-pyrazol-4-yl)-6-methylpyridin-2-yl)-3-methyl-3H-imidazo[4,5-b]pyridine (EXAMPLE 7, 1.0 g, 2.68 mmol) in THF (27 ml), was stirred at room temperature. To this solution was added NCS (0.448 g, 3.36 mmol), after which the reaction was cooled to 0° C. Then 1.0M lithium bis(trimethylsilyl)amide in THF (6.71 ml, 6.71 mmol) was added dropwise. The resulting mixture was allowed to slowly reach room temperature, and at 6 hours an additional 200 mg NCS and 3 ml of 1.0M lithium bis(trimethylsilyl)amide was added in and stirred overnight. Aqueous NaHCO$_3$ solution was added to quench the reaction, which was then extracted by EtOAc. The organic solution was washed with brine, dried over Na$_2$SO$_4$, filtered and the filtrate concentrated. The crude was purified by silica gel chromatography, eluting with 0 to 8% MeOH in DCM. The product containing fractions were concentrated and then dissolved in 35% EtOAc in hexane, concentrated to give the title compound. MS(M+1): 407.

TABLE 9

| Example | Structure | Name | MS(M + 1) |
|---|---|---|---|
| 151 | 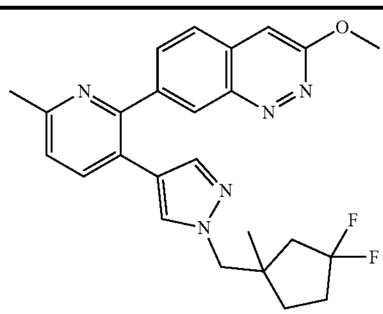 | (S or R)-7-(3-(1-((3,3-difluoro-1-methylcyclopentyl)methyl)-1H-pyrazol-4-yl)-6-methylpyridin-2-yl)-3-methoxycinnoline isomer B | 450 |

Example 153

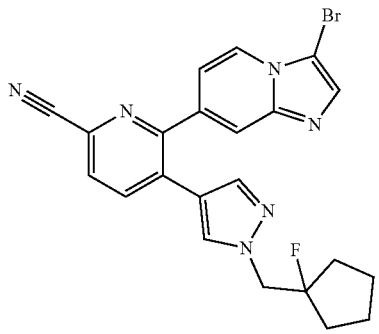 [SMILES: N#Cc1ccc(-c2cnn(CC3(F)CCCC3)c2)c(-c2ccn3c(Br)cnc3c2)n1]

6-(3-bromoimidazo[1,2-a]pyridin-7-yl)-5-(1-((1-fluorocyclopentyl)methyl)-1H-pyrazol-4-yl)picolinonitrile NBS (36.9 mg, 0.208 mmol) was added to a stirred mixture of 5-(1-((1-fluorocyclopentyl)methyl)-1H-pyrazol-4-yl)-6-(indolizin-7-yl)picolinonitrile (EXAMPLE 50, 40 mg, 0.104 mmol) in CH$_3$CN (4 ml) at 20° C. and the mixture was stirred at 70° C. for 1 hour. The mixture was filtered and the filtrate was concentrated to dryness. The residue was purified by preparative HPLC (reverse phase C-18 column), eluting with acetonitrile/water modified with 0.1% TFA, to give the title compound.

MS(M+1): 465, 467; $^1$H NMR (CDCl$_3$, 400 MHz): δ 8.25 (m, 1H), 7.94 (d, J=8.0 Hz, 1H), 7.85 (s, 1H), 7.76 (d, J=8.4 Hz, 1H), 7.38 (m, 3H), 4.32 (d, J=22.4 Hz, 2H), 1.75 (m, 8H).

Example 154

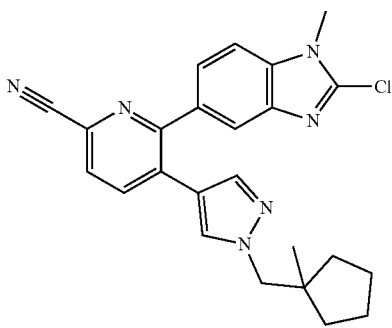 [SMILES: Cn1c(Cl)nc2cc(-c3nc(C#N)ccc3-c3cnn(CC4(C)CCCC4)c3)ccc21]

6-(2-chloro-1-methyl-1H-benzo[d]imidazol-5-yl)-5-(1-((1-methylcyclopentyl)methyl)-1H-pyrazol-4-yl)picolinonitrile Step 1: 6-(3-methyl-2-oxo-2,3-dihydro-1H-imidazo[4,5-b]pyridin-6-yl)-5-(1-((1-methylcyclopentyl)methyl)-1H-pyrazol-4-yl)picolinonitrile To a solution of 6-bromo-3-methyl-1H-imidazo[4,5-b]pyridin-2(3H)-one (CA, 30 mg, 0.132 mmol) and bis(pinacolato)diboron (40.1 mg, 0.158 mmol) in 1,4-dioxane (3 ml) were added potassium acetate (32.3 mg, 0.329 mmol) and PdCl$_2$(dppf) (19.25 mg, 0.026 mmol) under N$_2$. The reaction mixture was stirred at 70° C. for 2 hours. Then tripotassium phosphate trihydrate (52.6 mg, 0.197 mmol), 6-chloro-5-(1-((1-methylcyclopentyl)methyl)-1H-pyrazol-4-yl)picolinonitrile (INTERMEDIATE H1, 39.6 mg, 0.132 mmol) and water (0.7 ml) were added. The reaction mixture was stirred at 70° C. for 12 hours. The reaction mixture was diluted with water (50 mL) and extracted with EtOAc (30 mL×3). The combined organic layers were washed with brine (10 mL), dried over Na$_2$SO$_4$, filtered and the filtrate was concentrated in vacuo. The residue was purified by prep-TLC (SiO$_2$, 50% EtOAc in petroleum ether) to give the title compound. MS (M+H): 414.2.

Step 2: 6-(2-chloro-1-methyl-1H-benzo[d]imidazol-5-yl)-5-(1-((1-methylcyclopentyl)methyl)-1H-pyrazol-4-yl)picolinonitrile A solution of 6-(3-methyl-2-oxo-2,3-dihydro-1H-imidazo[4,5-b]pyridin-6-yl)-5-(1-((1-methylcyclopentyl)methyl)-1H-pyrazol-4-yl)picolinonitrile (30 mg, 0.073 mmol) in POCl$_3$ (2 ml, excess) was stirred at 80° C. for 13 hours and 90° C. for 3 additional hours. The reaction was then concentrated in vacuo. The residue was purified by preparative HPLC (CH$_3$CN/water with 0.1% TFA) to give the title compound. MS(M+H): 432; $^1$H NMR (CD$_3$OD, 400 MHz): δ 8.42 (s, 1H), 8.11 (d, J=7.6 Hz, 1H), 8.01 (s, 1H), 7.88 (d, J=7.6 Hz, 1H), 7.70-7.50 (m, 2H), 7.41 (s, 1H), 7.27 (s, 1H), 3.89 (s, 5H), 1.57-1.15 (m, 8H), 0.76 (s, 3H).

Example 155

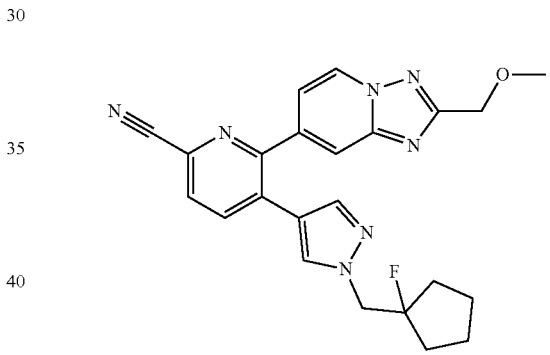

5-(1-((1-fluorocyclopentyl)methyl)-1H-pyrazol-4-yl)-6-(2-(methoxymethyl)-[1,2,4]triazolo[1,5-a]pyridin-7-yl)picolinonitrile 5-(1-((1-fluorocyclopentyl)methyl)-1H-pyrazol-4-yl)-6-(2-(hydroxymethyl)-[1,2,4]triazolo[1,5-a]pyridin-7-yl)picolinonitrile (EXAMPLE 66, 39 mg, 0.093 mmol) was dissolved in THF (1 ml) and cooled to 0° C. under a nitrogen atmosphere. Sodium hydride (4.5 mg, 0.112 mmol) was added, then after 2 minutes iodomethane (8.8 µl, 0.140 mmol) was added. The reaction was heated to 35° C. for 1 hour. Quenched with aqueous NH$_4$Cl, diluted with water and extracted twice with ethyl acetate. Filtered the organic over a bed of Na$_2$SO$_4$ and evaporated the filtrate. The crude isolate was purified on by silica gel chromatography, eluting with a gradient of 20-80% 3:1 EtOAc:EtOH in hexanes to give the title compound. MS(M+1): 432; $^1$H NMR (CDCl$_3$, 500 MHz): δ 8.55 (d, J=7.1 Hz, 1H), 7.94 (d, J=8 Hz, 1H), 7.84 (s, 1H), 7.76 (d, J=8 Hz, 1H), 7.42 (s, 1H), 7.31 (s, 1H), 7.11 (d, J=8.7 Hz, 1H), 4.78 (s, 2H), 4.29 (d, J=22 Hz, 2H), 3.57 (s, 3H), 1.80-1.50 (m, 8H).

EXAMPLE 82 was treated in a similar fashion as EXAMPLE 66 above to give the product shown in Table 11.

TABLE 11

| Example | Structure | Name | MS(M + 1) |
|---|---|---|---|
| 156 | 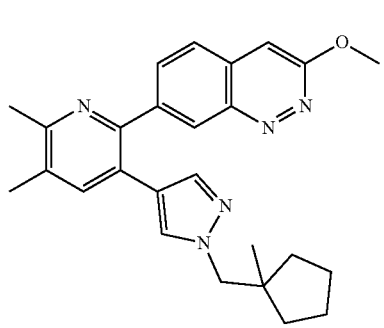 | 6-(2-(methoxymethyl)imidazo[1,2-a]pyridin-7-yl)-5-(1-((1-methylcyclopentyl)methyl)-1H-pyrazol-4-yl)picolinonitrile | 427 |

Example 157

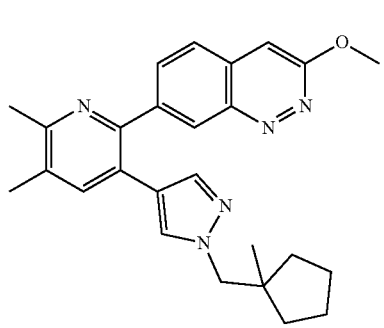

7-(5,6-dimethyl-3-(1-((1-methylcyclopentyl)methyl)-1H-pyrazol-4-yl)pyridin-2-yl)-3-methoxycinnoline 2,4,6-trimethyl-1,3,5,2,4,6-trioxatriborinane (5.7 mg, 0.046 mmol), 7-(6-chloro-5-methyl-3-(1-((1-methylcyclopentyl)methyl)-1H-pyrazol-4-yl)pyridin-2-yl)-3-methoxycinnoline (EXAMPLE 119, 0.017 g, 0.038 mmol) and 1,1'-bis(di-tert-butylphosphino)ferrocene palladium dichloride (2.5 mg, 3.79 µmol) were placed in a 4 mL reaction vial and evacuated and charged with nitrogen. Added 1,4-dioxane (1 ml) and 1M aqueous potassium carbonate (0.114 ml, 0.114 mmol) to the sealed vial and heated to 80° C. After 2 hours the reaction mixture was diluted with water (10 mL) and extracted with EtOAc (10 mL×3). The combined organic layers were washed with brine (10 mL), dried over $Na_2SO_4$, filtered and the filtrate was concentrated in vacuo. The crude was purified by prep HPLC (C18 column, 32-72% $CH_3CN$/water modified to pH 10 with $NH_4OH$) to give the title compound. MS(M+1): 428; $^1H$ NMR ($CDCl_3$, 500 MHz): δ 8.55 (s, 1H), 7.63 (s, 2H), 7.58 (s, 1H), 7.40 (s, 1H), 7.21 (s, 1H), 6.92 (s, 1H), 4.35 (s, 3H), 3.81 (s, 2H), 2.62 (s, 3H), 2.40 (s, 3H), 1.80-1.10 (m, 8H), 0.77 (s, 3H).

Example 158

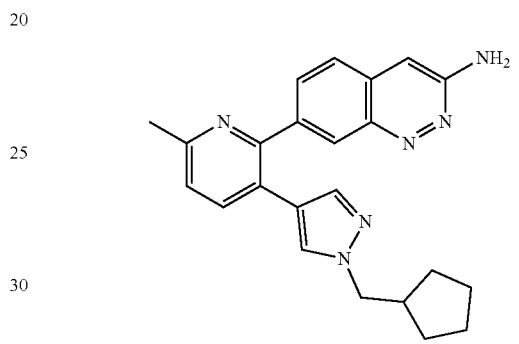

7-(3-(1-(cyclopentylmethyl)-1H-pyrazol-4-yl)-6-methylpyridin-2-yl)cinnolin-3-amine Step 1: 7-(3-(1-(cyclopentylmethyl)-1H-pyrazol-4-yl)-6-methylpyridin-2-yl)-N-(4-methoxybenzyl)cinnolin-3-amine 3-chloro-7-(3-(1-(cyclopentylmethyl)-1H-pyrazol-4-yl)-6-methylpyridin-2-yl)cinnoline (INTERMEDIATE Y1, 0.040 g, 0.099 mmol), cesium carbonate (0.129 g, 0.396 mmol), (RuPhos) palladium (II) phenethylamine chloride (7.2 mg, 9.90 µmol), and (4-methoxyphenyl)methanamine (0.014 g, 0.099 mmol) were added to a vial. t-Butanol (2 ml) was added followed by purging with nitrogen. The reaction was heated to 100° C. for 8 hours, then cooled to room temperature and filtered over a pad of celite. Washed the celite pad with EtOAc and the combined filtrates were evaporated to dryness. The crude isolate was purified on by silica gel chromatography, eluting with a gradient from 0-100% ethyl acetate in hexanes to provide the title compound. MS(M+1): 505.

Step 2: 7-(3-(1-(cyclopentylmethyl)-1H-pyrazol-4-yl)-6-methylpyridin-2-yl)cinnolin-3-amine 7-(3-(1-(cyclopentylmethyl)-1H-pyrazol-4-yl)-6-methylpyridin-2-yl)-N-(4-methoxybenzyl)cinnolin-3-amine (0.038 g, 0.075 mmol) was dissolved in DCE (0.375 ml) and stirred at room temperature. Trifluoroacetic acid (0.225 ml, 3.01 mmol) was added dropwise to the solution, which was then stirred at room temperature for 12 hours. The solution was evaporated to provide a dark oil which was dissolved in 1 ml of DMF and purified by prep HPLC (C18 column, 10-95% CH₃CN/water modified to pH 10 with NH₄OH) to give the title compound. MS(M+1): 385; ¹H NMR (CDCl₃, 500 MHz): δ 8.44 (s, 1H), 7.70 (d, J=8 Hz, 1H), 7.56 (d, J=8 Hz, 1H), 7.48 (d, J=8 Hz, 1H), 7.39 (s, 1H), 7.21 (d, J=8 Hz, 1H), 6.94 (s, 1H), 6.91 (s, 1H), 4.90 (s, 2H), 3.85 (d, J=20 Hz, 2H), 2.62 (s, 3H), 2.40 (s, 3H), 2.24 (m, 1H), 1.53 (m, 8H).

Example 159

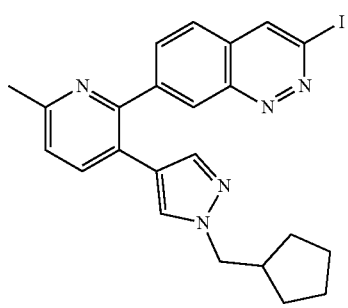 [SMILES: Cc1ccc(-c2cnn(CC3CCCC3)c2)c(-c2ccc3cc(I)nnc3c2)n1]

7-(3-(1-(cyclopentylmethyl)-1H-pyrazol-4-yl)-6-methylpyridin-2-yl)-3-iodocinnoline Step 1: 7-(3-(1-(cyclopentylmethyl)-1H-pyrazol-4-yl)-6-methylpyridin-2-yl)-3-(tributyl stannyl)cinnoline 3-Chloro-7-(3-(1-(cyclopentylmethyl)-1H-pyrazol-4-yl)-6-methylpyridin-2-yl)cinnoline (INTERMEDIATE Y1; 0.050 g, 0.124 mmol), hexabutylditin (0.069 ml, 0.136 mmol) and tetrakis(triphenylphosphine)palladium (0) (0.014 g, 0.012 mmol) were added to a vial. Dioxane (0.620 ml) was then added and nitrogen was bubbled through the solution. The vial was capped and heated to 110° C. until consumption of the chlorocinnoline was observed. The vial was cooled to room temperature and filtered over a pad of celite, washed with EtOAc (10 ml) and the combined filtrates evaporated. The crude isolate was purified on by silica gel chromatography, eluting with a gradient from 0-100% ethyl acetate in hexanes to provide the title compound. MS(M+18): 676.

Step 2: 7-(3-(1-(cyclopentylmethyl)-1H-pyrazol-4-yl)-6-methylpyridin-2-yl)-3-iodocinnoline 7-(3-(1-(cyclopentylmethyl)-1H-pyrazol-4-yl)-6-methylpyridin-2-yl)-3-(tributylstannyl)cinnoline (0.034 g, 0.052 mmol) was dissolved in DCM (0.258 ml). Iodine (0.052 g, 0.207 mmol) was than added and stirred at room temperature. Once reaction was complete the volatiles were evaporated.

The crude was purified directly by prep HPLC (C18 column, 10-95% CH₃CN/water (0.1% TFA)) to give the title compound. MS(M+1): 496.

Example 160

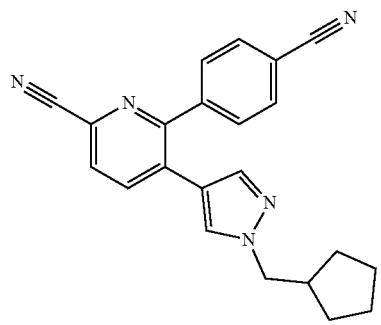 [SMILES: N#Cc1ccc(-c2nc(C#N)ccc2-c2cnn(CC3CCCC3)c2)cc1]

6-(4-cyanophenyl)-5-(1-(cyclopentylmethyl)-1H-pyrazol-4-yl)picolinonitrile

Step 1: 6-(4-cyanophenyl)-5-(1-(cyclopentylmethyl)-1H-pyrazol-4-yl)picolinic acid A mixture of methyl 6-chloro-5-(1-(cyclopentylmethyl)-1H-pyrazol-4-yl)picolinate (INTERMEDIATE H14, 200 mg, 0.625 mmol), (4-cyanophenyl)boronic acid (110 mg, 0.751 mmol), potassium phosphate (1.9 ml, 1.876 mmol) (1 M in water) and 1,1'-bis(di-tert-butylphosphino)ferrocene palladium dichloride (20.4 mg, 0.031 mmol) in dioxane (4 ml) was stirred at 100° C. under N₂ atmosphere overnight. Solvent was then evaporated to near dryness and the residue was partitioned between DCM (30 mL) and water (30 mL). The aqueous layer was adjusted to pH=3 with 2 M HCl, and was extracted with DCM (30 mL) twice. The combined organic layers were dried over anhydrous Na₂SO₄, and concentrated in vacuo to give the title compound. ¹H NMR (CDCl₃, 400 MHz): δ 8.25 (d, J=8 Hz, 1H), 8.03 (d, J=8 Hz, 1H), 7.71 (d, J=8 Hz, 2H), 7.59 (d, J=8 Hz, 2H), 7.38 (s, 1H), 7.01 (s, 1H), 3.95 (d, J=7.8 Hz, 2H), 2.33 (m, 1H), 1.63 (m, 6H), 1.15 (m, 2H).

Step 2: 6-(4-cyanophenyl)-5-(1-(cyclopentylmethyl)-1H-pyrazol-4-yl)picolinamide

The mixture of 6-(4-cyanophenyl)-5-(1-(cyclopentylmethyl)-1H-pyrazol-4-yl)picolinic acid (300 mg, 0.806 mmol), ammonium chloride (215 mg, 4.03 mmol), HATU (613 mg, 1.611 mmol) and Et₃N (0.561 ml, 4.03 mmol) in DMF (3 ml) was stirred at 50° C. for 4 hours. The mixture was then partitioned between DCM (30 mL) and water (30 mL). The aqueous layer was extracted with DCM (30 mL) twice. The combined organic layers were dried over anhydrous Na₂SO₄, and concentrated in vacuo. The crude product was purified by flash chromatography on silica gel (EtOAc) to give the title compound. ¹H NMR (CDCl₃, 400 MHz): δ 8.23 (d, J=8 Hz, 1H), 7.95 (d, J=8 Hz, 1H), 7.77 (br s, 1H), 7.68 (d, J=8.8 Hz, 2H), 7.59 (d, J=8.8 Hz, 2H), 7.35 (s, 1H), 7.00 (s, 1H), 5.62 (br s, 1H), 3.95 (d, J=7.6 Hz, 2H), 2.34 (m, 1H), 1.60 (m, 6H), 1.16 (m, 2H).

Step 3: 6-(4-cyanophenyl)-5-(1-(cyclopentylmethyl)-1H-pyrazol-4-yl)picolinonitrile The mixture of 6-(4-cyanophenyl)-5-(1-(cyclopentylmethyl)-1H-pyrazol-4-yl)picolinamide (80 mg, 0.215 mmol), trifluoroacetic anhydride (0.061 ml, 0.431 mmol) and Et₃N (0.090 ml, 0.646 mmol) in THF (3 ml) was stirred at 25° C. for 1 h. The mixture was partitioned between DCM (30 mL) and water (30 mL), and the aqueous layer was extracted with DCM (30 mL) twice. The combined organic layers were dried over anhydrous Na$_2$SO$_4$, and concentrated in vacuo. The crude was purified by prep HPLC (C18 column, 10-95% CH$_3$CN/water 0.1% TFA) to give the title compound. MS(M+1): 354; $^1$H NMR (CDCl$_3$, 400 MHz): δ 7.91 (d, J=8 Hz, 1H), 7.71 (m, 3H), 7.59 (d, J=8 Hz, 2H), 7.40 (s, 1H), 6.97 (s, 1H), 3.95 (d, J=7.6 Hz, 2H), 2.31 (m, 1H), 1.60 (m, 6H), 1.15 (m, 2H).

Example 161

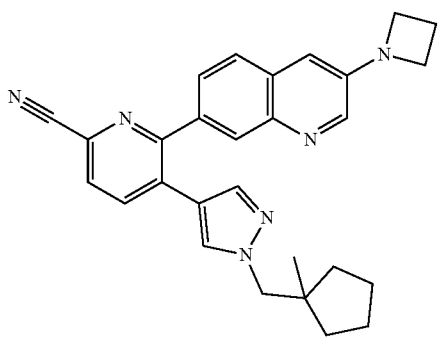 [SMILES: CC1(Cn2cc(-c3ccc(C#N)nc3-c3ccc4cc(N5CCC5)cnc4c3)cn2)CCCC1]

6-(3-(azetidin-1-yl)Quinolin-7-yl)-5-(1-((1-methylcyclopentyl)methyl)-1H-pyrazol-4-yl)picolinonitrile Step 1: 6-(3-chloroquinolin-7-yl)-5-(1-((1-methylcyclopentyl)methyl)-1H-pyrazol-4-yl)picolinonitrile To a solution of 6-chloro-5-(1-((1-methylcyclopentyl)methyl)-1H-pyrazol-4-yl)picolinonitrile (INTERMEDIATE H1, 300 mg, 0.997 mmol) in THF (5 ml) and water (1 ml) were added 3-chloro-7-(4,4,5,5-tetramethyl-1,3,2-dioxaborolan-2-yl)quinoline (INTERMEDIATE M24, 347 mg, 1.197 mmol), K$_3$PO$_4$ (529 mg, 2.493 mmol), and PdCl$_2$(dppf) (73.0 mg, 0.100 mmol) under nitrogen. The reaction mixture was stirred at 80° C. for 1 hour. After cooling to room temperature, the reaction mixture was diluted with water (50 mL) and extracted with EtOAc (30 mL×3). The combined organic layers were dried over MgSO$_4$, filtered and concentrated in vacuo. The crude was purified by prep HPLC (C18 column, 10-95% CH$_3$CN/water (pH 10 NH$_4$OH)) to give the title compound. MS(M+H) 428.

Step 2: 6-(3-(azetidin-1-yl)Quinolin-7-yl)-5-(1-((1-methylcyclopentyl)methyl)-1H-pyrazol-4-yl)picolinamide To a solution of 6-(3-chloroquinolin-7-yl)-5-(1-((1-methylcyclopentyl)methyl)-1H-pyrazol-4-yl)picolinonitrile (301 mg, 0.703 mmol) in THF (4 ml) were added chloro(2-dicyclohexylphosphino-2',6'-di-isopropoxy-1,1'-biphenyl)[2-(2-aminoethylphenyl)]palladium(II), methyl-tert-butylether adduct (86 mg, 0.106 mmol) and azetidine hydrochloride (79 mg, 0.844 mmol) under nitrogen. The reaction mixture was stirred at 25° C. for 10 minutes, then was added sodium t-butoxide (1.407 ml, 2.81 mmol) at 0° C. for 10 minutes. The reaction mixture was stirred at 50° C. for 3 hours. The reaction mixture was then diluted with water (50 mL) and extracted with EtOAc (30 mL×3). The combined organic layers were dried over MgSO$_4$, filtered and concentrated in vacuo to give the title compound, which was used in the next step without further purification. MS(M+H) 467.

Step 3: 6-(3-(azetidin-1-yl)quinolin-7-yl)-5-(1-((1-methylcyclopentyl)methyl)-1H-pyrazol-4-yl)picolinonitrile To a solution of 6-(3-(azetidin-1-yl)quinolin-7-yl)-5-(1-((1-methylcyclopentyl)methyl)-1H-pyrazol-4-yl)picolinamide (210 mg, 0.450 mmol) in DCM (5 ml) was added Et$_3$N (0.941 ml, 6.75 mmol) and 2,2,2-trifluoroacetic anhydride (851 mg, 4.05 mmol) dropwise at 0° C. for 1.5 hours. The reaction mixture was then diluted with water (10 mL) and extracted with EtOAc (30 mL×3). The combined organic layers were dried over MgSO$_4$, filtered and concentrated in vacuo. The crude was purified by prep HPLC (C18 column, 10-95% CH$_3$CN/water pH 10 NH$_4$OH) to give the title compound. MS(M+H) 449; $^1$H NMR (CD$_3$OD, 400 MHz): δ 8.28 (d, J=2.4 Hz, 1H), 8.13 (d, J=8 Hz, 1H), 7.90 (s, 1H), 7.86 (d, J=8 Hz, 1H), 7.74 (d, J=8.8 Hz, 1H), 7.47 (m, 2H), 7.18 (s, 1H), 7.10 (s, 1H), 4.09 (t, J=7.6 Hz, 4H), 3.83 (s, 2H), 2.51 (m, 2H), 1.50 (m, 4H), 1.31 (m, 2H), 1.07 (m, 2H), 0.71 (s, 3H).

Example 162

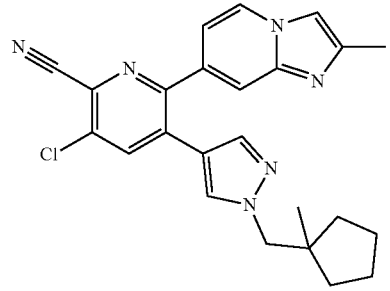

3-chloro-5-(1-((1-methylcyclopentyl)methyl)-1H-pyrazol-4-yl)-6-(2-methylimidazo[1,2-a]pyridin-7-yl)picolinonitrile Step 1: 3-amino-5-(1-((1-methylcyclopentyl)methyl)-1H-pyrazol-4-yl)-6-(2-methylimidazo[1,2-a]pyridin-7-yl)picolinonitrile To a solution of 7-bromo-2-methylimidazo[1,2-a]pyridine (50 mg, 0.237 mmol), bis(pinacolato)diboron (78 mg, 0.308 mmol) and potassium acetate (69.8 mg, 0.711 mmol) in 1,4-dioxane (1 mL) was added [1,1'-bis(diphenylphosphino)ferrocene]dichloropalladium(II) (8.7 mg, 0.012 mmol) under nitrogen atmosphere. Then the mixture was stirred at 60° C. for 1h. Then the mixture was added 3-amino-6-chloro-5-(1-((1-methylcyclopentyl)methyl)-1H-pyrazol-4-yl)picolinonitrile (INTERMEDIATE H9, 25 mg, 0.079 mmol), K$_3$PO$_4$.3H$_2$O (189 mg, 0.711 mmol), 1,1'-bis(di-tert-butylphosphino)ferrocene palladium dichloride (7.72 mg, 0.012 mmol) under nitrogen atmosphere. Then the mixture was stirred at 60° C. for 12 hours. The mixture was then treated with water (10 mL) and extracted with ethyl acetate (30 mL×2). The combined organic layers was washed with brine (30 mL×2), dried over Na₂SO₄, filtered and the filtrate evaporated. The product was purified by prep TLC (SiO₂, 100% EA) to give the title compound. MS(M+1): 412.

Step 2: 3-chloro-5-(1-((1-methylcyclopentyl)methyl)-1H-pyrazol-4-yl)-6-(2-methylimidazo[1,2-a]pyridin-7-yl)picolinonitrile To a solution of 3-amino-5-(1-((1-methylcyclopentyl)methyl)-1H-pyrazol-4-yl)-6-(2-methylimidazo[1,2-a]pyridin-7-yl)picolinonitrile (25 mg, 0.061 mmol) and sodium nitrite (6.3 mg, 0.091 mmol) in water (15 mL) was added 1 N hydrochloric acid (61 µL, 0.061 mmol) at 0° C. and stirred for 30 minutes. Then copper(I) chloride (7.8 mg, 0.079 mmol) was added in the mixture and stirred at 40° C. for 1 hour. Then the mixture was extracted with ethyl acetate (5 mL×3), dried over sodium sulfate, filtered and the filtrate evaporated. The crude was dissolved in DMF and purified by prep HPLC (C18 column, 10-95% CH₃CN/water 0.1% TFA) to give the title compound. MS(M+1): 431; ¹H NMR (CD₃OD, 400 MHz): δ 8.66 (d, J=7.2 Hz, 1H), 8.33 (s, 1H), 7.97 (d, J=12 Hz, 1H), 7.62 (s, 1H), 7.54 (s, 1H), 7.37 (d, J=6.8 Hz, 1H), 3.95 (s, 2H), 2.56 (s, 3H), 1.70-1.15 (m, 8H), 0.84 (s, 3H).

Example 163

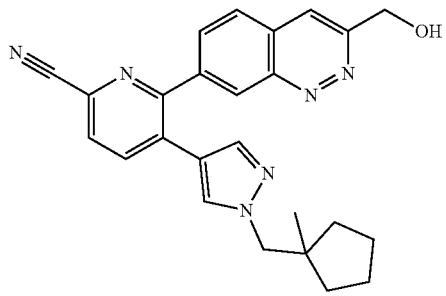 [SMILES: CC1(Cn2cc(-c3ccc(C#N)nc3-c3ccc4cc(CO)nnc4c3)cn2)CCCC1]

6-(3-(hydroxymethyl)cinnolin-7-yl)-5-(1-((1-methylcyclopentyl)methyl)-1H-pyrazol-4-yl)picolinonitrile Step 1: 5-(1-((1-methylcyclopentyl)methyl)-1H-pyrazol-4-yl)-6-(3-vinylcinnolin-7-yl)picolinonitrile To a solution of 6-(3-chlorocinnolin-7-yl)-5-(1-((1-methylcyclopentyl)methyl)-1H-pyrazol-4-yl)picolinonitrile (EXAMPLE 127; 200 mg, 0.466 mmol), potassium vinyltrifluoroborate (85.6 mg, 0.559 mmol) and K₃PO₄.3H₂O (372 mg, 1.398 mmol) in dioxane (6 mL) and H₂O (2 mL) was added Pd(dtbpf)Cl₂ (15.2 mg, 0.0233 mmol) under nitrogen atmosphere. Then the mixture was stirred at 60° C. for 16 h. LC-MS showed the reaction was complete. The mixture was extracted with ethyl acetate (30 mL×3). The organic phase was washed with brine (40 mL×2), dried over Na₂SO₄, filtered, concentrated in vacuo and purified by prep-TLC (SiO₂, petroleum ether: ethyl acetate=1:1) to yield the title compound. ¹H NMR (400 MHz, CD₃OD): δ 8.48 (1H, s), 8.27 (1H, s), 8.17 (1H, d, J=7.6 Hz), 8.03 (1H, d, J=8.4 Hz), 7.94 (1H, d, J=8.4 Hz), 7.87 (1H, d, J=8.4 Hz), 7.51 (1H, s), 7.20-7.33 (2H, m), 6.56 (1H, d, J=17.6 Hz), 5.76 (1H, d, J=11.2 Hz), 3.86 (2H, s), 1.47-1.51 (4H, m), 1.24-1.36 (2H, m), 1.08-1.09 (m, 2H), 0.70 (3H, s). MS (M+H): 421

Step 2: 6-(3-formylcinnolin-7-yl)-5-(1-((1-methylcyclopentyl)methyl)-1H-pyrazol-4-yl)picolinonitrile To a solution of 5-(1-((1-methylcyclopentyl)methyl)-1H-pyrazol-4-yl)-6-(3-vinylcinnolin-7-yl)picolinonitrile (40 mg, 0.095 mmol) in DCM (3 mL) and MeOH (0.5 mL) was bubbled an ozone-enriched stream of oxygen at −78° C. until the mixture turned light blue. Then the solution was purged with argon at −78° C. for 10 min to remove excess O₃. LC-MS showed target product formation. The mixture was concentrated in vacuo to give the title compound, which was used directly in the next step. MS(M+H): 423

Step 3: 6-(3-(hydroxymethyl)cinnolin-7-yl)-5-(1-((1-methylcyclopentyl)methyl)-1H-pyrazol-4-yl)picolinonitrile To a solution of 6-(3-formylcinnolin-7-yl)-5-(1-((1-methylcyclopentyl)methyl)-1H-pyrazol-4-yl)picolinonitrile (crude) in THF (2 mL) was added NaBH₄ (9.0 mg, 0.236 mmol) at 0° C. Then the mixture was stirred at 0° C. for 1 hour. LC-MS showed target product formation. The mixture was quenched with H₂O (2 mL) and extracted with EtOAc (10 mL×2). The organic phase was washed with brine (10 mL×2), dried over Na₂SO₄, filtered, concentrated in vacuo and purified by prep-TLC (SiO₂, petroleum ether: ethyl acetate=1:2) to yield the title compound. ¹H NMR (400 MHz, CD₃OD): δ 8.48 (1H, s), 8.25 (1H, s), 8.17 (1H, d, J=7.6 Hz), 8.05 (1H, d, J=8.4 Hz), 7.85-7.96 (2H, m), 7.47 (1H, s), 7.30 (1H, s), 5.16 (2H, s), 5.89 (1H, s), 3.84 (2H, s), 1.34-1.52 (3H, m), 1.28-1.31 (3H, m), 1.08-1.09 (m, 2H), 0.68 (3H, s).
MS(M+H): 425.

Example 164

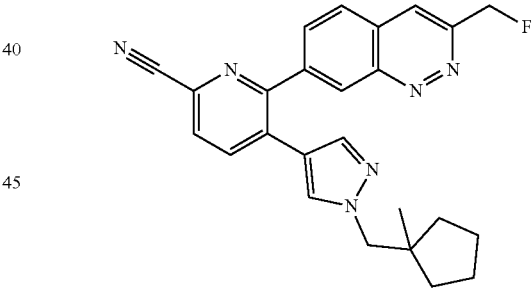

6-(3-(fluoromethyl)cinnolin-7-yl)-5-(1-((1-methylcyclopentyl)methyl)-1H-pyrazol-4-yl)picolinonitrile To a solution of 6-(3-(hydroxymethyl)cinnolin-7-yl)-5-6-(3-(hydroxymethyl) cinnolin-7-yl)-5-(1-((1-methylcyclopentyl)methyl)-1H-pyrazol-4-yl)picolinonitrile (EXAMPLE 163; 15 mg, 0.0353 mmol) in DCM (2 mL) was added DAST (81.5 mg, 0.506 mmol) at 0° C. Then the mixture was stirred at 0° C. C for 30 min. LC-MS showed formation of the target compound. The mixture was quenched with sat.NaHCO₃ (2 mL) and extracted with EtOAc (10 mL×2). The organic phase were washed with brine (10 mL×2), dried over Na₂SO₄, filtered, and the filtrate was concentrated in vacuo and purified by prep-HPLC (C18 column, 10-95% CH₃CN/water pH 10 NH₄OH) to yield the title compound. ¹H NMR (400 MHz, CD₃OD): δ 8.57 (1H, s), 8.32 (1H, s), 8.20 (1H, d, J=8.4 Hz), 8.13 (1H, d, J=8.4 Hz), 7.96 (2H, d, J=8.4 Hz), 7.49 (1H, s), 7.33 (1H, s), 5.90 (2H, d, J=48.0 Hz), 3.87 (2H, s), 1.32-1.52 (3H, m), 1.28-1.33 (3H, m), 1.08-1.09 (2H, m), 0.70 (3H, s). MS(M+H): 427

Example 165

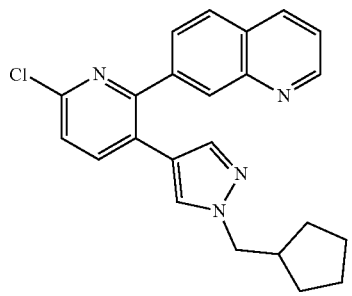 [SMILES: Clc1ccc(-c2cnn(CC3CCCC3)c2)c(-c2ccc3cccnc3c2)n1]

7-(6-chloro-3-(1-(cyclopentylmethyl)-1H-pyrazol-4-yl)pyridin-2-yl)quinoline

DMF (0.418 µl, 5.40 µmol) was added to a stirred mixture of 5-(1-(cyclopentylmethyl)-1H-pyrazol-4-yl)-6-(quinolin-7-yl)pyridin-2-ol (INTERMEDIATE AA1, 20 mg, 0.054 mmol) in POCl$_3$ (1 ml, 10.73 mmol) and the mixture was stirred at 60° C. for 18 h. The mixture was cooled, added into water (20 mL) slowly. The mixture was basified to pH=10 and the mixture was extracted with DCM (2×5 mL). The combined organic fractions were dried (Na$_2$SO$_4$), filtered and the solvent was evaporated under reduced pressure. The residue was purified by prep-TLC, eluting with PE/EA=1:1 to give the title compound. $^1$H NMR (CDCl$_3$, 400 MHz): δ 8.92 (d, J=2.8 Hz, 1H), 8.23 (s, 1H), 8.16 (d, J=8.4 Hz, 1H), 7.78 (m, 2H), 7.59 (m, 1H), 7.44-7.36 (m, 3H), 6.88 (s, 1H), 3.83 (d, J=7.6 Hz, 2H), 2.19 (m, 1H), 1.45 (m, 6H), 0.98 (m, 2H).

Example 166

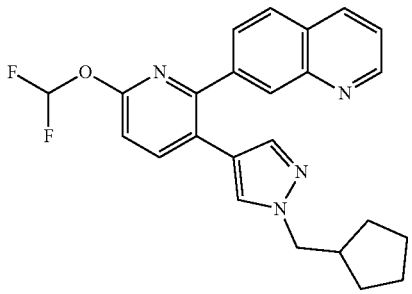 [SMILES: FC(F)Oc1ccc(-c2cnn(CC3CCCC3)c2)c(-c2ccc3cccnc3c2)n1]

7-(3-(1-(cyclopentylmethyl)-1H-pyrazol-4-yl)-6-(difluoromethoxy)pyridin-2-yl)quinoline A solution of 5-(1-(cyclopentylmethyl)-1H-pyrazol-4-yl)-6-(quinolin-7-yl)pyridin-2-ol (INTERMEDIATE AA1, 50 mg, 0.135 mmol), sodium 2-chloro-2,2-difluoroacetate (217 mg, 1.43 mmol) and potassium carbonate (18 mg, 0.130 mmol) in 5 mL of DMF was stirred at 90° C. for 3 hours. The mixture was partitioned between water and ethyl acetate. The organic was dried over sodium sulfate, filtered and the filtrate evaporated. The crude was purified by prep-HPLC (C18 column, 10-95% CH$_3$CN/water/0.1% TFA) to yield the title compound. $^1$H NMR (CDCl$_3$, 400 MHz): δ 9.19 (s, 1H), 8.62 (m, 2H), 7.94 (d, J=8.4 Hz, 1H), 7.80 (m, 3H), 7.57 (t, 1H, J=72 Hz), 7.18 (s, 2H), 7.00 (d, J=8.4 Hz, 1H), 3.93 (d, J=7.2 Hz, 2H), 2.31 (m, 1H), 1.55 (m, 6H), 1.10 (m, 2H).

Example 167

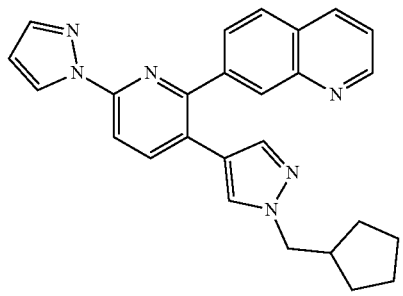 [SMILES: c1cnc2cc(-c3nc(-n4cccn4)ccc3-c3cnn(CC4CCCC4)c3)ccc2c1]

7-(3-(1-(cyclopentylmethyl)-1H-pyrazol-4-yl)-6-(1H-pyrazol-1-yl)pyridin-2-yl)quinoline To a solution of 7-(6-chloro-3-(1-(cyclopentylmethyl)-1H-pyrazol-4-yl)pyridin-2-yl)quinoline (EXAMPLE 165, 50 mg, 0.13 mmol) in 5 mL of DMSO was added pyrazole (44.2 mg, 0.65 mmol), N,N'-dimethylcyclohexane-1,2-diamine (7.4 mg, 0.05 mmol), potassium carbonate (36 mg, 0.26 mmol), and copper (I) iodide (4 mg, 0.03 mmol). The reaction was heated to 150° C. for 2 hours. The reaction was then quenched with water and extracted twice with ethyl acetate. The combined organic layers were dried over sodium sulfate, filtered and evaporated. The crude was purified by prep-TLC (petroleum ether:ethyl acetate 1:1) to give the title compound. $^1$H NMR (400 MHz, CD$_3$OD): δ 9.13 (1H, br s), 8.95 (1H, J=7.6 Hz, d), 8.67 (1H, s), 8.37 (1H, s), 8.22 (1H, J=8 Hz, d), 8.14 (2H, m), 8.07 (2H, m), 7.94 (1H, s), 7.44 (1H, s), 7.39 (1H, s), 6.58 (1H, s), 3.95 (2H, J=7.2 Hz, d), 2.29 (m, 1H), 1.54 (6H, m), 1.10 (2H, m). MS(M+H):421

Example 168

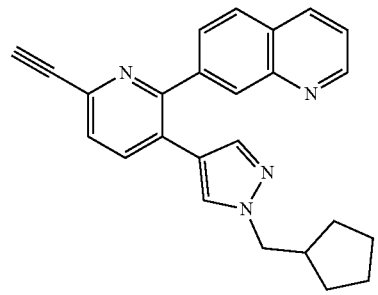 [SMILES: C#Cc1ccc(-c2cnn(CC3CCCC3)c2)c(-c2ccc3cccnc3c2)n1]

7-(3-(1-(cyclopentylmethyl)-1H-pyrazol-4-yl)-6-ethynylpyridin-2-yl)quinoline

Step 1: 7-(3-(1-(cyclopentylmethyl)-1H-pyrazol-4-yl)-6-iodopyridin-2-yl)quinoline A mixture of 7-(6-chloro-3-(1-(cyclopentylmethyl)-1H-pyrazol-4-yl)pyridin-2-yl)quinoline (EXAMPLE 165, 200 mg, 0.51 mmol) and sodium iodide (760 mg, 5.1 mmol) in $CH_3CN$ (5 mL) was stirred at room temperature briefly. Acetyl chloride (60 mg, 0.77 mmol) was then added dropwise at room temperature. Once acetyl chloride addition was complete the reaction was heated to reflux. Upon completion of the reaction yellow precipitate was observed. The reaction mixture was evaporated, then taken up in ethyl acetate and water. The aqueous was extracted 4× with ethyl acetate, then the combined layers were dried over sodium sulfate, filtered and evaporated. The crude isolate was then purified by silica gel chromatography, eluting with petroleum ether:ethyl acetate to give the title compound as the major isolate, which is less polar than the starting material. The material was carried to the next stage without characterization.

Step 2: 7-(3-(1-(cyclopentylmethyl)-1H-pyrazol-4-yl)-6-((trimethylsilyl)ethynyl)pyridin-2-yl)quinoline 7-(3-(1-(cyclopentylmethyl)-1H-pyrazol-4-yl)-6-iodopyridin-2-yl)quinoline (80 mg, 0.16 mmol), TMS-acetylene (25 mg, 0.25 mmol), 1,1'-bis(di-tert-butylphosphino)ferrocene palladium dichloride (11 mg, 0.016 mmol), copper (I) iodide (153 mg, 0.80 mmol) and triethylamine (80 mg, 0.80 mmol) was dissolved in 1,4-dioxane (3 mL). The reaction mixture was heated to 80° C. under $N_2$ atmosphere for 2 hours. The reaction mixture was then evaporated and taken up in ethyl acetate and water. The aqueous was extracted 2× with ethyl acetate, then the combined layers were dried over sodium sulfate, filtered and evaporated. The crude isolate was then purified by silica gel chromatography, eluting with petroleum ether:ethyl acetate to give the title compound which is more polar than the starting material. The material was carried to the next stage without characterization.

Step 3: 7-(3-(1-(cyclopentylmethyl)-1H-pyrazol-4-yl)-6-ethynylpyridin-2-yl)quinoline 7-(3-(1-(cyclopentylmethyl)-1H-pyrazol-4-yl)-6-((trimethylsilyl)ethynyl)pyridin-2-yl)quinoline (41 mg, 0.091 mmol) and potassium carbonate (37 mg, 0.27 mmol) were dissolved/suspended in methanol and stirred at room temperature. Upon reaction completion, the mixture was partitioned between ethyl acetate and water. The aqueous was extracted 4× more with ethyl acetate, dried over sodium sulfate, filtered and evaporated. The crude was purified by silica gel chromatography, eluting with petroleum ether: ethyl acetate to give the title compound. $^1$H NMR (CDCl$_3$, 400 MHz): δ 8.90 (s, 1H), 8.20 (s, 1H), 8.15 (d, J=7.6 Hz, 1H), 7.78 (d, J=8.4 Hz, 2H), 7.58 (d, J=8.4 Hz, 1H), 7.51 (d, J=8 Hz, 1H), 7.37 (s & br s, 2H), 6.83 (s, 1H), 3.79 (d, J=7.6 Hz, 2H), 3.17 (s, 1H), 2.16 (m, 1H), 1.44 (m, 6H), 0.95 (m, 2H).

Assay Protocol

The utility of the compounds as M4 muscarinic receptor allosteric modulators may be demonstrated by methodology known in the art, including by the assay described herein. CHO-K1 cells stably transfected with human M4 receptor and chimeric G-protein Gaqi5 are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed.

The following table shows representative data for the compounds of the Examples as modulators of the M4 muscarinic acetylcholine receptor as determined by the assays described herein. Such results are indicative of the intrinsic activity of the compounds for use as allosteric modulators of the M4 muscarinic acetylcholine receptor.

TABLE 8

| EXAMPLE | M4 FLIPPR Hu IP (nM) |
|---|---|
| 1 | 17 |
| 2 | 18 |
| 3 | 12 |
| 4 | 63 |
| 5 | 87 |
| 6 | 72 |
| 7 | 94 |
| 8 | 54 |
| 9 | 50 |
| 10 | 25 |
| 11 | 46 |
| 12 | 7 |
| 13 | 23 |
| 14 | 30 |
| 15 | 87 |
| 16 | 34 |
| 17 | 26 |
| 18 | 187 |
| 19 | 20 |
| 20 | 24 |
| 21 | 16 |
| 22 | 15 |
| 23 | 121 |
| 24 | 70 |
| 25 | 10 |
| 26 | 10 |
| 27 | 64 |
| 28 | 40 |
| 29 | 39 |
| 30 | 32 |
| 31 | 29 |
| 32 | 11 |
| 33 | 35 |
| 34 | 57 |
| 35 | 26 |
| 36 | 38 |
| 37 | 51 |
| 38 | 13 |
| 39 | 111 |
| 40 | 13 |
| 41 | 45 |
| 42 | 32 |
| 43 | 29 |
| 44 | 18 |
| 45 | 64 |
| 46 | 102 |

TABLE 8-continued

| EXAMPLE | M4 FLIPPR Hu IP (nM) |
|---|---|
| 47 | 56 |
| 48 | 41 |
| 49 | 107 |
| 50 | 27 |
| 51 | 22 |
| 52 | 10 |
| 53 | 76 |
| 54 | 36 |
| 55 | 35 |
| 56 | 41 |
| 57 | 16 |
| 58 | 15 |
| 59 | 43 |
| 60 | 110 |
| 61 | 37 |
| 62 | 62 |
| 63 | 63 |
| 64 | 22 |
| 65 | 28 |
| 66 | 89 |
| 67 | 64 |
| 68 | 38 |
| 69 | 25 |
| 70 | 49 |
| 71 | 26 |
| 72 | 41 |
| 73 | 41 |
| 74 | 58 |
| 75 | 31 |
| 76 | 23 |
| 77 | 66 |
| 78 | 29 |
| 79 | 80 |
| 80 | 65 |
| 81 | 82 |
| 82 | 20 |
| 83 | 26 |
| 84 | 33 |
| 85 | 37 |
| 86 | 18 |
| 87 | 11 |
| 88 | 24 |
| 89 | 67 |
| 90 | 42 |
| 91 | 33 |
| 92 | 4 |
| 93 | 34 |
| 94 | 35 |
| 95 | 80 |
| 96 | 35 |
| 97 | 68 |
| 98 | 82 |
| 99 | 83 |
| 100 | 100 |
| 101 | 69 |
| 102 | 232 |
| 103 | 45 |
| 104 | 20 |
| 105 | 17 |
| 106 | 82 |
| 107 | 36 |
| 108 | 86 |
| 109 | 69 |
| 110 | 23 |
| 111 | 38 |
| 112 | 46 |
| 113 | 79 |
| 114 | 140 |
| 115 | 21 |
| 116 | 61 |
| 117 | 45 |
| 118 | 48 |
| 119 | 5 |
| 120 | 44 |
| 121 | 50 |
| 122 | 59 |
| 123 | 63 |

TABLE 8-continued

| EXAMPLE | M4 FLIPPR Hu IP (nM) |
|---|---|
| 124 | 27 |
| 125 | 76 |
| 126 | 78 |
| 127 | 26 |
| 128 | 35 |
| 129 | 22 |
| 130 | 25 |
| 131 | 31 |
| 132 | 17 |
| 133 | 17 |
| 134 | 26 |
| 135 | 24 |
| 136 | 19 |
| 137 | 21 |
| 138 | 70 |
| 139 | 17 |
| 140 | 68 |
| 141 | 50 |
| 142 | 104 |
| 143 | 71 |
| 144 | 54 |
| 145 | 92 |
| 146 | 50 |
| 147 | 50 |
| 148 | 67 |
| 149 | 200 |
| 150 | 22 |
| 151 | 30 |
| 152 | 80 |
| 153 | 23 |
| 154 | 44 |
| 155 | 55 |
| 156 | 29 |
| 157 | 7 |
| 158 | 19 |
| 159 | 14 |
| 160 | 48 |
| 161 | 45 |
| 162 | 40 |
| 163 | 46 |
| 164 | 85 |
| 165 | 7 |
| 166 | 26 |
| 167 | 98 |
| 168 | 24 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

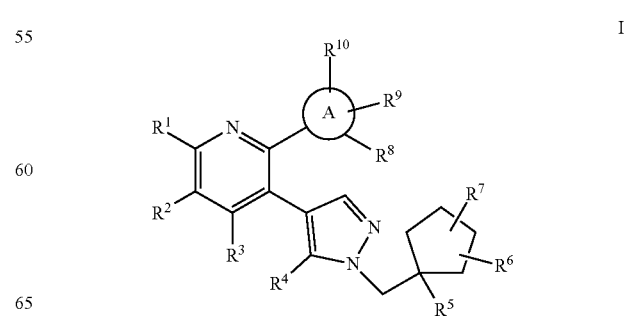

wherein:

A is selected from: benzoimidazole, benzoisoxazole, benzoxazole, benzotriazole, cinnoline, dihydrobenzofuranone, furopyridinone, imidazopyridine, indazole, isobenzofuranone, isoindolinone, isoquinoline, oxazolopyridine, phenyl, pyrazolopyridine, pyrrolopyridinone, quinoline, and triazolopyridine;

$R^1$ is selected from:
(1) hydrogen,
(2) halogen,
(3) —CN,
(4) —$C_{1-6}$alkyl, which is unsubstituted or substituted with a hydroxy, or 1-3 fluoro,
(5) —O—$C_{1-6}$alkyl, which is unsubstituted or substituted with a hydroxy, or 1-3 fluoro,
(6) —C≡CH,
(7) —pyrazolyl,
(8) —(C=O)—$NH_2$, and
(9) —(C=O)—NH(—$C_{1-6}$alkyl);

$R^2$ is selected from:
(1) hydrogen,
(2) halogen,
(3) —$C_{1-6}$alkyl, and
(4) —$NH_2$;

$R^3$ is selected from:
(1) hydrogen,
(2) halogen,
(3) —CN,
(4) —$C_{1-6}$alkyl, and
(5) —$NH_2$;

$R^4$ is selected from:
(1) hydrogen,
(2) —CN,
(3) chloro, and
(4) fluoro;

$R^5$ is selected from:
(1) hydrogen,
(2) fluoro, and
(3) —$CH_3$,
with the proviso that if A is isoindolinone or pyrrolopyridinone, then $R^5$ is fluoro;

each of $R^6$ and $R^7$ is independently selected from:
(1) hydrogen,
(2) fluoro, and
(2) $C_{1-6}$alkyl,
or $R^5$, $R^6$ and $R^7$ are joined together to form a bicycle [2.2.1]heptane ring, with the proviso that if A is pyrazolopyridine, then at least one of $R^6$ and $R^7$ is other than hydrogen;

each of $R^8$, $R^9$ and $R^{10}$ is independently selected from:
(1) hydrogen,
(2) halo,
(3) —OH,
(4) —$C_{1-6}$alkyl, which is unsubstituted or substituted with a hydroxy, —O$C_{1-6}$alkyl, cyclopropyl, cyclobutyl, or 1-3 fluoro,
(5) —O$C_{1-6}$alkyl, which is unsubstituted or substituted with a hydroxy, —O$C_{1-6}$alkyl, cyclopropyl, cyclobutyl, or 1-3 fluoro,
(6) —$C_{3-6}$cyclolkyl, which is unsubstituted or substituted with a hydroxy, methoxy, or 1-3 fluoro,
(7) —$NH_2$, —NH($C_{1-6}$alkyl), or —N($C_{1-6}$alkyl)$_2$, wherein the —$C_{1-6}$alkyl, is unsubstituted or substituted with hydroxy, methoxy, or 1-3 fluoro,
(8) azetidinyl, pyrrolidinyl, piperidinyl, or piperazinyl, wherein the azetidinyl, pyrrolidinyl, piperidinyl, or piperazinyl, is unsubstituted or substituted with hydroxy, methoxy, or 1-3 fluoro, and
(9) —CN;
or a pharmaceutically acceptable salt thereof.

2. The compound of claim 1 of the formula Ia:

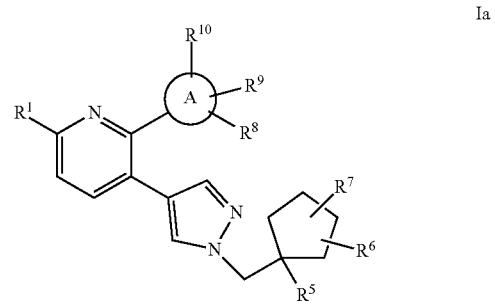

or a pharmaceutically acceptable salt thereof.

3. The compound of claim 1, or a pharmaceutically acceptable salt thereof, wherein
$R^2$ is hydrogen, $R^3$ is hydrogen and $R^1$ is selected from:
(1) hydrogen,
(2) fluoro,
(3) chloro,
(4) —CN, and
(5) methyl.

4. The compound of claim 1, or a pharmaceutically acceptable salt thereof, wherein $R^5$ is methyl.

5. The compound of claim 1, or a pharmaceutically acceptable salt thereof, wherein $R^5$ is fluoro.

6. The compound of claim 1, or a pharmaceutically acceptable salt thereof, wherein $R^6$ is selected from:
(1) hydrogen, and
(2) fluoro.

7. The compound of claim 1, or a pharmaceutically acceptable salt thereof, wherein $R^7$ is selected from:
(1) hydrogen, and
(2) fluoro.

8. The compound of claim 1, or a pharmaceutically acceptable salt thereof, wherein each of $R^8$, $R^9$ and $R^{10}$ is independently selected from:
(1) hydrogen,
(2) halo,
(3) —OH,
(4) —$C_{1-6}$alkyl, which is unsubstituted or substituted with a hydroxy, or 1-3 fluoro,
(5) —O$C_{1-6}$alkyl, which is unsubstituted or substituted with a hydroxy, or 1-3 fluoro, and
(6) cyclopropyl.

9. The compound of claim 1, or a pharmaceutically acceptable salt thereof, wherein each of $R^8$, $R^9$ and $R^{10}$ is independently selected from:
(1) hydrogen,
(2) fluoro,
(3) —$CH_3$,
(4) —$CF_3$, and
(5) —$OCH_3$, and
(6) cyclopropyl.

10. A compound which is selected from:
6-(3-(1-((1-fluorocyclopentyl)methyl)-1H-pyrazol-4-yl)-6-methylpyridin-2-yl)-2-methylisoindolin-1-one;
7-(3-(1-((1-fluorocyclopentyl)methyl)-1H-pyrazol-4-yl)-6-methylpyridin-2-yl)-3-methoxycinnoline;
5-(1-((1-fluorocyclopentyl)methyl)-1H-pyrazol-4-yl)-6-(2-methylimidazo[1,2-a]pyridin-7-yl)picolinonitrile;

7-(3-(1-(((3 S,4S)-3,4-difluorocyclopentyl)methyl)-1H-pyrazol-4-yl)pyridin-2-yl)-2-methylimidazo[1,2-a]pyridine;
7-(3-(1-(((3R,4R)-3,4-difluorocyclopentyl)methyl)-1H-pyrazol-4-yl)pyridin-2-yl)-2-methylimidazo[1,2-a]pyridine;
3-(1-(cyclopentylmethyl)-1H-pyrazol-4-yl)-6-methyl-2-(p-tolyl)pyridine;
6-(3-(1-(cyclopentylmethyl)-1H-pyrazol-4-yl)-6-methylpyridin-2-yl)-3-methyl-3H-imidazo[4,5-b]pyridine;
3-(4-(3-(1-(cyclopentylmethyl)-1H-pyrazol-4-yl)-6-methylpyridin-2-yl)phenyl)propan-1-ol;
1-(4-(3-(1-(cyclopentylmethyl)-1H-pyrazol-4-yl)-6-methylpyridin-2-yl)phenyl)-2,2,2-trifluoroethan-1-ol;
3-methoxy-7-(6-methyl-3-(1-((1-methylcyclopentyl)methyl)-1H-pyrazol-4-yl)pyridin-2-yl)quinolone;
5-(3-(1-(cyclopentylmethyl)-1H-pyrazol-4-yl)-6-methylpyridin-2-yl)-2-methylbenzo[d]oxazole;
7-(3-(1-(cyclopentylmethyl)-5-fluoro-1H-pyrazol-4-yl)-6-methylpyridin-2-yl)-3-methoxycinnoline;
7-(3-(1-(cyclopentylmethyl)-1H-pyrazol-4-yl)-6-methylpyridin-2-yl)-3-fluoroquinoline;
7-(3-(1-((1-fluorocyclopentyl)methyl)-1H-pyrazol-4-yl)-6-methylpyridin-2-yl)-3-(trifluoromethyl)quinoline;
6-(3-(1-((1-fluorocyclopentyl)methyl)-1H-pyrazol-4-yl)-6-methylpyridin-2-yl)-2-methyl-2H-indazole;
5-(3-(1-((1-fluorocyclopentyl)methyl)-1H-pyrazol-4-yl)-6-methylpyridin-2-yl)-1-methyl-1H-benzo[d]imidazole;
6-(3-(1-((1-fluorocyclopentyl)methyl)-1H-pyrazol-4-yl)-6-methylpyridin-2-yl)isoindolin-1-one;
6-(3-(1-((1-fluorocyclopentyl)methyl)-1H-pyrazol-4-yl)-6-methylpyridin-2-yl)-3-methyl-3H-imidazo[4,5-b]pyridine;
2-(cyclopropylmethyl)-6-(3-(1-((1-fluorocyclopentyl)methyl)-1H-pyrazol-4-yl)-6-methylpyridin-2-yl)isoindolin-1-one;
2-cyclopropyl-6-(3-(1-((1-fluorocyclopentyl)methyl)-1H-pyrazol-4-yl)-6-methylpyridin-2-yl)isoindolin-1-one;
3-fluoro-7-(3-(1-((1-fluorocyclopentyl)methyl)-1H-pyrazol-4-yl)-6-methylpyridin-2-yl)quinoline;
7-(3-(5-fluoro-1-((1-fluorocyclopentyl)methyl)-1H-pyrazol-4-yl)-6-methylpyridin-2-yl)quinoline;
6-(3-(5-fluoro-1-((1-fluorocyclopentyl)methyl)-1H-pyrazol-4-yl)-6-methylpyridin-2-yl)-3-methyl-3H-imidazo[4,5-b]pyridine;
5-(3-(5-fluoro-1-((1-fluorocyclopentyl)methyl)-1H-pyrazol-4-yl)-6-methylpyridin-2-yl)-1-methyl-1H-benzo[d]imidazole;
7-(3-(1-(bicyclo[2.2.1]heptan-1-ylmethyl)-1H-pyrazol-4-yl)-6-methylpyridin-2-yl)-3-methoxycinnoline;
7-(3-(1-(bicyclo[2.2.1]heptan-1-ylmethyl)-1H-pyrazol-4-yl)-6-methylpyridin-2-yl)quinoline;
7-(3-(1-(((3R,4 S)-3,4-difluorocyclopentyl)methyl)-1H-pyrazol-4-yl)-6-methylpyridin-2-yl)quinolone;
7-(3-(1-(((3 S,4R)-3,4difluorocyclopentyl)methyl)-1H-pyrazol-4-yl)-6-methylpyridin-2-yl)quinolone;
7-(3-(1-((3,3-difluorocyclopentyl)methyl)-1H-pyrazol-4-yl)-6-methylpyridin-2-yl)quinolone;
7-(3-(1-(((3 S,4S)-3,4-difluorocyclopentyl)methyl)-1H-pyrazol-4-yl)-6-methylpyridin-2-yl)quinolone;
7-(3-(1-(((3R,4R)-3,4-difluorocyclopentyl)methyl)-1H-pyrazol-4-yl)-6-methylpyridin-2-yl)quinolone;
7-(3-(1-(((1 S,3 S)-3-fluorocyclopentyl)methyl)-1H-pyrazol-4-yl)-6-methylpyridin-2-yl)quinoline;
7-(3-(1-(((1R,3R)-3-fluorocyclopentyl)methyl)-1H-pyrazol-4-yl)-6-methylpyridin-2-yl)quinoline;
7-(3-(1-(((1R,3 S)-3-fluorocyclopentyl)methyl)-1H-pyrazol-4-yl)-6-methylpyridin-2-yl)quinoline;
7-(3-(1-(((1 S,3R)-3-fluorocyclopentyl)methyl)-1H-pyrazol-4-yl)-6-methylpyridin-2-yl)quinoline;
3-fluoro-7-(6-methyl-3-(1-((1-methylcyclopentyl)methyl)-1H-pyrazol-4-yl)pyridin-2-yl)quinoline;
6-(6-methyl-3-(1-((1-methylcyclopentyl)methyl)-1H-pyrazol-4-yl)pyridin-2-yl)isobenzofuran-1(3H)-one;
2-methyl-6-(6-methyl-3-(1-((1-methylcyclopentyl)methyl)-1H-pyrazol-4-yl)pyridin-2-yl)-2H-indazole;
2-methyl-7-(6-methyl-3-(1-((1-methylcyclopentyl)methyl)-1H-pyrazol-4-yl)pyridin-2-yl)isoquinolin-1(2H)-one;
7-(3-(1-(cyclopentylfluoromethyl)-5-fluoro-1H-pyrazol-4-yl)-6-methylpyridin-2-yl)-3-methoxycinnoline;
7-(3-(1-((6,6-difluorobicyclo[3.1.0]hexan-3-yl)methyl)-1H-pyrazol-4-yl)-6-methylpyridin-2-yl)-3-methoxycinnoline;
5-(1-(cyclopentylmethyl)-1H-pyrazol-4-yl)-6-(pyrazolo[1,5-a]pyridin-6-yl)picolinonitrile;
5-(1-(cyclopentylmethyl)-1H-pyrazol-4-yl)-6-(2-methyl-1-oxo-1,2-dihydroisoquinolin-7-yl)picolinonitrile;
6-(2-cyclopropyl-3-oxoisoindolin-5-yl)-5-(1-((1-fluorocyclopentyl)methyl)-1H-pyrazol-4-yl)picolinonitrile;
5-(1-((1-fluorocyclopentyl)methyl)-1H-pyrazol-4-yl)-6-(6-methyl-5-oxo-6,7-dihydro-5H-pyrrolo[3,4-b]pyridin-3-yl)picolinonitrile;
6-([1,2,4]triazolo[4,3-a]pyridin-7-yl)-5-(1(1-fluorocyclopentyl)methyl)-1H-pyrazol-4-yl)picolinonitrile;
6-([1,2,4]triazolo[1,5-a]pyridin-7-yl)-5-(1(((1-fluorocyclopentyl)methyl)-1H-pyrazol-4-yl)picolinonitrile;
5-(1-((1-fluorocyclopentyl)methyl)-1H-pyrazol-4-yl)-6-(3-methyl-[1,2,4]triazolo[4,3-a]pyridin-7-yl)picolinonitrile;
5-(1-((1-fluorocyclopentyl)methyl)-1H-pyrazol-4-yl)-6-(1,1,2-trimethyl-3-oxoisoindolin-5-yl)picolinonitrile;
6-(1,1-dimethyl-3-oxoisoindolin-5-yl)-5-(1((1-fluorocyclopentyl)methyl)-1H-pyrazol-4-yl)picolinonitrile;
5-(1-((1-fluorocyclopentyl)methyl)-1H-pyrazol-4-yl)-6-(6-(2-fluoroethyl)-5-oxo-6,7-dihydro-5H-pyrrolo[3,4-b]pyridin-3-yl)picolinonitrile;
5-(1-((1-fluorocyclopentyl)methyl)-1H-pyrazol-4-yl)-6-(2-methyl-2H-indazol-6-yl)picolinonitrile;
5-(1-((1-fluorocyclopentyl)methyl)-1H-pyrazol-4-yl)-6-(2-methylbenzo[d]oxazol-5-yl)picolinonitrile;
5-(1-((1-fluorocyclopentyl)methyl)-1H-pyrazol-4-yl)-6-(imidazo[1,2-a]pyridin-7-yl)picolinonitrile;
5-(1-((1-fluorocyclopentyl)methyl)-1H-pyrazol-4-yl)-6-(2-(trifluoromethyl)imidazo[1,2-a]pyridin-7-yl)picolinonitrile;
6-(2-chloroimidazo[1,2-a]pyridin-7-yl)-5-(1-((1-fluorocyclopentyl)methyl)-1H-pyrazol-4-yl)picolinonitrile;
6-(2-cyclopropyloxazolo[5,4-b]pyridin-6-yl)-5-(1(((1-fluorocyclopentyl)methyl)-1H-pyrazol-4-yl)picolinonitrile;
6-(2-cyclopropylimidazo[1,2-a]pyridin-7-yl)-5-(1-((1-fluorocyclopentyl)methyl)-1H-pyrazol-4-yl)picolinonitrile;
6-(6-(cyclopropylmethyl)-5-oxo-6,7-dihydro-5H-pyrrolo[3,4-b]pyridin-3-yl)-5-(1-((1-fluorocyclopentyl)methyl)-1H-pyrazol-4-yl)picolinonitrile;
5-(1-((1-fluorocyclopentyl)methyl)-1H-pyrazol-4-yl)-6-(1-methyl-1H-benzo[d][1,2,3]triazol-5-yl)picolinonitrile;

6-(2-ethylimidazo[1,2-a]pyridin-7-yl)-5-(1-((1-fluorocyclopentyl)methyl)-1H-pyrazol-4-yl)picolinonitrile;

6-(2-(difluoromethyl)imidazo[1,2-a]pyridin-7-yl)-5-(1-((1-fluorocyclopentyl)methyl)-1H-pyrazol-4-yl)picolinonitrile;

6-(1,2-dimethyl-1H-benzo[d]imidazol-5-yl)-5-(1-((1-fluorocyclopentyl)methyl)-1H-pyrazol-4-yl)picolinonitrile;

5-(1-((1-fluorocyclopentyl)methyl)-1H-pyrazol-4-yl)-6-(2-methyl-[1,2,4]triazolo[1,5-a]pyridin-6-yl)picolinonitrile;

5-(1-((1-fluorocyclopentyl)methyl)-1H-pyrazol-4-yl)-6-(2-methyl-[1,2,4]triazolo[1,5-a]pyridin-7-yl)picolinonitrile;

6-(benzo[c]isoxazol-6-yl)-5-(1-((1-fluorocyclopentyl)methyl)-1H-pyrazol-4-yl)picolinonitrile;

6-(2,3-dimethyl-3H-imidazo[4, 5-b]pyridin-6-yl)-5-(1-((1-fluorocyclopentyl)methyl)-1H-pyrazol-4-yl)picolinonitrile;

5-(1-((1-fluorocyclopentyl)methyl)-1H-pyrazol-4-yl)-6-(2-methoxypyrazolo[1, 5-a]pyridin-6-yl)picolinonitrile;

6-(2-ethyl-[1,2,4]triazolo[1,5-a]pyridin-7-yl)-5-(1-((1-fluorocyclopentyl)methyl)-1H-pyrazol-4-yl)picolinonitrile;

5-(1-((1-fluorocyclopentyl)methyl)-1H-pyrazol-4-yl)-6-(2-(hydroxymethyl)-[1,2,4]triazolo[1,5-a]pyridin-7-yl)picolinonitrile;

5-(1-(((1 S,3 S)-3-fluorocyclopentyl)methyl)-1H-pyrazol-4-yl)-6-(3-methoxycinnolin-7-yl)picolinonitrile;

5-(1-(((1 S,3 S)-3-fluorocyclopentyl)methyl)-1H-pyrazol-4-yl)-6-(quinolin-7-yl)picolinonitrile;

5-(1-(((1 S,3 S)-3-fluorocyclopentyl)methyl)-1H-pyrazol-4-yl)-6-(2-methylimidazo[1,2-a]pyridin-7-yl)picolinonitrile;

5-(1-(((1R,3R)-3-fluorocyclopentyl)methyl)-1H-pyrazol-4-yl)-6-(1-methyl-1H-benzo[d]imidazol-5-yl)picolinonitrile;

5-(1-(((3 S,4S)-3,4-difluorocyclopentyl)methyl)-1H-pyrazol-4-yl)-6-(imidazo[1,2-a]pyridin-7-yl)picolinonitrile;

5-(1-(((3 S,4S)-3,4-difluorocyclopentyl)methyl)-1H-pyrazol-4-yl)-6-(1-methyl-1H-benzo[d]imidazol-5-yl)picolinonitrile;

5-(1-((1-methylcyclopentyl)methyl)-1H-pyrazol-4-yl)-6-(5-oxo-5,7-dihydrofuro[3,4-b]pyridin-3-yl)picolinonitrile;

6-(3-fluoroimidazo[1,2-a]pyridin-7-yl)-5-(1-((1-methylcyclopentyl)methyl)-1H-pyrazol-4-yl)picolinonitrile;

6-([1,2,4]triazolo[1,5-a]pyridin-7-yl)-5-(1-((1-methylcyclopentyl)methyl)-1H-pyrazol-4-yl)picolinonitrile;

6-(2-(difluoromethyl)imidazo[1,2-a]pyridin-7-yl)-5-(1-((1-methylcyclopentyl)methyl)-1H-pyrazol-4-yl)picolinonitrile;

6-(imidazo[1, 5-a]pyridin-7-yl)-5-(1-((1-methylcyclopentyl)methyl)-1H-pyrazol-4-yl)picolinonitrile;

6-(2-(fluoromethyl)-[1,2,4]triazolo[1, 5-a]pyridin-7-yl)-5-(1-((1-methylcyclopentyl)methyl)-1H-pyrazol-4-yl)picolinonitrile;

5-(1-((1-methylcyclopentyl)methyl)-1H-pyrazol-4-yl)-6-(pyrazolo[1,5-yl)picolinonitrile;

5-(1-((1-methylcyclopentyl)methyl)-1H-pyrazol-4-yl)-6-(2-methyloxazolo[5,4-b]pyridin-6-yl)picolinonitrile;

5-(5-chloro-1-((1-methylcyclopentyl)methyl)-1H-pyrazol-4-yl)-6-(imidazo[1,2-a]pyridin-7-yl)picolinonitrile;

6-(2-(hydroxymethyl)imidazo[1,2-a]pyridin-7-yl)-5-(1-((1-methylcyclopentyl)methyl)-1H-pyrazol-4-yl)picolinonitrile;

5-(1-(((3R,4R)-3, 4-difluorocyclopentyl)methyl)-1H-pyrazol-4-yl)-6-(2-methylimidazo[1,2-a]pyridin-7-yl)picolinonitrile;

5-(1-(((3R,4R)-3, 4-difluorocyclopentyl)methyl)-1H-pyrazol-4-yl)-6-(quinolin-7-yl)picolinonitrile;

3-fluoro-6-(3-methyl-3H-imidazo[4,5-b]pyridin-6-yl)-5-(1-((1-methylcyclopentyl)methyl)-1H-pyrazol-4-yl)picolinonitrile;

3-fluoro-6-(1-methyl-1H-benzo[d]imidazol-5-yl)-5-(1-((1-methylcyclopentyl)methyl)-1H-pyrazol-4-yl)picolinonitrile;

3-fluoro-6-(imidazo[1,2-a]pyridin-7-yl)-5-(1-((1-methylcyclopentyl)methyl)-1H-pyrazol-4-yl)picolinonitrile;

3-fluoro-5-(1-((1-methylcyclopentyl)methyl)-1H-pyrazol-4-yl)-6-(2-methylimidazo[1,2-a]pyridin-7-yl)picolinonitrile;

3-fluoro-5-(1-((1-fluorocyclopentyl)methyl)-1H-pyrazol-4-yl)-6-(2-methyl-2H-indazol-6-yl)picolinonitrile;

3-fluoro-5-(1-((1-fluorocyclopentyl)methyl)-1H-pyrazol-4-yl)-6-(3-methyl-[1,2,4]triazolo [4,3-a]pyridin-7-yl)picolinonitrile;

3-fluoro-5-(1-((1-fluorocyclopentyl)methyl)-1H-pyrazol-4-yl)-6-(2-(trifluoromethyl)imidazo[1,2-a]pyridin-7-yl)picolinonitrile;

7-(6-fluoro-3-(1-((1-methylcyclopentyl)methyl)-1H-pyrazol-4-yl)pyridin-2-yl)-3-methoxycinnoline;

7-(6-fluoro-5-methyl-3-(1-((1-methylcyclopentyl)methyl)-1H-pyrazol-4-yl)pyridin-2-yl)imidazo[1,2-a]pyridine;

7-(6-fluoro-3-(1-((1-fluorocyclopentyl)methyl)-1H-pyrazol-4-yl)-5-methylpyridin-2-yl)imidazo[1,2-a]pyridine;

7-(5-fluoro-3-(1-((1-fluorocyclopentyl)methyl)-1H-pyrazol-4-yl)pyridin-2-yl)quinoline;

7-(5-fluoro-3-(1-((1-fluorocyclopentyl)methyl)-1H-pyrazol-4-yl)pyridin-2-yl)-2-methylimidazo[1,2-a]pyridine;

7-(5-fluoro-3-(1-((1-fluorocyclopentyl)methyl)-1H-pyrazol-4-yl)pyridin-2-yl)-2, 3-dimethylimidazo[1,2-a]pyridine;

7-(5-fluoro-3-(1-((1-fluorocyclopentyl)methyl)-1H-pyrazol-4-yl)pyridin-2-yl)-2-(trifluoromethyl)-imidazo[1, 2-a]pyridine;

5-(5-fluoro-3-(1-(1-fluorocyclopentyl)methyl)-1H-pyrazol-4-yl)pyridin-2-yl)-1,2-dimethyl-1H-benzo[d]imidazole;

7-(5-fluoro-3-(1-(1-fluorocyclopentyl)methyl)-1H-pyrazol-4-yl)pyridin-2-yl)-3-methyl-[1,2,4]triazolo[4,3-a]pyridine;

2-cyclopropyl-6-(5-fluoro-3-(1-(1-fluorocyclopentyl)methyl)-1H-pyrazol-4-yl)pyridin-2-yl)isoindolin-1-one;

5-(3-(1-(((3R,4R)-3,4-difluorocyclopentyl)methyl)-1H-pyrazol-4-yl)-5-fluoropyridin-2-yl)-1,2-dimethyl-1H-benzo[d]imidazole;

3-(1-(1-methylcyclopentyl)methyl)-1H-pyrazol-4-yl)-2-(quinolin-7-yl)isonicotinonitrile;

7-(3-(1-(cyclopentylmethyl)-1H-pyrazol-4-yl)-6-(trifluoromethyl)pyridin-2-yl)quinoline;

6-(3-methoxycinnolin-7-yl)-2-methyl-5-(1-((1-methylcyclopentyl)methyl)-1H-pyrazol-4-yl)nicotinonitrile;

2-methyl-6-(3-methyl-3H-imidazo[4,5-b]pyridin-6-yl)-5-(1-(1-methylcyclopentyl)methyl)-1H-pyrazol-4-yl)nicotinonitrile;

6-(4-fluoro-3-(1-((1-methylcyclopentyl)methyl)-1H-pyrazol-4-yl)pyridin-2-yl)-3-methyl-3H-imidazo[4,5-b]pyridine;
6-(6-(difluoromethyl)-3-(1-(1-fluorocyclopentyl)methyl)-1H-pyrazol-4-yl)pyridin-2-yl)-3-methyl-3H-imidazo[4,5-b]pyridine;
6-(5-chloro-3-(1-(1-methylcyclopentyl)methyl)-1H-pyrazol-4-yl)pyridin-2-yl)-3-methyl-3H-imidazo[4,5-b]pyridine;
7-(5-chloro-3-(1-(1-fluorocyclopentyl)methyl)-1H-pyrazol-4-yl)pyridin-2-yl)-2-methylimidazo[1,2-a]pyridine;
7-(5-chloro-3-(1-(1-fluorocyclopentyl)methyl)-1H-pyrazol-4-yl)pyridin-2-yl)-2-(difluoromethyl)-imidazo[1,2-a]pyridine;
7-(5-methyl-3-(1-(1-methylcyclopentyl)methyl)-1H-pyrazol-4-yl)pyridin-2-yl)imidazo[1,2-a]pyridine;
7-(5-methyl-3-(1-(1-methylcyclopentyl)methyl)-1H-pyrazol-4-yl)pyridin-2-yl)-[1,2,4]triazolo[1,5-a]pyridine;
7-(5-fluoro-3-(1-(1-fluorocyclopentyl)methyl)-1H-pyrazol-4-yl)-6-methoxypyridin-2-yl)-2-methylimidazo[1,2-a]pyridine;
7-(6-chloro-3-(1-(1-methylcyclopentyl)methyl)-1H-pyrazol-4-yl)pyridin-2-yl)-2-methylimidazo[1,2-a]pyridine;
3-(6-chloro-3-(1-(1-fluorocyclopentyl)methyl)-1H-pyrazol-4-yl)-5-methylpyridin-2-yl)-6-(cyclopropylmethyl)-6,7-dihydro-5H-pyrrolo[3,4-b]pyridin-5-one;
6-(6-chloro-3-(1-((1-fluorocyclopentyl)methyl)-1H-pyrazol-4-yl)-5-methylpyridin-2-yl)-3-methyl-3H-imidazo[4,5-b]pyridine;
7-(6-chloro-3-(1-((1-fluorocyclopentyl)methyl)-1H-pyrazol-4-yl)-5-methylpyridin-2-yl)-[1,2,4]triazolo[4, 3-a]pyridine;
7-(6-chloro-5-methyl-3-(1-((1-methylcyclopentyl)methyl)-1H-pyrazol-4-yl)pyridin-2-yl)-3-methoxycinnoline;
5-(6-(difluoromethyl)-3-(1-(((1 S,3 S)-3-fluorocyclopentyl)methyl)-1H-pyrazol-4-yl)pyridin-2-y1)-1-methyl-1H-benzo[d]imidazole;
5-(6-(difluoromethyl)-3-(1-(((1R,3R)-3-fluorocyclopentyl)methyl)-1H-pyrazol-4-yl)pyridin-2-y1)-1-methyl-1H-benzo[d]imidazole;
7-(6-(difluoromethyl)-3-(1-(((1R,3R)-3-fluorocyclopentyl)methyl)-1H-pyrazol-4-yl)pyridin-2-y1)-3-methoxycinnoline;
7-(6-(difluoromethyl)-3-(1-(((1 S,3 S)-3-fluorocyclopentyl)methyl)-1H-pyrazol-4-yl)pyridin-2-y1)-3-methoxycinnoline;
6-(1-methyl-1H-benzo[d][1,2,3]triazol-5-yl)-5-(1-((1-methylcyclopentyl)methyl)-1H-pyrazol-4-yl)picolinonitrile;
6-(2-methyl-2H-benzo[d][1,2,3]triazol-5-yl)-5-(1-((1-methylcyclopentyl)methyl)-1H-pyrazol-4-yl)picolinonitrile;
6-(2-chloro-quinolin-7-yl)-5-(1-((1-methylcyclo-pentyl)methyl)-1H-pyrazol-4-yl)picolinonitrile;
6-(3-chlorocinnolin-7-yl)-5-(1-((1-methylcyclopentyl)methyl)-1H-pyrazol-4-yl)picolinonitrile;
6-(3-fluorocinnolin-7-yl)-5-(1-((1-methylcyclopentyl)methyl)-1H-pyrazol-4-yl)picolinonitrile;
7-(3-(1(3,3-difluorocyclopentyl)methyl)-1H-pyrazol-4-yl)-6-methylpyridin-2-yl)quinoline;
7-(3-(1-(((1 S,3 S)-3-fluorocyclopentyl)methyl)-1H-pyrazol-4-yl)-6-methylpyridin-2-yl)quinoline;
7-(3-(1-(((1R,3R)-3-fluorocyclopentyl)methyl)-1H-pyrazol-4-yl)-6-methylpyridin-2-yl)quinoline;
7-(3-(1-(((1R,3 S)-3-fluorocyclopentyl)methyl)-1H-pyrazol-4-yl)-6-methylpyridin-2-yl)quinoline;
7-(3-(1-(((1 S, 3R)-3-fluorocyclopentyl)methyl)-1H-pyrazol-4-yl)-6-methylpyridin-2-yl)quinoline;
5-(1-((1-fluorocyclopentyl)methyl)-1H-pyrazol-4-yl)-6-(2-(fluoromethyl)imidazo[7-yl)picolinonitrile;
3-fluoro-6-(2-(fluoromethyl)imidazo[1,2-a]pyridin-7-yl)-5-(1-((1-methylcyclopentyl)methyl)-1H-pyrazol-4-yl)picolinonitrile;
7-(5, 6-difluoro-3-(1-((1-methylcyclopentyl)methyl)-1H-pyrazol-4-yl)pyridin-2-yl)imidazo[1,2-a]pyridine;
6-(5, 6-difluoro-3-(1-((1-methylcyclopentyl)methyl)-1H-pyrazol-4-yl)pyridin-2-yl)-3-methyl-3H-imidazo[4,5-b]pyridine;
2-cyclobutyl-6-(3-(1-((1-fluorocyclopentyl)methyl)-1H-pyrazol-4-yl)pyridin-2-yl)isoindolin-1-one;
2-(cyclobutylmethyl)-6-(3-(1-((1-fluorocyclopentyl)methyl)-1H-pyrazol-4-yl)pyridin-2-yl)isoindolin-1-one;
5-(1-((1-fluorocyclopentyl)methyl)-1H-pyrazol-4-yl)-3-methyl-6-(2-methyl-[1,2,4]triazolo[1,5-a]pyridin-7-yl)picolinonitrile;
5-(1-((1-fluorocyclopentyl)methyl)-1H-pyrazol-4-yl)-3-methyl-6-(3-methyl-3H-imidazo[4,5-b]pyridin-6-yl)picolinonitrile;
6-([1,2,4]triazolo[1,5-a]pyridin-7-yl)-5-(1-((1-fluorocyclopentyl)methyl)-1H-pyrazol-4-yl)-3-methylpicolinonitrile;
5-(5-cyano- 1-((1-methylcyclopentyl)methyl)-1H-pyrazol-4-yl)-6-(imidazo[1,2-a]pyridin-7-yl)picolinonitrile;
3-methoxy-7-(6-methyl-3-(1-(spiro[2.4]heptan-5-ylmethyl)-1H-pyrazol-4-yl)pyridin-2-yl)cinnoline;
5-(1-(((1R,3 S) or (1 S,3R)-3-fluorocyclopentyl)methyl)-1H-pyrazol-4-yl)-6-(quinolin-7-yl)picolinonitrile;
7-(3-(1-(cyclopentylmethyl)-1H-pyrazol-4-yl)pyridin-2-yl)quinoline;
3-((4-(2-(3-methoxycinnolin-7-yl)-6-methylpyridin-3-yl)-1H-pyrazol-1-yl)methyl)-3-methylcyclopentan-1-one;
3-((4-(2-(3-methoxycinnolin-7-yl)-6-methylpyridin-3-yl)-1H-pyrazol-1-yl)methyl)-3-methylcyclopentan-1-one;
7-(3-(1-((3,3-difluoro-1-methylcyclopentyl)methyl)-1H-pyrazol-4-yl)-6-methylpyridin-2-yl)-3-methoxycinnoline;
7-(3-(1-((3,3-difluoro-1-methylcyclopentyl)methyl)-1H-pyrazol-4-yl)-6-methylpyridin-2-yl)-3-methoxycinnoline;
2-chloro-5-(3-(1-(cyclopentylmethyl)-1H-pyrazol-4-yl)-6-methylpyridin-2-yl)-1-methyl-1H-benzo[d]imidazole;
6-(3-bromoimidazo[1,2-a]pyridin-7-yl)-5-(1-((1-fluorocyclopentyl)methyl)-1H-pyrazol-4-yl)picolinonitrile;
6-(2-chloro-1-methyl-1H-benzo[d]imidazol-5-yl)-5-(1-((1-methylcyclopentyl)methyl)-1H-pyrazol-4-yl)picolinonitrile;
5-(1-((1-fluorocyclopentyl)methyl)-1H-pyrazol-4-yl)-6-(2-(methoxymethyl)-[1,2,4]triazolo[-a]pyridin-7-yl)picolinonitrile;
6-(2-(methoxymethyl)imidazo[1,2-a]pyridin-7-yl)-5-(1-((1-methylcyclopentyl)methyl)-1H-pyrazol-4-yl)picolinonitrile;
7-(5,6-dimethyl-3-(1-((1-methylcyclopentyl)methyl)-1H-pyrazol-4-yl)pyridin-2-yl)-3-methoxycinnoline;

7-(3-(1-(cyclopentylmethyl)-1H-pyrazol-4-yl)-6-methylpyridin-2-yl)cinnolin-3-amine;

7-(3-(1-(cyclopentylmethyl)-1H-pyrazol-4-yl)-6-methylpyridin-2-yl)-3-iodocinnoline;

6-(4-cyanophenyl)-5-(1-(cyclopentylmethyl)-1H-pyrazol-4-yl)picolinonitrile;

6-(3-(azetidin-1-yl)quinolin-7-yl)-5-(1-((1-methylcyclopentyl)methyl)-1H-pyrazol-4-yl)picolinonitrile;

3-chloro-5-(14(1-methylcyclopentyl)methyl)-1H-pyrazol-4-yl)-6-(2-methylimidazo[1,2-a]pyridin-7-yl)picolinonitrile;

6-(3-(hydroxymethyl)cinnolin-7-yl)-5-(1-((1-methylcyclopentyl)methyl)-1H-pyrazol-4-yl)picolinonitrile;

6-(3-(fluoromethyl)cinnolin-7-yl)-5-(1-((1-methylcyclopentyl)methyl)-1H-pyrazol-4-yl)picolinonitrile;

7-(6-chloro-3-(1-(cyclopentylmethyl)-1H-pyrazol-4-yl)pyridin-2-yl)quinoline;

7-(3-(1-(cyclopentylmethyl)-1H-pyrazol-4-yl)-6-(difluoromethoxy)pyridin-2-yl)quinoline;

7-(3-(1-(cyclopentylmethyl)-1H-pyrazol-4-yl)-6-(1H-pyrazol-1-yl)pyridin-2-yl)quinoline; and 7-(3-(1-(cyclopentylmethyl)-1H-pyrazol-4-yl)-6-ethynylpyridin-2-yl)quinoline;

or a pharmaceutically acceptable salt thereof.

11. A pharmaceutical composition which comprises an inert carrier and a compound of claim 1, or a pharmaceutically acceptable salt thereof.

12. A method for the treatment of a neurological and/or psychiatric disorder associated with muscarinic acetylcholine receptor dysfunction in a mammal comprising the step of administering at least one compound of claim 1, or a pharmaceutically acceptable salt of said compound, to a patient in need thereof in an amount effective to treat said disorder.

13. The method of claim 12, wherein the mammal has been diagnosed with a need for treatment of the disorder prior to the administering step.

14. The method of claim 12, wherein the disorder is a neurological and/or psychiatric disorder associated with mAChR M4 dysfunction.

15. The method of claim 12, wherein the disorder is a psychotic disorder.

16. The method of claim 15, wherein the psychotic disorder is selected from schizophrenia, psychotic disorder, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder.

17. The method of claim 12, wherein the disorder is a cognitive disorder.

18. The method of claim 17, wherein the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS dementical complex, dementia of the Alzheimer's type, age- related cognitive decline, and mild cognitive impairment.

* * * * *

UNITED STATES PATENT AND TRADEMARK OFFICE
CERTIFICATE OF CORRECTION

Page 1 of 1

PATENT NO. : 11,149,036 B2
APPLICATION NO. : 16/621959
DATED : October 19, 2021
INVENTOR(S) : John J. Acton, III et al.

It is certified that error appears in the above-identified patent and that said Letters Patent is hereby corrected as shown below:

On the Title Page

At Item (71), delete:
"John J. Acton, III, Bridgewater, NJ (US); Jianming Bao, San Mateo, CA (US); Qiaolin Deng, Princeton NJ (US); Melissa Egbertson, Ambler, PA (US); Ronald Ferguson, II, Scotch Plains, NJ (US); Xiaolei Gao, Bridgewater, NJ (US); Scott Timothy Harrison, Elkins Park, PA (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Zhaoyang Meng, Ambler, PA (US); Meng Na, Shanghai (CN); Michael T. Rudd, Collegeville, PA (US); Oleg Selyutin, West Windsor, NJ (US); David M. Tellers, Lansdale, PA (US); Ling Tong, Warren, NJ (US); and Fengqi Zhang, Edison, NJ (US)"

And insert:
--Merck Sharp & Dohme Corp., Rahway, NJ (US)
MSD R&D (China) Co., Ltd., Shanghai, (CN)--

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*